(12) United States Patent
Nishimura et al.

(10) Patent No.: US 9,138,434 B2
(45) Date of Patent: Sep. 22, 2015

(54) OCTAHYDROTHIENOQUINOLINE DERIVATIVE, PHARMACEUTICAL COMPOSITION COMPRISING DERIVATIVE, AND USE OF THESE

(75) Inventors: Toshihiro Nishimura, Azumino (JP); Hirotaka Teranishi, Azumino (JP); Masako Yoshida, Azumino (JP); Yasunori Ueno, Azumino (JP); Kiyoshi Kasai, Azumino (JP)

(73) Assignee: KISSEI PHARMACEUTICAL CO., LTD., Nagano (JP)

( * ) Notice: Subject to any disclaimer, the term of this patent is extended or adjusted under 35 U.S.C. 154(b) by 0 days.

(21) Appl. No.: 14/002,533

(22) PCT Filed: Mar. 12, 2012

(86) PCT No.: PCT/JP2012/056252
§ 371 (c)(1),
(2), (4) Date: Aug. 30, 2013

(87) PCT Pub. No.: WO2012/124649
PCT Pub. Date: Sep. 20, 2012

(65) Prior Publication Data
US 2014/0243311 A1 Aug. 28, 2014

(30) Foreign Application Priority Data
Mar. 14, 2011 (JP) .................. 2011-055154

(51) Int. Cl.
| A61K 31/496 | (2006.01) |
| C07D 495/04 | (2006.01) |
| A61K 45/06 | (2006.01) |
| A61K 31/4365 | (2006.01) |
| A61K 31/444 | (2006.01) |
| A61K 31/4545 | (2006.01) |

(52) U.S. Cl.
CPC ........... *A61K 31/496* (2013.01); *A61K 31/4365* (2013.01); *A61K 31/444* (2013.01); *A61K 31/4545* (2013.01); *A61K 45/06* (2013.01); *C07D 495/04* (2013.01)

(58) Field of Classification Search
CPC ............. C07D 495/04; A61K 31/4365; A61K 31/4545
USPC .................... 546/80; 514/210, 290
See application file for complete search history.

(56) References Cited

U.S. PATENT DOCUMENTS

| 4,526,892 A | 7/1985 | Salvati et al. |
| 4,826,986 A | 5/1989 | Huser et al. |

FOREIGN PATENT DOCUMENTS

| EP | 0013788 A1 | 8/1980 |
| EP | 0 160 502 A2 | 11/1985 |
| JP | 55-100385 A | 7/1980 |
| JP | 62-298589 A | 12/1987 |
| JP | 2005-129430 A | 5/2005 |

OTHER PUBLICATIONS

International Search Report for PCT/JP2012/056252, dated Apr. 24, 2012.

*Primary Examiner* — Rita Desai
(74) *Attorney, Agent, or Firm* — Sughrue Mion, PLLC

(57) ABSTRACT

The present invention provides compounds represented by the general formula (I): or pharmaceutical acceptable salts thereof, wherein $R^1$ is cyano or the like; $R^2$ and $R^3$ are hydrogen or the like; $R^4$ is $C_{1-6}$ alkyl or the like; $R^5$ is $C_{1-6}$ alkyl, halo-$C_{1-6}$ alkyl, cycloalkyl, cycloalkyl-$C_{1-6}$ alkyl, aralkyl or the like; $R^6$ and $R^7$ are each hydrogen, $C_{1-6}$ alkyl, halo-$C_{1-6}$ alkyl, cycloalkyl, $C_{1-6}$ alkoxy-$C_{1-6}$ alkyl, $R^{12}R^{13}N$—$C_{1-6}$ alkyl or the like, which exhibit potent dopamine $D_2$ receptor stimulating activities. The present invention also provides pharmaceutical compositions containing said compound, and uses thereof.

(I)

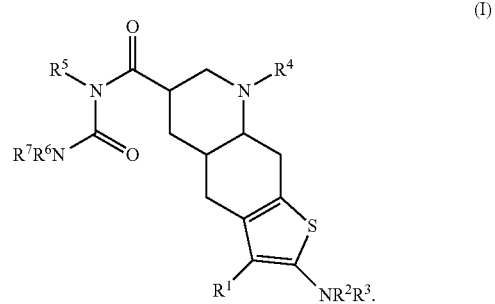

21 Claims, No Drawings

SEQUENCE LISTING

```
<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: Synthetic forward primer

<400> SEQUENCE: 1
caccatggat ccactgaatc tgtcc                                          25

<210> SEQ ID NO 2
<211> LENGTH: 22
<212> TYPE: DNA
<213> ORGANISM: Artificial Sequence
<220> FEATURE:
<223> OTHER INFORMATION: Synthetic reverse primer

<400> SEQUENCE: 2
tcagcagtgg aggatcttca gg                                             22

<210> SEQ ID NO 3
<211> LENGTH: 1332
<212> TYPE: DNA
<213> ORGANISM: Homo sapiens

<400> SEQUENCE: 3
atggatccac tgaatctgtc ctggtatgat gatgatctgg agaggcagaa ctggagccgg      60
cccttcaacg ggtcagacgg gaaggcggac agacccact acaactacta tgccacactg      120 ctcacccctgc tcatcgctgt catcgtcttc ggcaacgtgc tggtgtgcat ggctgtgtcc     180
```

```
cgcgagaagg cgctgcagac caccaccaac tacctgatcg tcagcctcgc agtggccgac    240
ctcctcgtcg ccacactggt catgcccctgg gttgtctacc tggaggtggt aggtgagtgg    300
aaattcagca ggattcactg tgacatcttc gtcactctgg acgtcatgat gtgcacggcg    360
agcatcctga acttgtgtgc catcagcatc gacaggtaca cagctgtggc catgcccatg    420
ctgtacaata cgcgctacag ctccaagcgc cgggtcaccg tcatgatctc catcgtctgg    480
gtcctgtcct tcaccatctc ctgcccactc ctcttcggac tcaataacgc agaccagaac    540
gagtgcatca ttgccaaccc ggccttcgtg gtctactcct ccatcgtctc cttctacgtg    600
cccttcattg tcaccctgct ggtctacatc aagatctaca ttgtcctccg cagacgccgc    660
aagcgagtca acaccaaacg cagcagccga gctttcaggg cccacctgag ggctccacta    720
aagggcaact gtactcaccc cgaggacatg aaactctgca ccgttatcat gaagtctaat    780
gggagtttcc cagtgaacag gcggagagtg gaggctgccc ggcgagccca ggagctggag    840
atggagatgc tctccagcac cagcccaccc gagaggaccc ggtacagccc catcccaccc    900
agccaccacc agctgactct ccccgacccg tcccaccacg tctccacag cactcccgac    960 agccccgcca aaccagagaa gaatgggcat gccaaagacc accccaagat tgccaagatc    1020
tttgagatcc agaccatgcc caatggcaaa acccggacct ccctcaagac catgagccgt    1080
aggaagctct cccagcagaa ggagaagaaa gccactcaga tgctcgccat tgttctcggc    1140
gtgttcatca tctgctggct gccccttcttc atcacacaca tcctgaacat acactgtgac    1200
tgcaacatcc cgcctgtcct gtacagcgcc ttcacgtggc tgggctatgt caacagcgcc    1260 gtgaaccccca tcatctacac caccttcaac attgagttcc gcaaggcctt cctgaagatc    1320
ctccactgct ga                                                         1332

<210> SEQ ID NO 4
<211> LENGTH: 22
<212> TYPE: DNA
<213> ORGANISM: Artificial Sequence
<220> FEATURE:
<223> OTHER INFORMATION: Synthetic forward primer

<400> SEQUENCE: 4
caccatggct ctctcttaca ga                                               22

<210> SEQ ID NO 5
<211> LENGTH: 18
<212> TYPE: DNA
<213> ORGANISM: Artificial Sequence
<220> FEATURE:
<223> OTHER INFORMATION: Synthetic reverse primer

<400> SEQUENCE: 5
atgtttgatg acaactgc                                                    18

<210> SEQ ID NO 6
<211> LENGTH: 1446
<212> TYPE: DNA
<213> ORGANISM: Homo sapiens

<400> SEQUENCE: 6
atggctctct cttacagagt gtctgaactt caaagcacaa ttcctgagca cattttgcag    60
agcacctttg ttcacgttat ctcttctaac tggtctggat tacagacaga atcaatacca    120
gaggaaatga aacagattgt tgaggaacag ggaaataaac tgcactgggc agctcttctg    180
```

```
atactcatgg tgataatacc cacaattggt ggaaatacccc ttgttattct ggctgtttca      240
ctggagaaga agctgcagta tgctactaat tactttctaa tgtccttggc ggtggctgat      300
ttgctggttg gattgtttgt gatgccaatt gccctcttga caataatgtt tgaggctatg      360
tggcccctcc cacttgttct atgtcctgcc tggttatttc ttgacgttct cttttcaacc      420
gcatccatca tgcatctctg tgccatttca gtggatcgtt acatagccat caaaaagcca      480
atccaggcca atcaatataa ctcacgggct acagcattca tcaagattac agtggtgtgg      540
ttaatttcaa taggcattgc cattccagtc cctattaaag ggatagagac tgatgtggac      600
aacccaaaca atatcacttg tgtgctgaca aaggaacgtt ttggcgattt catgctcttt      660
ggctcactgg ctgccttctt cacacctctt gcaattatga ttgtcaccta ctttctcact      720
atccatgctt tacagaagaa ggcttactta gtcaaaaaca agccacctca acgcctaaca      780
tggttgactg tgtctacagt tttccaaagg gatgaaacac cttgctcgtc accggaaaag      840
gtggcaatgc tggatggttc tcgaaaggac aaggctctgc ccaactcagg tgatgaaaca      900
cttatgcgaa gaacatccac aattgggaaa aagtcagtgc agaccatttc caacgaacag      960
agagcctcaa aggtcctagg gattgtgttt ttcctctttt tgcttatgtg gtgtcccttc     1020
tttattacaa atataacttt agttttatgt gattcctgta accaaactac tctccaaatg     1080
ctcctggaga tatttgtgtg gataggctat gttttcctcag gagtgaatcc tttggtctac     1140
accctcttca ataagacatt tcgggatgca tttggccgat atatcacctg caattaccgg     1200
gccacaaagt cagtaaaaac tctcagaaaa cgctccagta agatctactt ccggaatcca     1260
atggcagaga actctaagtt tttcaagaaa catggaattc gaaatgggat taaccctgcc     1320
atgtaccaga gtccaatgag gctccgaagt tcaaccattc agtcttcatc aatcattcta     1380
ctagatacgc ttctcctcac tgaaaatgaa ggtgacaaaa ctgaagagca agttagttat     1440
gtatag                                                                1446
```

OCTAHYDROTHIENOQUINOLINE DERIVATIVE, PHARMACEUTICAL COMPOSITION COMPRISING DERIVATIVE, AND USE OF THESE

CROSS REFERENCE TO RELATED APPLICATIONS

This is a National Stage of International Application No. PCT/JP2012/056252, filed Mar. 12, 2012, claiming priority from Japanese Patent Application No. 2011-055154, filed Mar. 14, 2011, the contents of all of which are incorporated herein by reference in their entirety.

TECHNICAL FIELD

The present invention relates to novel octahydrothienoquinoline derivatives, which exhibit dopamine $D_2$ receptor agonistic activities, pharmaceutical compositions containing the same, and their uses.

Parkinson's disease is a progressive neurodegenerating disease which usually affects elderly patients, and the number of parkinsonian patients is growing with progressive aging of society. Parkinson's disease pathogenesis is characterized by impairment in coordinated motor function such as rest tremor, rigidity, akinesia, postural instability and the like. It is thought that Parkinson's disease results from deficiency of dopamine in the striatum, which is caused by degeneration of dopamine neuron in the substantia nigra. For that reasons, L-dopa or dopamine $D_2$ receptor agonists are used for the treatment of Parkinson's disease.

L-dopa is a precursor of dopamine, and is metabolized to dopamine which exerts its efficacy in the brain. Since L-dopa has a very short serum half-life, L-dopa is administered usually in combination with a peripheral aromatic L-amino acid decarboxylase inhibitor and/or a catechol-O-methyltransferase inhibitor, which are the metabolizing enzyme inhibitors of L-dopa.

Dopamine $D_2$ receptor agonists exert an anti-Parkinson's effect by directly stimulating dopamine $D_2$ receptors of the striatum. And, it is known that the dopamine $D_2$ receptor agonists are useful for treating restless legs syndrome, hyperprolactinemia or the like (for example, see Non-patent literature 1 or 2).

Various ergot or non-ergot dopamine $D_2$ receptor agonists are known as dopamine $D_2$ receptor agonist (for example, see Patent literature 1 to 3 about ergot dopamine $D_2$ receptor agonist, and see Patent literature 4 to 6 about non-ergot dopamine $D_2$ receptor agonist).

The non-ergot dopamine $D_2$ receptor agonists have the disadvantage duration of action is shorter than the ergot dopamine $D_2$ receptor agonists, since the serum half-life of them is shorter than the ergot dopamine $D_2$ receptor agonists (for example, see Non-patent literature 3). And more, the non-ergot dopamine $D_2$ receptor agonists have problems of side effects such as sudden onset of sleep, somnolence or the like.

The ergot dopamine $D_2$ agonists show the long-term effectiveness compared to the non-ergot dopamine $D_2$ receptor agonists. However, recently it has been reported that the risk of onset of cardiac valvular disease increases when taken long-term high dose of pergolide which was is a typical ergot dopamine $D_2$ receptor agonist. So, the periodic monitoring of echocardiography and the like are required during administering the ergot dopamine $D_2$ receptor agonists. Since it is reported that cardiac valvular disease is caused by the growth stimulation of the cardiac valvular cells by the stimulation activity of 5-$HT_{2B}$ receptor as pathogenesis of cardiac valvular disease, the relevance of cardiac valvular diseases and the stimulation activity of 5-$HT_{2B}$ receptor is strongly suggested (for example, see Non-patent literature 4).

Accordingly, it has been expected for novel dopamine $D_2$ receptor agonists exhibiting potent and lasting dopamine $D_2$ receptor agonistic activities with less 5-$HT_{2B}$ receptor stimulating activities.

A compound represented by the formula:

[Chem. 1]

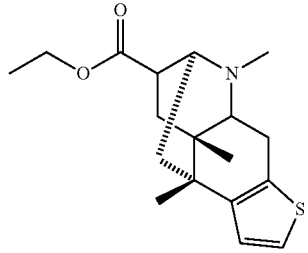

is known as 4,4a,5,6,7,8,8a,9-octahydrothieno[3,2g]quinoline derivative (see Non-patent literature 5). However, any pharmacological effects of the compound are not described at all in the Non-patent literature 5.

CITATION LIST

Patent Literature

Patent literature 1: U.S. Pat. No. 4,166,182
Patent literature 2: U.S. Pat. No. 3,752,814
Patent literature 3: U.S. Pat. No. 4,526,892
Patent literature 4: U.S. Pat. No. 4,452,808
Patent literature 5: U.S. Pat. No. 3,804,849
Patent literature 6: U.S. Pat. No. 4,886,812

Non-Patent Literature

Non-patent literature 1: Happe, S. et al, "CNS Drugs", 2004, vol. 18(1), pp. 27-36
Non-patent literature 2: Crosignani, P. G. et al, "Eur. J. Obstetrics & Gynecology and Reproductive Biology", 2006, vol. 125, pp. 152-164
Non-patent literature 3: Prikhojan, A. et al, "J. Neural Transm.", 2000, vol. 107, pp. 1159-1164
Non-patent literature 4: Setola, V. et al, "Mol. Pharmacol.", 2003, vol. 63, pp. 1223-1229
Non-patent literature 5: Bosch, J. et al, "J. Heterocyclic Chem.", 1980, vol. 17, pp. 745-747

SUMMARY OF THE INVENTION

Object to be Solved by the Invention

An object of the present invention is to provide a novel compound having potent dopamine $D_2$ receptor stimulating activities, and more preferably a compound alleviated 5-$HT_{2B}$ receptor stimulating activities.

Means for Solving the Object

The inventors of the present invention diligently worked to achieve the foregoing object and found surprisingly that compounds represented by the general formula (I) show highly potent dopamine $D_2$ receptor simulating activities as compared to 5-$HT_{2B}$ receptor simulating activities. Based on these findings, the present invention has been accomplished.

That is, the present invention therefore provides a compound represented by the general formula (I):

[Chem. 2]

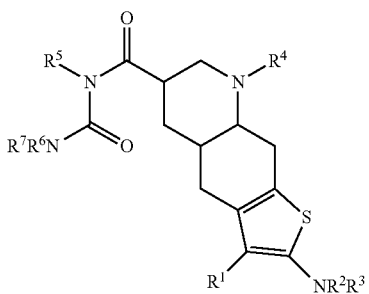

(I)

or a pharmaceutically acceptable salt thereof,
wherein
$R^1$ is any one of the following a) to d):
  a) a cyano group,
  b) a carbamoyl group,
  c) a $C_{2-7}$ alkoxycarbonyl group, or
  d) a carboxy group;
$R^2$ and $R^3$ are each independently a hydrogen atom, a $C_{1-6}$ alkyl group, a $C_{1-7}$ acyl group, or a $C_{2-7}$ alkoxycarbonyl group;
$R^4$ is a hydrogen atom, a $C_{1-6}$ alkyl group, or a halo-$C_{1-6}$ alkyl group;
$R^5$ is any one of the following a) to j):
  a) a $C_{1-6}$ alkyl group,
  b) a halo-$C_{1-6}$ alkyl group,
  c) a cycloalkyl group,
  d) a benzo-fuzed cycloalkyl group,
  e) a cycloalkyl-$C_{1-6}$ alkyl group,
  f) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group, and a hydroxy-$C_{1-6}$ alkyl group,
  g) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and a $C_{1-6}$ alkoxy group,
  h) a $C_{2-6}$ alkenyl group,
  i) a $C_{1-6}$ alkoxy-$C_{1-6}$ alkyl group, or
  j) a $R^{10}R^{11}N$—$C_{1-6}$ alkyl group;
$R^6$ and $R^7$ are each independently any one of the following a) to k):
  a) a hydrogen atom,
  b) a $C_{1-6}$ alkyl group,
  c) a halo-$C_{1-6}$ alkyl group,
  d) a heterocycloalkyl group,
  e) a heterocycloalkyl-$C_{1-6}$ alkyl group,
  f) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group, and a $R^{10}R^{11}N$—$C_{1-6}$ alkyl group,
  g) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and a $C_{1-6}$ alkoxy group,
  h) a $C_{1-6}$ alkoxy-$C_{1-6}$ alkyl group,
  i) a $R^{12}R^{13}N$—$C_{1-6}$ alkyl group,
  j) a $R^{12}R^{13}N$—$C_{1-6}$ alkoxy-$C_{1-6}$ alkyl group, or
  k) a $R^{12}R^{13}N$—$C(O)$—$C_{1-6}$ alkyl group;
$R^{10}$ and $R^{11}$ are each independently a hydrogen atom, a $C_{1-6}$ alkyl group or a hydroxy-$C_{1-6}$ alkyl group, or $R^{10}$ and $R^{11}$, together with the nitrogen atom to which they are bonded, form a cyclic amino group, wherein the cyclic amino group is unsubstituted or substituted with 1 or 2 $C_{1-6}$ alkyl groups; and
$R^{12}$ and $R^{13}$ are each independently a hydrogen atom, a $C_{1-6}$ alkyl group, a hydroxy-$C_{1-6}$ alkyl group or an aryl group, or $R^{12}$ and $R^{13}$, together with the nitrogen atom to which they are bonded, form a cyclic amino group, wherein the cyclic amino group is unsubstituted or substituted with 1 or 2 $C_{1-6}$ alkyl groups.

In another aspect, the present invention provides a pharmaceutical composition which comprises, as an active ingredient, a compound represented by the general formula (I) or a pharmaceutically acceptable salt thereof.

In still another aspect, the present invention provides a treating or preventing agent of Parkinson's disease, restless legs syndrome or hyperprolactinemia which comprises a compound represented by the general formula (I) or a pharmaceutically acceptable salt thereof.

In still another aspect, the present invention provides a dopamine $D_2$ receptor agonist which comprises a compound represented by the general formula (I) or a pharmaceutically acceptable salt thereof.

In still another aspect, the present invention provides a pharmaceutical agent which comprises (1) a compound of the general formula (I) or a pharmaceutically acceptable salt thereof and (2) at least one anti-Parkinson drug selected from L-dopa, dopamine $D_2$ receptor agonists, anticholinergic agents, adenosine $A_{2A}$ receptor antagonists, NMDA receptor antagonists, monoamine oxidase B inhibitors, COMT inhibitors, aromatic L-amino acid decarboxylase inhibitors, droxidopa, melevodopa, threodops, zonisamide and amantadine hydrochloride.

Effects of the Invention

The compounds of the present invention exhibit potent dopamine $D_2$ receptor simulating activities. Moreover, compounds of the present invention have a desirable safety profile since compounds of the present invention have extremely slight 5-$HT_{2B}$ receptor stimulating activities. Accordingly, compounds of the present invention are useful as a therapeutic or prophylactic agent for Parkinson's disease, restless legs syndrome or hyperprolactinemia.

EMBODIMENTS FOR CARRYING OUT THE INVENTION

In a compound represented by the general formula (I), the following terms have the following meanings unless otherwise specified.

The term "halogen atom" refers to a fluorine, chlorine, bromine or iodine atom.

The term "$C_{1-6}$ alkyl group" refers to a straight chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group and the like. Preferred $C_{1-6}$ alkyl groups for $R^4$ are a $C_{1-3}$ alkyl group, and more preferably a methyl group. Preferred $C_{1-6}$ alkyl groups for $R^{10}$, $R^{11}$, $R^{12}$ and $R^{13}$ are a $C_{1-3}$ alkyl group, and more preferably a methyl or ethyl group.

The term "halo-$C_{1-6}$ alkyl group" refers to an alkyl group having 1 to 6 carbon atoms substituted with the same or different 1 to 3 halogen atoms such as a fluoromethyl group, a 2-fluoroethyl group, a difluoromethyl group, a trifluoromethyl group, a 2,2,2-trifluoroethyl group, a 3,3,3-trifluoropropyl group, a 4,4,4-trifluorobutyl group and the like.

The term "hydroxyl-$C_{1-6}$ alkyl group" refers to an alkyl group having 1 to 6 carbon atoms substituted with a hydroxy group such as a hydroxymethyl group, a 1-hydroxyethyl group, a 1-hydroxy-1,1-dimethylmethyl group, a 2-hydroxyethyl group, a 2-hydroxy-2-methylpropyl group, a 3-hydroxypropyl group and the like.

The term "$C_{1-6}$ alkoxy group" refers to a straight chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, a hexyloxy group and the like.

The term "$C_{2-7}$ alkoxycarbonyl group" refers to a ($C_{1-6}$ alkoxy)-C(O)— such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, a hexyloxycarbonyl group and the like.

The term "$C_{1-7}$ acyl group" refers to a formyl group or a group represented by a ($C_{1-6}$ alkyl)-C(O)— such as a formyl group, an acetyl group, a propionyl group, a butyryl group, an isobutyryl group, a pivaloyl group, a valeryl group, an isovaleryl group and the like.

The term "cycloalkyl group" refers to a 3- to 7-membered saturated cyclic hydrocarbon such as a cyclopropyl group, a cyclobutyl group, a cyclopentyl group, a cyclohexyl group and a cycloheptyl group.

The term "benzo-fuzed cycloalkyl group" refers to a cycloalkyl group fuzed with a benzene ring such as an indan-1-yl group, an indan-2-yl group, a tetrahydro-naphthalen-1-yl group and the like.

The term "heterocycloalkyl group" refers to a 4- to 7-membered saturated heterocyclic group which contains —NH—, —O— or —S— as a member of the ring and is bonded via a carbon atom. Examples of heterocycloalkyl groups include an azetidin-3-yl group, a tetrahydrofuryl group, a tetrahydrothienyl group, a tetrahydro-pyranyl group, a pyrrolidin-2-yl group, a pyrrolidin-3-yl group, a piperidin-2-yl group, a piperidin-3-yl group, a piperidin-4-yl group and the like.

The heterocycloalkyl group may be optionally substituted with 1 or 2 $C_{1-6}$ alkyl groups such as a 1-methylazetidin-3-yl group, a 1-methylpyrrolidin-3-yl group, a 1-methylpiperidin-4-yl group, a 1-methyl-piperidin-3-yl group and the like.

The term "cycloalkyl-$C_{1-6}$ alkyl group" refers to a cyclopropylmethyl group, a cyclopentylmethyl group, a cyclohexylmethyl group and the like, preferably a cyclopropylmethyl group.

The term "heterocycloalkyl-$C_{1-6}$ alkyl group" refers to a 1-methylazetidin-3-ylmethyl group, 1-methylpiperidin-4-ylmethyl group and the like.

The term "aryl group" refers to a $C_{6-10}$ aromatic hydrocarbon group such as a phenyl group, a 1-naphtyl group and a 2-naphtyl group, preferably a phenyl group.

The term "heteroaryl group" refers to a 5- or 6-membered monocyclic aromatic heterocycle having 1 to 5 carbon atoms and 1 to 4 heteroatoms selected independently from the group consisting of an oxygen, nitrogen and sulfur atom, or a 8- to 10-membered bicyclic aromatic heterocycle having 1 to 9 carbon atoms and 1 to 4 heteroatoms selected independently from the group consisting of an oxygen, nitrogen atom and sulfur atom, provided that said heterocycles do not include adjacent oxygen and/or sulfur atoms. Examples of monocyclic aromatic heteroaryl groups include pyrrolyl, furyl, thienyl, imidazolyl, pyrazolyl, oxazolyl, isoxazolyl, 1,2,4-oxadiazolyl, 1,3,4-oxadiazolyl, tetrazolyl, thiazolyl, isothiazolyl, 1,2,3-thiadiazolyl, triazolyl, pyridyl, pyrazinyl, pyrimidyl, pyridazinyl and the like, preferably thienyl, imidazolyl, thiazolyl or pyridyl. Examples of bicyclic aromatic heteroaryl groups include indazolyl, benzofuranyl, benzothienyl, benzothiazolyl, quinolyl, isoquinolyl, phthalazinyl, benzimidazolyl, benzoxazolyl and the like. The heterocycles include all position isomers such as 2-pyridyl, 3-pyridyl or 4-pyridyl.

The term "aralkyl group" refers to an aryl-$C_{1-6}$ alkyl group such as a benzyl group, a phenethyl group, a 1-phenylethyl group, a 3-phenylpropyl group, a 4-phenyl-butyl group, a naphthylmethyl group and the like. Preferred aralkyl groups for $R^5$, $R^6$ and $R^7$ are a phenyl-$C_{1-6}$ alkyl group, and more preferably a benzyl or phenethyl group.

The term "heteroaryl-$C_{1-6}$ alkyl group" refers to a 2-pyridylmethyl group, a 3-pyridylmethyl group, a 4-pyridylmethyl group, a 2-pyridylethyl group, a 3-pyridylethyl group, a 4-pyridylethyl group, a 2-thienylmethyl group, an imidazol-1-ylmethyl group, an 2-imidazol-3-ylmethyl group, an 2-imidazol-1-ylethyl group, an 3-imidazol-1-ylpropyl group, a 2-thiazolylmethyl group and the like.

The term "$C_{2-6}$ alkenyl group" refers to a straight chained or branched unsaturated hydrocarbon group having 2 to 6 carbon atoms such as $CH_2=CHCH_2$—, $CH_2=CHCH_2CH_2$—, $CH_3CH=CHCH_2$— and the like.

The term "$C_{1-6}$ alkoxy-$C_{1-6}$ alkyl group" includes a 2-methoxyethyl group, a 3-methoxypropyl group, an 2-ethoxyethyl group, an 3-ethoxypropyl group and the like.

The term "cyclic amino group" refers to a 5- to 7-membered saturated cyclic amine which may contain —NH—, —O— or —S— as a member of the ring. Examples of cyclic amino groups include a 1-pyrrolidyl group, a piperidinyl group, a piperazinyl group, a morpholinyl group, a thiomorpholinyl group, a [1,4]diazepam-1-yl group and the like.

The numbering of the ring atoms of the compound represented by the general formula (I) is given as follows:

[Chem. 3]

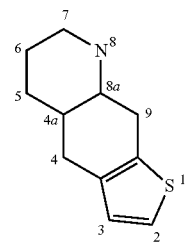

In a chemical name in the present description, the marks "*" mean the relative configuration of the asymmetric carbon atom. For example, 1-{[(4aR*,6R*,8aR*)-2-amino-3-cyano-8-methyl-4H,4aH,5H,6H,7H, 8H, 8aH,9H-thieno[3,2-g]quinolin-6-yl]carbonyl}-1-butyl-3-[2-(dimethylamino)

ethyl]urea (Compound 1-24) means that the asymmetric carbons at 4a, 6 and 8a positions are relative configurations.

In the case where a compound represented by the general formula (I) of the present invention contains one or more asymmetric carbon atoms, all stereoisomers in the R- or S-configuration at each of asymmetric carbons and their mixture are contemplated within the scope of the present invention. In such cases, racemic compounds, racemic mixtures, racemic solid solutions, individual enantiomers and mixtures of diastereomers are also contemplated within the scope of the present invention. In the case where a compound represented by the general formula (I) has the geometrical isomers, all geometrical isomers are also contemplated within the scope of the present invention. In the case where a compound represented by the general formula (I) has the atropisomers, all atropisomers are also contemplated within the scope of the present invention. A compound represented by the general formula (I) or a pharmaceutically acceptable salt thereof includes a solvate with a pharmaceutically acceptable solvent such as water, ethanol and the like.

Compounds represented by the general formula (I) of the present invention may exist in the form of salts. Examples of such salts include acid addition salts formed with mineral acids such as hydrochloric acid, hydrobromic acid, hydroiodic acid, sulfuric acid, nitric acid, phosphoric acid and the like; acid addition salts formed with organic acids such as formic acid, acetic acid, trifluoroacetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like; basic salts formed with inorganic bases such as lithium, sodium, potassium, calcium, magnesium and the like; basic salts formed with organic bases such as triethylamine, piperidine, morpholine, lysine and the like.

In an embodiment of a compound represented by the general formula (I) of the present invention,
preferably $R^1$ is a cyano group;
$R^2$ and $R^3$ are preferably a hydrogen atom;
$R^4$ is preferably a hydrogen atom or a $C_{1-6}$ alkyl group, and even more preferably a methyl group;
$R^5$ is preferably any one of the following a) to h):
a) a $C_{1-6}$ alkyl group,
b) a halo-$C_{1-6}$ alkyl group,
c) a cycloalkyl-$C_{1-6}$ alkyl group,
d) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group and a hydroxy-$C_{1-6}$ alkyl group,
e) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and a $C_{1-6}$ alkoxy group,
f) a $C_{2-6}$ alkenyl group,
g) a $C_{1-6}$ alkoxy-$C_{1-6}$ alkyl group, or
h) a $R^{10}R^{11}N$—$C_{1-6}$ alkyl group;
more preferably $R^5$ is any one of the following a) to f):
a) a $C_{1-6}$ alkyl group,
b) a cycloalkyl-$C_{1-6}$ alkyl group,
c) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group and a hydroxy-$C_{1-6}$ alkyl group,
d) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and a $C_{1-6}$ alkoxy group,
e) a $C_{1-6}$ alkoxy-$C_{1-6}$ alkyl group, or
f) a $R^{10}R^{11}N$—$C_{1-6}$ alkyl group;
even more preferably $R^5$ is any one of the following a) to d):
a) a $C_{1-6}$ alkyl group,
b) a cycloalkyl-$C_{1-6}$ alkyl group,
c) a $C_{1-6}$ alkoxy-$C_{1-6}$ alkyl group, or
d) a $R^{10}R^{11}N$—$C_{1-6}$ alkyl group;
$R^6$ is preferably a hydrogen atom,
$R^7$ is preferably any one of the following a) to i):
a) a $C_{1-6}$ alkyl group,
b) a halo-$C_{1-6}$ alkyl group,
c) a heterocycloalkyl-$C_{1-6}$ alkyl group,
d) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group, and a $R^{10}R^{11}N$—$C_{1-6}$ alkyl group,
e) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and a $C_{1-6}$ alkoxy group,
f) a $C_{1-6}$ alkoxy-$C_{1-6}$ alkyl group,
g) a $R^{12}R^{13}N$—$C_{1-6}$ alkyl group,
h) a $R^{12}R^{13}N$—$C_{1-6}$ alkoxy-$C_{1-6}$ alkyl group, or
i) a $R^{12}R^{13}N$—$C(O)$—$C_{1-6}$ alkyl group;
more preferably $R^7$ is any one of the following a) to f):
a) a $C_{1-6}$ alkyl group,
b) a halo-$C_{1-6}$ alkyl group,
c) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group, and a $R^{10}R^{11}N$—$C_{1-6}$ alkyl group,
d) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group and a $C_{1-6}$ alkoxy group,
e) a $C_{1-6}$ alkoxy-$C_{1-6}$ alkyl group, or
f) a $R^{12}R^{13}N$—$C_{1-6}$ alkyl group;
even more preferably $R^7$ is any one of the following a) to d):
a) a $C_{1-6}$ alkyl group,
b) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group, and a $R^{10}R^{11}N$—$C_{1-6}$ alkyl group,
c) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group and a $C_{1-6}$ alkoxy group, or
d) a $R^{12}R^{13}N$—$C_{1-6}$ alkyl group;
especially preferable $R^7$ is any one of the following a) to b):
a) a $C_{1-6}$ alkyl group, or
b) a $R^{12}R^{13}N$—$C_{1-6}$ alkyl group; and
preferably $R^{10}$ and $R^{11}$ are each independently a $C_{1-6}$ alkyl group, or $R^{10}$ and $R^{11}$, together with the nitrogen atom to which they are bonded, form a cyclic amino group, wherein the cyclic amino group is unsubstituted or substituted with 1 or 2 $C_{1-6}$ alkyl groups; or preferably $R^{12}$ and $R^{13}$ are each independently a $C_{1-6}$ alkyl group, or $R^{12}$ and $R^{13}$, together with the nitrogen atom to which they are bonded, form a cyclic amino group, wherein the cyclic amino group is unsubstituted or substituted with 1 or 2 $C_{1-6}$ alkyl groups.

In an embodiment of a compound represented by the general formula (I), a compound represented by the general formula (I) is preferably a general formula (II), wherein

[Chem. 4]

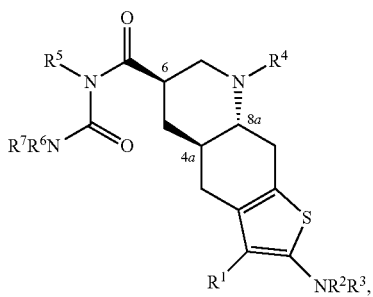

(II)

and the configuration at 4a, 6 and 8a positions of the quinoline ring of 4H, 4aH,5H,6H,7H,8H,8aH,9H-thieno[3,2-g]quinoline is represented by relative configuration, more preferably a compound represented by the general formula (I) is a general formula (III), wherein

[Chem. 5]

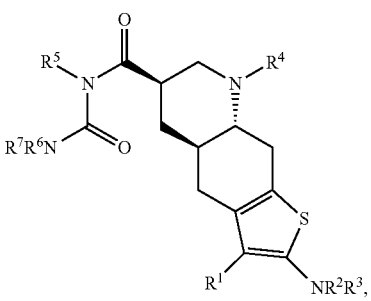

(III)

and the configuration at 4a, 6 and 8a positions of the quinoline ring of 4H, 4aH,5H,6H,7H,8H,8aH,9H-thieno[3,2-g]quinoline is represented by absolute configuration.

In a preferable embodiment of the present invention,
$R^1$ is a cyano group.

In a more preferable embodiment of the present invention,
$R^1$ is a cyano group; and
$R^2$ and $R^3$ are a hydrogen atom.

In an even more preferable embodiment of the present invention,
$R^1$ is a cyano group;
$R^2$ and $R^3$ are a hydrogen atom; and
$R^4$ is a hydrogen atom or a $C_{1-6}$ alkyl group.

In an even more preferable embodiment of the present invention,
$R^1$ is a cyano group;
$R^2$ and $R^3$ are a hydrogen atom;
$R^4$ is a hydrogen atom or a $C_{1-6}$ alkyl group;
$R^6$ is a hydrogen atom; and
$R^7$ is any one of the following a) to i):
a) a $C_{1-6}$ alkyl group,
b) a halo-$C_{1-6}$ alkyl group,
c) a heterocycloalkyl-$C_{1-6}$ alkyl group,
d) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group and a $R^{10}R^{11}N$—$C_{1-6}$ alkyl group,
e) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and a $C_{1-6}$ alkoxy group,
f) a $C_{1-6}$ alkoxy-$C_{1-6}$ alkyl group,
g) a $R^{12}R^{13}N$—$C_{1-6}$ alkyl group,
h) a $R^{12}R^{13}N$—$C_{1-6}$ alkoxy-$C_{1-6}$ alkyl group, or
i) a $R^{12}R^{13}N$—$C(O)$—$C_{1-6}$ alkyl group.

In an even more preferable embodiment of the present invention,
$R^1$ is a cyano group;
$R^2$ and $R^3$ are a hydrogen atom;
$R^4$ is a hydrogen atom or a $C_{1-6}$ alkyl group;
$R^5$ is any one of the following a) to h):
a) a $C_{1-6}$ alkyl group,
b) a halo-$C_{1-6}$ alkyl group,
c) a cycloalkyl-$C_{1-6}$ alkyl group,
d) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group and a hydroxy-$C_{1-6}$ alkyl group,
e) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group and a $C_{1-6}$ alkoxy group,
f) a $C_{2-6}$ alkenyl group,
g) a $C_{1-6}$ alkoxy-$C_{1-6}$ alkyl group, or
h) a $R^{10}R^{11}N$—$C_{1-6}$ alkyl group;
$R^6$ is a hydrogen atom; and
$R^7$ is any one of the following a) to i):
a) a $C_{1-6}$ alkyl group,
b) a halo-$C_{1-6}$ alkyl group,
c) a heterocycloalkyl-$C_{1-6}$ alkyl group,
d) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group and a $R^{10}R^{11}N$—$C_{1-6}$ alkyl group,
e) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group and a $C_{1-6}$ alkoxy group,
f) a $C_{1-6}$ alkoxy-$C_{1-6}$ alkyl group,
g) a $R^{12}R^{13}N$—$C_{1-6}$ alkyl group,
h) a $R^{12}R^{13}N$—$C_{1-6}$ alkoxy-$C_{1-6}$ alkyl group, or
i) a $R^{12}R^{13}N$—$C(O)$—$C_{1-6}$ alkyl group.

In an even more preferable embodiment of the present invention,
$R^1$ is a cyano group;
$R^2$ and $R^3$ are a hydrogen atom;
$R^4$ is a hydrogen atom or a $C_{1-6}$ alkyl group;
$R^5$ is any one of the following a) to h):
a) a $C_{1-6}$ alkyl group,
b) a halo-$C_{1-6}$ alkyl group,
c) a cycloalkyl-$C_{1-6}$ alkyl group,
d) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group and a hydroxy-$C_{1-6}$ alkyl group, e) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group and a $C_{1-6}$ alkoxy group,
f) a $C_{2-6}$ alkenyl group,
g) a $C_{1-6}$ alkoxy-$C_{1-6}$ alkyl group, or
h) a $R^{10}R^{11}N$—$C_{1-6}$ alkyl group;
  $R^6$ is a hydrogen atom; and
  $R^7$ is any one of the following a) to f):
a) a $C_{1-6}$ alkyl group,
b) a halo-$C_{1-6}$ alkyl group,
c) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group and a $R^{10}R^{11}N$—$C_{1-6}$ alkyl group,
d) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group and a $C_{1-6}$ alkoxy group,
e) a $C_{1-6}$ alkoxy-$C_{1-6}$ alkyl group, or
f) a $R^{12}R^{13}N$—$C_{1-6}$ alkyl group.

In an even more preferable embodiment of the present invention,
  $R^1$ is a cyano group;
  $R^2$ and $R^3$ are a hydrogen atom;
  $R^4$ is a methyl group;
  $R^5$ is any one of the following a) to f):
a) a $C_{1-6}$ alkyl group,
b) a cycloalkyl-$C_{1-6}$ alkyl group,
c) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group and a hydroxy-$C_{1-6}$ alkyl group,
d) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group and a $C_{1-6}$ alkoxy group,
e) a $C_{1-6}$ alkoxy-$C_{1-6}$ alkyl group, or
f) a $R^{10}R^{11}N$—$C_{1-6}$ alkyl group;
  $R^6$ is a hydrogen atom; and
  $R^7$ is any one of the following a) to d):
a) a $C_{1-6}$ alkyl group,
b) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group and a $R^{10}R^{11}N$—$C_{1-6}$ alkyl group,
c) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group and a $C_{1-6}$ alkoxy group, or
d) a $R^{12}R^{13}N$—$C_{1-6}$ alkyl group.

In an even more preferable embodiment of the present invention,
  $R^1$ is a cyano group;
  $R^2$ and $R^3$ are a hydrogen atom;
  $R^4$ is a methyl group;
  $R^5$ is any one of the following a) to d):
a) a $C_{1-6}$ alkyl group,
b) a cycloalkyl-$C_{1-6}$ alkyl group,
c) a $C_{1-6}$ alkoxy-$C_{1-6}$ alkyl group, or
d) a $R^{10}R^{11}N$—$C_{1-6}$ alkyl group;
  $R^6$ is a hydrogen atom, and
  $R^7$ is any one of the following a) to b):
a) a $C_{1-6}$ alkyl group, or
b) a $R^{12}R^{13}N$—$C_{1-6}$ alkyl group.

Specific examples of preferred embodiments of the present invention are compounds selected form the group consisting of:
1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[2-(dimethylamino)ethyl]-1-propylurea (Compound 1-1);
1-{[(4aR,6R,8aR)-2-amino-3-cyano-8-methyl-4H,4aH,5H,6H,7H,8H,8aH,9H-thieno[3,2-g]quinolin-6-yl]carbonyl}-1-butyl-3-[2-(diethylamino)ethyl]urea (Compound 1-3);
1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[3-(dimethylamino)-2,2-dimethylpropyl]-1-ethylurea (Compound 1-4);
1-{[(4aR,6R,8aR)-2-amino-3-cyano-8-methyl-4H,4aH,5H,6H,7H,8H,8aH,9H-thieno[3,2-g]quinolin-6-yl]carbonyl}-3-ethyl-1-[2-(pyrrolidin-1-yl)ethyl]urea (Compound 1-6);
1-{[(4aR*,6R*,8aR*)-2-amino-3-cyano-8-methyl-4H,4aH,5H,6H,7H,8H,8aH,9H-thieno[3,2-g]quinolin-6-yl]carbonyl}-1-butyl-3-[2-(dimethylamino)ethyl]urea (Compound 1-24);
1-{[(4aR*,6R*,8aR*)-2-amino-3-cyano-8-methyl-4H,4aH,5H,6H,7H,8H,8aH,9H-thieno[3,2-g]quinolin-6-yl]carbonyl}-3-[2-(dimethylamino)ethyl]-1-(2-phenylethyl)urea (Compound 1-30);
1-{[(4aR*,6R*,8aR*)-2-amino-3-cyano-8-methyl-4H,4aH,5H,6H,7H,8H,8aH,9H-thieno[3,2-g]quinolin-6-yl]carbonyl}-3-[2-(dimethylamino)ethyl]-1-(3-methylbutyl)urea (Compound 1-43);
1-{[(4aR*,6R*,8aR*)-2-amino-3-cyano-8-methyl-4H,4aH,5H,6H,7H,8H,8aH,9H-thieno[3,2-g]quinolin-6-yl]carbonyl}-1-butyl-3-[2-(piperidin-1-yl)ethyl]urea (Compound 1-46);
1-{[(4aR*,6R*,8aR*)-2-amino-3-cyano-8-methyl-4H,4aH,5H,6H,7H,8H,8aH,9H-thieno[3,2-g]quinolin-6-yl]carbonyl}-3-[2-(dimethylamino)ethyl]-1-(2,2-di-methylpropyl)urea (Compound 1-56);
1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[(2S)-1-(dimethylamino)propan-2-yl]-1-ethylurea (Compound 1-57);
1-{[(4aR*,6R*,8aR*)-2-amino-3-cyano-8-methyl-4H,4aH,5H,6H,7H,8H,8aH,9H-thieno[3,2-g]quinolin-6-yl]carbonyl}-3-[2-(dimethylamino)-2-methylpropyl]-1-propylurea (Compound 1-82);
1-{[(4aR*,6R*,8aR*)-2-amino-3-cyano-8-methyl-4H,4aH,5H,6H,7H,8H,8aH,9H-thieno[3,2-g]quinolin-6-yl]carbonyl}-3-[2-(dimethylamino)-2-ethylbutyl]-1-ethylurea (Compound 1-84);
1-{[(4aR,6R,8aR)-2-amino-3-cyano-8-methyl-4H,4aH,5H,6H,7H,8H,8aH,9H-thieno[3,2-g]quinolin-6-yl]carbonyl}-1-(cyclopropylmethyl)-3-[3-(dimethylamino)-2,2-dimethyl-propyl]urea (Compound 1-104);
1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[2-(diethylamino)ethyl]-1-ethylurea (Compound 1-105);
1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[1-(dimethylamino)-2-methylpropan-2-yl]-1-ethylurea (Compound 1-106);
1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[2-(dimethylamino)-2-ethylbutyl]-1-ethylurea (Compound 1-107);

1-{[(4aR,6R,8aR)-2-amino-3-cyano-8-methyl-4H,4aH,5H, 6H,7H,8H,8aH,9H-thieno[3,2-g]quinolin-6-yl]carbonyl}-3-[2-(dimethylamino)ethyl]-1-ethylurea (Compound 1-108); and 1-{[(4aR,6R,8aR)-2-amino-3-cyano-8-methyl-4H,4aH,5H, 6H,7H,8H,8aH,9H-thieno[3,2-g]quinolin-6-yl]carbonyl}-1-(cyclopropylmethyl)-3-[2-(dimethylamino)ethyl]urea (Compound 1-109), or a pharmaceutically acceptable salt thereof.

Compounds represented by the general formula (I) of the present invention can be prepared by methods as illustrated in schemes 1 and 2.

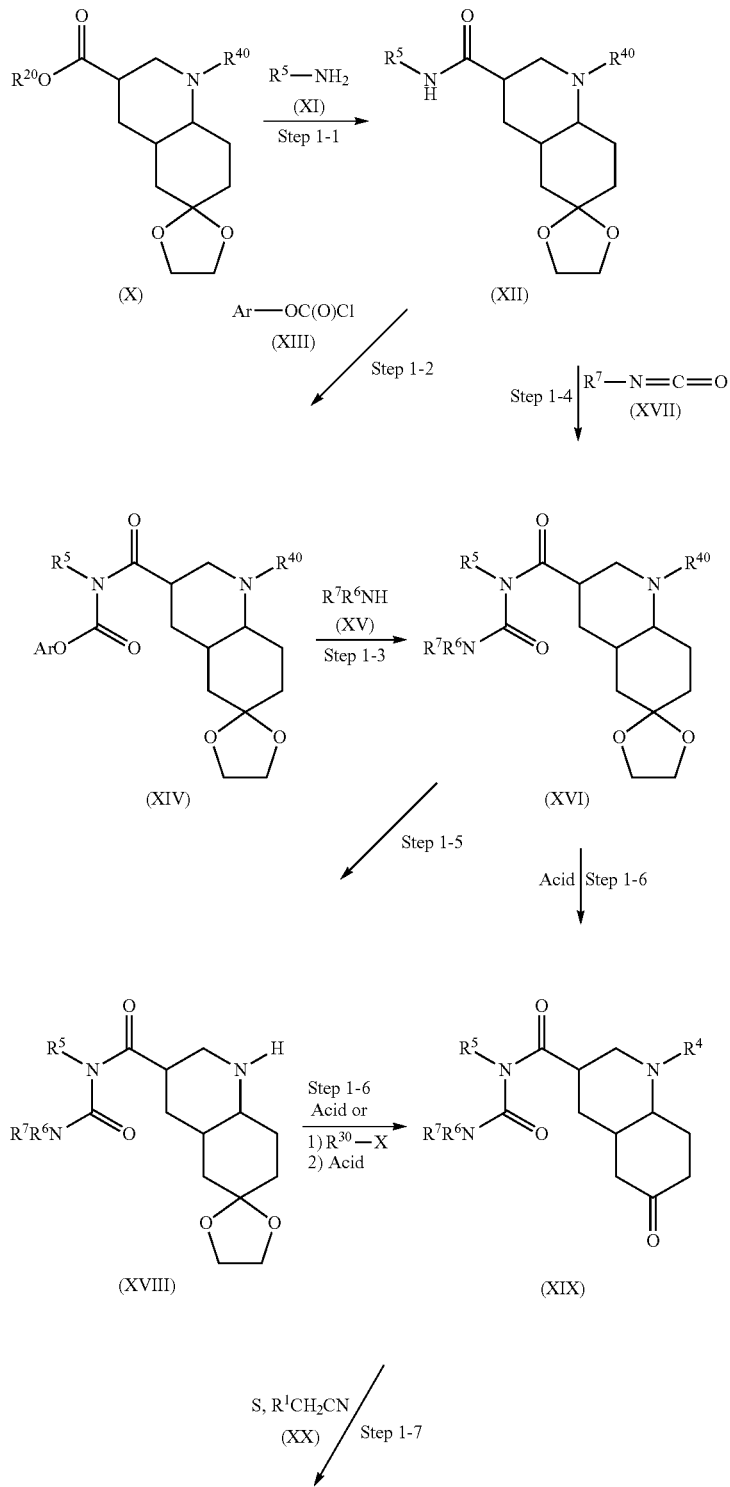

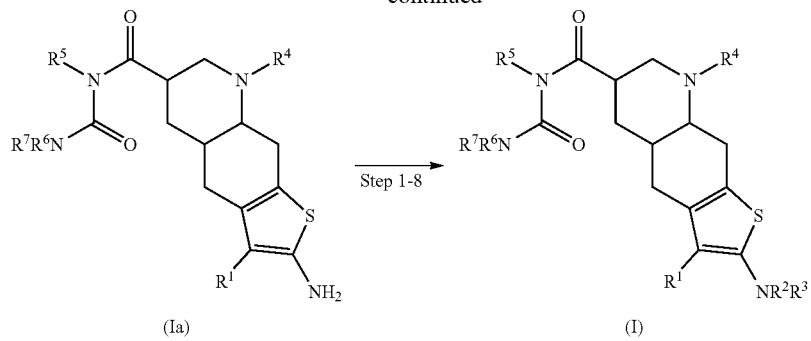

In the formula, $R^1$, $R^2$, $R^3$, $R^4$, $R^5$, $R^6$ and $R^7$ have the same meanings as defined above; and $R^{20}$ is a $C_{1-6}$ alkyl group, $R^{30}$ is a halo-$C_{1-6}$ alkyl group, X represents an leaving group such as an iodine atom, a trifluoromethanesulfonyloxy group or the like, $R^{40}$ is a $C_{1-6}$ alkyl group or a benzyl group, Ar represents an aryl group such as a phenyl group, a 2-chlorophenyl group, a 4-nitrophenyl group or the like.

Step 1-1

A carboxylic acid derivative can be prepared by alkaline hydrolysis of an ester derivative (X) in a suitable solvent. As the solvent used in the reaction, for example, methanol, ethanol, water, tetrahydrofuran, a mixed solvent thereof and the like can be illustrated. As the base, for example, sodium hydroxide, potassium hydroxide, lithium hydroxide and the like can be illustrated. The reaction temperature is usually at 0° C. to reflux temperature, the reaction time is usually 10 minutes to 24 hours, varying based on the starting materials employed, the solvent, the reaction temperature and the like.

An amide derivative (XII) can be prepared by condensing a carboxylic acid derivative with amine (XI) in the presence of a condensing reagent in an inert solvent. As the inert solvent, for example, acetonitrile, N,N-dimethylformamide, tetrahydrofuran, methylene chloride, a mixed solvent thereof and the like can be illustrated. As the condensing reagent, for example, dicyclohexylcarbodiimide, 1-(3-dimethylaminopropyl)-3-ethylcarbodiimide hydrochloride, diphenylphosphoryl azide, 4-(4,6-dimethoxy-1,3,5-triazin-2-yl)-4-methylmorpholinium hydrochloride and the like can be illustrated. The reaction temperature is usually at −20° C. to 100° C., the reaction time is usually 10 minutes to 24 hours, varying based on the starting materials employed, the solvent, the reaction temperature and the like.

Alternatively, the amide derivative (XII) can be also prepared by converting a carboxylic acid to its reactive derivatives (for example; an acid halide, an acid anhydride, a mixed acid anhydride, a benzotriazol-1-yl-ester, a 4-nitrophenyl ester, a 2,5-dioxopyrrolidine ester and the like) according to conventional methods, followed by the condensation with amine (XI) or the salt thereof in a suitable solvent in the presence or absence of a base. As the solvent used in the condensation reaction, for example, acetonitrile, N,N-dimethylforamide, tetrahydrofuran, methylene chloride, a mixed solvent thereof and the like can be illustrated. As the base, for example, potassium carbonate, triethylamine, N,N-diisopropylethylamine, pyridine, N-methylmorphorine, N,N-dimethylaniline and the like can be illustrated. The reaction temperature is usually at −20° C. to reflux temperature, the reaction time is usually 1 hour to 24 hours, varying based on the starting materials employed, the solvent, the reaction temperature and the like.

Alternatively, the amide derivative (XII) can be also prepared by irradiating microwave to a mixture of the ester derivative (X) and amine (XI) in a suitable solvent. As the solvent used in the reaction, for example, ethanol, 2-propanol, a mixed solvent thereof and the like can be illustrated. The reaction temperature is usually at 100° C. to 250° C., the reaction time is usually 1 hour to 24 hours, varying based on the starting materials employed, the solvent, the reaction temperature and the like.

Step 1-2

An aryl carbamate derivative (XIV) can be prepared by allowing an amide derivative (XII) to react with an aryl chloroformate (XIII) in an inert solvent in the presence of a base. As the inert solvent used in the reaction, for example, tetrahydrofuran and the like can be illustrated. As the base, for example, sodium hexamethyldisilazide, lithium hexamethyldisilazide, potassium tert-butoxide and the like can be illustrated. The reaction temperature is usually at −78° C. to 50° C., the reaction time is usually 15 minutes to 24 hours, varying based on the starting materials employed, the solvent, the reaction temperature and the like.

Step 1-3

An acyl urea derivative (XVI) can be prepared by allowing an aryl carbamate derivative (XIV) to react with amine (XV) or salt thereof in an inert solvent in the presence or absence of a base. As the inert solvent used in the reaction, for example, 2-propanol, tetrahydrofuran, methylene chloride, 1,4-dioxane, a mixed solvent thereof and the like can be illustrated. As the base, for example, potassium carbonate, triethylamine, N,N-diisopropylethylamine, pyridine, N-methylmorphorine, N,N-dimethylaniline and the like can be illustrated. The reaction temperature is usually at 0° C. to 150° C., the reaction time is usually 15 minutes to 24 hours, varying based on the starting materials employed, the solvent, the reaction temperature and the like.

Step 1-4

An acyl urea derivative (XVI) can be prepared by allowing an amide derivative (XII) to react with isocyanate (XVII) in an inert solvent with metal catalyst in the presence or absence of ligand. As the inert solvent used in the reaction, for example, methylene chloride, 1,2-dichloroethane, chloroform, toluene, acetonitrile, N,N-dimethylformamide, a mixed solvent thereof and the like can be illustrated. As the metal catalyst, for example, copper(I) chloride, copper(II) chloride, copper(I) bromide, copper(I) iodide and the like can be illustrated. As the ligand, for example, triphenylphospine, tri-para-tolylphosphine and the like can be illustrated. The reaction temperature is usually at 0° C. to 120° C., the reaction time is usually 15 minutes to 24 hours, varying based on the starting materials employed, the solvent, the reaction temperature and the like.

Step 1-5

An octahydro-1H-quinoline derivative (XVIII) can be prepared by removing a benzyl group of an acyl urea derivative (XVI) wherein $R^{40}$ is a benzyl group in a suitable solvent under an atmosphere of hydrogen in the presence of metal catalyst. As the solvent used in the reaction, for example, methanol, ethanol, N,N-dimethylforamide, tetrahydrofuran and the like can be illustrated. As the metal catalyst, for example, palladium-carbon, platinum dioxide and the like can be illustrated. The reaction temperature is usually at room temperature to 80° C., the reaction time is usually 30 minutes to 12 hours, varying based on the starting materials employed, the solvent, the reaction temperature and the like.

Step 1-6

A 6-oxodecaquinoline derivative (XIX) wherein $R^4$ is a $C_{1-6}$ alkyl group and a 6-oxodecaquinoline derivative (XIX) wherein $R^4$ is a hydrogen atom can be prepared by acid hydrolysis of a ketal derivative (XVI) wherein $R^{40}$ is a $C_{1-6}$ alkyl group and a ketal derivative (XVIII) in a suitable solvent. As the solvent used in the reaction, for example, tetrahydrofuran, dimethoxyethane, 1,4-dioxane, methylene chloride, 1,2-dichloroethane, chloroform, water, a mixed solvent thereof and the like can be illustrated. As the acid, for example, sulfuric acid, hydrochloric acid, phosphoric acid, acetic acid, methanesulfonic acid, benzenesulfonic acid and the like can be illustrated. The reaction temperature is usually at -50° C. to 100° C., the reaction time is usually 10 minutes to 24 hours, varying based on the starting materials employed, the solvent, the reaction temperature and the like.

Alternatively, a 6-oxodecaquinoline (XIX) wherein $R^4$ is a halo-$C_{1-6}$ alkyl group can be prepared by allowing a ketal derivative (XVIII) to react with an alkylating reagent ($R^{30}$—X) in an inert solvent in the presence of a base, and then hydrolyze the ketal ring by the same method as defined above. As the inert solvent used in the alkylation reaction, for example, acetonitrile, tetrahydrofuran, N,N-dimethylformamide, dimethoxyethane, 1,4-dioxane, methylene chloride and the like can be illustrated. As the base, for example, potassium carbonate, cesium carbonate, triethylamine, N,N-diisopropylethylamine and the like can be illustrated. The reaction temperature is usually at 0° C. to reflux temperature, the reaction time is usually 1 hour to 24 hours, varying based on the starting materials employed, the solvent, the reaction temperature and the like.

Step 1-7

An octahydrothienoquinoline derivative (Ia) can be prepared by allowing a 6-oxodecaquinoline derivative (XIX) to react with compound (XX) and sulfur in an inert solvent in the presence or absence of a base. As the inert solvent used in the reaction, for example, ethanol, methanol, 1,4-dioxane and the like can be illustrated. As the base, for example, morpholine, piperidine, triethylamine and the like can be illustrated. The reaction temperature is usually at 0° C. to reflux temperature, the reaction time is usually 15 minutes to 24 hours, varying based on the starting materials employed, the solvent, the reaction temperature and the like.

Step 1-8

An acyl amide derivative (I) can be prepared by allowing an octahydrothienoquinoline derivative (Ia) to react with an acylating reagent in an inert solvent in the presence or absence of a base. As the inert solvent used in the reaction, for example, tetrahydrofuran, 1,4-dioxane, methylene chloride, benzene and the like can be illustrated. As the acylating reagent, for example, an acid halide, an acid anhydride, a mixed acid anhydride and the like can be illustrated. As the base, for example, potassium carbonate, triethylamine, N,N-diisopropylethylamine, pyridine, N-methylmorphorine, N,N-dimethylaniline and the like can be illustrated. The reaction temperature is usually at 0° C. to reflux temperature, the reaction time is usually 15 minutes to 24 hours, varying based on the starting materials employed, the solvent, the reaction temperature and the like.

Alternatively, an octahydrothienoquinoline derivative (I) wherein $R^2$ is a hydrogen atom and $R^3$ is a $R_{2-7}$ alkoxycarbonyl group can be prepared by allowing an octahydrothienoquinoline derivative (Ia) to react with 1,1'-carbonyldiimidazole in an inert solvent, and then to react with a $C_{1-6}$ alcohol. As the inert solvent used in the reaction, for example, methylene chloride and the like can be illustrated. The reaction temperature is usually at -20° C. to 60° C., the reaction time is usually 1 hour to 48 hours, varying based on the starting materials employed, the solvent, the reaction temperature and the like.

Scheme 2

[Chem. 7]

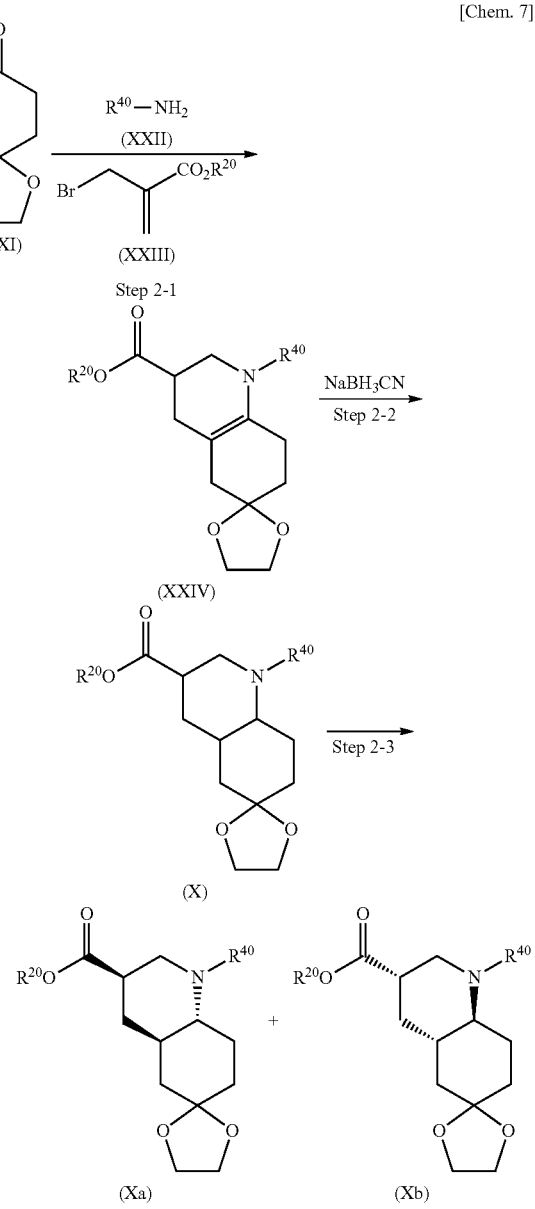

In the formula, $R^{20}$ and $R^{40}$ have the same meanings as defined above.

Step 2-1

Compound (XXIV) can be prepared by conducting coupling reaction of 1,4-cyclohexanedione monoethylene ketal (XXI), amine (XXII) and 2-(bromomethyl)-acrylic acid ester (XXIII) in an inert solvent. As the inert solvent used in the reaction, for example, toluene, benzene and the like can be illustrated. The reaction temperature is usually at −50° C. to reflux temperature, the reaction time is usually 1 hour to 24 hours, varying based on the starting materials employed, the solvent, the reaction temperature and the like.

Step 2-2

Compound (X) can be prepared by reduction of a compound (XXIV) in a suitable solvent in the presence of an acid by using a reducing reagent such as sodium cyanoborohydride, sodium borohydride, sodium triacetoxyborohyride or the like. As the solvent used in the reaction, for example, tetrahydrofuran, methanol, ethanol, ethyl acetate, 1,4-dioxane, a mixed solvent thereof and the like can be illustrated. As the acid, for example, sulfuric acid, hydrochloric acid, acetic acid and the like can be illustrated. The reaction temperature is usually at −50° C. to 50° C., the reaction time is usually 10 minutes to 12 hours, varying based on the starting materials employed, the solvent, the reaction temperature and the like.

Step 2-3

The optical active compounds (Xa) and (Xb) can be prepared by allowing compound (X) to separate by mean of optical resolution by crystallization such as preferential crystallization, diastereomeric salt formation, inclusion complexation, preference enrichment and the like, enzymatic optical resolution or direct optical resolution using chiral column chromatography.

As the chiral column used in the direct optical resolution by the chiral column chromatography, for example, CHIRALPAK (registered mark of Daicel Chemical Industries) AY-H column, AD-H column, IA column and the like can be illustrated. As the eluting solvent, hexane, methanol, ethanol, 2-propanol, diethylamine, a mixed solvent thereof and the like can be illustrated. The eluting flow rate is 0.5 mL/min to 10 ml/min. The eluting temperature is usually at 10° C. to 60° C., and the detection wavelength is 200 nm to 270 nm.

The forementioned schemes are exemplary for preparing compounds of the present invention and synthetic intermediates thereof. Those ordinarily skilled in the art will appreciate that various changes or modifications of the forementioned schemes may be made without departing from the scope of the invention.

Compounds represented by the general formula (I) of the present invention and intermediates for preparing the compounds of the present invention can be isolated or purified, if required, according to conventional isolation or purification techniques well known to those in the art of the relevant field, such as solvent extraction, crystallization, recrystallization, chromatography, preparative high performance liquid chromatography or the like.

Compounds of the present invention prepared in the abovementioned schemes exhibit excellent dopamine $D_2$ receptor stimulating activities, and are accordingly useful as a treating or prophylactic agent for the various diseases dopamine $D_2$ receptor mediated. For example, the compounds of the present invention are useful as a treating or prophylactic agent such as Parkinson's disease, restless legs syndrome, hyperprolactinemia or the like, especially useful as a treating or preventing agent such as Parkinson's disease.

Compounds of the present invention can be also used, if required, in combination with other anti-Parkinson drugs. As the other anti-Parkinson drugs include, for example, L-dopa; dopamine $D_2$ receptor agonists such as cabergoline, bromocriptine mesylate, terguride, talipexole hydrochloride, ropinirole hydrochloride, pergolide mesylate, pramipexole hydrochloride, rotigotine, apomorphine and the like; anticholinergic agents such as profenamine, trihexyphenidyl hydrochloride, mazaticol hydrochloride, piperiden, piroheptine hydrochloride, methixene hydrochloride and the like; adenosine $A_{2A}$ receptor antagonists such as istradefylline and the like; NMDA receptor antagonists such as budipine and the like; monoamine oxidase B inhibitors such as selegiline hydrochloride, rasagiline mesylate, safinamide mesylate and the like; COMT inhibitors such as entacapone and the like; aromatic L-amino acid decarboxylase inhibitors such as carbidopa, benserazide and the like; droxidopa, melevodopa, threodops; zonisamide; amantadine hydrochloride and the like.

Pharmaceutical compositions comprising a compound represented by the general formula (I) of the present invention or a pharmaceutically acceptable salt thereof as an active ingredient can be administered in various dosage forms depending on their usages. Exemplary dosage forms include powders, granules, fine granules, dry syrups, tablets, capsules, injections, liquids, ointments, suppositories, poultices and the like, which are administered orally or parenterally.

Pharmaceutical compositions comprising a compound represented by the general formula (I) of the present invention or a pharmaceutically acceptable salt thereof can be formulated by using a compound represented by the general formula (I) or a pharmaceutically acceptable salt thereof and at least one pharmaceutical additive. These pharmaceutical compositions can be formulated by admixing, diluting or dissolving with appropriate pharmaceutical additives such as excipients, disintegrants, binders, lubricants, diluents, buffers, tonicity agents, preservatives, wetting agents, emulsifying agents, dispersing agents, stabilizing agents, solubilizing agents and the like, according to a conventional formulation procedure depending upon their dosage forms.

The dosage of a compound represented by the general formula (I) or a pharmaceutically acceptable salt thereof is appropriately determined depending on the age, sex or body weight of the individual patient, the severity of the disease, the condition to be treated and the like, which is approximately within the range of from about 0.1 mg to about 300 mg per day per adult human, preferably about 0.5 mg to about 30 mg, in the case of oral administration, and approximately within the range of from about 0.01 mg to about 50 mg per day per adult human, preferably about 0.05 mg to about 10 mg, in the case of parenteral administration. The dosages may be administered in single or divided doses, for example one to several times daily.

A pharmaceutical combination comprising a compound represented by the general formula (I) of the present invention or a pharmaceutically acceptable salt thereof and other anti-Parkinson drugs can be administered as a single pharmaceutical composition comprising all of active ingredients, or as separately formulated pharmaceutical compositions each of which comprises a single active ingredient. Where separately formulated pharmaceutical compositions are used, the compositions may be administered separately, concurrently or at different intervals. Alternatively, where separately formulated pharmaceutical compositions are used, the compositions may be mixed together with an appropriate diluent, and administered simultaneously.

A pharmaceutical combination comprising a compound represented by the general formula (I) of the present invention or a pharmaceutically acceptable salt thereof, and any other anti-Perkinson drugs is preferably used for the treating or preventing agent of Parkinson's disease, restless legs syndrome, hyperprolactinemia or the like, especially used for the treating or preventing agent of Parkinson's disease.

In a pharmaceutical combination comprising a compound represented by the general formula (I) or a pharmaceutically acceptable salt thereof and other anti-Parkinson drugs, the compounding ratio of medicament can be appropriately determined depending on the age, sex or body weight of the individual patient, the severity of the disease, administration time, dosage form, administration method, combination of medicaments and the like.

The present invention is further illustrated in more detail by way of the following Reference Examples, Examples and Test Examples. However, the present invention is not limited thereto.

EXAMPLES

Reference Example 1-1

Ethyl 1'-methyl-2',3',4',5',7',8'-hexahydro-1'H-spiro[1,3-dioxolane-2,6'-quinoline]-3'-carboxylate To a mixture of ethyl 2-(bromomethyl)acrylate (20.42 g) and toluene (320 mL) was added dropwise a mixture of a 40% methylamine-methanol solution (240.1 mL) and toluene (80 mL) under ice cooling while stirring. The mixture was stirred for 3 minutes. To the mixture was added a mixture of 1,4-cyclohexandione monoethylene ketal (14.00 g) and toluene (100 mL) under the same conditions. The mixture was refluxed with the Dean-Stark apparatus for 4.5 hours. After cooling to room temperature, the mixture was passed through a layer of Celite (registered mark). The filtrate was concentrated under reduced pressure. The residue was purified by aminopropyl silica gel column chromatography (eluent: 0%-40% ethyl acetate/hexane, gradient elution) to give the title compound (22.92 g).

$^1$H-NMR (CDCl$_3$) δ ppm: 1.20-1.35 (4H, m), 1.70-1.85 (2H, m), 1.95-2.10 (1H, m), 2.15-2.35 (4H, m), 2.60 (3H, s), 2.75-3.00 (2H, m), 3.10-3.20 (1H, m), 3.85-4.05 (4H, m), 4.15 (2H, q, J=7.1 Hz)

Reference examples 1-2 to 1-3 were prepared in a manner similar to those as described in reference example 1-1 using the corresponding amines instead of methylamine. These were illustrated in Table 1.

TABLE 1

| Reference example | Strucutre |
|---|---|
| 1-1 | (structure) |
| 1-2 | (structure) |
| 1-3 | (structure) |

The physical data of reference examples 1-2 to 1-3 were shown below.

Reference Example 1-2

$^1$H-NMR (CDCl$_3$) δ ppm: 1.15-1.35 (4H, m), 1.80-1.90 (2H, m), 1.95-2.10 (1H, m), 2.15-2.50 (5H, m), 2.65-2.80 (1H, m), 2.90-3.00 (1H, m), 3.05-3.20 (1H, m), 3.90-4.20 (7H, m), 7.20-7.40 (5H, m)

Reference Example 1-3

$^1$H-NMR (CDCl$_3$) δ ppm: 0.86 (3H, t, J=7.4 Hz), 1.26 (3H, t, J=7.1 Hz), 1.35-1.60 (2H, m), 1.70-1.90 (2H, m), 1.90-2.05 (1H, m), 2.10-2.40 (5H, m), 2.65-2.90 (3H, m), 2.90-3.05 (1H, m), 3.15-3.25 (1H, m), 3.90-4.05 (4H, m), 4.14 (2H, q, J=7.1 Hz)

Reference Example 2-1

Ethyl (3'R*,4'aR*,8'aR*)-1'-methyloctahydro-1'H-spiro[1,3-dioxolane-2,6'-quinoline]-3'-carboxylate To a mixture of ethyl 1'-methyl-2',3',4',5',7',8'-hexahydro-1'H-spiro[1,3-dioxolane-2,6'-quinoline]-3'-carboxylate (reference example 1-1) (22.92 g), tetrahydrofuran (260 mL) and methanol (65 mL) was added a 4 mol/L hydrogen chloride-dioxane solution (21.4 mL), followed by sodium cyanoborohydride (6.14 g) under ice bath cooling while stirring. The mixture was stirred for 10 minutes. The mixture was concentrated under reduced pressure, added a saturated aqueous solution of sodium bicarbonate, and extracted with ethyl acetate. The separated organic layer was washed with brine, dried over anhydrous magnesium sulfate, and concentrated under reduced pressure. The residue was purified by silica gel column chromatography (eluent: 0%-22% methanol/ethyl acetate, gradient elution) to give the title compound (8.33 g). The structure was illustrated in Table 2.

$^1$H-NMR (CDCl$_3$) δ ppm: 1.10-1.30 (4H, m), 1.30-1.75 (6H, m), 1.75-1.85 (1H, m), 1.85-2.00 (1H, m), 2.00-2.10

(1H, m), 2.17 (1H, t, J=11.6 Hz), 2.30 (3H, s), 2.60-2.75 (1H, m), 3.05-3.15 (1H, m), 3.93 (4H, s), 4.12 (2H, q, J=7.1 Hz)

Reference examples 2-2 to 2-3 were prepared in a manner similar to those as described in reference example 2-1 using the corresponding enamines instead of ethyl 1'-methyl-2',3', 4',5',7',8'-hexahydro-1'H-spiro[1,3-dioxolane-2,6'-quinoline]-3'-carboxylate. These structures were illustrated in Table 2.

The physical data of reference examples 2-2 to 2-3 were shown below.

Reference Example 2-2

$^1$H-NMR (CDCl$_3$) δ ppm: 1.15-1.30 (4H, m), 1.35-1.95 (8H, m), 2.05-2.25 (2H, m), 2.50-2.65 (1H, m), 3.00-3.10 (1H, m), 3.25 (1H, d, J=13.9 Hz), 3.95 (4H, s), 4.00-4.15 (3H, m), 7.15-7.40 (5H, m)

Reference Example 2-3

$^1$H-NMR (CDCl$_3$) δ ppm: 0.85 (3H, t, J=7.3 Hz), 1.17 (1H, dd, J=24.9, 12.5 Hz), 1.25 (3H, t, J=7.1 Hz), 1.30-1.70 (7H, m), 1.75-1.85 (2H, m), 1.85-1.95 (1H, m), 1.95-2.10 (1H, m), 2.31 (1H, t, J=11.4 Hz), 2.40-2.55 (1H, m), 2.55-2.70 (2H, m), 3.10-3.20 (1H, m), 3.93 (4H, s), 4.12 (2H, q, J=7.1 Hz)

Reference Example 2-4

Ethyl (3'R*,4'aR*,8'aR*)-1'-ethyloctahydro-1'H-spiro[1,3-dioxolane-2,6'-quinoline]-3'-carboxylate To a mixture of ethyl (3'R*,4'aR*,8'aR*)-1'-benzyl-octahydro-1'H-spiro[1,3-dioxolane-2,6'-quinoline]-3'-carboxylate (reference example 2-2) (200 mg) and ethanol (4.0 mL) was added 10% palladium-carbon (86 mg). The mixture was stirred at room temperature for 12 hours under a hydrogen atmosphere. The mixture was passed through a layer of Celite (registered mark) and the filtrate was concentrated under reduced pressure to give ethyl (3'R*,4'aR*,8'aR*)octahydro-1'H-spiro[1,3-dioxolane-2,6'-quinoline]-3'-carboxylate (154 mg).

$^1$H-NMR (CDCl$_3$) δ ppm: 1.25 (3H, t, J=7.1 Hz), 1.25-1.55 (4H, m), 1.55-1.70 (2H, m), 1.70-1.85 (2H, m), 1.90-2.00 (1H, m), 2.10-2.20 (1H, m), 2.40-2.55 (1H, m), 2.73 (1H, t, J=12.0 Hz), 3.25-3.35 (1H, m), 3.94 (4H, s), 4.12 (2H, q, J=7.1 Hz)

To a mixture of ethyl (3'R*,4'aR*,8'aR*)octahydro-1'H-spiro[1,3-dioxolane-2,6'-quinoline]-3'-carboxylate (154 mg) and N,N-dimethylformamide (2.8 mL) was added potassium carbonate (184 mg), followed by iodoethane (0.053 mL), and the mixture was stirred at room temperature for 18 hours. To the reaction mixture was added brine, and extracted with ethyl acetate. After the separated organic layer was dried over anhydrous sodium sulfate, it was concentrated under reduced pressure to give the title compound (157 mg). The structure was illustrated in Table 2.

$^1$H-NMR (CDCl$_3$) δ ppm: 0.99 (3H, t, J=7.2 Hz), 1.17 (1H, dd, J=24.9, 12.4 Hz), 1.25 (3H, t, J=7.1 Hz), 1.30-1.50 (2H, m), 1.50-1.75 (3H, m), 1.75-1.95 (3H, m), 2.00-2.10 (1H, m), 2.32 (1H, t, J=11.6 Hz), 2.55-2.75 (2H, m), 2.75-2.90 (1H, m), 3.05-3.20 (1H, m), 3.93 (4H, s), 4.12 (2H, q, J=7.2 Hz)

TABLE 2

| Reference example | Structure |
|---|---|
| 2-1 | 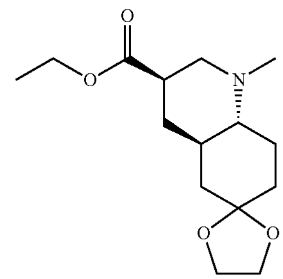 [SMILES: CCOC(=O)[C@@H]1C[C@@H]2CC3(CC[C@H]2N(C)C1)OCCO3] |
| 2-2 | 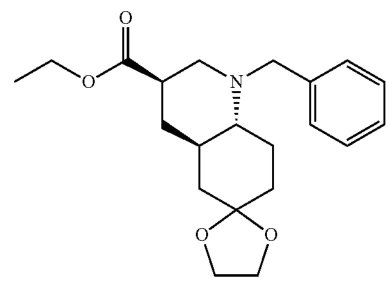 [SMILES: CCOC(=O)[C@@H]1C[C@@H]2CC3(CC[C@H]2N(Cc2ccccc2)C1)OCCO3] |
| 2-3 | 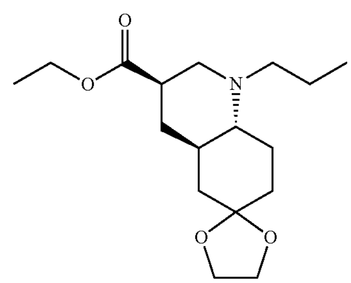 [SMILES: CCCN1C[C@H](C(=O)OCC)C[C@@H]2CC3(CC[C@H]21)OCCO3] |
| 2-4 | 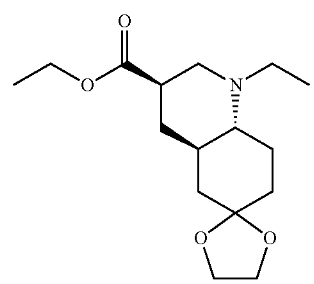 |

The structures of the reference example 2-1 to 2-4 in Table 2 indicate relative configuration.

Reference Example 3

Ethyl (3'R,4'aR,8'aR)-1'-methyloctahydro-1'H-spiro[1,3-dioxolane-2,6'-quinoline]-3'-carboxylate To ethyl (3'R*,4'aR*,8'aR*)-1'-methyloctahydro-1'H-spiro[1,3-dioxolane-2,6'-quinoline]-3'-carboxylate (reference example 2-1) (14.4 g) was repeated chromatography using a CHIRALPAK (registered mark) AY-H (Daicel Chemical Industries) column (250 mm×20 mm I.D.) with the following condition:
Solvent system; hexane:ethanol:diethylamine=50:50:0.1 (V/V)
Detection wavelength; 220 nm
Flow rate; 5.0 mL/min
Column oven temperature; 40° C.

The eluted component of the second peak was collected, and concentrated to give the title compound (6.9 g).

$^1$H-NMR (CDCl$_3$) δ ppm: 1.10-1.30 (4H, m), 1.30-1.75 (6H, m), 1.75-1.85 (1H, m), 1.85-2.00 (1H, m), 2.00-2.10 (1H, m), 2.17 (1H, t, J=11.6 Hz), 2.30 (3H, s), 2.60-2.75 (1H, m), 3.05-3.15 (1H, m), 3.93 (4H, s), 4.12 (2H, q, J=7.1 Hz) [α]$_D^{29}$=−11.50° (c=1.06, MeOH)

Reference Example 4-1

(3'R,4'aR,8'aR)-1'-Methyl-N-propyloctahydro-1'H-spiro[1,3-dioxolane-2,6'-quinoline]-3'-carboxamide To a mixture of ethyl (3'R,4'aR,8'aR)-1'-methyloctahydro-1'H-spiro[1,3-dioxolane-2,6'-quinoline]-3'-carboxylate (reference example 3) (1.995 g) and ethanol (35 mL) was added a 5 mol/L aqueous solution of sodium hydroxide (7.06 mL) while stirring at room temperature. The mixture was heated at 80° C. and stirred for 1.5 hours. After cooling in ice bath, it was neutralized by the addition of 6 mol/L hydrochloric acid (5.88 mL). The mixture was concentrated under reduced pressure to give (3'R,4'aR,8'aR)-1'-methyloctahydro-1'H-spiro[1,3-dioxolane-2,6'-quinoline]-3'-carboxylic acid.

To a mixture of (3'R,4'aR,8'aR)-1'-methyloctahydro-1'H-spiro[1,3-dioxolane-2,6'-quinoline]-3'-carboxylic acid, 1-propylamine (0.638 mL), triethylamine (2.16 mL) and methylene chloride (54 mL) was added 1-hydroxybenzotriazole (1.19 g), followed by 1-(3-dimethylaminopropyl)-3-ethylcarbodiimide hydrochloride (1.49 g) while stirring at room temperature. The mixture was stirred for 11 hours. The mixture was passed through a layer of Celite (registered mark) and the filtrate was concentrated under reduced pressure. The residue was purified by aminopropyl silica gel column chromatography (eluent: 0%-5% methanol/ethyl acetate, gradient elution) to give the title compound (1.812 g).

$^1$H-NMR (CDCl$_3$) δ ppm: 0.91 (3H, t, J=7.4 Hz), 1.25-1.70 (9H, m), 1.70-1.85 (2H, m), 2.00-2.10 (1H, m), 2.20-2.35 (4H, m), 2.40-2.50 (1H, m), 2.90-3.05 (1H, m), 3.15-3.25 (2H, m), 3.85-4.00 (4H, m), 5.30-5.50 (1H, m) [α]$_D^{28}$=−8.00° (c=0.30, MeOH)

Reference Example 4-4

(3'R,4'aR,8'aR)—N-[(1S)-2,3-Dihydro-1H-inden-1-yl]-1'-methyloctahydro-1'H-spiro-[1,3-dioxolane-2,6'-quinoline]-3'-carboxamide To a mixture of ethyl (3'R,4'aR,8'aR)-1'-methyl-octahydro-1'H-spiro[1,3-dioxolane-2,6'-quinoline]-3'-carboxylate (reference example 3) (100 mg) and ethanol (35 mL) was added a 1 mol/L aqueous solution of sodium hydroxide (0.42 mL), and the mixture was stirred at room temperature for 2 hours. The reaction mixture was neutralized by the addition of 1 mol/L hydrochloric acid (0.42 mL). The mixture was concentrated under reduced pressure to give (3'R,4'aR,8'aR)-1'-methyloctahydro-1'H-spiro[1,3-dioxolane-2,6'-quinoline]-3'-carboxylic acid.

To a mixture of (3'R,4'aR,8'aR)-1'-methyloctahydro-1'H-spiro[1,3-dioxolane-2,6'-quinoline]-3'-carboxylic acid, (1S)-2,3-dihydro-1H-inden-1-amine (64 mg) and methylene chloride (1 mL) was added 1-hydroxybenzotriazole (60 mg), followed by 1-(3-dimethylaminopropyl)-3-ethylcarbodiimide hydrochloride (85 mg) while stirring at room temperature, and the mixture was stirred for 12 hours. The mixture was passed through a layer of Celite (registered mark) and the filtrate was concentrated under reduced pressure. The residue was purified by aminopropyl silica gel column chromatography (eluent: 0%-7% methanol/ethyl acetate, gradient elution) to give the title compound (105 mg).

$^1$H-NMR (CDCl$_3$) δ ppm: 1.30-1.50 (3H, m), 1.50-1.85 (7H, m), 2.00-2.10 (1H, m), 2.25-2.35 (4H, m), 2.45-2.55 (1H, m), 2.55-2.70 (1H, m), 2.80-3.05 (3H, m), 3.90-4.00 (4H, m), 5.45-5.55 (1H, m), 5.55-5.65 (1H, m), 7.20-7.30 (4H, m) [α]$_D^{29}$=−75.00° (c=0.21, MeOH)

After dissolving a mixture of (3'R,4'aR,8'aR)—N-[(1S)-2,3-dihydro-1H-inden-1-yl]-1'-methyloctahydro-1'H-spiro-[1,3-dioxolane-2,6'-quinoline]-3'-carboxamide (reference example 4-4) (3 mg) and acetonitrile (1.2 mL) by heating at 50° C., it was allowed to remain at room temperature for 6 days to give a single crystal. The absolute configuration of reference example 4-4 was determined by X-ray crystallographic analysis of the obtained single crystal.

By determining the absolute configuration of (3'R,4'aR,8'aR)—N-[(1S)-2,3-dihydro-1H-inden-1-yl]-1'-methyloctahyd-ro-1'H-spiro[1,3-dioxolane-2,6'-quinoline]-3'-carboxamide (reference example 4-4), ethyl (3'R,4'aR,8'aR)-1'-methylocta-hydro-1'H-spiro[1,3-dioxolane-2,6'-quinoline]-3'-carboxyl-ate (reference example 3) as its starting material, was demonstrated the same configuration.

Reference Example 4-5

(3'R*,4'aR*,8'aR*)-1'-Methyl-N-propyloctahydro-1'H-spiro-[1,3-dioxolane-2,6'-quinoline]-3'-carboxamide To a mixture of ethyl (3'R*,4'aR*,8'aR*)-1'-methyl-octahydro-1'H-spiro-[1,3-dioxolane-2,6'-quinoline]-3'-carboxylate (reference example 2-1) (16.67 g) and ethanol (39 mL) was added a 5 mol/L aqueous solution of sodium hydroxide (58.8 mL) under water bath cooling, and the mixture was stirred at the same temperature for 1 hour. After cooling in ice salt bath, it was neutralized by the addition of 6 mol/L hydrochloric acid (49 mL). The mixture was concentrated under reduced pressure to give (3'R*,4'aR*,8'aR*)-1'-methyloc-tahydro-1'H-spiro[1,3-dioxo-lane-2,6'-quinoline]-3'-carboxylic acid.

To a mixture of (3'R*,4'aR*,8'aR*)-1'-methyloctahydro-1'H-spiro[1,3-dioxolane-2,6'-quinoline]-3'-carboxylic acid, 1-propylamine (5.32 mL), triethylamine (9.01 mL) and methylene chloride (131 mL) was added 1-hydroxybenzotriazole (9.9 g), followed by 1-(3-dimethylaminopropyl)-3-ethylcarbodiimide hydrochloride (12.4 g) while stirring at room temperature, and the mixture was stirred for 14 hours. The mixture was passed through a layer of Celite (registered mark) and the filtrate was washed with a 1 mol/L aqueous solution of sodium hydroxide, dried over anhydrous sodium sulfate, and concentrated under reduced pressure. The residue was purified by aminopropyl silica gel column chromatography (eluent: 0%-5% methanol/ethyl acetate, gradient elution) to give the title compound (16.18 g).

$^1$H-NMR (CDCl$_3$) δ ppm: 0.91 (3H, t, J=7.6 Hz), 1.25-1.90 (11H, m), 2.00-2.15 (1H, m), 2.20-2.35 (4H, m), 2.35-2.50 (1H, m), 2.90-3.05 (1H, m), 3.15-3.25 (2H, m), 3.85-4.00 (4H, m), 5.35-5.50 (1H, m)

Reference examples 4-2 to 4-3 and reference examples 4-6 to 4-33 were prepared in a manner similar to those as described in reference example 4-1 or reference example 4-5 using the corresponding decahydroquinoline-3-carboxylate esters and amines instead of ethyl (3'R,4'aR,8'aR)-1'-methy-loctahydro-1'H-spiro[1,3-dioxolane-2,6'-quinoline]-3'-carboxylate and 1-propylamine. These were illustrated in Table 3.

TABLE 3

| Reference example | Structure |
|---|---|
| 4-1 | (Chiral) |
| 4-2 | (Chiral) |
| 4-3 | (Chiral) |
| 4-4 | (Chiral) |
| 4-5 | 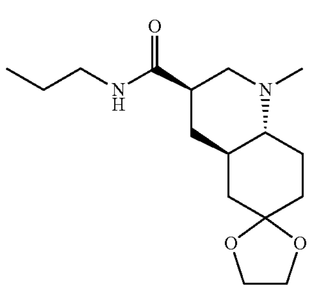 [SMILES: CCCNC(=O)[C@@H]1C[C@@H]2CC3(CC[C@H]2N(C)C1)OCCO3] |

TABLE 3-continued

| Reference example | Structure |
|---|---|
| 4-6 | 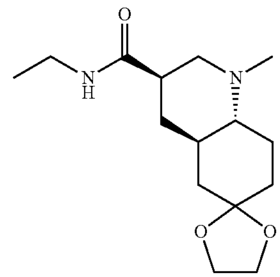 [SMILES: CCNC(=O)[C@@H]1C[C@@H]2CC3(CC[C@H]2N(C)C1)OCCO3] |
| 4-7 | 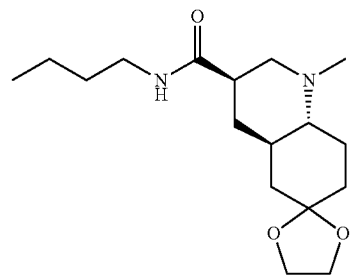 |
| 4-8 | 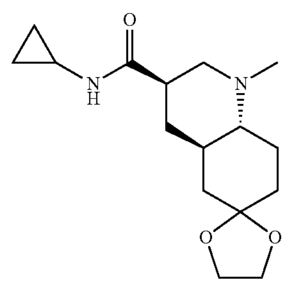 [SMILES: CN1C[C@H](C(=O)NC2CC2)C[C@@H]2CC3(CC[C@H]21)OCCO3] |
| 4-9 | 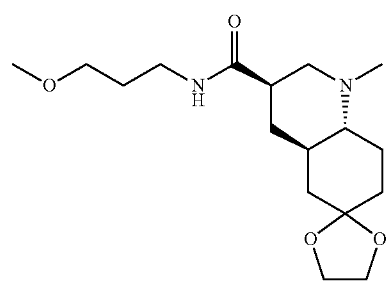 [SMILES: COCCCNC(=O)[C@@H]1C[C@@H]2CC3(CC[C@H]2N(C)C1)OCCO3] |
| 4-10 | 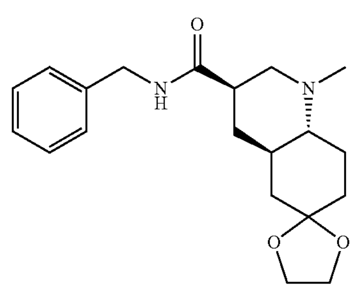 [SMILES: CN1C[C@H](C(=O)NCc2ccccc2)C[C@@H]2CC3(CC[C@H]21)OCCO3] |

TABLE 3-continued

| Reference example | Structure |
|---|---|
| 4-11 | *(structure)* |
| 4-12 | *(structure)* |
| 4-13 | *(structure)* |
| 4-14 | *(structure)* |
| 4-15 | *(structure)* |
| 4-16 | *(structure)* |
| 4-17 | *(structure)* |
| 4-18 | *(structure)* |
| 4-19 | *(structure)* |
| 4-20 | *(structure)* |

TABLE 3-continued
| Reference example | Structure |
|---|---|
| 4-21 | 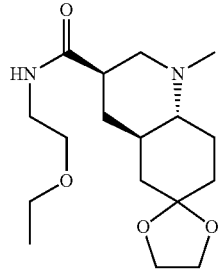 [SMILES: CCOCCNC(=O)[C@@H]1C[C@@H]2CC3(CC[C@H]2N(C)C1)OCCO3] |
| 4-22 | 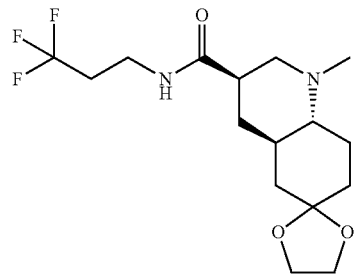 [SMILES: CN1C[C@H](C(=O)NCCC(F)(F)F)C[C@@H]2CC3(CC[C@H]21)OCCO3] |
| 4-23 | 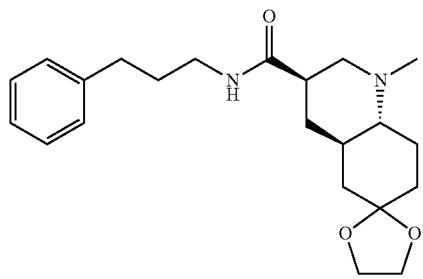 [SMILES: CN1C[C@H](C(=O)NCCCc2ccccc2)C[C@@H]2CC3(CC[C@H]21)OCCO3] |
| 4-24 | 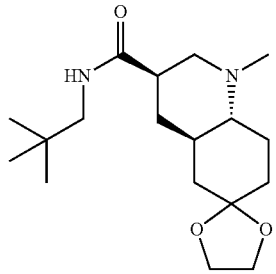 [SMILES: CN1C[C@H](C(=O)NCC(C)(C)C)C[C@@H]2CC3(CC[C@H]21)OCCO3] |
| 4-25 | 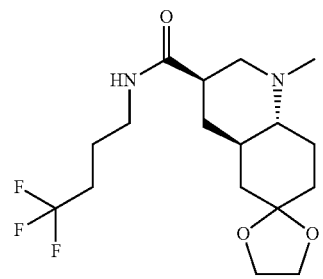 [SMILES: CN1C[C@H](C(=O)NCCCC(F)(F)F)C[C@@H]2CC3(CC[C@H]21)OCCO3] |
TABLE 3-continued
| Reference example | Structure |
|---|---|
| 4-26 | 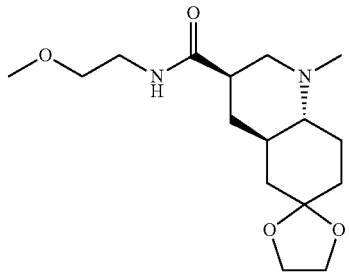 [SMILES: COCCNC(=O)[C@@H]1C[C@@H]2CC3(CC[C@H]2N(C)C1)OCCO3] |
| 4-27 | 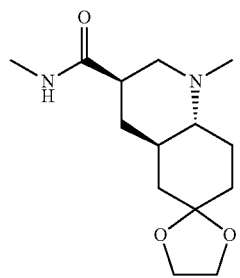 [SMILES: CNC(=O)[C@@H]1C[C@@H]2CC3(CC[C@H]2N(C)C1)OCCO3] |
| 4-28 | 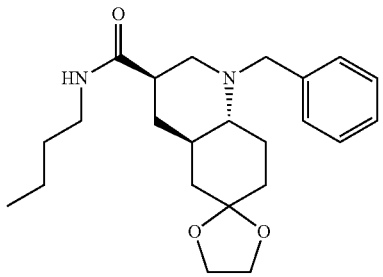 [SMILES: CCCCNC(=O)[C@@H]1C[C@@H]2CC3(CC[C@H]2N(Cc2ccccc2)C1)OCCO3] |
| 4-29 | 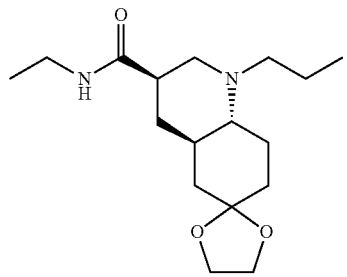 [SMILES: CCCN1C[C@H](C(=O)NCC)C[C@@H]2CC3(CC[C@H]21)OCCO3] |
| 4-30 | 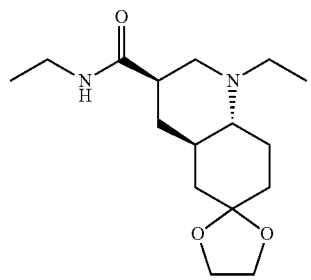 [SMILES: CCNC(=O)[C@@H]1C[C@@H]2CC3(CC[C@H]2N(CC)C1)OCCO3] |

TABLE 3-continued

| Reference example | Structure |
|---|---|
| 4-31 | (structure: propyl amide, benzyl piperidine fused to cyclohexane with dioxolane spiro) |
| 4-32 | (structure: ethyl amide, benzyl piperidine fused to cyclohexane with dioxolane spiro) |
| 4-33 | Chiral (structure: cyclopropylmethyl amide, N-methyl piperidine fused to cyclohexane with dioxolane spiro) |

The structures of the reference example 4-1 to 4-4 and 4-33 in Table 3 indicate absolute configuration, and the structures of the reference example 4-5 to 4-32 in Table 3 indicate relative configuration.

The physical data of reference examples 4-2 to 4-3 and reference examples 4-6 to 4-33 were shown below.

Reference Example 4-2

$^1$H-NMR (CDCl$_3$) δ ppm: 0.92 (3H, t, J=8 Hz), 1.20-1.90 (11H, m), 2.00-2.15 (1H, m), 2.20-2.50 (6H, m), 2.90-3.05 (1H, m), 3.15-3.35 (3H, m), 3.85-4.00 (4H, m), 5.30-5.50 (1H, m)

Reference Example 4-3

$^1$H-NMR (CDCl$_3$) δ ppm: 1.13 (3H, t, J=7.2 Hz), 1.25-1.90 (9H, m), 2.00-2.10 (1H, m), 2.20-2.35 (4H, m), 2.35-2.50 (1H, m), 2.90-3.10 (1H, m), 3.20-3.40 (2H, m), 3.85-4.00 (4H, m), 5.39 (1H, brs)
[α]$_D^{27}$=−20.25° (c=0.32, MeOH)

Reference Example 4-6

$^1$H-NMR (CDCl$_3$) δ ppm: 1.08-1.17 (3H, m), 1.20-1.90 (9H, m), 2.00-2.10 (1H, m), 2.20-2.35 (4H, m), 2.38-2.50 (1H, m), 2.90-3.10 (1H, m), 3.20-3.41 (2H, m), 3.93 (4H, s), 5.38 (1H, brs)

Reference Example 4-7

$^1$H-NMR (CDCl$_3$) δ ppm: 0.92 (3H, t, J=8 Hz), 1.20-1.90 (11H, m), 2.00-2.15 (1H, m), 2.20-2.50 (6H, m), 2.90-3.05 (1H, m), 3.15-3.35 (3H, m), 3.85-4.00 (4H, m), 5.30-5.50 (1H, m)

Reference Example 4-8

MS (ESI, m/z): 295 (M+H)+

Reference Example 4-9

$^1$H-NMR (CDCl$_3$) δ ppm: 1.21-1.87 (11H, m), 2.01-2.10 (1H, m), 2.19-2.33 (4H, m), 2.39-2.51 (1H, m), 2.92-3.04 (1H, m), 3.28-3.40 (5H, m), 3.44-3.51 (2H, m), 3.93 (4H, s), 6.14 (1H, brs)

Reference Example 4-10

$^1$H-NMR (CDCl$_3$) δ ppm: 1.30-1.90 (8H, m), 2.00-2.10 (1H, m), 2.25-2.40 (4H, m), 2.40-2.60 (1H, m), 2.95-3.10 (1H, m), 3.10-3.30 (1H, m), 3.85-4.00 (4H, m), 4.30-4.55 (2H, m), 5.65-5.80 (1H, m), 7.20-7.40 (5H, m)

Reference Example 4-11

MS (ESI, m/z): 359 (M+H)+

Reference Example 4-12

$^1$H-NMR (CDCl$_3$) δ ppm: 0.90 (6H, d, J=6.8 Hz), 1.25-1.46 (3H, m), 1.48-1.85 (7H, m), 2.00-2.15 (1H, m), 2.20-2.35 (4H, m), 2.40-2.54 (1H, m), 2.90-3.03 (1H, m), 3.03-3.12 (2H, m), 3.90-3.98 (4H, m), 5.35-5.55 (1H, m)

Reference Example 4-13

$^1$H-NMR (CDCl$_3$) δ ppm: 0.10-0.25 (2H, m), 0.40-0.60 (2H, m), 0.85-1.00 (1H, m), 1.20-1.90 (9H, m), 1.95-2.15 (1H, m), 2.20-2.35 (4H, m), 2.40-2.55 (1H, m), 2.90-3.05 (1H, m), 3.05-3.20 (2H, m), 3.80-4.00 (4H, m), 5.40-5.60 (1H, m)

Reference Example 4-14

$^1$H-NMR (CDCl$_3$) δ ppm: 1.25-1.45 (3H, m), 1.45-1.70 (4H, m), 1.70-1.85 (2H, m), 2.00-2.10 (1H, m), 2.25-2.35 (4H, m), 2.40-2.55 (1H, m), 2.95-3.05 (1H, m), 3.90-4.00 (4H, m), 4.50-4.70 (2H, m), 5.75-5.90 (1H, m), 6.90-7.00 (2H, m), 7.20-7.25 (1H, m)

Reference Example 4-15

$^1$H-NMR (CDCl$_3$) δ ppm: 1.30-1.50 (3H, m), 1.50-1.70 (4H, m), 1.75-1.85 (2H, m), 2.00-2.10 (1H, m), 2.25-2.35 (4H, m), 2.50-2.65 (1H, m), 3.00-3.10 (1H, m), 3.90-4.00 (4H, m), 4.75 (2H, ddd, J=18.4, 16.3, 5.6 Hz), 6.25-6.35 (1H, m), 7.30 (1H, d, J=3.3 Hz), 7.71 (1H, d, J=3.3 Hz)

Reference Example 4-16

$^1$H-NMR (CDCl$_3$) δ ppm: 1.20-1.90 (9H, m), 2.00-2.10 (1H, m), 2.20-2.40 (4H, m), 2.40-2.60 (1H, m), 2.90-3.10 (1H, m), 3.80-4.00 (6H, m), 5.00-5.30 (2H, m), 5.40-5.60 (1H, brs), 5.70-6.00 (1H, m)

Reference Example 4-17

$^1$H-NMR (CDCl$_3$) δ ppm: 0.89 (3H, t, J=7.0 Hz), 1.20-1.70 (12H, m), 1.70-1.85 (3H, m), 2.00-2.10 (1H, m), 2.20-2.35

(4H, m), 2.40-2.50 (1H, m), 2.90-3.05 (1H, m), 3.15-3.30 (2H, m), 3.85-4.00 (4H, m), 5.35-5.50 (1H, m)

Reference Example 4-18

¹H-NMR (CDCl₃) δ ppm: 0.80 (2H, m), 1.05-1.90 (18H, m), 2.00-2.10 (1H, m), 2.20-2.35 (4H, m), 2.40-2.55 (1H, m), 2.90-3.15 (3H, m), 3.85-4.00 (4H, m), 5.35-5.55 (1H, m)

Reference Example 4-19

¹H-NMR (CDCl₃) δ ppm: 1.20-1.90 (9H, m), 2.00-2.10 (1H, m), 2.20-2.40 (7H, m), 2.40-2.60 (1H, m), 2.90-3.10 (1H, m), 3.80-4.00 (4H, m), 4.30-4.50 (2H, m), 5.40-5.60 (1H, m), 7.10-7.30 (4H, m)

Reference Example 4-20

¹H-NMR (CDCl₃) δ ppm: 0.91 (6H, d, J=6.6 Hz), 1.20-1.70 (10H, m), 1.70-1.85 (2H, m), 2.00-2.15 (1H, m), 2.20-2.35 (4H, m), 2.35-2.55 (1H, m), 2.90-3.05 (1H, m), 3.20-3.30 (2H, m), 3.85-4.00 (4H, m), 5.30-5.45 (1H, m)

Reference Example 4-21

¹H-NMR (CDCl₃) δ ppm: 1.20 (3H, t, J=7.0 Hz), 1.25-1.90 (9H, m), 2.00-2.10 (1H, m), 2.20-2.35 (4H, m), 2.40-2.55 (1H, m), 2.95-3.05 (1H, m), 3.35-3.55 (6H, m), 3.85-4.00 (4H, m), 5.75-5.95 (1H, m)

Reference Example 4-22

¹H-NMR (CDCl₃) δ ppm: 1.20-1.46 (3H, m), 1.46-1.90 (6H, m), 2.00-2.15 (1H, m), 2.15-2.55 (7H, m), 2.90-3.05 (1H, m), 3.50 (2H, q, J=6.4 Hz), 3.85-4.00 (4H, m), 5.65-5.80 (1H, m)

Reference Example 4-23

¹H-NMR (CDCl₃) δ ppm: 1.15-1.90 (11H, m), 2.00-2.10 (1H, m), 2.22 (1H, t, J=11.2 Hz), 2.28 (3H, s), 2.33-2.46 (1H, m), 2.64 (2H, t, J=7.2 Hz), 2.85-3.00 (1H, m), 3.28 (2H, q, J=6.8 Hz), 3.85-4.05 (4H, m), 5.30-5.50 (1H, m), 7.14-7.24 (3H, m), 7.24-7.34 (2H, m)

Reference Example 4-24

¹H-NMR (CDCl₃) δ ppm: 0.89 (9H, s), 1.25-1.85 (9H, m), 2.00-2.15 (1H, m), 2.20-2.35 (4H, m), 2.40-2.55 (1H, m), 2.90-3.05 (1H, m), 3.05 (2H, d, J=6.3 Hz), 3.94 (4H, s), 5.35-5.50 (1H, m)

Reference Example 4-25

¹H-NMR (CDCl₃) δ ppm: 1.25-1.47 (3H, m), 1.47-1.70 (4H, m), 1.70-1.90 (4H, m), 2.00-2.20 (3H, m), 2.20-2.35 (4H, m), 2.40-2.55 (1H, m), 2.90-3.05 (1H, m), 3.25-3.40 (2H, m), 3.85-4.00 (4H, m), 5.50-5.75 (1H, m)

Reference Example 4-26

MS (ESI, m/z): 313 (M+H)+

Reference Example 4-27

¹H-NMR (CDCl₃) δ ppm: 1.25-1.70 (7H, m), 1.70-1.85 (2H, m), 2.00-2.10 (1H, m), 2.20-2.35 (4H, m), 2.40-2.55 (1H, m), 2.80 (3H, d, J=4.8 Hz), 2.90-3.05 (1H, m), 3.90-4.00 (4H, m), 5.35-5.50 (1H, m)

Reference Example 4-28

¹H-NMR (CDCl₃) δ ppm: 0.89 (3H, t, J=7.3 Hz), 1.19-1.77 (11H, m), 1.78-1.93 (2H, m), 2.13-2.24 (2H, m), 2.27-2.39 (1H, m), 2.87-2.97 (1H, m), 3.06-3.25 (3H, m), 3.88-4.01 (4H, m), 4.04-4.13 (1H, m), 5.20-5.36 (1H, m), 7.17-7.36 (5H, m)

Reference Example 4-29

MS (ESI, m/z): 311 (M+H)+

Reference Example 4-30

¹H-NMR (CDCl₃) δ ppm: 0.90-1.05 (3H, m), 1.05-1.20 (3H, m), 1.25-1.50 (3H, m), 1.50-1.90 (6H, m), 2.00-2.10 (1H, m), 2.30-2.50 (2H, m), 2.60-2.90 (2H, m), 2.95-3.05 (1H, m), 3.20-3.35 (2H, m), 3.85-4.00 (4H, m), 5.41 (1H, brs)

Reference Example 4-31

¹H-NMR (CDCl₃) δ ppm: 0.86 (3H, t, J=7.4 Hz), 1.20-1.95 (11H, m), 2.10-2.25 (2H, m), 2.25-2.40 (1H, m), 2.90-3.00 (1H, m), 3.05-3.25 (3H, m), 3.90-4.00 (4H, m), 4.10 (1H, d, J=13.8 Hz), 5.25-5.40 (1H, m), 7.15-7.35 (5H, m)

Reference Example 4-32

¹H-NMR (CDCl₃) δ ppm: 1.07 (3H, t, J=7.3 Hz), 1.25-1.78 (7H, m), 1.79-1.93 (2H, m), 2.13-2.25 (2H, m), 2.27-2.39 (1H, m), 2.88-2.99 (1H, m), 3.10-3.31 (3H, m), 3.87-4.00 (4H, m), 4.05-4.15 (1H, m), 5.17-5.39 (1H, m), 7.16-7.36 (5H, m)

Reference Example 4-33

¹H-NMR (CDCl₃) δ ppm: 0.10-0.25 (2H, m), 0.40-0.60 (2H, m), 0.80-1.00 (1H, m), 1.20-1.48 (3H, m), 1.48-1.70 (4H, m), 1.70-1.90 (2H, m), 2.00-2.15 (1H, m), 2.20-2.35 (4H, m), 2.40-2.55 (1H, m), 2.90-3.05 (1H, m), 3.05-3.14 (2H, m), 3.90-4.00 (4H, m), 5.49 (1H, brs)

[α]_D^{27}=−18.52° (c=0.30, MeOH)

Reference Example 5-1

(3'R,4'aR,8'aR)-1'-Methyl-N-[2-(pyrrolidin-1-yl)ethyl]octa-hydro-1'H-spiro[1,3-dioxolane-2,6'-quinoline]-3'-carboxamide A mixture of ethyl (3'R,4'aR,8'aR)-1'-methyloctahydro-1'H-spiro[1,3-dioxolane-2,6'-quinoline]-3'-carboxylate (reference example 3) (100 mg) and 1-(2-aminoethyl)pyrrolidine (0.22 mL) was stirred under microwave irradiation to 210° C. for 12 hours. The mixture was purified by aminopropyl silica gel column chromatography (eluent: 0%-10% methanol/ethyl acetate, gradient elution) to give the title compound (73 mg).

¹H-NMR (CDCl₃) δ ppm: 1.24-1.46 (3H, m), 1.48-1.70 (4H, m), 1.70-1.86 (6H, m), 2.01-2.11 (1H, m), 2.23-2.33

(1H, m), 2.29 (3H, s), 2.43-2.53 (5H, m), 2.53-2.60 (2H, m), 2.94-3.01 (1H, m), 3.28-3.37 (2H, m), 3.90-3.97 (4H, m), 6.05-6.18 (1H, m)

Reference Example 5-2

(3'R*,4'aR*,8'aR*)-N-[3-(Dimethylamino)propyl]-1'-methyl-octahydro-1'H-spiro-[1,3-dioxolane-2,6'-quinoline]-3'-carboxamide A mixture of ethyl (3'R*,4'aR*,8'aR*)-1'-methyloctahydro-1'H-spiro[1,3-dioxolane-2,6'-quinoline]-3'-carboxylate (reference example 2-1) (2.053 g) and (3-aminopropyl)dimethylamine (4.44 mL) was stirred under microwave irradiation to 210° C. for 10 hours. The mixture was purified by aminopropyl silica gel column chromatography (eluent: 0%-10% methanol/ethyl acetate, gradient elution) to give the title compound (2.557 g).

$^1$H-NMR (CDCl$_3$) δ ppm: 1.20-1.90 (11H, m), 2.00-2.15 (1H, m), 2.15-2.55 (13H, m), 2.95-3.05 (1H, m), 3.25-3.40 (2H, m), 3.85-4.00 (4H, m), 7.35-7.50 (1H, m)

Reference examples 5-3 to 5-8 were prepared in a manner similar to those as described in reference example 5-2 using the corresponding decahydroquinoline-3-carboxylate esters and amines instead of ethyl (3'R*,4'aR*,8'aR*)-1'-methyloctahydro-1'H-spiro[1,3-dioxolane-2,6'-quinoline]-3'-carboxylate (reference example 2-1) and (3-aminopropyl)dimethylamine. These were illustrated in Table 4.

TABLE 4

| Reference example | Structure |
|---|---|
| 5-1 | (Chiral structure) |
| 5-2 | (structure) |
| 5-3 | (structure) |
| 5-4 | (structure) |
| 5-5 | (structure) |
| 5-6 | (structure) |
| 5-7 | (structure) |
| 5-8 | (structure) |

The structure of the reference example 5-1 in Table 4 indicates absolute configuration, and the structures of the reference example 5-2 to 5-8 in Table 4 indicate relative configuration.

The physical data of reference examples 5-3 to 5-8 were shown below.

Reference Example 5-3

MS (ESI, m/z): 368 (M+H)+

Reference Example 5-4

¹H-NMR (CDCl₃) δ ppm: 1.20-1.90 (8H, m), 2.00-2.10 (1H, m), 2.15-2.35 (11H, m), 2.38 (2H, t, J=6.4 Hz), 2.42-2.55 (1H, m), 2.90-3.05 (1H, m), 3.20-3.35 (2H, m), 3.90-4.01 (4H, m), 6.00-6.15 (1H, m)

Reference Example 5-5

MS (ESI, m/z): 354 (M+H)+

Reference Example 5-6

¹H-NMR (CDCl₃) δ ppm: 1.24-1.87 (13H, m), 2.01-2.11 (1H, m), 2.22-2.35 (1H, m), 2.29 (3H, s), 2.41-2.62 (7H, m), 2.94-3.02 (1H, m), 3.27-3.37 (2H, m), 3.89-3.98 (4H, m), 6.05-6.18 (1H, m)

Reference Example 5-7

¹H-NMR (CDCl₃) δ ppm: 0.84 (3H, t, J=7.3 Hz), 1.20-1.70 (9H, m), 1.70-1.90 (3H, m), 1.95-2.10 (1H, m), 2.20-2.25 (7H, m), 2.30-2.55 (5H, m), 2.55-2.70 (1H, m), 3.00-3.10 (1H, m), 3.25-3.40 (2H, m), 3.85-4.00 (4H, m), 7.35-7.45 (1H, m)

Reference Example 5-8

¹H-NMR (CDCl₃) δ ppm: 0.98 (3H, t, J=7.1 Hz), 1.20-1.50 (3H, m), 1.50-1.70 (4H, m), 1.70-1.90 (3H, m), 2.00-2.10 (1H, m), 2.15-2.30 (7H, m), 2.30-2.50 (4H, m), 2.60-2.75 (1H, m), 2.75-2.90 (1H, m), 3.00-3.10 (1H, m), 3.25-3.40 (2H, m), 3.85-4.00 (4H, m), 7.30-7.45 (1H, m)

Reference Example 6-1

Phenyl N-{[(3'R,4'aR,8'aR)-1'-methyloctahydro-1'H-spiro[1,3-dioxolane-2,6'-quinolin]-3'-yl]carbonyl}-N-propylcarbamate To a mixture of (3'R,4'aR,8'aR)-1'-methyl-N-propyloctahydro-1'H-spiro-[1,3-dioxolane-2,6'-quinoline]-3'-carboxamide (reference example 4-1) (1.816 g) and tetrahydrofuran (31 mL) was added a 1 mol/L sodium hexamethyldisilazide-tetrahydrofuran solution (7.97 mL) at −42° C. After stirring at the same temperature for 20 minutes, phenyl chloroformate (0.999 mL) was added to the mixture, and then stirred for 1.5 hours. After warming to room temperature, water and ethyl acetate were added. The separated organic layer was dried over anhydrous magnesium sulfate, and concentrated under reduced pressure. The residue was purified by silica gel column chromatography (eluent: 0%-15% methanol/ethyl acetate, gradient elution) to give the title compound (2.402 g).

¹H-NMR (CDCl₃) δ ppm: 0.95 (3H, t, J=7.5 Hz), 1.15-1.50 (3H, m), 1.50-1.85 (7H, m), 1.90-2.10 (2H, m), 2.29 (3H, s), 2.38 (1H, t, J=11.3 Hz), 2.95-3.05 (1H, m), 3.65-3.80 (1H, m), 3.80-3.95 (6H, m), 7.10-7.20 (2H, m), 7.25-7.35 (1H, m), 7.35-7.50 (2H, m)

Reference Example 6-5

Phenyl N-{[(3'R*,4'aR*,8'aR*)-1'-methyloctahydro-1'H-spiro-[1,3-dioxolane-2,6'-quinolin]-3'-yl]carbonyl}-N-propylcarbamate To a mixture of (3'R*,4'aR*,8'aR*)-1'-methyl-N-propyloctahydro-1'H-spiro-[1,3-dioxolane-2,6'-quinoline]-3'-carboxamide (reference example 4-5) (539 mg) and tetrahydrofuran (3.6 mL) was added a 1 mol/L sodium hexamethyldisilazide-tetrahydrofuran solution (2.4 mL) at −20° C. After stirring at the same temperature for 20 minutes, phenyl chloroformate (0.298 mL) was added to the mixture, and then stirred for 1 hour. After warming to room temperature, water and ethyl acetate were added. The separated organic layer was dried over anhydrous sodium sulfate, and concentrated under reduced pressure. The residue was purified by silica gel column chromatography (eluent: 0%-9% methanol/ethyl acetate, gradient elution) to give the title compound (622 mg).

¹H-NMR (CDCl₃) δ ppm: 0.95 (3H, t, J=7.6 Hz), 1.10-1.50 (3H, m), 1.50-1.85 (7H, m), 1.85-2.10 (2H, m), 2.28 (3H, s), 2.38 (1H, t, J=10.8 Hz), 2.90-3.10 (1H, m), 3.65-4.00 (7H, m), 7.10-7.20 (2H, m), 7.20-7.35 (1H, m), 7.35-7.50 (2H, m)

Reference examples 6-2 to 6-4 and reference examples 6-6 to 6-40 were prepared in a manner similar to those as described in reference example 6-1 or reference example 6-5 using the corresponding amides and aryl chloroformates instead of (3'R,4'aR,8'aR)-1'-methyl-N-propyloctahydro-1'H-spiro[1,3-dioxolane-2,6'-quinoline]-3'-carboxamide and phenyl chloroformate. These were illustrated in Table 5.

TABLE 5

| Reference example | Structure |
| --- | --- |
| 6-1 | (Chiral structure shown) |

TABLE 5-continued

| Reference example | Structure | |
|---|---|---|
| 6-2 | 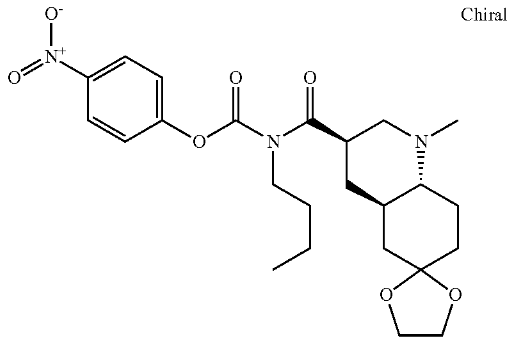 [SMILES: CCCCN(C(=O)Oc1ccc([N+](=O)[O-])cc1)C(=O)[C@@H]1C[C@@H]2CC3(CC[C@H]2N(C)C1)OCCO3] | Chiral |
| 6-3 | 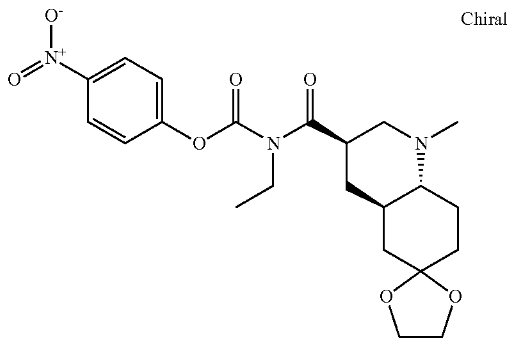 [SMILES: CCN(C(=O)Oc1ccc([N+](=O)[O-])cc1)C(=O)[C@@H]1C[C@@H]2CC3(CC[C@H]2N(C)C1)OCCO3] | Chiral |
| 6-4 | 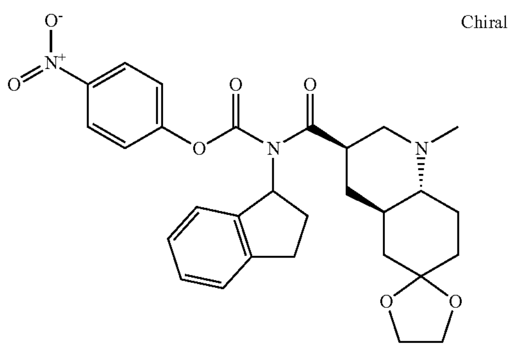 [SMILES: CN1C[C@H](C(=O)N(C(=O)Oc2ccc([N+](=O)[O-])cc2)C2CCc3ccccc32)C[C@@H]2CC3(CC[C@H]21)OCCO3] | Chiral |
| 6-5 | 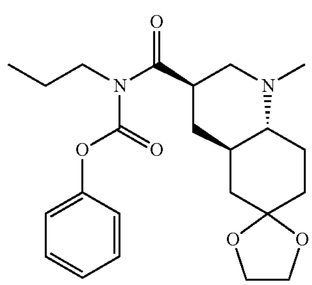 [SMILES: CCCN(C(=O)Oc1ccccc1)C(=O)[C@@H]1C[C@@H]2CC3(CC[C@H]2N(C)C1)OCCO3] | |

TABLE 5-continued
| Reference example | Structure |
|---|---|
| 6-6 | 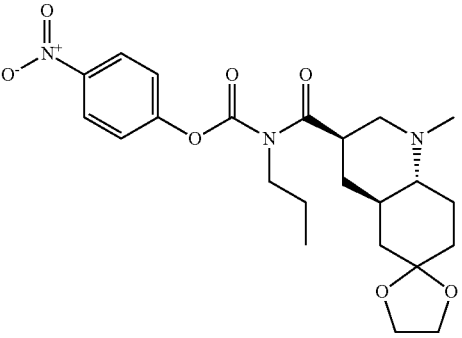 [SMILES: CCCN(C(=O)Oc1ccc([N+](=O)[O-])cc1)C(=O)[C@@H]1C[C@@H]2CC3(CC[C@H]2N(C)C1)OCCO3] |
| 6-7 | 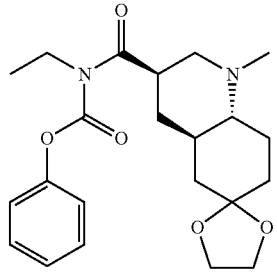 [SMILES: CCN(C(=O)Oc1ccccc1)C(=O)[C@@H]1C[C@@H]2CC3(CC[C@H]2N(C)C1)OCCO3] |
| 6-8 | 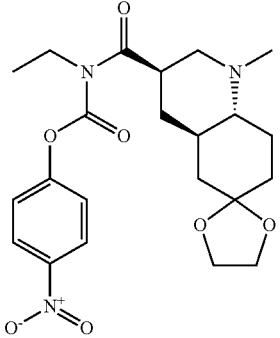 [SMILES: CCN(C(=O)Oc1ccc([N+](=O)[O-])cc1)C(=O)[C@@H]1C[C@@H]2CC3(CC[C@H]2N(C)C1)OCCO3] |
| 6-9 | 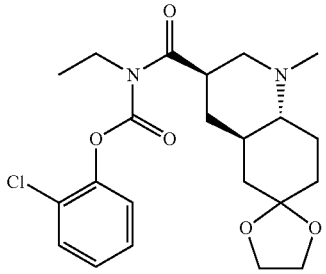 [SMILES: CCN(C(=O)Oc1ccccc1Cl)C(=O)[C@@H]1C[C@@H]2CC3(CC[C@H]2N(C)C1)OCCO3] |
| 6-10 | 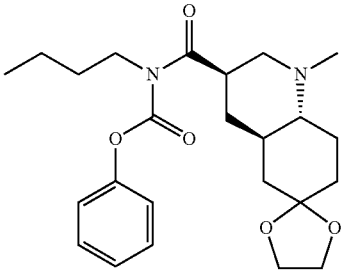 [SMILES: CCCCN(C(=O)Oc1ccccc1)C(=O)[C@@H]1C[C@@H]2CC3(CC[C@H]2N(C)C1)OCCO3] |

TABLE 5-continued
| Reference example | Structure |
|---|---|
| 6-11 | 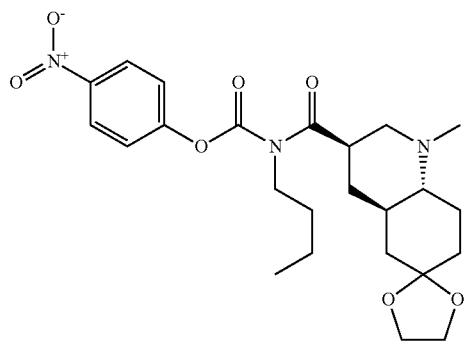 [SMILES: CCCCN(C(=O)Oc1ccc([N+](=O)[O-])cc1)C(=O)[C@@H]1C[C@@H]2CC3(CC[C@H]2N(C)C1)OCCO3] |
| 6-12 | 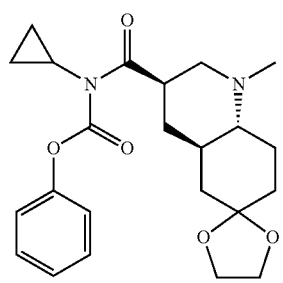 [SMILES: CN1C[C@H](C(=O)N(C(=O)Oc2ccccc2)C2CC2)C[C@@H]2CC3(CC[C@H]21)OCCO3] |
| 6-13 | 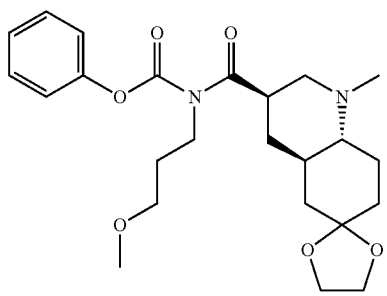 [SMILES: COCCCN(C(=O)Oc1ccccc1)C(=O)[C@@H]1C[C@@H]2CC3(CC[C@H]2N(C)C1)OCCO3] |
| 6-14 | 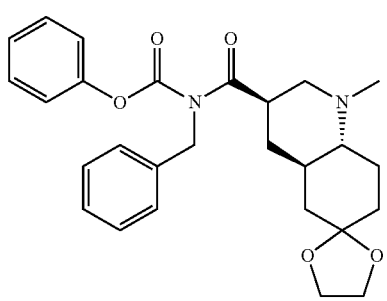 [SMILES: CN1C[C@H](C(=O)N(Cc2ccccc2)C(=O)Oc2ccccc2)C[C@@H]2CC3(CC[C@H]21)OCCO3] |
| 6-15 | 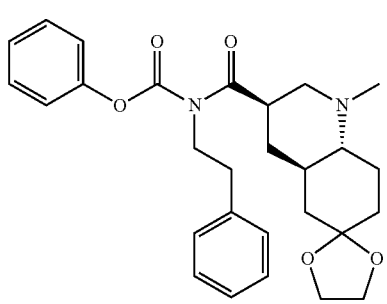 [SMILES: CN1C[C@H](C(=O)N(CCc2ccccc2)C(=O)Oc2ccccc2)C[C@@H]2CC3(CC[C@H]21)OCCO3] |

TABLE 5-continued

| Reference example | Structure |
|---|---|
| 6-16 | 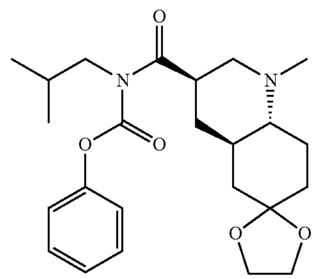 [SMILES: CC(C)CN(C(=O)Oc1ccccc1)C(=O)[C@@H]1C[C@@H]2CC3(CC[C@H]2N(C)C1)OCCO3] |
| 6-17 | 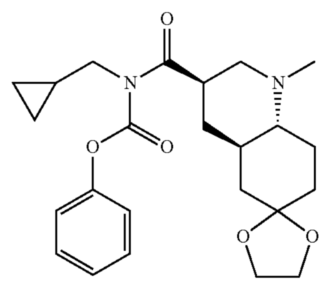 [SMILES: CN1C[C@H](C(=O)N(CC2CC2)C(=O)Oc2ccccc2)C[C@@H]2CC3(CC[C@H]21)OCCO3] |
| 6-18 | 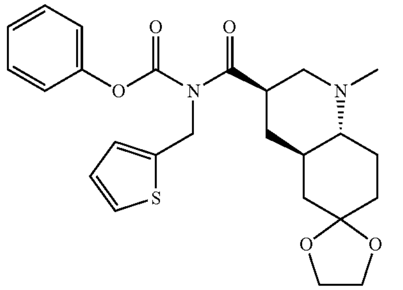 [SMILES: CN1C[C@H](C(=O)N(Cc2cccs2)C(=O)Oc2ccccc2)C[C@@H]2CC3(CC[C@H]21)OCCO3] |
| 6-19 | 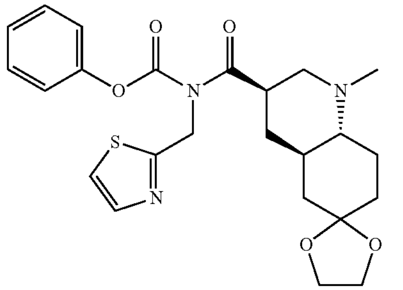 [SMILES: CN1C[C@H](C(=O)N(Cc2nccs2)C(=O)Oc2ccccc2)C[C@@H]2CC3(CC[C@H]21)OCCO3] |
| 6-20 | 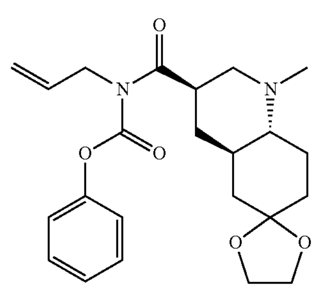 [SMILES: C=CCN(C(=O)Oc1ccccc1)C(=O)[C@@H]1C[C@@H]2CC3(CC[C@H]2N(C)C1)OCCO3] |

TABLE 5-continued

| Reference example | Structure |
|---|---|
| 6-21 | 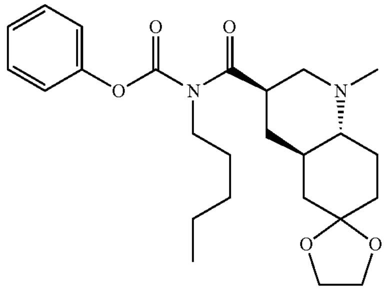 |
| 6-22 | 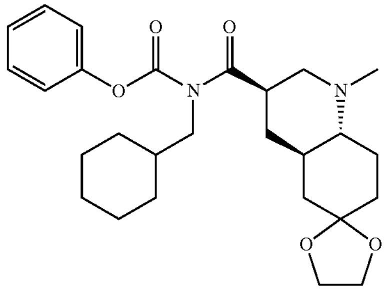 [SMILES: CN1C[C@H](C(=O)N(CC2CCCCC2)C(=O)Oc2ccccc2)C[C@@H]2CC3(CC[C@H]21)OCCO3] |
| 6-23 | 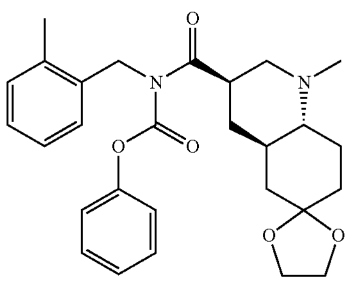 [SMILES: Cc1ccccc1CN(C(=O)Oc1ccccc1)C(=O)[C@@H]1C[C@@H]2CC3(CC[C@H]2N(C)C1)OCCO3] |
| 6-24 | 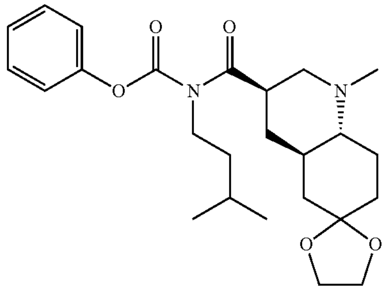 [SMILES: CC(C)CCN(C(=O)Oc1ccccc1)C(=O)[C@@H]1C[C@@H]2CC3(CC[C@H]2N(C)C1)OCCO3] |
| 6-25 | 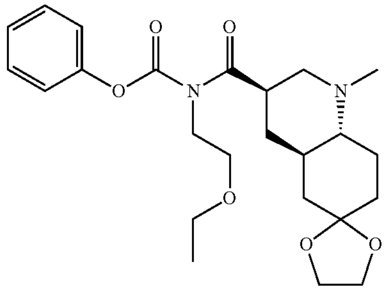 [SMILES: CCOCCN(C(=O)Oc1ccccc1)C(=O)[C@@H]1C[C@@H]2CC3(CC[C@H]2N(C)C1)OCCO3] |

TABLE 5-continued

| Reference example | Structure |
|---|---|
| 6-26 | 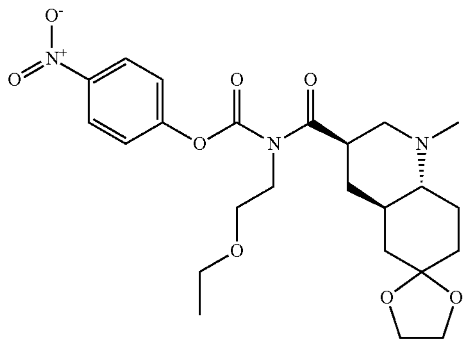 [SMILES: CCOCCN(C(=O)Oc1ccc([N+](=O)[O-])cc1)C(=O)[C@@H]1C[C@@H]2CC3(CC[C@H]2N(C)C1)OCCO3] |
| 6-27 | 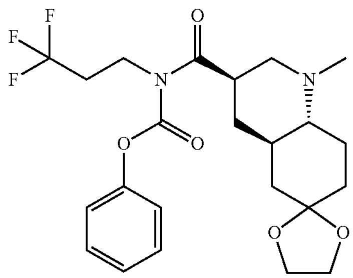 [SMILES: CN1C[C@H](C(=O)N(CCC(F)(F)F)C(=O)Oc2ccccc2)C[C@@H]2CC3(CC[C@H]21)OCCO3] |
| 6-28 | 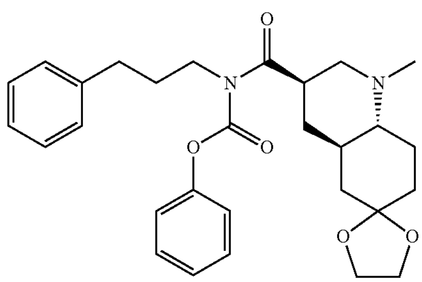 [SMILES: CN1C[C@H](C(=O)N(CCCc2ccccc2)C(=O)Oc2ccccc2)C[C@@H]2CC3(CC[C@H]21)OCCO3] |
| 6-29 | 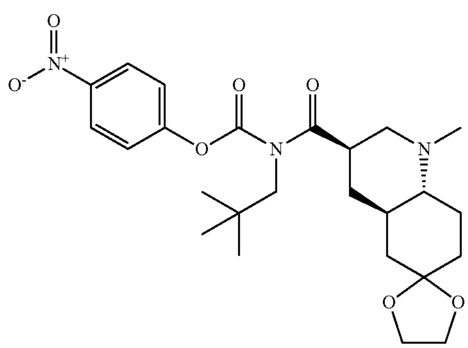 [SMILES: CN1C[C@H](C(=O)N(CC(C)(C)C)C(=O)Oc2ccc([N+](=O)[O-])cc2)C[C@@H]2CC3(CC[C@H]21)OCCO3] |
| 6-30 | 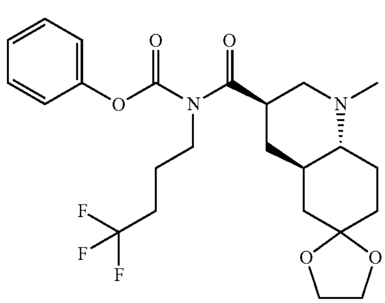 [SMILES: CN1C[C@H](C(=O)N(CCCC(F)(F)F)C(=O)Oc2ccccc2)C[C@@H]2CC3(CC[C@H]21)OCCO3] |

TABLE 5-continued

| Reference example | Structure |
|---|---|
| 6-31 | 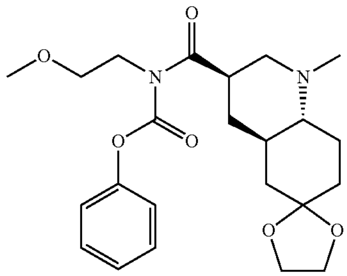 [SMILES: COCCN(C(=O)Oc1ccccc1)C(=O)[C@@H]1C[C@@H]2CC3(CC[C@H]2N(C)C1)OCCO3] |
| 6-32 | 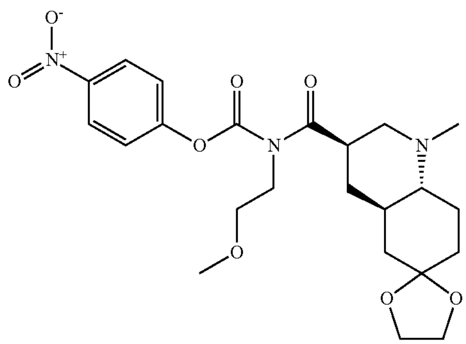 [SMILES: COCCN(C(=O)Oc1ccc([N+](=O)[O-])cc1)C(=O)[C@@H]1C[C@@H]2CC3(CC[C@H]2N(C)C1)OCCO3] |
| 6-33 | 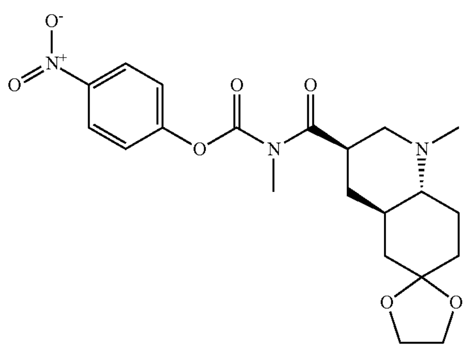 [SMILES: CN(C(=O)Oc1ccc([N+](=O)[O-])cc1)C(=O)[C@@H]1C[C@@H]2CC3(CC[C@H]2N(C)C1)OCCO3] |
| 6-34 | 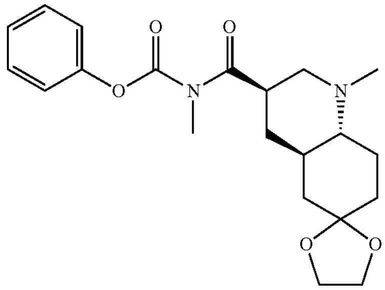 [SMILES: CN(C(=O)Oc1ccccc1)C(=O)[C@@H]1C[C@@H]2CC3(CC[C@H]2N(C)C1)OCCO3] |

TABLE 5-continued

| Reference example | Structure |
|---|---|
| 6-35 | 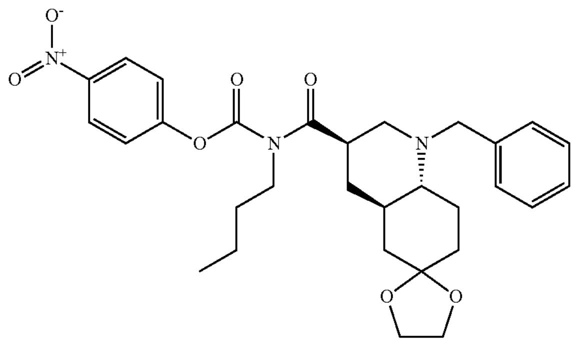 [SMILES: CCCCN(C(=O)Oc1ccc([N+](=O)[O-])cc1)C(=O)[C@@H]1C[C@@H]2CC3(CC[C@H]2N(Cc2ccccc2)C1)OCCO3] |
| 6-36 | 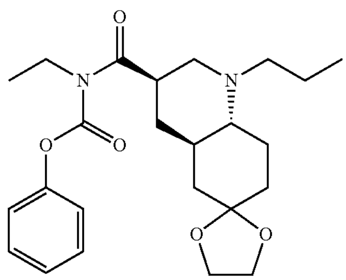 [SMILES: CCCN1C[C@H](C(=O)N(CC)C(=O)Oc2ccccc2)C[C@@H]2CC3(CC[C@H]21)OCCO3] |
| 6-37 | 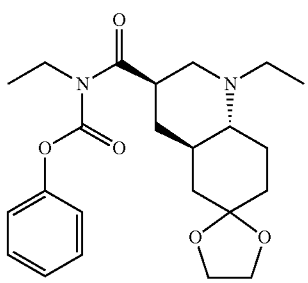 [SMILES: CCN(C(=O)Oc1ccccc1)C(=O)[C@@H]1C[C@@H]2CC3(CC[C@H]2N(CC)C1)OCCO3] |
| 6-38 | 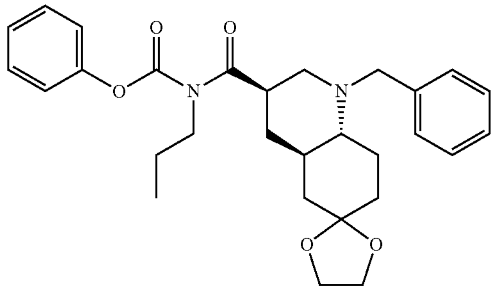 [SMILES: CCCN(C(=O)Oc1ccccc1)C(=O)[C@@H]1C[C@@H]2CC3(CC[C@H]2N(Cc2ccccc2)C1)OCCO3] |
| 6-39 | Chiral |

TABLE 5-continued

| Reference example | Structure |
|---|---|
| 6-40 | 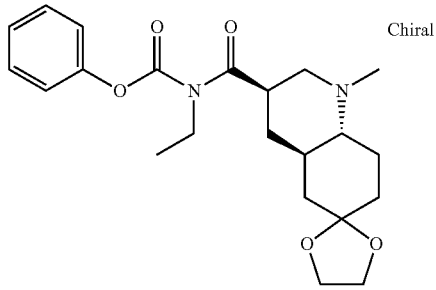 [SMILES: CCN(C(=O)Oc1ccccc1)C(=O)[C@@H]1C[C@@H]2CC3(CC[C@H]2N(C)C1)OCCO3] Chiral |

The structures of the reference example 6-1 to 6-4 and 6-39 to 6-40 in Table 5 indicate absolute configuration, and the structures of the reference example 6-5 to 6-38 in Table 5 indicate relative configuration.

The physical data of reference examples 6-2 to 6-4 and reference examples 6-6 to 6-40 were shown below.

Reference Example 6-2

$^1$H-NMR (CDCl$_3$) δ ppm: 0.96 (3H, t, J=7.2 Hz), 1.20-1.90 (11H, m), 2.00-2.15 (2H, m), 2.20-2.40 (4H, m), 2.95-3.10 (1H, m), 3.65-3.80 (1H, m), 3.80-4.00 (6H, m), 7.30-7.40 (2H, m), 8.25-8.35 (2H, m)

Reference Example 6-3

MS (ESI, m/z): 448 (M+H)+

Reference Example 6-4

MS (ESI, m/z): 536 (M+H)+

Reference Example 6-6

MS (ESI, m/z): 462 (M+H)+

Reference Example 6-7

$^1$H-NMR (CDCl$_3$) δ ppm: 1.10-1.50 (6H, m), 1.50-1.85 (5H, m), 1.85-2.10 (2H, m), 2.29 (3H, s), 2.38 (1H, t, J=11.2 Hz), 2.90-3.05 (1H, m), 3.65-3.85 (1H, m), 3.85-4.00 (6H, m), 7.12-7.20 (2H, m), 7.25-7.32 (1H, m), 7.38-7.46 (2H, m)

Reference Example 6-8

$^1$H-NMR (CDCl$_3$) δ ppm: 1.20-1.75 (10H, m), 1.75-1.85 (1H, m), 1.85-1.95 (1H, m), 1.95-2.10 (1H, m), 2.30 (3H, s), 2.37 (1H, t, J=11.2 Hz), 2.95-3.05 (1H, m), 3.65-3.80 (1H, m), 3.85-4.00 (6H, m), 7.30-7.40 (2H, m), 8.25-8.35 (2H, m)

Reference Example 6-9

$^1$H-NMR (CDCl$_3$) δ ppm: 1.15-1.50 (6H, m), 1.50-1.85 (5H, m), 1.90-2.10 (2H, m), 2.29 (3H, s), 2.38 (1H, t, J=11.3 Hz), 2.85-3.10 (1H, m), 3.70-3.85 (1H, m), 3.85-3.95 (4H, m), 3.97 (2H, q, J=7.1 Hz), 7.20-7.30 (2H, m), 7.30-7.40 (1H, m), 7.45-7.50 (1H, m)

Reference Example 6-10

$^1$H-NMR (CDCl$_3$) δ ppm: 0.95 (3H, t, J=7.2 Hz), 1.15-1.50 (6H, m), 1.50-1.88 (6H, m), 1.88-2.10 (2H, m), 2.29 (3H, s), 2.38 (1H, t, J=11.2 Hz), 2.95-3.05 (1H, m), 3.65-3.80 (1H, m), 3.80-4.00 (6H, m), 7.12-7.18 (2H, m), 7.26-7.32 (1H, m), 7.38-7.46 (2H, m)

Reference Example 6-11

$^1$H-NMR (CDCl$_3$) δ ppm: 0.96 (3H, t, J=7.3 Hz), 1.20-1.50 (6H, m), 1.50-1.75 (5H, m), 1.75-1.85 (1H, m), 1.85-1.95 (1H, m), 1.95-2.10 (1H, m), 2.30 (3H, s), 2.37 (1H, t, J=11.2 Hz), 2.95-3.10 (1H, m), 3.65-3.80 (1H, m), 3.80-3.95 (6H, m), 7.30-7.40 (2H, m), 8.25-8.35 (2H, m)

Reference Example 6-12

MS (ESI, m/z): 415 (M+H)+

Reference Example 6-13

MS (ESI, m/z): 447 (M+H)+

Reference Example 6-14

MS (ESI, m/z): 465 (M+H)+

Reference Example 6-15

$^1$H-NMR (CDCl$_3$) δ ppm: 1.20-1.50 (4H, m), 1.50-1.70 (2H, m), 1.75-1.85 (1H, m), 1.95-2.10 (1H, m), 2.20-2.40 (4H, m), 2.80-3.20 (6H, m), 3.75-4.00 (6H, m), 6.95-7.05 (2H, m), 7.15-7.35 (6H, m), 7.35-7.45 (2H, m)

Reference Example 6-16

MS (ESI, m/z): 431 (M+H)+

Reference Example 6-17

$^1$H-NMR (CDCl$_3$) δ ppm: 0.30-0.40 (2H, m), 0.45-0.60 (2H, m), 1.15-1.50 (4H, m), 1.50-1.85 (5H, m), 1.90-2.10 (2H, m), 2.29 (3H, s), 2.38 (1H, t, J=11.2 Hz), 2.95-3.10 (1H, m), 3.70-3.85 (3H, m), 3.85-3.95 (4H, m), 7.10-7.20 (2H, m), 7.25-7.35 (1H, m), 7.35-7.50 (2H, m)

Reference Example 6-18

MS (ESI, m/z): 471 (M+H)+

Reference Example 6-19

$^1$H-NMR (CDCl$_3$) δ ppm: 1.20-1.50 (3H, m), 1.50-1.85 (5H, m), 1.95-2.10 (2H, m), 2.30 (3H, s), 2.42 (1H, t, J=11.2

Hz), 3.00-3.15 (1H, m), 3.80-4.00 (5H, m), 5.41 (2H, dd, J=17.3, 16.0 Hz), 7.05-7.10 (2H, m), 7.20-7.30 (1H, m), 7.31 (1H, d, J=3.3 Hz), 7.35-7.45 (2H, m), 7.75 (1H, d, J=3.3 Hz)

Reference Example 6-20

MS (ESI, m/z): 415 (M+H)+

Reference Example 6-21

MS (ESI, m/z): 445 (M+H)+

Reference Example 6-22

MS (ESI, m/z): 471 (M+H)+

Reference Example 6-23

MS (ESI, m/z): 479 (M+H)+

Reference Example 6-24

MS (ESI, m/z): 445 (M+H)+

Reference Example 6-25

MS (ESI, m/z): 447 (M+H)+

Reference Example 6-26

$^1$H-NMR (CDCl$_3$) δ ppm: 1.16 (3H, t, J=7.0 Hz), 1.20-1.50 (3H, m), 1.50-1.75 (4H, m), 1.75-1.85 (1H, m), 1.85-2.10 (2H, m), 2.30 (3H, s), 2.37 (1H, t, J=11.2 Hz), 3.00-3.10 (1H, m), 3.45-3.55 (2H, m), 3.55-3.75 (3H, m), 3.85-3.95 (4H, m), 4.05-4.15 (2H, m), 7.30-7.40 (2H, m), 8.25-8.35 (2H, m)

Reference Example 6-27

$^1$H-NMR (CDCl$_3$) δ ppm: 1.10-1.50 (3H, m), 1.50-1.85 (5H, m), 1.85-2.10 (2H, m), 2.29 (3H, s), 2.33-2.42 (1H, m), 2.42-2.55 (2H, m), 2.95-3.05 (1H, m), 3.70-3.85 (1H, m), 3.85-4.00 (4H, m), 4.10-4.25 (2H, m), 7.10-7.20 (2H, m), 7.25-7.35 (1H, m), 7.40-7.50 (2H, m)

Reference Example 6-28

$^1$H-NMR (CDCl$_3$) δ ppm: 1.10-1.50 (3H, m), 1.50-1.85 (5H, m), 1.85-2.10 (4H, m), 2.28 (3H, s), 2.37 (1H, t, J=9.2 Hz), 2.68 (2H, t, J=6.4 Hz), 2.95-3.05 (1H, m), 3.70-3.80 (1H, m), 3.85-3.95 (6H, m), 7.08-7.14 (2H, m), 7.14-7.22 (3H, m), 7.24-7.32 (3H, m), 7.38-7.46 (2H, m)

Reference Example 6-29

MS (ESI, m/z): 490 (M+H)+

Reference Example 6-30

MS (ESI, m/z): 485 (M+H)+

Reference Example 6-31

MS (ESI, m/z): 433 (M+H)+

Reference Example 6-32

$^1$H-NMR (CDCl$_3$) δ ppm: 1.20-1.50 (3H, m), 1.50-1.75 (4H, m), 1.75-1.85 (1H, m), 1.85-2.10 (2H, m), 2.30 (3H, s), 2.37 (1H, t, J=11.3 Hz), 3.00-3.10 (1H, m), 3.35 (3H, s), 3.58 (2H, t, J=5.4 Hz), 3.60-3.75 (1H, m), 3.85-3.95 (4H, m), 4.05-4.15 (2H, m), 7.30-7.40 (2H, m), 8.25-8.35 (2H, m)

Reference Example 6-33

$^1$H-NMR (CDCl$_3$) δ ppm: 1.20-1.75 (7H, m), 1.75-1.85 (1H, m), 1.85-2.10 (2H, m), 2.30 (3H, s), 2.38 (1H, t, J=11.2 Hz), 2.95-3.10 (1H, m), 3.37 (3H, s), 3.70-3.85 (1H, m), 3.85-3.95 (4H, m), 7.30-7.40 (2H, m), 8.25-8.35 (2H, m)

Reference Example 6-34

MS (ESI, m/z): 389 (M+H)+

Reference Example 6-35

$^1$H-NMR (CDCl$_3$) δ ppm: 0.92 (3H, t, J=7.4 Hz), 1.20-2.00 (13H, m), 2.10-2.20 (1H, m), 2.24 (1H, t, J=11.2 Hz), 2.95-3.05 (1H, m), 3.18 (1H, d, J=13.8 Hz), 3.55-3.70 (1H, m), 3.70-3.85 (2H, m), 3.85-4.00 (4H, m), 4.05-4.20 (1H, m), 7.15-7.35 (7H, m), 8.25-8.35 (2H, m)

Reference Example 6-36

MS (ESI, m/z): 431 (M+H)+

Reference Example 6-37

MS (ESI, m/z): 417 (M+H)+

Reference Example 6-38

$^1$H-NMR (CDCl$_3$) δ ppm: 0.90 (3H, t, J=7.4 Hz), 1.20-1.35 (1H, m), 1.37 (1H, t, J=12.8 Hz), 1.40-1.85 (7H, m), 1.85-2.00 (2H, m), 2.05-2.20 (1H, m), 2.28 (1H, t, J=11.1 Hz), 2.90-3.05 (1H, m), 3.21 (1H, d, J=13.9 Hz), 3.65-3.80 (3H, m), 3.85-3.95 (4H, m), 4.08 (1H, d, J=13.9 Hz), 7.00-7.10 (2H, m), 7.15-7.35 (6H, m), 7.35-7.45 (2H, m)

Reference Example 6-39

MS (ESI, m/z): 474 (M+H)+

Reference Example 6-40

MS (ESI, m/z): 403 (M+H)+

Reference Example 7-1

1-{[(3'R,4'aR,8'aR)-1'-Methyloctahydro-1'H-spiro[1,3-dioxolane-2,6'-quinolin]-3'-yl]-carbonyl}-3-ethyl-1-[2-(pyrrolidin-1-yl)ethyl]urea To a mixture of (3'R,4'aR,8'aR)-1'-methyl-N-[2-(pyrrolidin-1-yl)ethyl]octahydro-1'H-spiro[1,3-dioxolane-2,6'-quinoline]-3'-carboxamide (reference example 5-1) (73 mg) and 1,2-dichloroethane (1 mL) was added copper(I) chloride (21 mg) and ethyl isocyanate (0.049 mL) at room temperature, and the mixture was stirred for 2.5 hours. The mixture was purified by aminopropyl silica gel column chromatography (eluent: 0%-5% methanol/ethyl acetate, gradient elution) to give the title compound (46 mg).

$^1$H-NMR (CDCl$_3$) δ ppm: 1.16 (3H, t, J=7.3 Hz), 1.28-1.48 (3H, m), 1.51-1.73 (4H, m), 1.74-1.91 (6H, m), 2.00-2.10

(1H, m), 2.29 (3H, s), 2.30-2.39 (1H, m), 2.52-2.75 (6H, m), 2.90-3.01 (1H, m), 3.14-3.33 (3H, m), 3.55-4.00 (6H, m), 9.28-9.65 (1H, m)

Reference Example 7-2

1-{[(3'R*,4'aR*,8'aR*)-1'-Methyloctahydro-1'H-spiro[1,3-dioxolane-2,6'-quinolin]-3'-yl]carbonyl}-1-[3-(dimethylamino)propyl]-3-ethylurea To a mixture of (3'R*,4'aR*,8'aR*)-N-[3-(dimethylamino)propyl]-1'-methyloctahydro-1'H-spiro[1,3-dioxolane-2,6'-quinoline]-3'-carboxamide (reference example 5-2) (2.512 g) and 1,2-dichloroethane (25 mL) were added copper(I) chloride (732 mg) and ethyl isocyanate (1.75 mL) at room temperature, and the mixture was stirred for 1 hour. The mixture was purified by aminopropyl silica gel column chromatography (eluent: 2% methanol/ethyl acetate) to give the title compound (2.309 g).

$^1$H-NMR (CDCl$_3$) δ ppm: 1.16 (3H, t, J=7.4 Hz), 1.30-1.50 (3H, m), 1.50-1.90 (8H, m), 2.00-2.15 (1H, m), 2.15-2.40 (12H, m), 2.85-3.00 (1H, m), 3.05-3.35 (3H, m), 3.55-3.90 (2H, m), 3.90-4.00 (4H, m), 9.37 (1H, br)

Reference examples 7-3 to 7-9 were prepared in a manner similar to those as described in reference example 7-2 using the corresponding amides and isocyanates instead of (3'R,4'aR,8'aR)-1'-methyl-N-[2-(pyrrolidin-1-yl)ethyl]-octahydro-1'H-spiro-[1,3-dioxolane-2,6'-quinoline]-3'-carboxamide and ethyl isocyanate. These were illustrated in Table 6.

| Reference example | Structure |
|---|---|
| 7-1 | 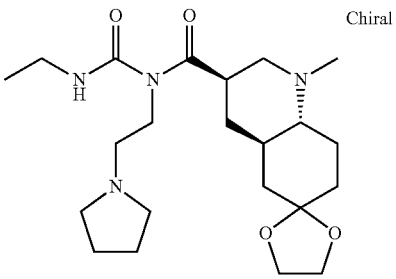 [SMILES: CCNC(=O)N(CCN1CCCC1)C(=O)[C@@H]1C[C@@H]2CC3(CC[C@H]2N(C)C1)OCCO3] Chiral |
| 7-2 | 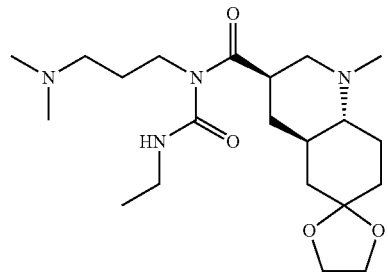 [SMILES: CCNC(=O)N(CCCN(C)C)C(=O)[C@@H]1C[C@@H]2CC3(CC[C@H]2N(C)C1)OCCO3] |
| 7-3 | 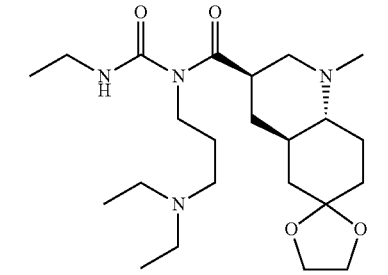 [SMILES: CCNC(=O)N(CCCN(CC)CC)C(=O)[C@@H]1C[C@@H]2CC3(CC[C@H]2N(C)C1)OCCO3] |
| 7-4 | 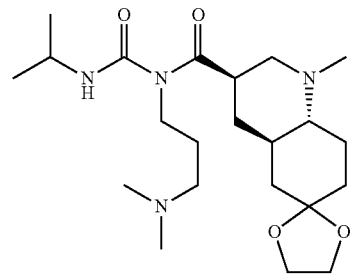 [SMILES: CC(C)NC(=O)N(CCCN(C)C)C(=O)[C@@H]1C[C@@H]2CC3(CC[C@H]2N(C)C1)OCCO3] |
| 7-5 | 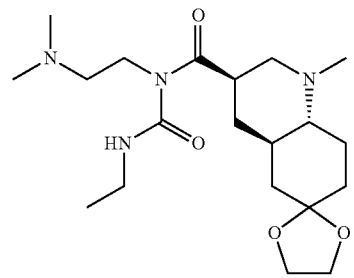 [SMILES: CCNC(=O)N(CCN(C)C)C(=O)[C@@H]1C[C@@H]2CC3(CC[C@H]2N(C)C1)OCCO3] |
| 7-6 | 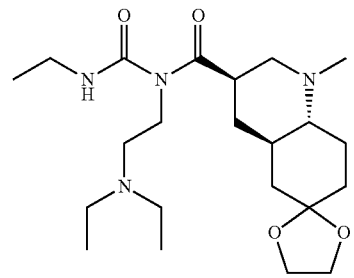 [SMILES: CCNC(=O)N(CCN(CC)CC)C(=O)[C@@H]1C[C@@H]2CC3(CC[C@H]2N(C)C1)OCCO3] |
| 7-7 | 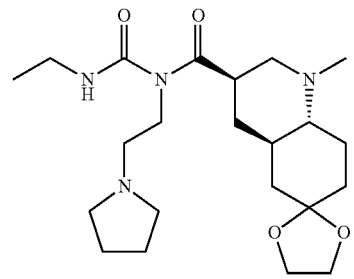 [SMILES: CCNC(=O)N(CCN1CCCC1)C(=O)[C@@H]1C[C@@H]2CC3(CC[C@H]2N(C)C1)OCCO3] |
| 7-8 | 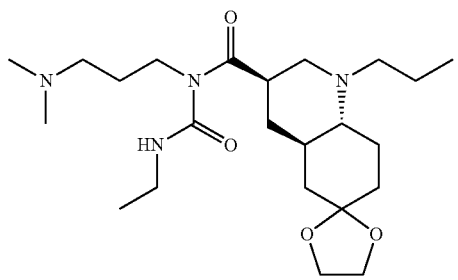 [SMILES: CCCN1C[C@H](C(=O)N(CCCN(C)C)C(=O)NCC)C[C@@H]2CC3(CC[C@H]21)OCCO3] |

| Reference example | Structure |
|---|---|
| 7-9 | (structure shown) |

The structure of the reference example 7-1 in Table 6 indicates absolute configuration, and the structures of the reference example 7-2 to 7-9 in Table 6 indicate relative configuration.

The physical data of reference examples 7-3 to 7-9 were shown below.

Reference Example 7-3

$^1$H-NMR (CDCl$_3$) δ ppm: 1.01 (6H, t, J=7.2 Hz), 1.10-1.30 (6H, m), 1.30-1.50 (3H, m), 1.50-1.90 (5H, m), 2.00-2.10 (1H, m), 2.29 (3H, s), 2.34 (1H, t, J=11.2 Hz), 2.40-2.65 (5H, m), 2.85-3.00 (1H, m), 3.10-3.35 (4H, m), 3.65-3.85 (2H, m), 3.90-4.00 (4H, m), 9.33 (1H, brs)

Reference Example 7-4

$^1$H-NMR (CDCl$_3$) δ ppm: 1.10-1.25 (7H, m), 1.25-1.50 (3H, m), 1.50-1.90 (7H, m), 2.00-2.10 (1H, m), 2.15-2.40 (12H, m), 2.85-3.00 (1H, m), 3.05-3.25 (1H, m), 3.50-4.05 (7H, m), 9.33 (1H, brs)

Reference Example 7-5

MS (ESI, m/z): 397 (M+H)+

Reference Example 7-6

$^1$H-NMR (CDCl$_3$) δ ppm: 1.02 (6H, t, J=7.2 Hz), 1.16 (3H, t, J=7.3 Hz), 1.23-1.49 (3H, m), 1.50-1.74 (4H, m), 1.75-1.95 (2H, m), 1.99-2.09 (1H, m), 2.29 (3H, s), 2.31-2.41 (1H, m), 2.44-2.65 (6H, m), 2.88-3.00 (1H, m), 3.16-3.39 (3H, m), 3.42-3.66 (1H, m), 3.68-3.84 (1H, m), 3.87-4.00 (4H, m), 9.47-9.96 (1H, m)

Reference Example 7-7

$^1$H-NMR (CDCl$_3$) δ ppm: 1.16 (3H, t, J=7.3 Hz), 1.29-1.49 (3H, m), 1.51-1.91 (10H, m), 2.00-2.10 (1H, m), 2.29 (3H, s), 2.29-2.40 (1H, m), 2.50-2.78 (6H, m), 2.90-3.00 (1H, m), 3.11-3.34 (3H, m), 3.56-4.02 (6H, m), 9.33-9.64 (1H, m)

Reference Example 7-8

$^1$H-NMR (CDCl$_3$) δ ppm: 0.84 (3H, t, J=7.4 Hz), 1.16 (3H, t, J=7.3 Hz), 1.25-1.85 (12H, m), 1.85-1.95 (1H, m), 1.95-2.10 (1H, m), 2.22 (6H, s), 2.25-2.40 (2H, m), 2.40-2.55 (2H, m), 2.55-2.70 (1H, m), 2.95-3.05 (1H, m), 3.05-3.20 (1H, m), 3.20-3.35 (2H, m), 3.60-3.90 (2H, m), 3.94 (4H, s), 9.36 (1H, brs)

Reference Example 7-9

$^1$H-NMR (CDCl$_3$) δ ppm: 0.98 (3H, t, J=7.1 Hz), 1.16 (3H, t, J=7.3 Hz), 1.25-1.50 (3H, m), 1.50-1.70 (3H, m), 1.70-1.85 (4H, m), 1.85-1.95 (1H, m), 2.00-2.10 (1H, m), 2.22 (6H, s), 2.25-2.40 (2H, m), 2.49 (1H, t, J=11.2 Hz), 2.65-2.85 (2H, m), 2.90-3.00 (1H, m), 3.05-3.20 (1H, m), 3.20-3.35 (2H, m), 3.60-3.90 (2H, m), 3.94 (4H, s), 9.37 (1H, brs)

Reference Example 8-1

1-{[(3'R,4'aR,8'aR)-1'-Methyloctahydro-1'H-spiro[1,3-dioxolane-2,6'-quinolin]3'-yl]-carbonyl}-3-[2-(dimethylamino)ethyl]-1-propylurea To a mixture of phenyl N-{[(3'R,4'aR,8'aR)-1'-methyloctahydro-1'H-spiro-[1,3-dioxolane-2,6'-quinolin]-3'-yl]carbonyl}-N-propylcarbamate (reference example 6-1) (2.401 g) and 2-propanol (30 mL) was added N,N-dimethyl ethylenediamine (1.26 mL) while stirring at room temperature. The mixture was heated at 53° C. and stirred for 13 hours. After cooling to room temperature, the reaction mixture was concentrated under reduced pressure. The residue was purified by aminopropyl silica gel column chromatography (eluent: 0%-100% ethyl acetate/hexane, gradient elution) to give the title compound (2.383 g).

$^1$H-NMR (CDCl$_3$) δ ppm: 0.92 (3H, t, J=7.4 Hz), 1.35-1.50 (3H, m), 1.50-1.90 (8H, m), 2.00-2.15 (1H, m), 2.26 (6H, s), 2.31 (3H, s), 2.37 (1H, t, J=11.2 Hz), 2.46 (2H, t, J=6.4 Hz), 2.85-3.10 (2H, m), 3.35-3.45 (2H, m), 3.60-3.70 (1H, m), 3.70-3.80 (1H, m), 3.90-4.00 (4H, m), 9.33 (1H, br)

[α]$_D^{28}$=−6.62° (c=0.31, MeOH)

Reference Example 8-6

1-{[(3'R*,4'aR*,8'aR*)-1'-Methyloctahydro-1'H-spiro[1,3-dioxolane-2,6'-quinolin]-3'-yl]carbonyl}-3-[2-(dimethylamino)ethyl]-1-propylurea To a mixture of phenyl N-{[(3'R*,4'aR*,8'aR*)-1'-methyloctahydro-1'H-spiro-[1,3-dioxolane-2,6'-quinolin]-3'-yl]carbonyl}-N-propylcarbamate (reference example 6-5) (2.025 g) and 2-propanol (26 mL) was added N,N-dimethyl ethylenediamine (1.06 mL) while stirring at room temperature, and the mixture was heated at 50° C. and stirred for 12 hours. After cooling to room temperature, the reaction mixture was concentrated under reduced pressure. The residue was purified by aminopropyl silica gel column chromatography (eluent: 0%-75% ethyl acetate/hexane, gradient elution) to give the title compound (1.984 g).

$^1$H-NMR (CDCl$_3$) δ ppm: 0.80-1.00 (3H, m), 1.30-1.90 (11H, m), 2.00-2.20 (1H, m), 2.25 (6H, s), 2.31 (3H, s), 2.32-2.50 (3H, m), 2.80-3.10 (2H, m), 3.30-3.50 (2H, m), 3.60-3.85 (2H, m), 3.90-4.00 (4H, m), 9.32 (1H, brs)

Reference examples 8-2 to 8-5, reference examples 8-7 to 8-83, reference examples 8-85 to 8-89, and reference examples 8-91 to 8-96 were prepared in a manner similar to those as described in reference example 8-1 or reference example 8-6 using the corresponding phenyl carbamates and amines instead of phenyl N-{[(3'R,4'aR,8'aR)-1'-methyloctahydro-1'H-spiro[1,3-dioxolane-2,6'-quinolin]-3'-yl]-carbonyl}-N-propylcarbamate and N,N-dimethyl ethylenediamine. These were illustrated in Table 7.

Reference Example 8-84

1-{[(3'R*,4'aR*,8'aR*)-1'-Methyloctahydro-1'H-spiro[1,3-dioxolane-2,6'-quinolin]-3'-yl]carbonyl}-1-[3-(dimethylamino)propyl]-3-(2-fluoroethyl)urea To a mixture of (3'R*,4'aR*,8'aR*)-N-[3-(dimethylamino)propyl]-1'-methyloctahydro-1'H-spiro[1,3-dioxolane-2,6'-quinoline]-3'-carboxamide (reference example 5-2) (300 mg) and tetrahydrofuran (10 mL) was added a 1 mol/L sodium hexamethyldisilazide-tetrahydrofuran solution (1.2 mL) at −40° C. After stirring at the same temperature for 35 minutes, a mixture of 4-nitrophenyl chloroformate (232 mg) and tetrahydrofuran (1 mL) was added to the mixture, and then stirred for 1.5 hours. After warming to room temperature and stirring for 20 minutes, 2-fluoroethylamine hydrochloride (176 mg) and triethylamine (0.246 mL) were added to the reaction mixture, and then stirred at the same temperature for 4 hours. A saturated aqueous solution of sodium bicarbonate was added to the reaction mixture, and extracted with ethyl acetate. After the separated organic layer was dried over anhydrous sodium sulfate, the residue was purified by aminopropyl silica gel column chromatography (eluent: 0%-10% methanol/ethyl acetate, gradient elution) to give the title compound (195 mg). The structure was illustrated in Table 7.

$^1$H-NMR (CDCl$_3$) δ ppm: 1.30-1.90 (11H, m), 2.00-2.10 (1H, m), 2.16-2.39 (3H, m), 2.22 (6H, s), 2.30 (3H, s), 2.88-2.99 (1H, m), 3.12-3.32 (1H, m), 3.44-3.86 (4H, m), 3.88-3.97 (4H, m), 4.46 (1H, t, J=4.8 Hz), 4.58 (1H, t, J=4.8 Hz), 9.88-10.09 (1H, m)

Reference Example 8-90 was prepared in a manner similar to those as described in reference example 8-84 using the corresponding nitrophenyl carbamate and amine instead of (3'R*,4'aR*,8'aR*)-N-[3-(dimethylamino)propyl]-1'-methyloctahydro-1'H-spiro[1,3-dioxolane-2,6'-quinoline]-3'-carboxamide and 2-fluoroethylamine hydrochloride. This was illustrated in Table 7.

Reference Example 8-97

1-{[(3'R*,4'aR*,8'aR*)-1'-(2-Fluoroethyl)octahydro-1'H-spiro[1,3-dioxolane-2,6'-quinolin]-3'-yl]carbonyl}-3-[2-(dimethylamino)ethyl]-1-propylurea To a mixture of 1-{[(3'R*,4'aR*,8'aR*)octahydro-1'H-spiro[1,3-dioxolane-2,6'-quinolin]-3'-yl]carbonyl}-3-[2-(dimethylamino)ethyl]-1-propylurea (reference example 9-4) (111 mg) and N,N-dimethylformamide (1.0 mL) was added potassium carbonate (85 mg), followed by 1-fluoro-2-iodoethane (124 mg), and the mixture was stirred at room temperature for 18 hours. Water was added to the reaction mixture, and extracted with ethyl acetate. After the separated organic layer was dried over anhydrous sodium sulfate, it was concentrated under reduced pressure. The residue was purified by aminopropyl silica gel column chromatography (eluent: 10%-100% ethyl acetate/hexane, gradient elution) to give the title compound (23 mg).

$^1$H-NMR (CDCl$_3$) δ ppm: 0.94 (3H, t, J=7.2 Hz), 1.30-1.90 (10H, m), 1.90-2.10 (2H, m), 2.25 (6H, s), 2.45 (2H, t, J=6.4 Hz), 2.66 (1H, t, J=10.8 Hz), 2.75-3.15 (4H, m), 3.3-3.45 (2H, m), 3.60-3.80 (2H, m), 3.85-4.00 (4H, m), 4.40-4.53 (1H, m), 4.53-4.65 (1H, m), 9.28 (1H, brs)

Reference examples 8-98 to 8-100 were prepared in a manner similar to those as described in reference example 8-97 using the corresponding decahydroquinolines, and alkyl halides or alkyl triflates instead of 1-{[(3'R*,4'aR*,8'aR*)octahydro-1'H-spiro-[1,3-dioxolane-2,6'-quinolin]-3'-yl]carbonyl}-3-[2-(dimethylamino)ethyl]-1-propylurea and 1-fluoro-2-iodoethane. These were illustrated in Table 7.

TABLE 7

| Reference example | Structure |
|---|---|
| 8-1 | 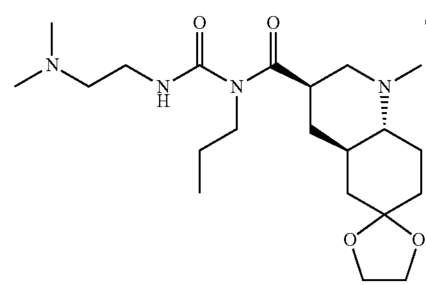 |
| 8-2 | 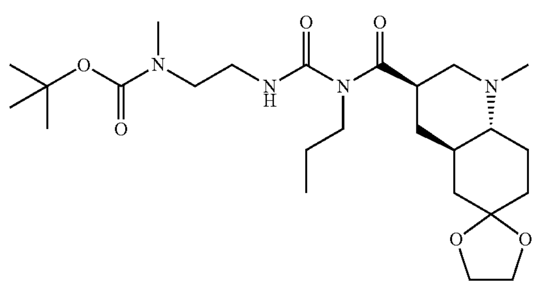 |

TABLE 7-continued
| Reference example | Structure |
|---|---|
| 8-3 | 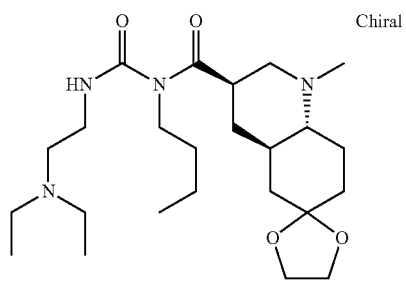 [SMILES: CCCCN(C(=O)NCCN(CC)CC)C(=O)[C@@H]1C[C@@H]2CC3(CC[C@H]2N(C)C1)OCCO3] Chiral |
| 8-4 | 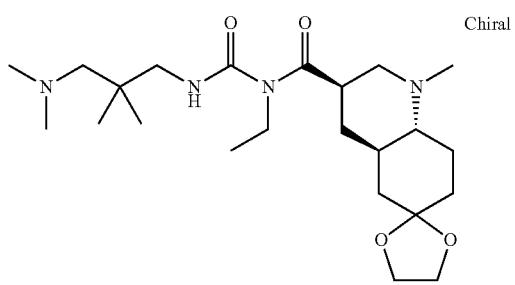 [SMILES: CCN(C(=O)NCC(C)(C)CN(C)C)C(=O)[C@@H]1C[C@@H]2CC3(CC[C@H]2N(C)C1)OCCO3] Chiral |
| 8-5 | 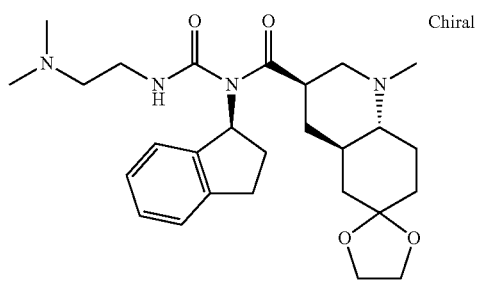 [SMILES: CN(C)CCNC(=O)N(C(=O)[C@@H]1C[C@@H]2CC3(CC[C@H]2N(C)C1)OCCO3)[C@H]1CCc2ccccc21] Chiral |
| 8-6 | 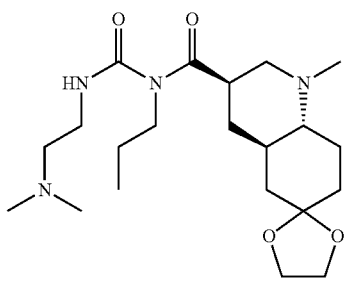 [SMILES: CCCN(C(=O)NCCN(C)C)C(=O)[C@@H]1C[C@@H]2CC3(CC[C@H]2N(C)C1)OCCO3] |
| 8-7 | 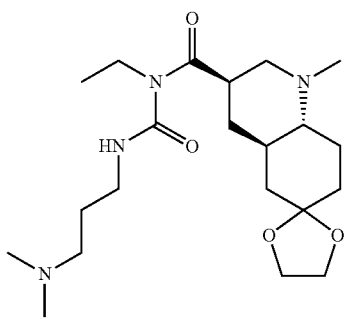 [SMILES: CCN(C(=O)NCCCN(C)C)C(=O)[C@@H]1C[C@@H]2CC3(CC[C@H]2N(C)C1)OCCO3] |

TABLE 7-continued
| Reference example | Structure |
|---|---|
| 8-8 | 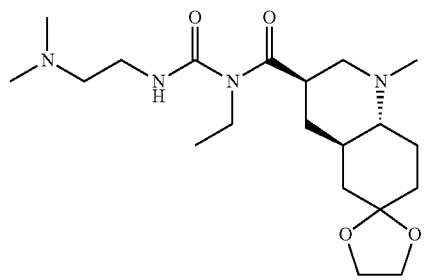 [SMILES: CCN(C(=O)NCCN(C)C)C(=O)[C@@H]1C[C@@H]2CC3(CC[C@H]2N(C)C1)OCCO3] |
| 8-9 | 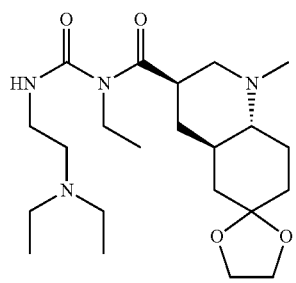 [SMILES: CCN(CC)CCNC(=O)N(CC)C(=O)[C@@H]1C[C@@H]2CC3(CC[C@H]2N(C)C1)OCCO3] |
| 8-10 | 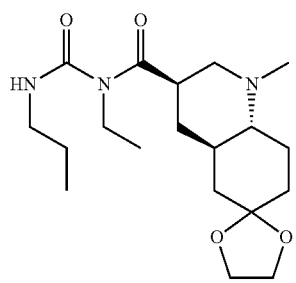 [SMILES: CCCNC(=O)N(CC)C(=O)[C@@H]1C[C@@H]2CC3(CC[C@H]2N(C)C1)OCCO3] |
| 8-11 | 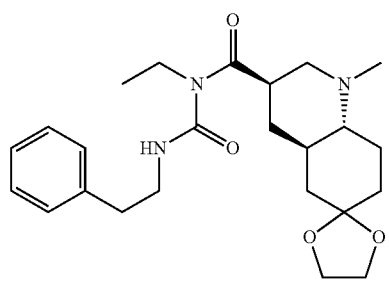 |
| 8-12 | 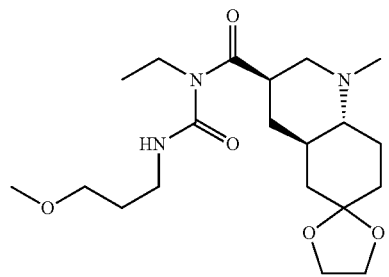 [SMILES: CCN(C(=O)NCCCOC)C(=O)[C@@H]1C[C@@H]2CC3(CC[C@H]2N(C)C1)OCCO3] |

TABLE 7-continued

| Reference example | Structure |
| --- | --- |
| 8-13 | 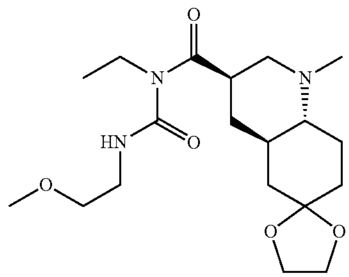 [SMILES: CCN(C(=O)NCCOC)C(=O)[C@@H]1C[C@@H]2CC3(CC[C@H]2N(C)C1)OCCO3] |
| 8-14 | 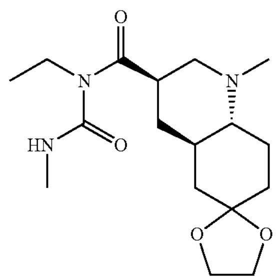 [SMILES: CCN(C(=O)NC)C(=O)[C@@H]1C[C@@H]2CC3(CC[C@H]2N(C)C1)OCCO3] |
| 8-15 | 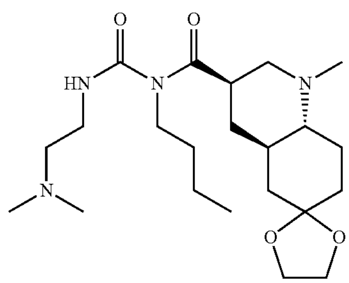 [SMILES: CCCCN(C(=O)NCCN(C)C)C(=O)[C@@H]1C[C@@H]2CC3(CC[C@H]2N(C)C1)OCCO3] |
| 8-16 | 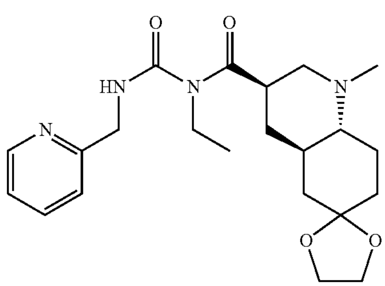 [SMILES: CCN(C(=O)NCc1ccccn1)C(=O)[C@@H]1C[C@@H]2CC3(CC[C@H]2N(C)C1)OCCO3] |
| 8-17 | 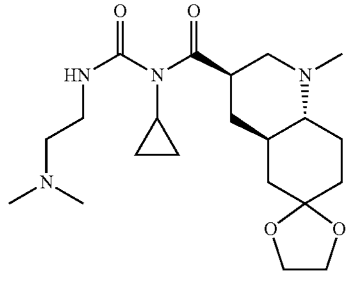 [SMILES: CN(C)CCNC(=O)N(C(=O)[C@@H]1C[C@@H]2CC3(CC[C@H]2N(C)C1)OCCO3)C1CC1] |

TABLE 7-continued

| Reference example | Structure |
|---|---|
| 8-18 | 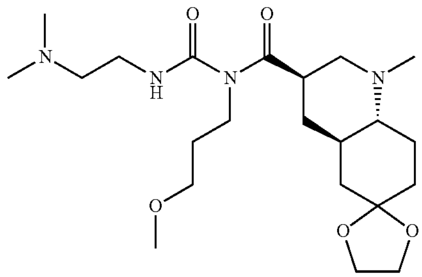 [SMILES: COCCCN(C(=O)NCCN(C)C)C(=O)[C@@H]1C[C@@H]2CC3(CC[C@H]2N(C)C1)OCCO3] |
| 8-19 | 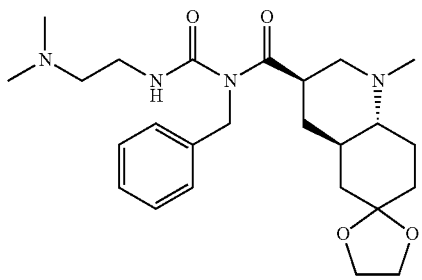 [SMILES: CN(C)CCNC(=O)N(Cc1ccccc1)C(=O)[C@@H]1C[C@@H]2CC3(CC[C@H]2N(C)C1)OCCO3] |
| 8-20 | 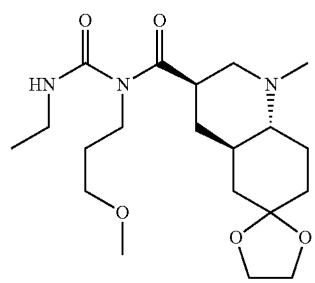 [SMILES: CCNC(=O)N(CCCOC)C(=O)[C@@H]1C[C@@H]2CC3(CC[C@H]2N(C)C1)OCCO3] |
| 8-21 | 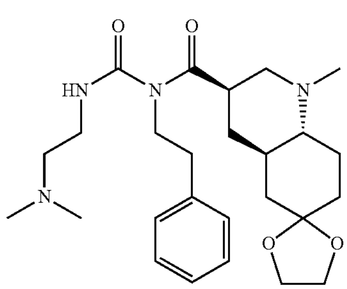 [SMILES: CN(C)CCNC(=O)N(CCc1ccccc1)C(=O)[C@@H]1C[C@@H]2CC3(CC[C@H]2N(C)C1)OCCO3] |
| 8-22 | 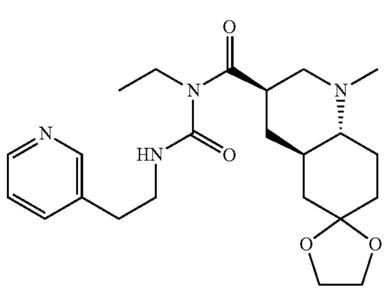 [SMILES: CCN(C(=O)NCCc1cccnc1)C(=O)[C@@H]1C[C@@H]2CC3(CC[C@H]2N(C)C1)OCCO3] |

TABLE 7-continued
| Reference example | Structure |
|---|---|
| 8-23 | 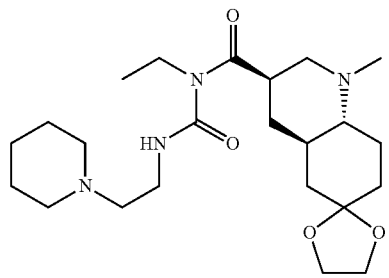 [SMILES: CCN(C(=O)NCCN1CCCCC1)C(=O)[C@@H]1C[C@@H]2CC3(CC[C@H]2N(C)C1)OCCO3] |
| 8-24 | 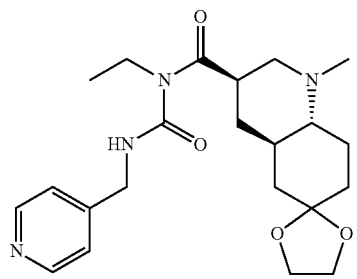 [SMILES: CCN(C(=O)NCc1ccncc1)C(=O)[C@@H]1C[C@@H]2CC3(CC[C@H]2N(C)C1)OCCO3] |
| 8-25 | 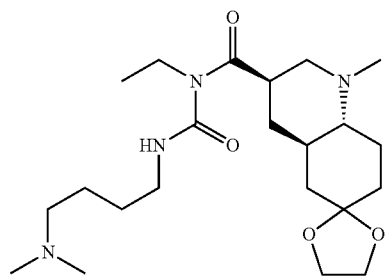 [SMILES: CCN(C(=O)NCCCCN(C)C)C(=O)[C@@H]1C[C@@H]2CC3(CC[C@H]2N(C)C1)OCCO3] |
| 8-26 | 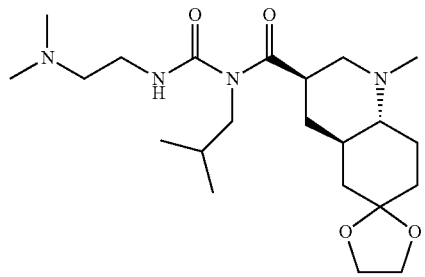 [SMILES: CC(C)CN(C(=O)NCCN(C)C)C(=O)[C@@H]1C[C@@H]2CC3(CC[C@H]2N(C)C1)OCCO3] |
| 8-27 | 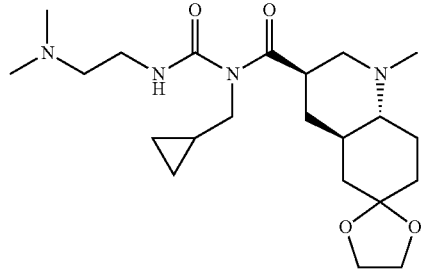 [SMILES: CN(C)CCNC(=O)N(CC1CC1)C(=O)[C@@H]1C[C@@H]2CC3(CC[C@H]2N(C)C1)OCCO3] |

TABLE 7-continued
| Reference example | Structure |
|---|---|
| 8-28 | 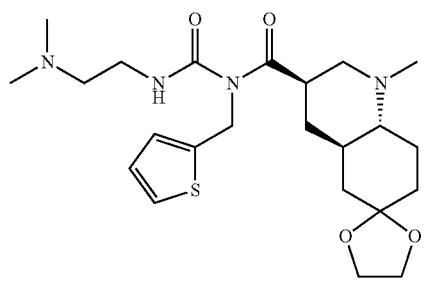 [SMILES: CN(C)CCNC(=O)N(Cc1cccs1)C(=O)[C@@H]1C[C@@H]2CC3(CC[C@H]2N(C)C1)OCCO3] |
| 8-29 | 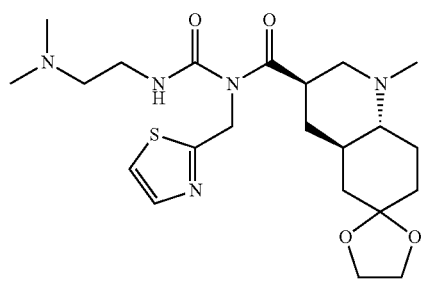 [SMILES: CN(C)CCNC(=O)N(Cc1nccs1)C(=O)[C@@H]1C[C@@H]2CC3(CC[C@H]2N(C)C1)OCCO3] |
| 8-30 | 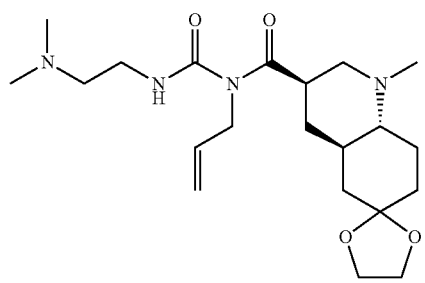 [SMILES: C=CCN(C(=O)NCCN(C)C)C(=O)[C@@H]1C[C@@H]2CC3(CC[C@H]2N(C)C1)OCCO3] |
| 8-31 | 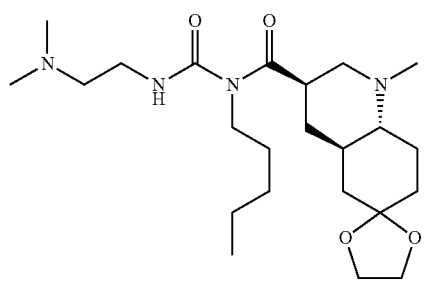 [SMILES: CCCCCN(C(=O)NCCN(C)C)C(=O)[C@@H]1C[C@@H]2CC3(CC[C@H]2N(C)C1)OCCO3] |
| 8-32 | 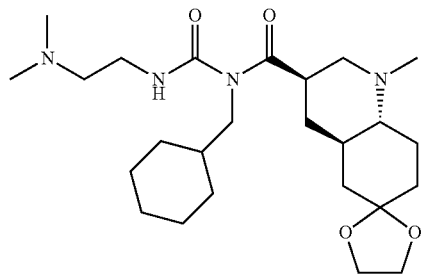 [SMILES: CN(C)CCNC(=O)N(CC1CCCCC1)C(=O)[C@@H]1C[C@@H]2CC3(CC[C@H]2N(C)C1)OCCO3] |

TABLE 7-continued
| Reference example | Structure |
|---|---|
| 8-33 | 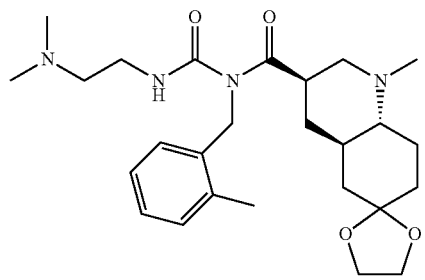 [SMILES: Cc1ccccc1CN(C(=O)NCCN(C)C)C(=O)[C@@H]1C[C@@H]2CC3(CC[C@H]2N(C)C1)OCCO3] |
| 8-34 | 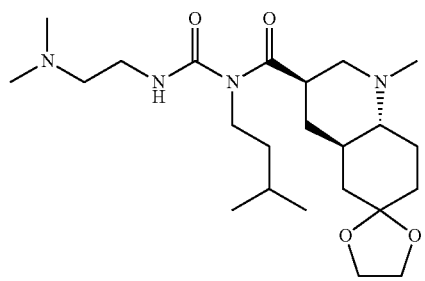 [SMILES: CC(C)CCN(C(=O)NCCN(C)C)C(=O)[C@@H]1C[C@@H]2CC3(CC[C@H]2N(C)C1)OCCO3] |
| 8-35 | 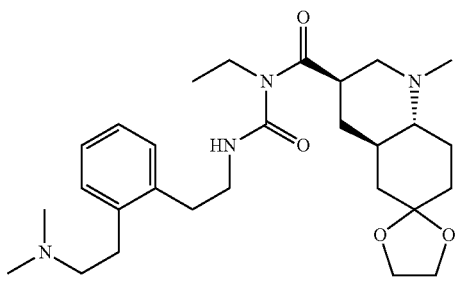 [SMILES: CCN(C(=O)NCCc1ccccc1CCN(C)C)C(=O)[C@@H]1C[C@@H]2CC3(CC[C@H]2N(C)C1)OCCO3] |
| 8-36 | 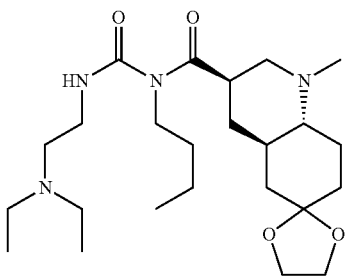 [SMILES: CCCCN(C(=O)NCCN(CC)CC)C(=O)[C@@H]1C[C@@H]2CC3(CC[C@H]2N(C)C1)OCCO3] |
| 8-37 | 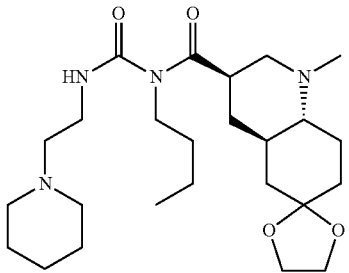 [SMILES: CCCCN(C(=O)NCCN1CCCCC1)C(=O)[C@@H]1C[C@@H]2CC3(CC[C@H]2N(C)C1)OCCO3] |

TABLE 7-continued

| Reference example | Structure |
|---|---|
| 8-38 | 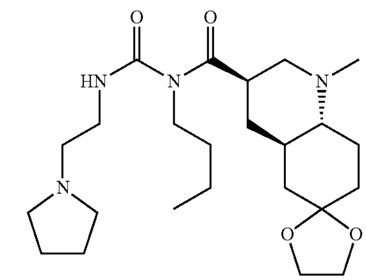 [SMILES: CCCCN(C(=O)NCCN1CCCC1)C(=O)[C@@H]1C[C@@H]2CC3(CC[C@H]2N(C)C1)OCCO3] |
| 8-39 | 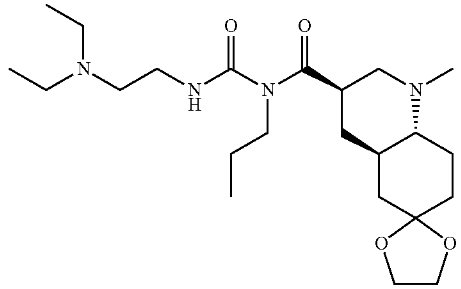 [SMILES: CCCN(C(=O)NCCN(CC)CC)C(=O)[C@@H]1C[C@@H]2CC3(CC[C@H]2N(C)C1)OCCO3] |
| 8-40 | 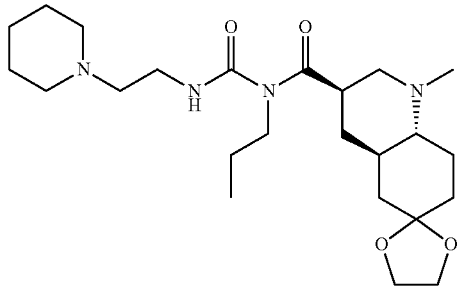 [SMILES: CCCN(C(=O)NCCN1CCCCC1)C(=O)[C@@H]1C[C@@H]2CC3(CC[C@H]2N(C)C1)OCCO3] |
| 8-41 | 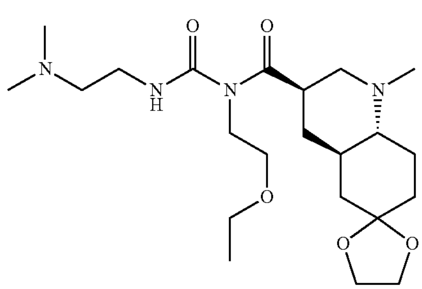 |
| 8-42 | 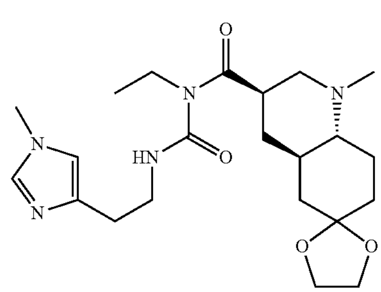 [SMILES: CCN(C(=O)NCCc1cn(C)cn1)C(=O)[C@@H]1C[C@@H]2CC3(CC[C@H]2N(C)C1)OCCO3] |

TABLE 7-continued
| Reference example | Structure |
|---|---|
| 8-43 | 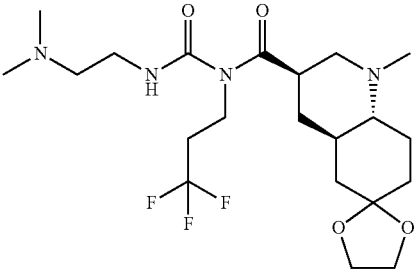 [SMILES: CN(C)CCNC(=O)N(CCC(F)(F)F)C(=O)[C@@H]1C[C@@H]2CC3(CC[C@H]2N(C)C1)OCCO3] |
| 8-44 | 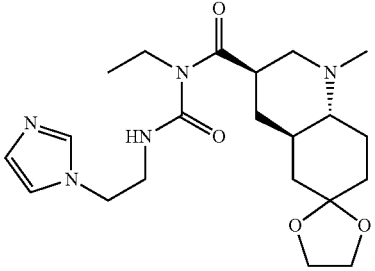 [SMILES: CCN(C(=O)NCCn1ccnc1)C(=O)[C@@H]1C[C@@H]2CC3(CC[C@H]2N(C)C1)OCCO3] |
| 8-45 | 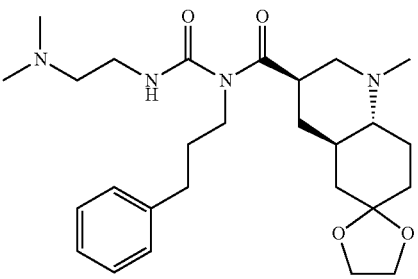 [SMILES: CN(C)CCNC(=O)N(CCCc1ccccc1)C(=O)[C@@H]1C[C@@H]2CC3(CC[C@H]2N(C)C1)OCCO3] |
| 8-46 | 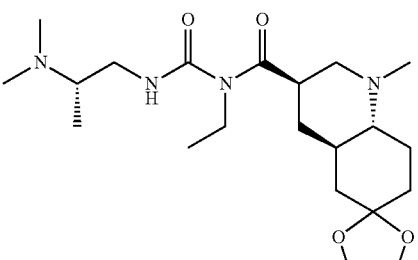 |
| 8-47 | 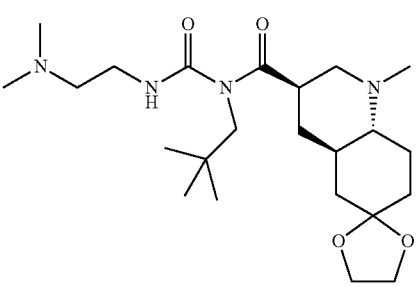 [SMILES: CN(C)CCNC(=O)N(CC(C)(C)C)C(=O)[C@@H]1C[C@@H]2CC3(CC[C@H]2N(C)C1)OCCO3] |

TABLE 7-continued
| Reference example | Structure |
|---|---|
| 8-48 | 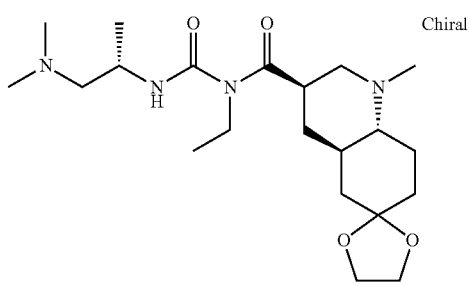 [SMILES: CCN(C(=O)N[C@@H](C)CN(C)C)C(=O)[C@@H]1C[C@@H]2CC3(CC[C@H]2N(C)C1)OCCO3] Chiral |
| 8-49 | 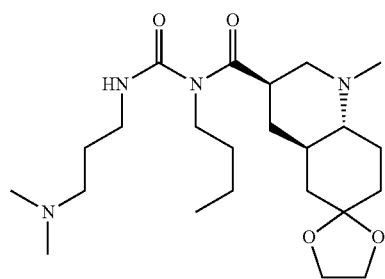 [SMILES: CCCCN(C(=O)NCCCN(C)C)C(=O)[C@@H]1C[C@@H]2CC3(CC[C@H]2N(C)C1)OCCO3] |
| 8-50 | 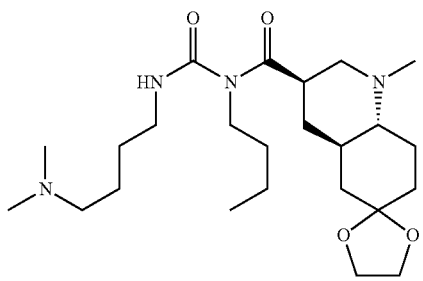 [SMILES: CCCCN(C(=O)NCCCCN(C)C)C(=O)[C@@H]1C[C@@H]2CC3(CC[C@H]2N(C)C1)OCCO3] |
| 8-51 | 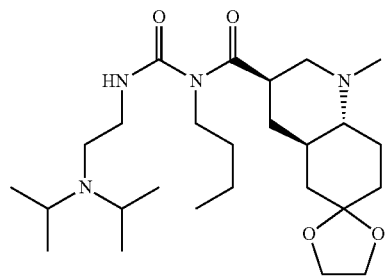 [SMILES: CCCCN(C(=O)NCCN(C(C)C)C(C)C)C(=O)[C@@H]1C[C@@H]2CC3(CC[C@H]2N(C)C1)OCCO3] |
| 8-52 | 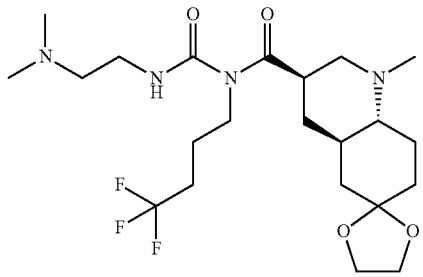 [SMILES: CN(C)CCNC(=O)N(CCCC(F)(F)F)C(=O)[C@@H]1C[C@@H]2CC3(CC[C@H]2N(C)C1)OCCO3] |

TABLE 7-continued

| Reference example | Structure |
|---|---|
| 8-53 | 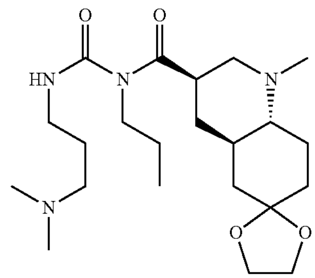 [SMILES: CCCN(C(=O)NCCCN(C)C)C(=O)[C@@H]1C[C@@H]2CC3(CC[C@H]2N(C)C1)OCCO3] |
| 8-54 | 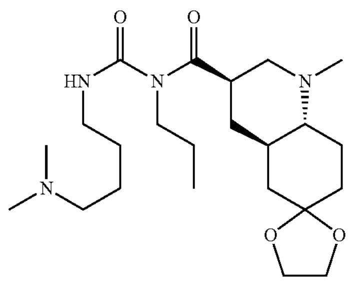 [SMILES: CCCN(C(=O)NCCCCN(C)C)C(=O)[C@@H]1C[C@@H]2CC3(CC[C@H]2N(C)C1)OCCO3] |
| 8-55 | 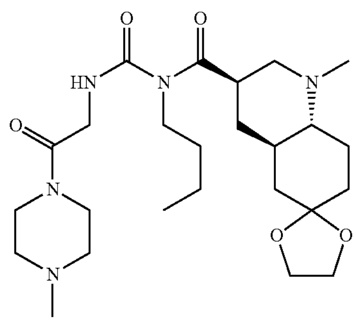 [SMILES: CCCCN(C(=O)NCC(=O)N1CCN(C)CC1)C(=O)[C@@H]1C[C@@H]2CC3(CC[C@H]2N(C)C1)OCCO3] |
| 8-56 | 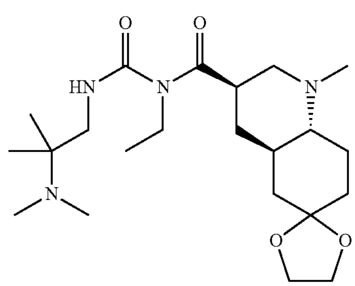 [SMILES: CCN(C(=O)NCC(C)(C)N(C)C)C(=O)[C@@H]1C[C@@H]2CC3(CC[C@H]2N(C)C1)OCCO3] |
| 8-57 | 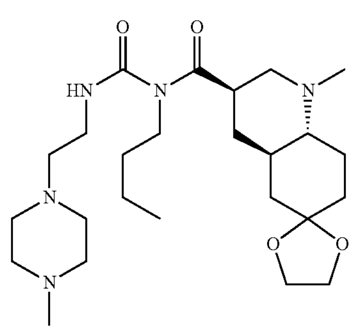 [SMILES: CCCCN(C(=O)NCCN1CCN(C)CC1)C(=O)[C@@H]1C[C@@H]2CC3(CC[C@H]2N(C)C1)OCCO3] |

TABLE 7-continued

| Reference example | Structure |
|---|---|
| 8-58 | 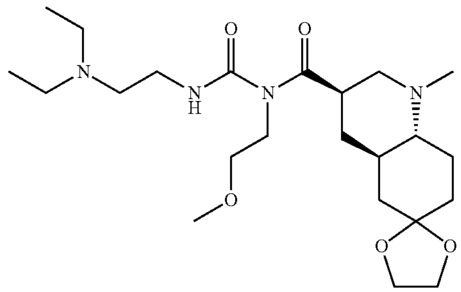 [SMILES: CCN(CC)CCNC(=O)N(CCOC)C(=O)[C@@H]1C[C@@H]2CC3(CC[C@H]2N(C)C1)OCCO3] |
| 8-59 | 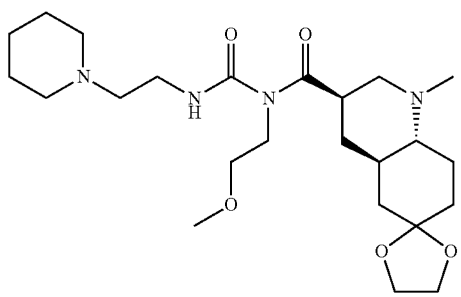 [SMILES: COCCN(C(=O)NCCN1CCCCC1)C(=O)[C@@H]1C[C@@H]2CC3(CC[C@H]2N(C)C1)OCCO3] |
| 8-60 | 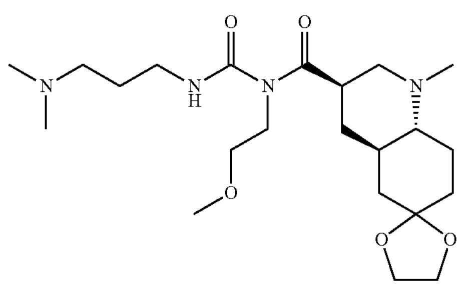 [SMILES: COCCN(C(=O)NCCCN(C)C)C(=O)[C@@H]1C[C@@H]2CC3(CC[C@H]2N(C)C1)OCCO3] |
| 8-61 | 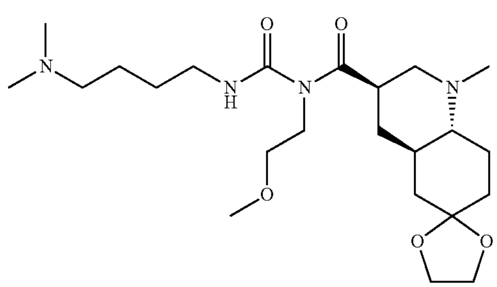 [SMILES: COCCN(C(=O)NCCCCN(C)C)C(=O)[C@@H]1C[C@@H]2CC3(CC[C@H]2N(C)C1)OCCO3] |
| 8-62 | 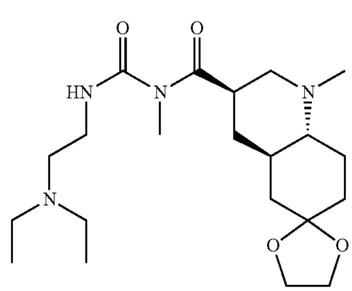 [SMILES: CCN(CC)CCNC(=O)N(C)C(=O)[C@@H]1C[C@@H]2CC3(CC[C@H]2N(C)C1)OCCO3] |

TABLE 7-continued

| Reference example | Structure |
|---|---|
| 8-63 | 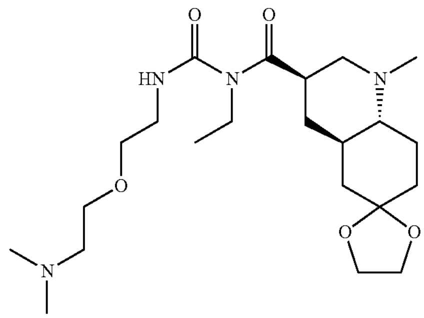 [SMILES: CCN(C(=O)NCCOCCN(C)C)C(=O)[C@@H]1C[C@@H]2CC3(CC[C@H]2N(C)C1)OCCO3] |
| 8-64 | 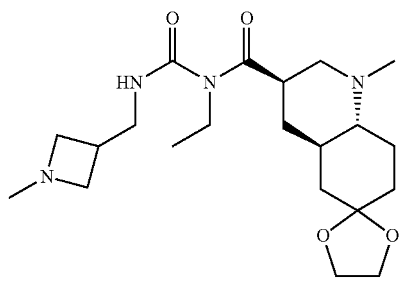 [SMILES: CCN(C(=O)NCC1CN(C)C1)C(=O)[C@@H]1C[C@@H]2CC3(CC[C@H]2N(C)C1)OCCO3] |
| 8-65 | 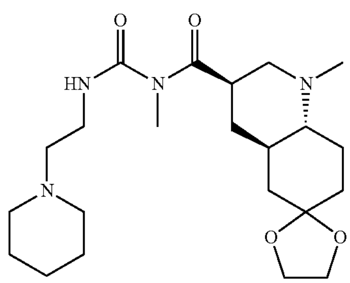 [SMILES: CN(C(=O)NCCN1CCCCC1)C(=O)[C@@H]1C[C@@H]2CC3(CC[C@H]2N(C)C1)OCCO3] |
| 8-66 | 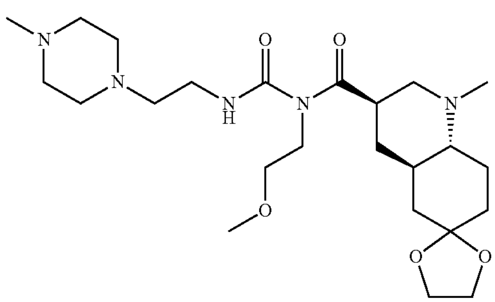 [SMILES: COCCN(C(=O)NCCN1CCN(C)CC1)C(=O)[C@@H]1C[C@@H]2CC3(CC[C@H]2N(C)C1)OCCO3] |
| 8-67 | 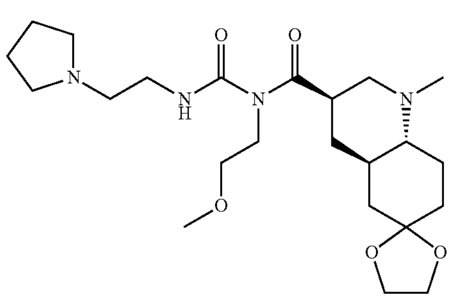 [SMILES: COCCN(C(=O)NCCN1CCCC1)C(=O)[C@@H]1C[C@@H]2CC3(CC[C@H]2N(C)C1)OCCO3] |

TABLE 7-continued

| Reference example | Structure |
|---|---|
| 8-68 | 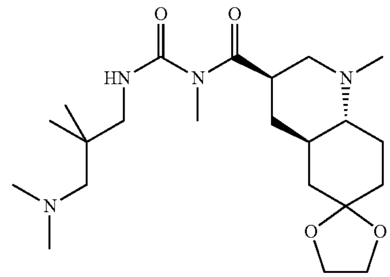 [SMILES: CN(C)CC(C)(C)CNC(=O)N(C)C(=O)[C@@H]1C[C@@H]2CC3(CC[C@H]2N(C)C1)OCCO3] |
| 8-69 | 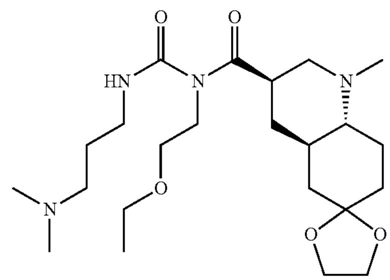 [SMILES: CCOCCN(C(=O)NCCCN(C)C)C(=O)[C@@H]1C[C@@H]2CC3(CC[C@H]2N(C)C1)OCCO3] |
| 8-70 | 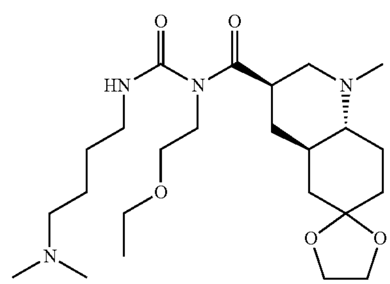 [SMILES: CCOCCN(C(=O)NCCCCN(C)C)C(=O)[C@@H]1C[C@@H]2CC3(CC[C@H]2N(C)C1)OCCO3] |
| 8-71 | 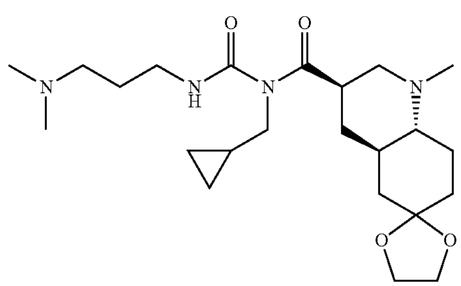 [SMILES: CN(C)CCCNC(=O)N(CC1CC1)C(=O)[C@@H]1C[C@@H]2CC3(CC[C@H]2N(C)C1)OCCO3] |
| 8-72 | 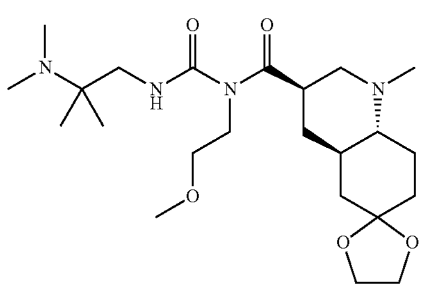 [SMILES: COCCN(C(=O)NCC(C)(C)N(C)C)C(=O)[C@@H]1C[C@@H]2CC3(CC[C@H]2N(C)C1)OCCO3] |

TABLE 7-continued
| Reference example | Structure |
|---|---|
| 8-73 | 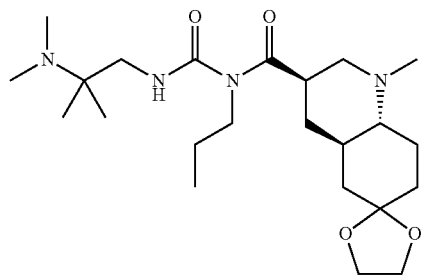 [SMILES: CCCN(C(=O)NCC(C)(C)N(C)C)C(=O)[C@@H]1C[C@@H]2CC3(CC[C@H]2N(C)C1)OCCO3] |
| 8-74 | 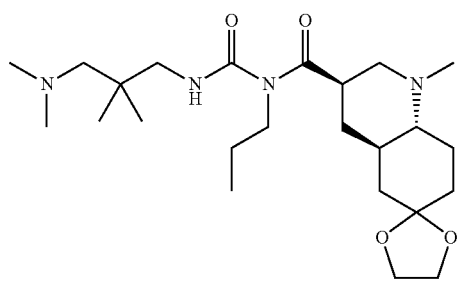 [SMILES: CCCN(C(=O)NCC(C)(C)CN(C)C)C(=O)[C@@H]1C[C@@H]2CC3(CC[C@H]2N(C)C1)OCCO3] |
| 8-75 | 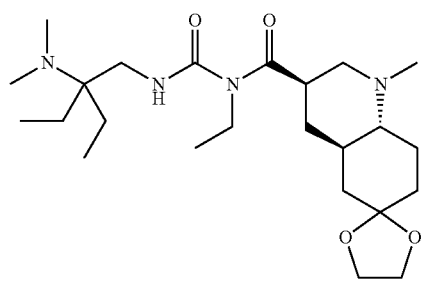 [SMILES: CCN(C(=O)NCC(CC)(CC)N(C)C)C(=O)[C@@H]1C[C@@H]2CC3(CC[C@H]2N(C)C1)OCCO3] |
| 8-76 | 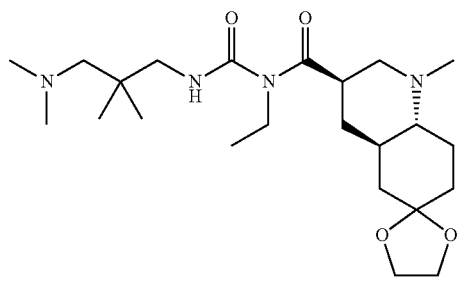 [SMILES: CCN(C(=O)NCC(C)(C)CN(C)C)C(=O)[C@@H]1C[C@@H]2CC3(CC[C@H]2N(C)C1)OCCO3] |
| 8-77 | 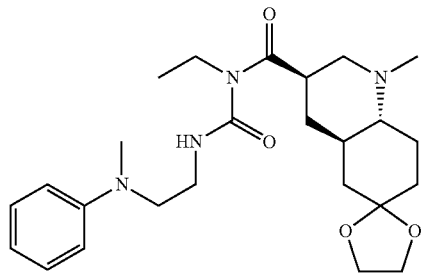 [SMILES: CCN(C(=O)NCCN(C)c1ccccc1)C(=O)[C@@H]1C[C@@H]2CC3(CC[C@H]2N(C)C1)OCCO3] |

TABLE 7-continued
| Reference example | Structure |
|---|---|
| 8-78 | 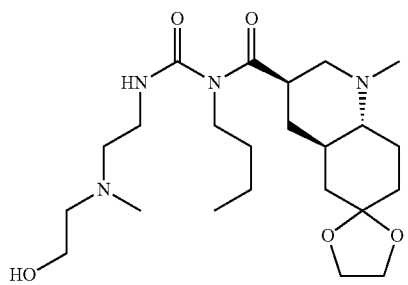 [SMILES: CCCCN(C(=O)NCCN(C)CCO)C(=O)[C@@H]1C[C@@H]2CC3(CC[C@H]2N(C)C1)OCCO3] |
| 8-79 | 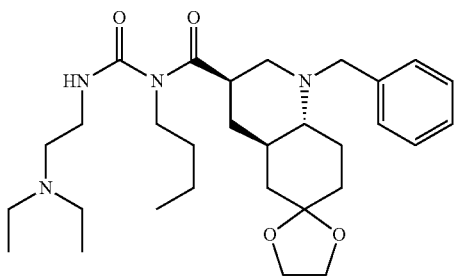 [SMILES: CCCCN(C(=O)NCCN(CC)CC)C(=O)[C@@H]1C[C@@H]2CC3(CC[C@H]2N(Cc2ccccc2)C1)OCCO3] |
| 8-80 | 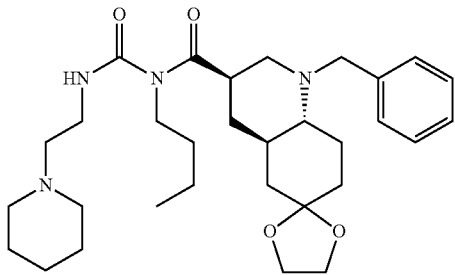 [SMILES: CCCCN(C(=O)NCCN1CCCCC1)C(=O)[C@@H]1C[C@@H]2CC3(CC[C@H]2N(Cc2ccccc2)C1)OCCO3] |
| 8-81 | 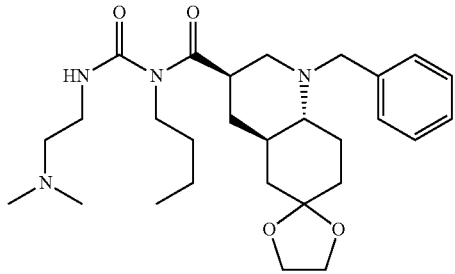 [SMILES: CCCCN(C(=O)NCCN(C)C)C(=O)[C@@H]1C[C@@H]2CC3(CC[C@H]2N(Cc2ccccc2)C1)OCCO3] |
| 8-82 | 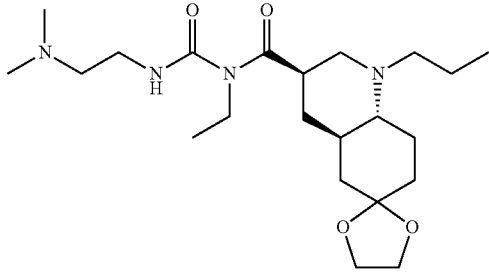 [SMILES: CCCN1C[C@H](C(=O)N(CC)C(=O)NCCN(C)C)C[C@@H]2CC3(CC[C@H]21)OCCO3] |

TABLE 7-continued

| Reference example | Structure |
| --- | --- |
| 8-83 | 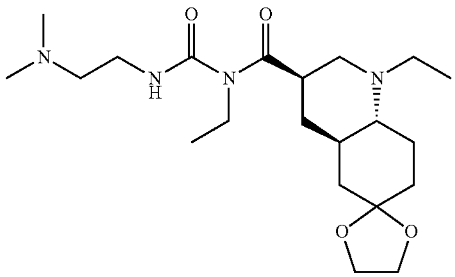 [SMILES: CCN(C(=O)NCCN(C)C)C(=O)[C@@H]1C[C@@H]2CC3(CC[C@H]2N(CC)C1)OCCO3] |
| 8-84 | 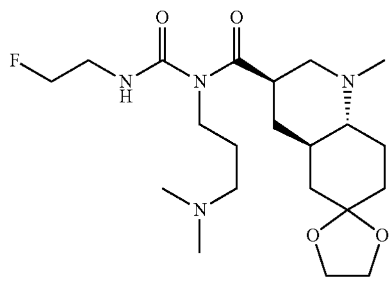 [SMILES: CN(C)CCCN(C(=O)NCCF)C(=O)[C@@H]1C[C@@H]2CC3(CC[C@H]2N(C)C1)OCCO3] |
| 8-85 | 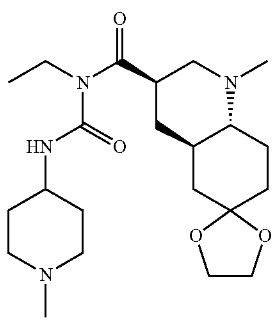 [SMILES: CCN(C(=O)NC1CCN(C)CC1)C(=O)[C@@H]1C[C@@H]2CC3(CC[C@H]2N(C)C1)OCCO3] |
| 8-86 | 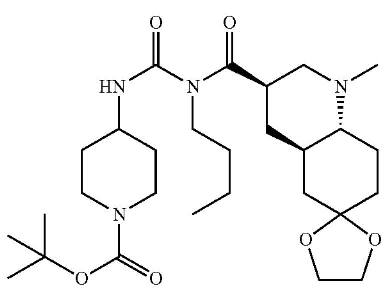 [SMILES: CCCCN(C(=O)NC1CCN(C(=O)OC(C)(C)C)CC1)C(=O)[C@@H]1C[C@@H]2CC3(CC[C@H]2N(C)C1)OCCO3] |
| 8-87 | 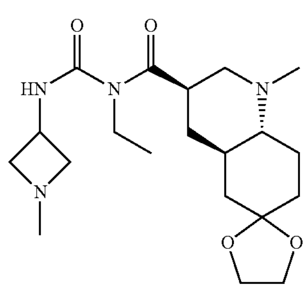 [SMILES: CCN(C(=O)NC1CN(C)C1)C(=O)[C@@H]1C[C@@H]2CC3(CC[C@H]2N(C)C1)OCCO3] |

TABLE 7-continued

| Reference example | Structure |
|---|---|
| 8-88 | 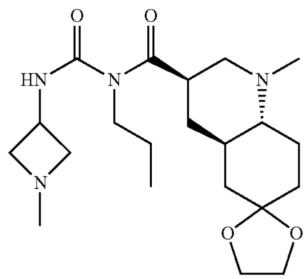 [SMILES: CCCN(C(=O)NC1CN(C)C1)C(=O)[C@@H]1C[C@@H]2CC3(CC[C@H]2N(C)C1)OCCO3] |
| 8-89 | 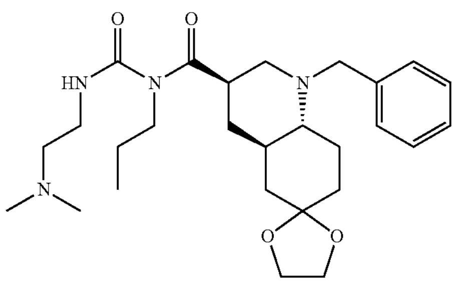 [SMILES: CCCN(C(=O)NCCN(C)C)C(=O)[C@@H]1C[C@@H]2CC3(CC[C@H]2N(Cc2ccccc2)C1)OCCO3] |
| 8-90 | 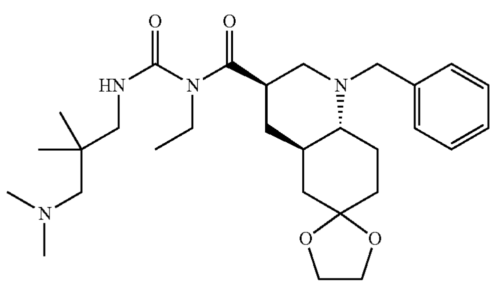 [SMILES: CCN(C(=O)NCC(C)(C)CN(C)C)C(=O)[C@@H]1C[C@@H]2CC3(CC[C@H]2N(Cc2ccccc2)C1)OCCO3] |
| 8-91 | Chiral |
| 8-92 | Chiral |

TABLE 7-continued
| Reference example | Structure |
|---|---|
| 8-93 | 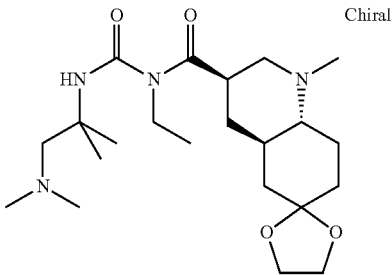 [SMILES: CCN(C(=O)NC(C)(C)CN(C)C)C(=O)[C@@H]1C[C@@H]2CC3(CC[C@H]2N(C)C1)OCCO3] Chiral |
| 8-94 | 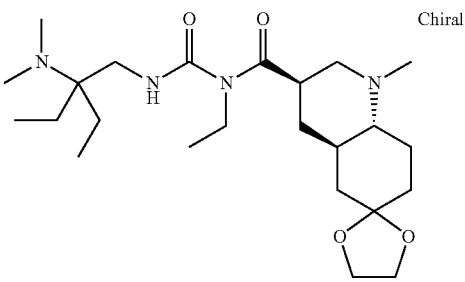 [SMILES: CCN(C(=O)NCC(CC)(CC)N(C)C)C(=O)[C@@H]1C[C@@H]2CC3(CC[C@H]2N(C)C1)OCCO3] Chiral |
| 8-95 | 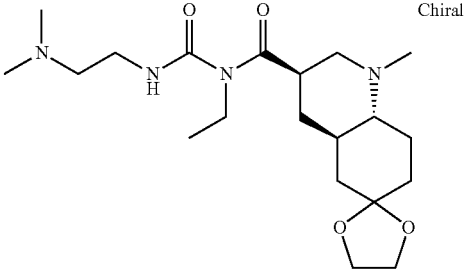 [SMILES: CCN(C(=O)NCCN(C)C)C(=O)[C@@H]1C[C@@H]2CC3(CC[C@H]2N(C)C1)OCCO3] Chiral |
| 8-96 | 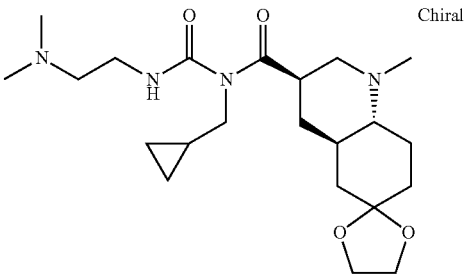 [SMILES: CN(C)CCNC(=O)N(CC1CC1)C(=O)[C@@H]1C[C@@H]2CC3(CC[C@H]2N(C)C1)OCCO3] Chiral |
| 8-97 | 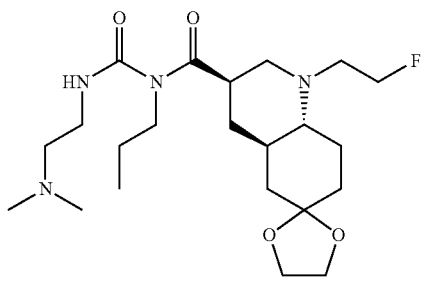 [SMILES: CCCN(C(=O)NCCN(C)C)C(=O)[C@@H]1C[C@@H]2CC3(CC[C@H]2N(CCF)C1)OCCO3] |

TABLE 7-continued

| Reference example | Structure |
|---|---|
| 8-98 | 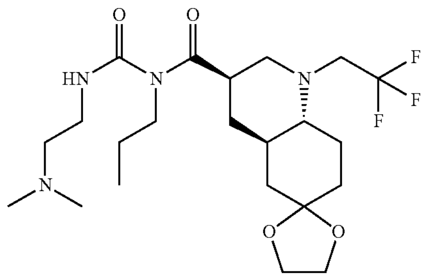 [SMILES: CCCN(C(=O)NCCN(C)C)C(=O)[C@@H]1C[C@@H]2CC3(CC[C@H]2N(CC(F)(F)F)C1)OCCO3] |
| 8-99 | 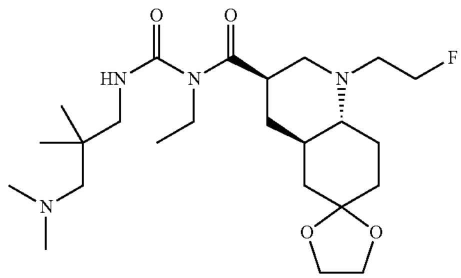 [SMILES: CCN(C(=O)NCC(C)(C)CN(C)C)C(=O)[C@@H]1C[C@@H]2CC3(CC[C@H]2N(CCF)C1)OCCO3] |
| 8-100 | 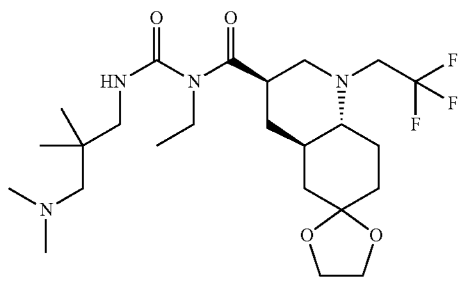 [SMILES: CCN(C(=O)NCC(C)(C)CN(C)C)C(=O)[C@@H]1C[C@@H]2CC3(CC[C@H]2N(CC(F)(F)F)C1)OCCO3] |

The structures of the reference example 8-1 to 8-5, 8-48 and 8-91 to 8-96 in Table 7 indicate absolute configuration, and the structures of the reference example 8-6 to 8-47, 8-49 to 8-90 and 8-97 to 8-100 in Table 7 indicate relative configuration.

The physical data of reference examples 8-2 to 8-5, reference examples 8-7 to 8-83, reference examples 8-85 to 8-96 and reference examples 8-98 to 8-100 were shown below.

Reference Example 8-2

MS (ESI, m/z): 497 (M+H)+

Reference Example 8-3

$^1$H-NMR (CDCl$_3$) δ ppm: 0.94 (3H, t, J=7.4 Hz), 1.02 (6H, t, J=7.2 Hz), 1.26-1.48 (5H, m), 1.51-1.88 (8H, m), 2.02-2.13 (1H, m), 2.31 (3H, s), 2.33-2.41 (1H, m), 2.49-2.60 (6H, m), 2.87-3.07 (2H, m), 3.30-3.39 (2H, m), 3.61-3.86 (2H, m), 3.90-4.01 (4H, m), 9.15-9.38 (1H, m)

Reference Example 8-4

$^1$H-NMR (CDCl$_3$) δ ppm: 0.91 (6H, s), 1.22 (3H, t, J=7.2 Hz), 1.35-1.50 (3H, m), 1.50-1.90 (6H, m), 2.00-2.20 (3H, m), 2.25-2.45 (10H, m), 2.90-3.15 (2H, m), 3.15-3.25 (2H, m), 3.75-4.00 (6H, m), 9.30-9.50 (1H, m)

Reference Example 8-5

$^1$H-NMR (CDCl$_3$) δ ppm: 1.30-1.75 (7H, m), 1.75-1.85 (1H, m), 2.00-2.10 (7H, m), 2.10-2.25 (3H, m), 2.29 (3H, s), 2.30-2.45 (1H, m), 2.45-2.60 (1H, m), 2.85-3.00 (1H, m), 3.00-3.20 (5H, m), 3.90-3.95 (4H, m), 6.05-6.20 (1H, m) 7.10-7.25 (4H, m)

Reference Example 8-7

$^1$H-NMR (CDCl$_3$) δ ppm: 1.17-1.27 (3H, m), 1.34-1.49 (3H, m), 1.51-1.87 (8H, m), 2.03-2.13 (1H, m), 2.21 (6H, s), 2.27-2.41 (6H, m), 2.89-3.10 (2H, m), 3.27-3.36 (2H, m), 3.76-3.90 (2H, m), 3.91-4.00 (4H, m), 9.28 (1H, brs)

Reference Example 8-8

MS (ESI, m/z): 397 (M+H)+

Reference Example 8-9

$^1$H-NMR (CDCl$_3$) δ ppm: 1.02 (6H, t, J=7.2 Hz), 1.22 (3H, t, J=7.1 Hz), 1.35-1.50 (3H, m), 1.50-1.90 (6H, m), 2.00-2.15 (1H, m), 2.32 (3H, s), 2.37 (1H, t, J=11.3 Hz), 2.50-2.65 (6H, m), 2.85-3.10 (2H, m), 3.30-3.40 (2H, m), 3.70-4.00 (6H, m), 9.29 (1H, brs)

Reference Example 8-10

¹H-NMR (CDCl₃) δ ppm: 0.94 (3H, t, J=7.4 Hz), 1.15-1.30 (4H, m), 1.35-1.50 (3H, m), 1.50-1.90 (7H, m), 2.00-2.15 (1H, m), 2.32 (3H, s), 2.36 (1H, t, J=11.3 Hz), 2.90-3.10 (2H, m), 3.15-3.30 (2H, m), 3.75-4.00 (6H, m), 9.15-9.35 (1H, m)

Reference Example 8-11

¹H-NMR (CDCl₃) δ ppm: 1.23 (3H, t, J=6.9 Hz), 1.32-1.49 (3H, m), 1.51-1.88 (6H, m), 2.02-2.12 (1H, m), 2.27-2.40 (1H, m), 2.32 (3H, s), 2.79-3.09 (4H, m), 3.46-3.58 (2H, m), 3.75-3.90 (2H, m), 3.92-3.98 (4H, m), 7.16-7.35 (5H, m), 9.24-9.39 (1H, m)

Reference Example 8-12

¹H-NMR (CDCl₃) δ ppm: 1.22 (3H, t, J=7.0 Hz), 1.35-1.50 (3H, m), 1.50-1.90 (8H, m), 2.00-2.15 (1H, m), 2.25-2.45 (4H, m), 2.90-3.10 (2H, m), 3.30-3.40 (5H, m), 3.44 (2H, t, J=6.2 Hz), 3.75-4.00 (6H, m), 9.32 (1H, brs)

Reference Example 8-13

¹H-NMR (CDCl₃) δ ppm: 1.24 (3H, t, J=7.0 Hz), 1.33-1.88 (9H, m), 2.01-2.13 (1H, m), 2.32 (3H, s), 2.33-2.43 (1H, m), 2.87-3.10 (2H, m), 3.37 (3H, s), 3.43-3.54 (4H, m), 3.75-4.00 (6H, m), 9.33-9.48 (1H, m)

Reference Example 8-14

¹H-NMR (CDCl₃) δ ppm: 1.24 (3H, t, J=7.0 Hz), 1.33-1.88 (9H, m), 2.03-2.14 (1H, m), 2.28-2.41 (1H, m), 2.32 (3H, s), 2.85 (3H, d, J=4.8 Hz), 2.88-3.11 (2H, m), 3.74-4.02 (6H, m), 9.06-9.26 (1H, m)

Reference Example 8-15

MS (ESI, m/z): 425 (M+H)+

Reference Example 8-16

¹H-NMR (CDCl₃) δ ppm: 1.26 (3H, t, J=7.0 Hz), 1.35-1.90 (9H, m), 2.00-2.15 (1H, m), 2.32 (3H, s), 2.41 (1H, t, J=11.4 Hz), 2.90-3.00 (1H, m), 3.00-3.15 (1H, m), 3.80-4.00 (6H, m), 4.63 (2H, d, J=5.0 Hz), 7.15-7.25 (1H, m), 7.25-7.30 (1H, m), 7.60-7.70 (1H, m), 8.55-8.65 (1H, m), 9.98 (1H, brs)

Reference Example 8-17

MS (ESI, m/z): 409 (M+H)+

Reference Example 8-18

MS (ESI, m/z): 441 (M+H)+

Reference Example 8-19

MS (ESI, m/z): 459 (M+H)+

Reference Example 8-20

MS (ESI, m/z): 398 (M+H)+

Reference Example 8-21

¹H-NMR (CDCl₃) δ ppm: 1.20-1.65 (8H, m), 1.75-1.85 (1H, m), 2.00-2.10 (1H, m), 2.20-2.35 (10H, m), 2.46 (2H, t, J=6.5 Hz), 2.75-2.85 (1H, m), 2.85-3.00 (3H, m), 3.35-3.45 (2H, m), 3.85-4.05 (6H, m), 7.20-7.40 (5H, m), 9.31 (1H, br)

Reference Example 8-22

¹H-NMR (CDCl₃) δ ppm: 1.22 (3H, t, J=7.0 Hz), 1.31-1.48 (3H, m), 1.51-1.88 (6H, m), 2.02-2.14 (1H, m), 2.28-2.39 (1H, m), 2.31 (3H, s), 2.81-3.07 (4H, m), 3.47-3.58 (2H, m), 3.74-4.01 (6H, m), 7.19-7.29 (1H, m), 7.51-7.58 (1H, m), 8.43-8.52 (2H, m), 9.34-9.44 (1H, m)

Reference Example 8-23

¹H-NMR (CDCl₃) δ ppm: 1.23 (3H, t, J=7.1 Hz), 1.33-1.48 (5H, m), 1.50-1.87 (10H, m), 2.01-2.13 (1H, m), 2.28-2.52 (7H, m), 2.32 (3H, s), 2.88-3.09 (2H, m), 3.33-3.45 (2H, m), 3.73-4.00 (6H, m), 9.16-9.40 (1H, m)

Reference Example 8-24

¹H-NMR (CDCl₃) δ ppm: 1.26 (3H, t, J=7.1 Hz), 1.35-1.49 (3H, m), 1.50-1.91 (6H, m), 2.00-2.14 (1H, m), 2.29-2.42 (1H, m), 2.32 (3H, s), 2.90-3.13 (2H, m), 3.78-4.05 (6H, m), 4.48 (2H, d, J=5.8 Hz), 7.10-7.32 (2H, m), 8.48-8.64 (2H, m), 9.69-9.88 (1H, m)

Reference Example 8-25

¹H-NMR (CDCl₃) δ ppm: 1.23 (3H, t, J=7.1 Hz), 1.33-1.89 (13H, m), 2.02-2.12 (1H, m), 2.20 (6H, s), 2.23-2.29 (2H, m), 2.29-2.39 (1H, m), 2.32 (3H, s), 2.88-3.08 (2H, m), 3.22-3.33 (2H, m), 3.75-4.01 (6H, m), 9.19-9.35 (1H, m)

Reference Example 8-26

¹H-NMR (CDCl₃) δ ppm: 0.90 (6H, d, J=6.4 Hz), 1.30-1.95 (10 nH, m), 2.00-2.15 (1H, m), 2.20-2.40 (10H, m), 2.40-2.55 (2H, m), 2.85-2.95 (1H, m), 3.00-3.15 (1H, m), 3.30-3.45 (2H, m), 3.55-3.75 (2H, m), 3.90-4.00 (4H, m), 9.32 (1H, brs)

Reference Example 8-27

MS (ESI, m/z): 423 (M+H)+

Reference Example 8-28

¹H-NMR (CDCl₃) δ ppm: 1.30-1.50 (3H, m), 1.50-1.65 (5H, m), 1.75-1.90 (1H, m), 2.00-2.10 (1H, m), 2.25 (6H, s), 2.27 (3H, s), 2.35 (1H, t, J=11.3 Hz), 2.45 (2H, t, J=6.3 Hz), 2.80-2.95 (1H, m), 3.15-3.30 (1H, m), 3.35-3.50 (2H, m), 3.90-4.00 (4H, m), 5.19 (2H, dd, J=34.2, 16.4 Hz), 6.90-7.05 (2H, m), 7.15-7.25 (1H, m), 9.24 (1H, br)

Reference Example 8-29

MS (ESI, m/z): 466 (M+H)+

Reference Example 8-30

MS (ESI, m/z): 409 (M+H)+

Reference Example 8-31

MS (ESI, m/z): 439 (M+H)+

Reference Example 8-32

¹H-NMR (CDCl₃) δ ppm: 0.85-1.30 (5H, m), 1.30-1.50 (3H, m), 1.50-1.90 (12H, m), 2.00-2.15 (1H, m), 2.25 (6H, s), 2.25-2.40 (4H, m), 2.44 (2H, t, J=6.4 Hz), 2.85-2.95 (1H, m), 3.00-3.15 (1H, m), 3.30-3.45 (2H, m), 3.55-3.65 (1H, m), 3.65-3.80 (1H, m), 3.90-4.05 (4H, m), 9.30 (1H, br)

Reference Example 8-33

$^1$H-NMR (CDCl$_3$) δ ppm: 1.20-1.70 (6H, m), 1.70-1.85 (1H, m), 1.90-2.05 (1H, m), 2.10-2.55 (16H, m), 2.75-2.95 (2H, m), 3.35-3.50 (2H, m), 3.80-4.00 (4H, m), 5.01 (2H, s), 6.85-6.95 (1H, m), 7.10-7.25 (3H, m)

Reference Example 8-34

$^1$H-NMR (CDCl$_3$) δ ppm: 0.93 (6H, d, J=6.6 Hz), 1.30-1.90 (12H, m), 2.00-2.15 (1H, m), 2.26 (6H, s), 2.31 (3H, s), 2.38 (1H, t, J=11.3 Hz), 2.47 (2H, t, J=6.4 Hz), 2.85-2.95 (1H, m), 2.95-3.10 (1H, m), 3.35-3.45 (2H, m), 3.60-3.75 (1H, m), 3.75-3.85 (1H, m), 3.90-4.00 (4H, m), 9.33 (1H, brs)

Reference Example 8-35

$^1$H-NMR (CDCl$_3$) δ ppm: 1.23 (3H, t, J=7.0 Hz), 1.33-1.49 (3H, m), 1.52-1.88 (6H, m), 2.01-2.14 (1H, m), 2.25-2.39 (1H, m), 2.32 (6H, s), 2.32 (3H, s), 2.43-2.52 (2H, m), 2.77-3.09 (6H, m), 3.43-3.54 (2H, m), 3.77-3.99 (6H, m), 7.10-7.22 (4H, m), 9.28-9.42 (1H, m)

Reference Example 8-36

$^1$H-NMR (CDCl$_3$) δ ppm: 0.94 (3H, t, J=7.4 Hz), 1.02 (6H, t, J=7.2 Hz), 1.26-1.48 (5H, m), 1.51-1.88 (8H, m), 2.02-2.13 (1H, m), 2.31 (3H, s), 2.33-2.41 (1H, m), 2.49-2.60 (6H, m), 2.87-3.07 (2H, m), 3.30-3.39 (2H, m), 3.61-3.86 (2H, m), 3.90-4.01 (4H, m), 9.15-9.38 (1H, m)

Reference Example 8-37

$^1$H-NMR (CDCl$_3$) δ ppm: 0.94 (3H, t, J=7.3 Hz), 1.28-1.48 (7H, m), 1.50-1.88 (12H, m), 2.01-2.13 (1H, m), 2.28-2.51 (7H, m), 2.31 (3H, s), 2.87-3.09 (2H, m), 3.32-3.45 (2H, m), 3.61-3.86 (2H, m), 3.89-4.02 (4H, m), 9.13-9.37 (1H, m)

Reference Example 8-38

$^1$H-NMR (CDCl$_3$) δ ppm: 0.94 (3H, t, J=7.3 Hz), 1.28-1.48 (5H, m), 1.50-1.88 (12H, m), 2.01-2.12 (1H, m), 2.31 (3H, s), 2.31-2.42 (1H, m), 2.47-2.58 (4H, m), 2.58-2.67 (2H, m), 2.88-3.08 (2H, m), 3.36-3.47 (2H, m), 3.61-3.86 (2H, m), 3.90-4.00 (4H, m), 9.17-9.42 (1H, m)

Reference Example 8-39

$^1$H-NMR (CDCl$_3$) δ ppm: 0.92 (3H, t, J=7.2 Hz), 1.02 (6H, t, J=7.2 Hz), 1.30-1.50 (3H, m), 1.50-1.90 (8H, m), 2.00-2.15 (1H, m), 2.31 (3H, s), 2.33-2.41 (1H, m), 2.45-2.65 (6H, m), 2.85-3.10 (2H, m), 3.25-3.40 (2H, m), 3.55-3.85 (2H, m), 3.88-4.02 (4H, m), 9.27 (1H, brs)

Reference Example 8-40

MS (ESI, m/z): 451 (M+H)+

Reference Example 8-41

$^1$H-NMR (CDCl$_3$) δ ppm: 1.16 (3H, t, J=7.0 Hz), 1.25-1.50 (3H, m), 1.50-1.90 (6H, m), 2.00-2.10 (1H, m), 2.20-2.40 (10H, m), 2.45 (2H, t, J=6.5 Hz), 2.90-3.00 (1H, m), 3.30-3.60 (7H, m), 3.80-4.05 (6H, m), 9.14 (1H, br)

Reference Example 8-42

$^1$H-NMR (CDCl$_3$) δ ppm: 1.23 (3H, t, J=7.1 Hz), 1.34-1.48 (3H, m), 1.51-1.87 (6H, m), 2.02-2.12 (1H, m), 2.28-2.42 (1H, m), 2.31 (3H, s), 2.75-2.83 (2H, m), 2.89-3.07 (2H, m), 3.51-3.59 (2H, m), 3.63 (3H, s), 3.75-3.99 (6H, m), 6.65-6.70 (1H, m), 7.30-7.35 (1H, m), 9.17-9.41 (1H, m)

Reference Example 8-43

MS (ESI, m/z): 465 (M+H)+

Reference Example 8-44

$^1$H-NMR (CDCl$_3$) δ ppm: 1.23 (3H, t, J=7.1 Hz), 1.33-1.48 (3H, m), 1.51-1.88 (6H, m), 2.02-2.12 (1H, m), 2.27-2.39 (1H, m), 2.31 (3H, s), 2.88-3.07 (2H, m), 3.55-3.64 (2H, m), 3.74-4.01 (6H, m), 4.08-4.17 (2H, m), 6.91-6.96 (1H, m), 7.04-7.11 (1H, m), 7.40-7.50 (1H, m), 9.38-9.50 (1H, m)

Reference Example 8-45

MS (ESI, m/z): 487 (M+H)+

Reference Example 8-46

$^1$H-NMR (CDCl$_3$) δ ppm: 0.96 (3H, d, J=6.8 Hz), 1.23 (3H, t, J=6.9 Hz), 1.33-1.90 (9H, m), 2.01-2.13 (1H, m), 2.25 (6H, s), 2.26-2.43 (1H, m), 2.31 (3H, s), 2.62-2.75 (1H, m), 2.87-3.08 (2H, m), 3.14-3.24 (1H, m), 3.27-3.39 (1H, m), 3.74-4.02 (6H, m), 9.18-9.43 (1H, m)

Reference Example 8-47

$^1$H-NMR (CDCl$_3$) δ ppm: 0.91 (9H, s), 1.30-1.50 (3H, m), 1.50-1.90 (6H, m), 2.00-2.10 (1H, m), 2.20-2.35 (10H, m), 2.44 (2H, t, J=6.4 Hz), 2.85-2.95 (1H, m), 3.10-3.25 (1H, m), 3.30-3.40 (2H, m), 3.78 (2H, brs), 3.90-4.00 (4H, m), 8.89 (1H, br)

Reference Example 8-48

$^1$H-NMR (CDCl$_3$) δ ppm: 1.19 (3H, d, J=6.6 Hz), 1.23 (3H, t, J=7.0 Hz), 1.33-1.49 (3H, m), 1.51-1.94 (6H, m), 2.03-2.12 (1H, m), 2.13-2.20 (1H, m), 2.24 (6H, s), 2.29-2.43 (2H, m), 2.31 (3H, s), 2.89-3.08 (2H, m), 3.67-4.03 (7H, m), 9.13-9.27 (1H, m)

Reference Example 8-49

$^1$H-NMR (CDCl$_3$) δ ppm: 0.94 (3H, t, J=7.3 Hz), 1.29-1.49 (5H, m), 1.49-1.88 (10H, m), 2.01-2.12 (1H, m), 2.21 (6H, s), 2.25-2.41 (3H, m), 2.31 (3H, s), 2.87-3.09 (2H, m), 3.25-3.36 (2H, m), 3.60-3.85 (2H, m), 3.89-4.01 (4H, m), 9.20-9.38 (1H, m)

Reference Example 8-50

$^1$H-NMR (CDCl$_3$) δ ppm: 0.94 (3H, t, J=7.3 Hz), 1.26-1.90 (17H, m), 2.01-2.13 (1H, m), 2.20 (6H, s), 2.22-2.39 (3H, m), 2.31 (3H, s), 2.87-3.07 (2H, m), 3.22-3.33 (2H, m), 3.61-3.86 (2H, m), 3.90-4.01 (4H, m), 9.21-9.36 (1H, m)

Reference Example 8-51

$^1$H-NMR (CDCl$_3$) δ ppm: 0.94 (3H, t, J=7.3 Hz), 1.00 (12H, d, J=6.5 Hz), 1.24-1.88 (13H, m), 2.02-2.14 (1H, m), 2.30-2.42 (1H, m), 2.31 (3H, s), 2.50-2.61 (2H, m), 2.86-3.08 (4H, m), 3.21-3.31 (2H, m), 3.61-3.86 (2H, m), 3.88-4.00 (4H, m), 9.11-9.37 (1H, m)

Reference Example 8-52

MS (ESI, m/z): 479 (M+H)+

Reference Example 8-53

$^1$H-NMR (CDCl$_3$) δ ppm: 0.93 (3H, t, J=7.4 Hz), 1.30-1.50 (3H, m), 1.50-1.90 (10H, m), 2.00-2.15 (1H, m), 2.21 (6H, s), 2.25-2.40 (6H, m), 2.85-3.10 (2H, m), 3.25-3.35 (2H, m), 3.60-3.85 (2H, m), 3.90-4.00 (4H, m), 9.30 (1H, s)

Reference Example 8-54

$^1$H-NMR (CDCl$_3$) δ ppm: 0.93 (3H, t, J=7.4 Hz), 1.30-1.90 (15H, m), 2.00-2.15 (1H, m), 2.15-2.40 (12H, m), 2.85-3.10 (2H, m), 3.20-3.35 (2H, m), 3.60-3.85 (2H, m), 3.90-4.00 (4H, m), 9.20-9.35 (1H, m)

Reference Example 8-55

$^1$H-NMR (CDCl$_3$) δ ppm: 0.93 (3H, t, J=7.3 Hz), 1.29-1.88 (13H, m), 2.01-2.12 (1H, m), 2.30 (6H, s), 2.34-2.47 (5H, m), 2.88-3.08 (2H, m), 3.35-3.47 (2H, m), 3.59-3.86 (4H, m), 3.89-4.00 (4H, m), 4.07-4.15 (2H, m), 9.73-10.02 (1H, m)

Reference Example 8-56

$^1$H-NMR (CDCl$_3$) δ ppm: 1.02 (6H, s), 1.24 (3H, t, J=6.9 Hz), 1.35-1.89 (9H, m), 2.01-2.12 (1H, m), 2.22 (6H, s), 2.31 (3H, s), 2.35-2.46 (1H, m), 2.90-3.10 (2H, m), 3.26 (2H, d, J=4.8 Hz), 3.75-4.01 (6H, m), 9.16-9.46 (1H, m)

Reference Example 8-57

$^1$H-NMR (CDCl$_3$) δ ppm: 0.94 (3H, t, J=7.3 Hz), 1.28-1.89 (14H, m), 2.00-2.12 (1H, m), 2.22-2.74 (10H, m), 2.29 (3H, s), 2.31 (3H, s), 2.85-3.10 (2H, m), 3.33-3.46 (2H, m), 3.60-3.87 (2H, m), 3.88-4.02 (4H, m), 9.13-9.42 (1H, m)

Reference Example 8-58

MS (ESI, m/z): 455 (M+H)+

Reference Example 8-59

MS (ESI, m/z): 467 (M+H)+

Reference Example 8-60

MS (ESI, m/z): 441 (M+H)+

Reference Example 8-61

MS (ESI, m/z): 455 (M+H)+

Reference Example 8-62

$^1$H-NMR (CDCl$_3$) δ ppm: 1.02 (6H, t, J=7.2 Hz), 1.29-1.48 (3H, m), 1.51-1.87 (6H, m), 2.02-2.12 (1H, m), 2.26-2.38 (1H, m), 2.31 (3H, s), 2.49-2.63 (6H, m), 2.89-2.98 (1H, m), 3.03-3.16 (1H, m), 3.31-3.40 (2H, m), 3.34 (3H, s), 3.86-4.02 (4H, m), 9.16-9.36 (1H, m)

Reference Example 8-63

$^1$H-NMR (CDCl$_3$) δ ppm: 1.23 (3H, t, J=6.9 Hz), 1.35-1.49 (3H, m), 1.51-1.88 (6H, m), 2.01-2.13 (1H, m), 2.26 (6H, s), 2.30-2.41 (1H, m), 2.31 (3H, s), 2.48-2.55 (2H, m), 2.88-3.08 (2H, m), 3.44-3.51 (2H, m), 3.52-3.61 (4H, m), 3.75-4.02 (6H, m), 9.30-9.45 (1H, m)

Reference Example 8-64

$^1$H-NMR (CDCl$_3$) δ ppm: 1.23 (3H, t, J=6.9 Hz), 1.33-1.49 (3H, m), 1.49-1.88 (6H, m), 2.01-2.13 (1H, m), 2.28 (3H, s), 2.29-2.40 (1H, m), 2.31 (3H, s), 2.56-2.68 (1H, m), 2.84-3.09 (4H, m), 3.30-3.38 (2H, m), 3.41-3.49 (2H, m), 3.75-4.01 (6H, m), 9.27-9.38 (1H, m)

Reference Example 8-65

$^1$H-NMR (CDCl$_3$) δ ppm: 1.30-1.87 (15H, m), 2.03-2.12 (1H, m), 2.28-2.52 (7H, m), 2.31 (3H, s), 2.89-2.99 (1H, m), 3.04-3.16 (1H, m), 3.34 (3H, s), 3.36-3.45 (2H, m), 3.88-4.00 (4H, m), 9.18-9.33 (1H, m)

Reference Example 8-66

MS (ESI, m/z): 482 (M+H)+

Reference Example 8-67

MS (ESI, m/z): 453 (M+H)+

Reference Example 8-68

$^1$H-NMR (CDCl$_3$) δ ppm: 0.91 (6H, s), 1.29-1.89 (8H, m), 2.03-2.12 (1H, m), 2.15 (2H, s), 2.24-2.40 (2H, m), 2.28 (6H, s), 2.32 (3H, s), 2.91-3.01 (1H, m), 3.07-3.20 (1H, m), 3.19 (2H, d, J=5.5 Hz), 3.33 (3H, s), 3.88-4.00 (4H, m), 9.39-9.51 (1H, m)

Reference Example 8-69

$^1$H-NMR (CDCl$_3$) δ ppm: 1.17 (3H, t, J=7.0 Hz), 1.23-1.88 (11H, m), 1.99-2.11 (1H, m), 2.22 (6H, s), 2.25-2.36 (3H, m), 2.29 (3H, s), 2.91-3.01 (1H, m), 3.23-3.62 (7H, m), 3.77-4.06 (6H, m), 8.28-9.94 (1H, m)

Reference Example 8-70

$^1$H-NMR (CDCl$_3$) δ ppm: 1.17 (3H, t, J=7.0 Hz), 1.25-1.88 (13H, m), 2.00-2.10 (1H, m), 2.21 (6H, s), 2.23-2.38 (3H, m), 2.29 (3H, s), 2.89-3.00 (1H, m), 3.20-3.62 (7H, m), 3.75-4.10 (6H, m), 8.55-9.77 (1H, m)

Reference Example 8-71

$^1$H-NMR (CDCl$_3$) δ ppm: 0.30-0.55 (4H, m), 0.90-1.05 (1H, m), 1.35-1.90 (11H, m), 2.00-2.15 (1H, m), 2.24 (6H, s), 2.30-2.45 (6H, m), 2.90-3.00 (1H, m), 3.10-3.25 (1H, m), 3.25-3.35 (2H, m), 3.75 (2H, d, J=6.7 Hz), 3.90-4.00 (4H, m), 9.32 (1H, brs)

Reference Example 8-72

$^1$H-NMR (CDCl$_3$) δ ppm: 1.02 (6H, s), 1.29-1.49 (3H, m), 1.50-1.88 (6H, m), 1.98-2.10 (1H, m), 2.22 (6H, s), 2.28-2.40 (1H, m), 2.30 (3H, s), 2.91-3.02 (1H, m), 3.16-3.39 (3H, m), 3.33 (3H, s), 3.46-3.58 (2H, m), 3.76-4.07 (6H, m), 8.26-9.55 (1H, m)

Reference Example 8-73

$^1$H-NMR (CDCl$_3$) δ ppm: 0.93 (3H, t, J=7.4 Hz), 1.02 (6H, s), 1.33-1.87 (11H, m), 2.02-2.12 (1H, m), 2.23 (6H, s), 2.31

(3H, s), 2.35-2.45 (1H, m), 2.85-3.10 (2H, m), 3.25 (2H, d, J=4.8 Hz), 3.60-3.84 (2H, m), 3.88-4.01 (4H, m), 9.09-9.47 (1H, m)

Reference Example 8-74

$^1$H-NMR (CDCl$_3$) δ ppm: 0.86-0.97 (3H, m), 0.91 (6H, s), 1.34-1.50 (3H, m), 1.51-1.88 (8H, m), 2.02-2.12 (1H, m), 2.14 (2H, s), 2.28 (6H, s), 2.31 (3H, s), 2.33-2.42 (1H, m), 2.88-3.11 (2H, m), 3.19 (2H, d, J=5.5 Hz), 3.59-3.83 (2H, m), 3.88-4.02 (4H, m), 9.29-9.52 (1H, m)

Reference Example 8-75

$^1$H-NMR (CDCl$_3$) δ ppm: 0.87 (6H, t, J=7.4 Hz), 1.23 (3H, t, J=7.0 Hz), 1.34-1.88 (13H, m), 2.01-2.13 (1H, m), 2.31 (3H, s), 2.32 (6H, s), 2.35-2.43 (1H, m), 2.90-3.10 (2H, m), 3.30 (2H, d, J=5.0 Hz), 3.75-4.01 (6H, m), 9.10-9.45 (1H, m)

Reference Example 8-76

$^1$H-NMR (CDCl$_3$) δ ppm: 0.91 (6H, s), 1.22 (3H, t, J=7.1 Hz), 1.34-1.50 (3H, m), 1.51-1.89 (6H, m), 2.01-2.12 (1H, m), 2.14 (2H, s), 2.28 (6H, s), 2.32 (3H, s), 2.33-2.42 (1H, m), 2.90-3.12 (2H, m), 3.19 (2H, d, J=5.8 Hz), 3.75-4.00 (6H, m), 9.33-9.47 (1H, m)

Reference Example 8-77

$^1$H-NMR (CDCl$_3$) δ ppm: 1.22 (3H, t, J=7.1 Hz), 1.30-1.47 (3H, m), 1.51-1.75 (5H, m), 1.79-1.88 (1H, m), 2.00-2.12 (1H, m), 2.24-2.37 (1H, m), 2.31 (3H, s), 2.85-2.93 (1H, m), 2.94-3.05 (1H, m), 2.96 (3H, s), 3.41-3.56 (4H, m), 3.73-4.00 (6H, m), 6.63-6.78 (3H, m), 7.17-7.25 (2H, m), 9.30-9.41 (1H, m)

Reference Example 8-78

$^1$H-NMR (CDCl$_3$) δ ppm: 0.93 (3H, t, J=7.3 Hz), 1.28-1.89 (13H, m), 2.02-2.13 (1H, m), 2.27 (3H, s), 2.31 (3H, s), 2.33-2.43 (1H, m), 2.52-2.63 (4H, m), 2.86-3.08 (2H, m), 3.34-3.45 (2H, m), 3.55-3.87 (4H, m), 3.89-4.01 (4H, m), 9.45-9.69 (1H, m)

Reference Example 8-79

$^1$H-NMR (CDCl$_3$) δ ppm: 0.92 (3H, t, J=7.3 Hz), 0.99 (6H, t, J=7.2 Hz), 1.22-1.36 (2H, m), 1.38-2.02 (11H, m), 2.12-2.26 (2H, m), 2.46-2.59 (6H, m), 2.82-2.95 (2H, m), 3.14-3.22 (1H, m), 3.25-3.34 (2H, m), 3.48-3.66 (2H, m), 3.91-4.03 (4H, m), 4.07-4.19 (1H, m), 7.17-7.35 (5H, m), 9.10-9.34 (1H, m)

Reference Example 8-80

$^1$H-NMR (CDCl$_3$) δ ppm: 0.92 (3H, t, J=7.3 Hz), 1.22-2.01 (19H, m), 2.12-2.26 (2H, m), 2.28-2.49 (6H, m), 2.81-2.94 (2H, m), 3.14-3.22 (1H, m), 3.28-3.40 (2H, m), 3.47-3.65 (2H, m), 3.90-4.03 (4H, m), 4.08-4.19 (1H, m), 7.16-7.34 (5H, m), 9.07-9.34 (1H, m)

Reference Example 8-81

$^1$H-NMR (CDCl$_3$) δ ppm: 0.92 (3H, t, J=7.4 Hz), 1.21-1.36 (2H, m), 1.39-2.01 (11H, m), 2.12-2.26 (2H, m), 2.22 (6H, s), 2.36-2.44 (2H, m), 2.80-2.95 (2H, m), 3.13-3.22 (1H, m), 3.29-3.38 (2H, m), 3.48-3.66 (2H, m), 3.90-4.03 (4H, m), 4.08-4.19 (1H, m), 7.17-7.35 (5H, m), 9.18-9.36 (1H, m)

Reference Example 8-82

MS (ESI, m/z): 425 (M+H)+

Reference Example 8-83

MS (ESI, m/z): 411 (M+H)+

Reference Example 8-85

$^1$H-NMR (CDCl$_3$) δ ppm: 1.23 (3H, t, J=7.0 Hz), 1.33-1.87 (11H, m), 1.90-2.00 (2H, m), 2.03-2.20 (3H, m), 2.27 (3H, s), 2.31-2.41 (1H, m), 2.32 (3H, s), 2.60-2.82 (2H, m), 2.91-3.10 (2H, m), 3.59-4.02 (7H, m), 9.16-9.40 (1H, m)

Reference Example 8-86

$^1$H-NMR (CDCl$_3$) δ ppm: 0.94 (3H, t, J=7.4 Hz), 1.28-1.49 (8H, m), 1.45 (9H, s), 1.51-1.96 (9H, m), 2.02-2.12 (1H, m), 2.27-2.40 (1H, m), 2.31 (3H, s), 2.86-3.08 (4H, m), 3.61-4.05 (9H, m), 9.30-9.45 (1H, m)

Reference Example 8-87

$^1$H-NMR (CDCl$_3$) δ ppm: 1.15-1.30 (3H, m), 1.33-1.50 (3H, m), 1.50-1.95 (6H, m), 2.00-2.13 (1H, m), 2.25-2.40 (7H, m), 2.80-2.91 (2H, m), 2.91-2.98 (1H, m), 2.98-3.08 (1H, m), 3.65-3.75 (2H, m), 3.75-3.90 (2H, m), 3.90-4.00 (4H, m), 4.35-4.50 (1H, m), 9.59 (1H, d, J=6.4 Hz)

Reference Example 8-88

$^1$H-NMR (CDCl$_3$) δ ppm: 0.92 (3H, t, J=7.2 Hz), 1.30-1.50 (3H, m), 1.50-1.95 (8H, m), 2.00-2.15 (1H, m), 2.25-2.45 (7H, m), 2.80-2.96 (3H, m), 2.97-3.10 (1H, m), 3.50-3.80 (4H, m), 3.90-4.00 (4H, m), 4.30-4.50 (1H, m), 9.59 (1H, d, J=6.4 Hz)

Reference Example 8-89

$^1$H-NMR (CDCl$_3$) δ ppm: 0.87 (3H, t, J=7.4 Hz), 1.35-1.90 (10H, m), 1.90-2.00 (1H, m), 2.10-2.30 (8H, m), 2.44 (2H, t, J=6.5 Hz), 2.80-2.95 (2H, m), 3.21 (1H, d, J=13.5 Hz), 3.30-3.40 (2H, m), 3.45-3.60 (2H, m), 3.90-4.05 (4H, m), 4.13 (1H, d, J=13.5 Hz), 7.15-7.35 (5H, m), 9.30 (1H, br)

Reference Example 8-90

$^1$H-NMR (CDCl$_3$) δ ppm: 0.85-0.90 (6H, m), 1.12 (3H, t, J=7.0 Hz), 1.35-2.05 (10H, m), 2.11 (2H, s), 2.15-2.35 (7H, m), 2.85-3.00 (2H, m), 3.05-3.20 (2H, m), 3.21 (1H, d, J=13.7 Hz), 3.60-3.75 (2H, m), 3.90-4.00 (4H, m), 4.14 (1H, d, J=13.7 Hz), 7.15-7.35 (5H, m), 9.34 (1H, br)

Reference Example 8-91

$^1$H-NMR (CDCl$_3$) δ ppm: 0.35-0.42 (2H, m), 0.44-0.52 (2H, m), 0.91 (6H, s), 0.93-1.05 (1H, m), 1.35-1.50 (3H, m), 1.50-1.73 (4H, m), 1.74-1.88 (2H, m), 2.00-2.11 (1H, m), 2.15 (2H, s), 2.20-2.44 (10H, m), 2.90-3.00 (1H, m), 3.10-3.30 (3H, m), 3.76 (2H, d, J=6.4 Hz), 3.90-4.00 (4H, m), 9.42 (1H, brs) [α]$_D^{28}$=−10.39° (c=0.28, MeOH)

Reference Example 8-92

$^1$H-NMR (CDCl$_3$) δ ppm: 1.20 (6H, t, J=7.2 Hz), 1.22 (3H, t, J=6.8 Hz), 1.34-1.90 (8H, m), 2.00-2.15 (1H, m), 2.25-2.45

(4H, m), 2.45-2.65 (7H, m), 2.85-3.10 (2H, m), 3.30-3.40 (2H, m), 3.70-3.91 (2H, m), 3.91-4.00 (4H, m), 9.27 (1H, brs)

Reference Example 8-93

$^1$H-NMR (CDCl$_3$) δ ppm: 1.21 (3H, t, J=7.2 Hz), 1.34 (6H, s), 1.35-1.90 (9H, m), 2.00-2.15 (1H, m), 2.20-2.45 (10H, m), 2.49 (2H, s), 2.90-3.10 (2H, m), 3.70-3.88 (2H, m), 3.88-4.00 (4H, m), 9.35 (1H, brs)

Reference Example 8-94

$^1$H-NMR (CDCl$_3$) δ ppm: 0.87 (6H, t, J=7.6 Hz), 1.23 (3H, t, J=7.0 Hz), 1.30-1.90 (13H, m), 2.00-2.15 (1H, m), 2.20-2.45 (10H, m), 2.90-3.10 (2H, m), 3.30 (2H, d), 3.75-4.00 (6H, m), 9.15-9.45 (1H, m)

Reference Example 8-95

$^1$H-NMR (CDCl$_3$) δ ppm: 1.24 (3H, t), 1.35-1.50 (3H, m), 1.50-1.90 (6H, m), 2.00-2.15 (1H, m), 2.20-2.50 (12H, m), 2.85-3.10 (2H, m), 3.30-3.45 (2H, m), 3.75-4.00 (6H, m), 9.20-9.40 (1H, m)
[α]$_D^{27}$=−12.97° (c=0.33, MeOH)

Reference Example 8-96

$^1$H-NMR (CDCl$_3$) δ ppm: 0.35-0.45 (2H, m), 0.45-0.55 (2H, m), 0.90-1.05 (1H, m), 1.30-1.90 (9H, m), 2.00-2.15 (1H, m), 2.25 (6H, s), 2.31 (3H, s), 2.38 (1H, t, J=11.2 Hz), 2.44 (2H, t, J=6.8 Hz), 2.90-3.00 (1H, m), 3.10-3.25 (1H, m), 3.33-3.45 (2H, m), 3.76 (2H, d, J=6.8 Hz), 3.90-4.00 (4H, m), 9.29 (1H, brs)

Reference Example 8-98

$^1$H-NMR (CDCl$_3$) δ ppm: 0.95 (3H, t, J=7.2 Hz), 1.30-1.90 (8H, m), 1.90-2.02 (1H, m), 2.10-2.22 (1H, m), 2.25 (6H, s), 2.44 (2H, t, J=7.2 Hz), 2.70-3.32 (6H, m), 3.33-3.45 (2H, m), 3.60-3.80 (2H, m), 3.90-4.00 (5H, m), 9.23 (1H, brs)

Reference Example 8-99

$^1$H-NMR (CDCl$_3$) δ ppm: 0.91 (6H, s), 1.23 (3H, t, J=7.0 Hz), 1.35-1.50 (3H, m), 1.50-1.90 (6H, m), 1.95-2.10 (2H, m), 2.15 (2H, s), 2.28 (6H, s), 2.60-2.70 (1H, m), 2.75-3.15 (3H, m), 3.19 (2H, d, J=5.6 Hz), 3.70-4.00 (6H, m), 4.40-4.65 (2H, m), 9.38 (1H, brs)

Reference Example 8-100

MS (ESI, m/z): 507 (M+H)+

Reference Example 9-1

1-{[(3'R*,4'aR*,8'aR*)Octahydro-1'H-spiro[1,3-dioxolane-2,6'-quinolin]-3'-yl]carbonyl}-1-butyl-3-[2-(diethylamino)ethyl]urea To a mixture of 1-{[(3'R*,4'aR*,8'aR*)-1'-benzyloctahydro-1'H-spiro[1,3-dioxolane-2,6'-quinolin]-3'-yl]carbonyl}-1-butyl-3-[2-(diethylamino)ethyl]urea (reference example 8-79) (177 mg) and ethanol (6.0 mL) was added 10% palladium-carbon (70 mg), and the mixture was stirred at room temperature for 2 hours under a hydrogen atmosphere. The mixture was passed through a layer of Celite (registered mark) and the filtrate was concentrated under reduced pressure to give the title compound (142 mg).

$^1$H-NMR (CDCl$_3$) δ ppm: 0.95 (3H, t, J=7.5 Hz), 1.02 (6H, t, J=7.2 Hz), 1.29-1.86 (13H, m), 2.18-2.30 (1H, m), 2.48-2.62 (6H, m), 2.76-2.95 (2H, m), 3.13-3.22 (1H, m), 3.28-3.38 (2H, m), 3.62-3.83 (2H, m), 3.90-4.01 (4H, m), 9.05-9.40 (1H, m)

Reference examples 9-2 to 9-5 were prepared in a manner similar to those as described in reference example 9-1 using the corresponding benzylamines instead of 1-{[(3'R*,4'aR*,8'aR*)-1'-benzyloctahydro-1'H-spiro[1,3-dioxolane-2,6'-quinolin]-3'-yl]carbonyl}-1-butyl-3-[2-(diethylamino)ethyl]urea. These were illustrated in Table 8.

TABLE 8

| Reference example | Structure |
|---|---|
| 9-1 | 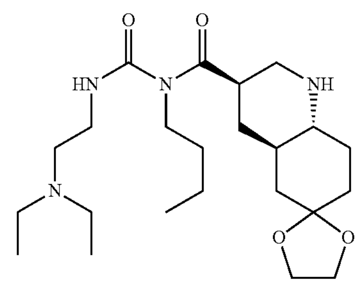 [SMILES: CCCCN(C(=O)NCCN(CC)CC)C(=O)[C@H]1CN[C@@H]2CCC3(C[C@H]2C1)OCCO3] |
| 9-2 | 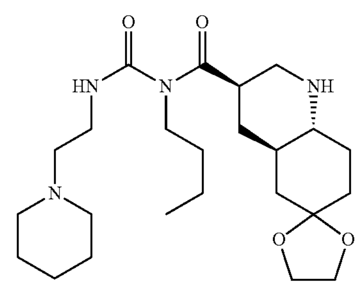 [SMILES: CCCCN(C(=O)NCCN1CCCCC1)C(=O)[C@H]1CN[C@@H]2CCC3(C[C@H]2C1)OCCO3] |
| 9-3 | 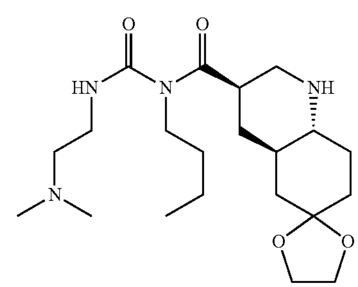 [SMILES: CCCCN(C(=O)NCCN(C)C)C(=O)[C@H]1CN[C@@H]2CCC3(C[C@H]2C1)OCCO3] |
| 9-4 | 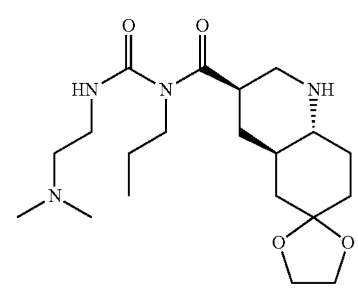 |

TABLE 8-continued

| Reference example | Structure |
|---|---|
| 9-5 | (structure shown) |

The structures of the reference example 9-1 to 9-5 in Table 8 indicate relative configuration.

The physical data of reference examples 9-2 to 9-5 were shown below.

Reference Example 9-2

$^1$H-NMR (CDCl$_3$) δ ppm: 0.95 (3H, t, J=7.3 Hz), 1.29-1.87 (19H, m), 2.17-2.53 (7H, m), 2.74-2.95 (2H, m), 3.12-3.22 (1H, m), 3.33-3.44 (2H, m), 3.62-3.83 (2H, m), 3.90-4.01 (4H, m), 8.98-9.47 (1H, m)

Reference Example 9-3

$^1$H-NMR (CDCl$_3$) δ ppm: 0.95 (3H, t, J=7.3 Hz), 1.27-1.87 (13H, m), 2.17-2.29 (1H, m), 2.25 (6H, s), 2.39-2.48 (2H, m), 2.73-2.97 (2H, m), 3.12-3.23 (1H, m), 3.31-3.42 (2H, m), 3.63-3.84 (2H, m), 3.91-4.02 (4H, m), 9.14-9.46 (1H, m)

Reference Example 9-4

MS (ESI, m/z): 397 (M+H)+

Reference Example 9-5

MS (ESI, m/z): 425 (M+H)+

Reference Example 10-1

1-{[(3R,4aR,8aR)-1-Methyl-6-oxodecahydroquino-lin-3-yl]carbonyl}-3-[2-(dimethylamino)ethyl]-1-propylurea To 1-{[(3'R,4'aR,8'aR)-1'-methyloctahydro-1'H-spiro[1,3-dioxolane-2,6'-quinolin]-3'-yl]carbonyl}-3-[2-(dimethylamino)ethyl]-1-propylurea (reference example 8-1) (2.366 g) was added 2 mol/L hydrochloric acid (30 mL) and the mixture was stirred at room temperature for 2 hours. After diethyl ether was added to the reaction mixture and washed, the aqueous layer was made alkaline with potassium carbonate. The mixture was extracted with methylene chloride/methanol mixed solvent (methylene chloride:methanol=9:1). After the organic layer was dried over anhydrous sodium sulfate, it was concentrated under reduced pressure to give the title compound (1.605 g).

$^1$H-NMR (CDCl$_3$) δ ppm: 0.94 (3H, t, J=7.4 Hz), 1.45-1.90 (6H, m), 1.95-2.05 (1H, m), 2.10-2.55 (17H, m), 2.90-3.10 (2H, m), 3.30-3.45 (2H, m), 3.60-3.80 (2H, m), 9.22 (1H, brs)
[α]$_D^{28}$=−37.56° (c=0.38, MeOH)

Reference Example 10-7

1-{[(3R*,4aR*,8aR*)-1-Methyl-6-oxodecahydro-quinolin-3-yl]carbonyl}-1-[3-(dimethylamino)pro-pyl]-3-ethylurea To 1-{[(3'R*,4'aR*,8'aR*)-1'-methyloctahydro-1'H-spiro[1,3-dioxolane-2,6'-quinolin]-3'-yl]carbonyl}-1-[3-(dimethylamino)propyl]-3-ethylurea (reference example 7-2) (2.305 g) was added 2 mol/L hydrochloric acid (103 mL) and the mixture was stirred at room temperature for 2 hours. The reaction mixture was made alkaline with potassium carbonate. The mixture was extracted with methylene chloride/methanol mixed solvent (methylene chloride:methanol=9:1). After the organic layer was dried over anhydrous sodium sulfate, it was concentrated under reduced pressure to give the title compound (2.084 g).

MS (ESI, m/z): 367 (M+H)+

Reference examples 10-2 to 10-6 and reference examples 10-8 to 10-108 were prepared in a manner similar to those as described in reference example 10-1 or reference example 10-7 using the corresponding ketals instead of 1-{[(3'R,4'aR,8'aR)-1'-methyloctahydro-1'H-spiro[1,3-dioxolane-2,6'-quinolin]-3'-yl]-carbonyl}-3-[2-(dimethylamino)ethyl]-1-propylurea. These were illustrated in Table 9.

TABLE 9

| Reference example | Structure |
|---|---|
| 10-1 | (structure shown, Chiral) |
| 10-2 | (structure shown, Chiral) |
| 10-3 | (structure shown, Chiral) |

TABLE 9-continued
| Reference example | Structure |
|---|---|
| 10-4 | 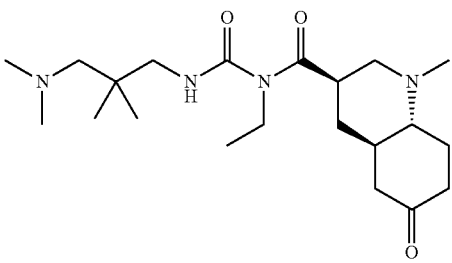 Chiral |
| 10-5 | 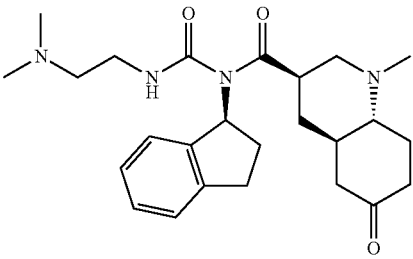 Chiral |
| 10-6 | 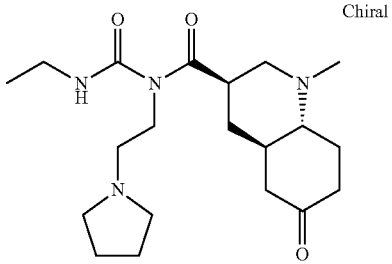 [SMILES: CCNC(=O)N(CCN1CCCC1)C(=O)[C@@H]1C[C@@H]2CC(=O)CC[C@H]2N(C)C1] Chiral |
| 10-7 | 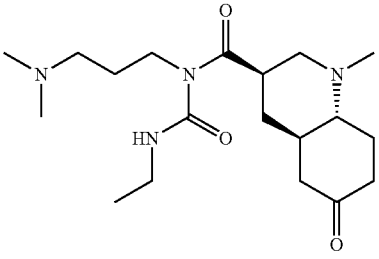 |
| 10-8 | 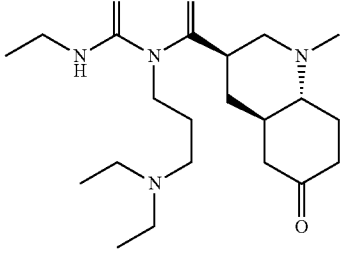 |
| 10-9 | 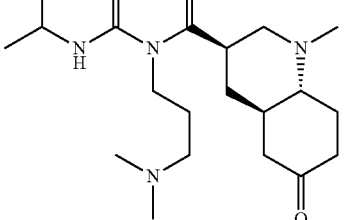 |
| 10-10 | 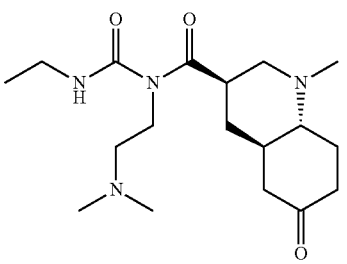 [SMILES: CCNC(=O)N(CCN(C)C)C(=O)[C@@H]1C[C@@H]2CC(=O)CC[C@H]2N(C)C1] |
| 10-11 | 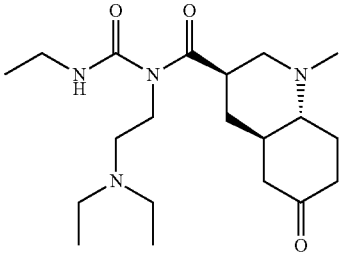 [SMILES: CCNC(=O)N(CCN(CC)CC)C(=O)[C@@H]1C[C@@H]2CC(=O)CC[C@H]2N(C)C1] |
| 10-12 | 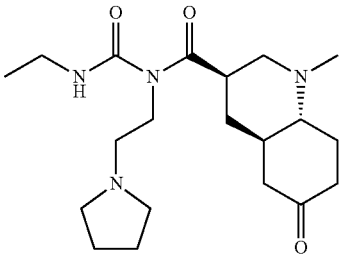 [SMILES: CCNC(=O)N(CCN1CCCC1)C(=O)[C@@H]1C[C@@H]2CC(=O)CC[C@H]2N(C)C1] |
| 10-13 | 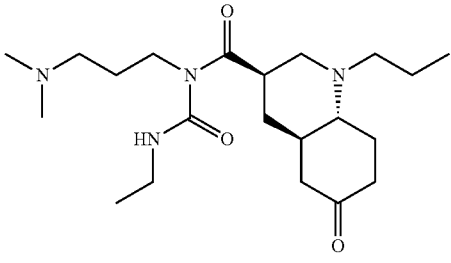 [SMILES: CCCN1C[C@H](C(=O)N(CCCN(C)C)C(=O)NCC)C[C@@H]2CC(=O)CC[C@H]21] |

TABLE 9-continued

| Reference example | Structure |
|---|---|
| 10-14 | 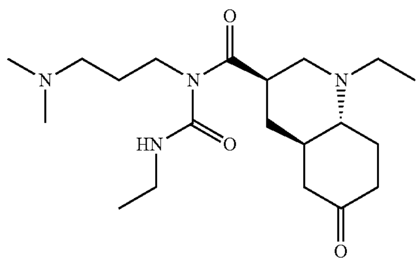 [SMILES: CCNC(=O)N(CCCN(C)C)C(=O)[C@@H]1C[C@@H]2CC(=O)CC[C@H]2N(CC)C1] |
| 10-15 | 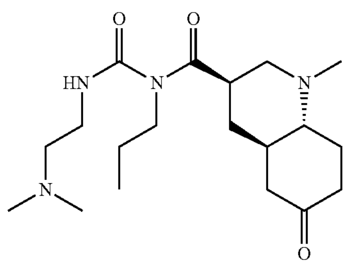 |
| 10-16 | 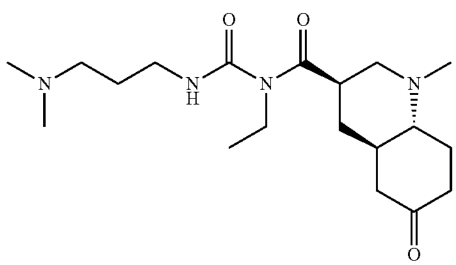 |
| 10-17 | 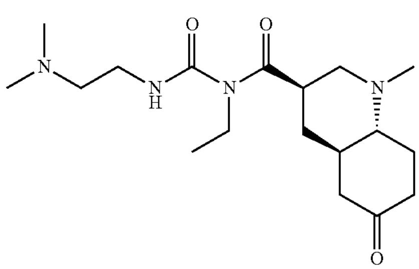 |
| 10-18 | 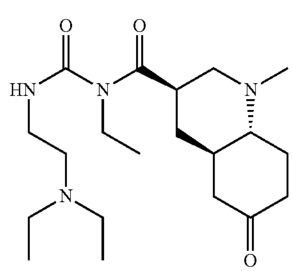 [SMILES: CCN(CC)CCNC(=O)N(CC)C(=O)[C@@H]1C[C@@H]2CC(=O)CC[C@H]2N(C)C1] |
| 10-19 | |
| 10-20 | |
| 10-21 | |
| 10-22 | |
| 10-23 | |

TABLE 9-continued

| Reference example | Structure |
|---|---|
| 10-24 | 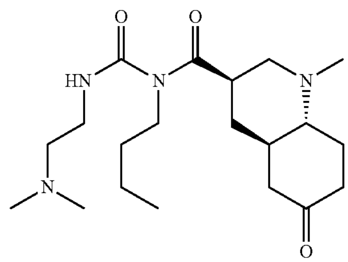 |
| 10-25 | 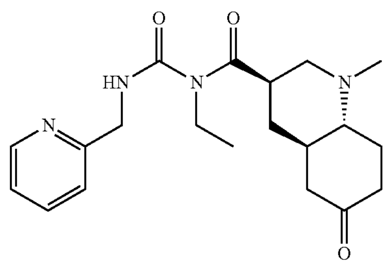 [SMILES: CCN(C(=O)NCc1ccccn1)C(=O)[C@@H]1C[C@@H]2CC(=O)CC[C@H]2N(C)C1] |
| 10-26 | 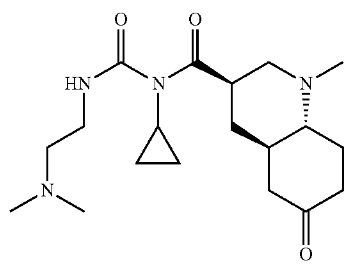 |
| 10-27 | 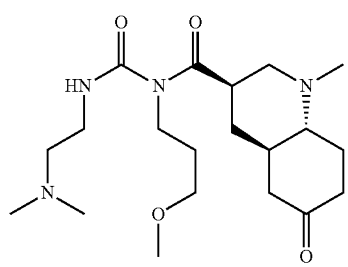 |
| 10-28 | 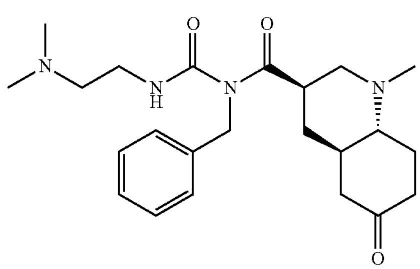 |
| 10-29 | |
| 10-30 | |
| 10-31 | |
| 10-32 | |
| 10-33 | |

TABLE 9-continued

| Reference example | Structure |
|---|---|
| 10-34 | 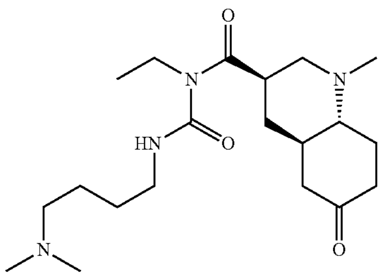 |
| 10-35 | 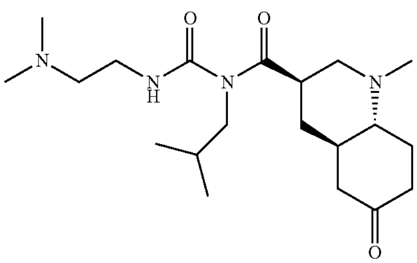 |
| 10-36 | 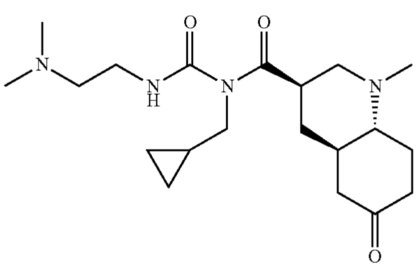 |
| 10-37 | 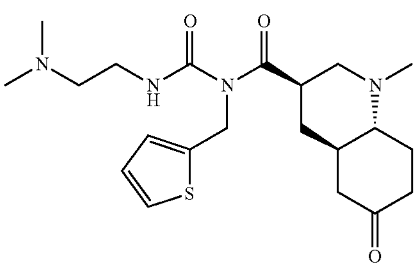 |
| 10-38 | 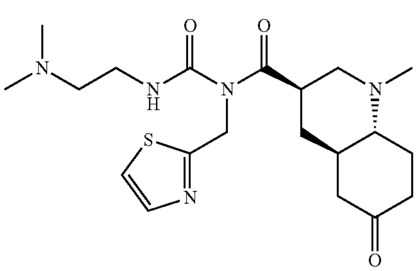 |
| 10-39 | |
| 10-40 | |
| 10-41 | |
| 10-42 | |
| 10-43 | |

TABLE 9-continued

| Reference example | Structure |
|---|---|
| 10-44 | 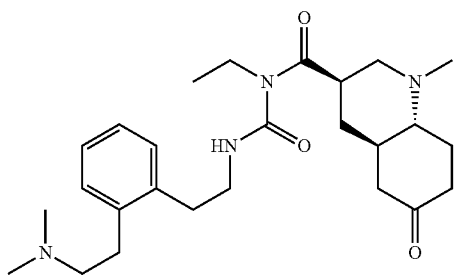 |
| 10-45 | 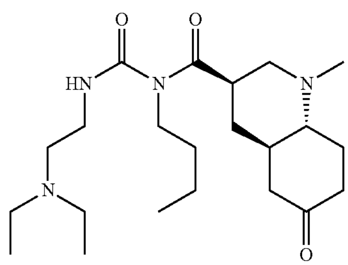 [SMILES: CCCCN(C(=O)NCCN(CC)CC)C(=O)[C@@H]1C[C@@H]2CC(=O)CC[C@H]2N(C)C1] |
| 10-46 | 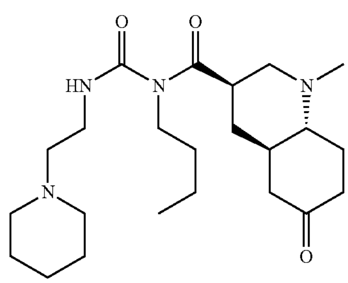 [SMILES: CCCCN(C(=O)NCCN1CCCCC1)C(=O)[C@@H]1C[C@@H]2CC(=O)CC[C@H]2N(C)C1] |
| 10-47 | 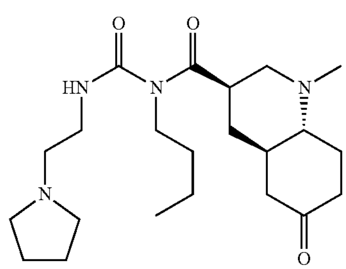 [SMILES: CCCCN(C(=O)NCCN1CCCC1)C(=O)[C@@H]1C[C@@H]2CC(=O)CC[C@H]2N(C)C1] |
| 10-48 | 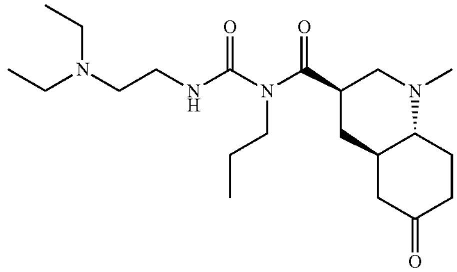 [SMILES: CCCN(C(=O)NCCN(CC)CC)C(=O)[C@@H]1C[C@@H]2CC(=O)CC[C@H]2N(C)C1] |
| 10-49 | |
| 10-50 | |
| 10-51 | |
| 10-52 | |
| 10-53 | |

TABLE 9-continued

| Reference example | Structure |
|---|---|
| 10-54 | 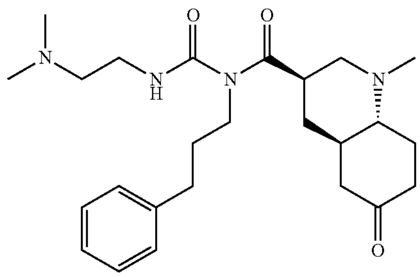 |
| 10-55 | 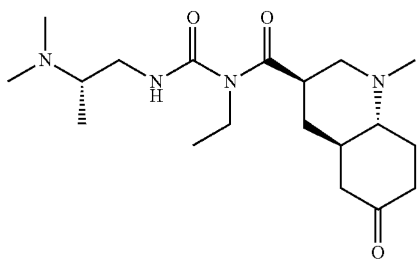 |
| 10-56 | 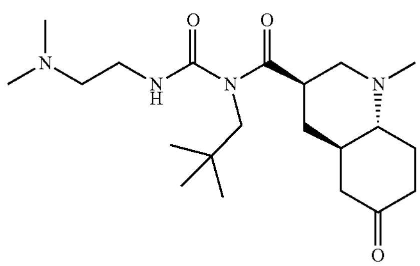 |
| 10-57 | (Chiral) |
| 10-58 | 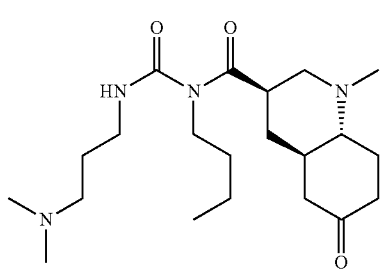 |
| 10-59 | |
| 10-60 | |
| 10-61 | |
| 10-62 | |
| 10-63 | |

TABLE 9-continued

| Reference example | Structure |
|---|---|
| 10-64 | 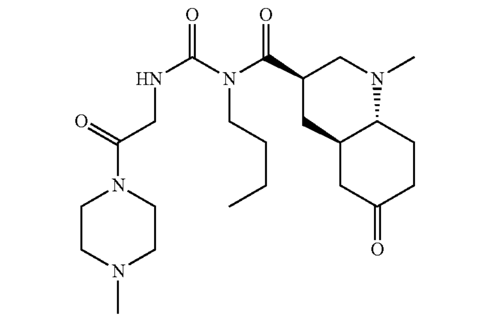 [SMILES: CCCCN(C(=O)NCC(=O)N1CCN(C)CC1)C(=O)[C@@H]1C[C@@H]2CC(=O)CC[C@H]2N(C)C1] |
| 10-65 | 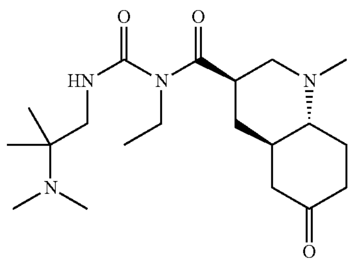 [SMILES: CCN(C(=O)NCC(C)(C)N(C)C)C(=O)[C@@H]1C[C@@H]2CC(=O)CC[C@H]2N(C)C1] |
| 10-66 | 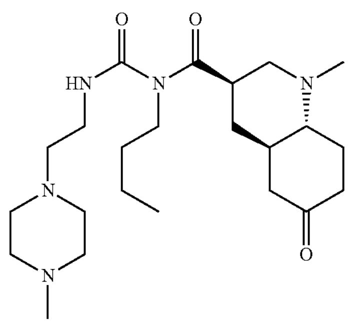 [SMILES: CCCCN(C(=O)NCCN1CCN(C)CC1)C(=O)[C@@H]1C[C@@H]2CC(=O)CC[C@H]2N(C)C1] |
| 10-67 | 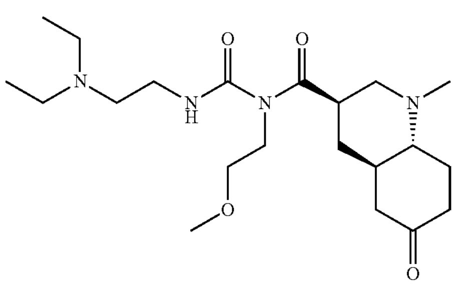 [SMILES: CCN(CC)CCNC(=O)N(CCOC)C(=O)[C@@H]1C[C@@H]2CC(=O)CC[C@H]2N(C)C1] |
| 10-68 | 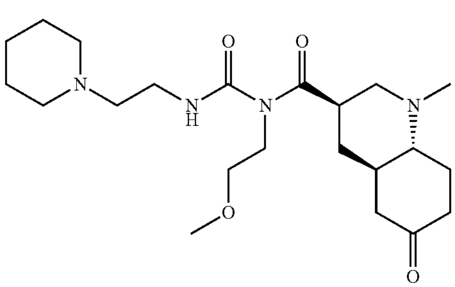 [SMILES: COCCN(C(=O)NCCN1CCCCC1)C(=O)[C@@H]1C[C@@H]2CC(=O)CC[C@H]2N(C)C1] |
| 10-69 | |
| 10-70 | |
| 10-71 | |
| 10-72 | |
| 10-73 | |

TABLE 9-continued

| Reference example | Structure |
|---|---|
| 10-74 | 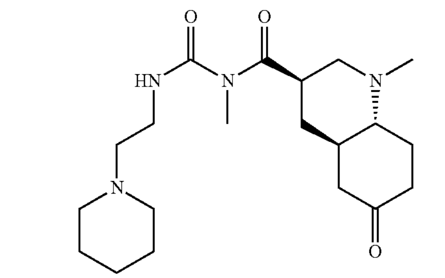 [SMILES: CN(C(=O)NCCN1CCCCC1)C(=O)[C@@H]1C[C@@H]2CC(=O)CC[C@H]2N(C)C1] |
| 10-75 | 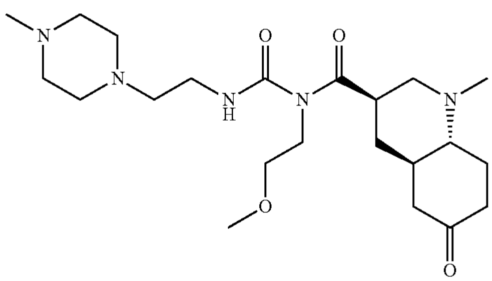 |
| 10-76 | 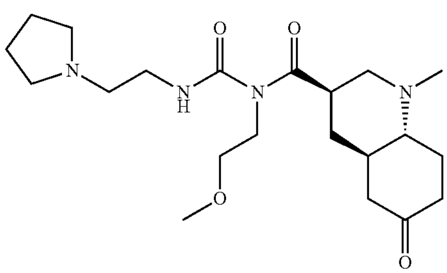 [SMILES: COCCN(C(=O)NCCN1CCCC1)C(=O)[C@@H]1C[C@@H]2CC(=O)CC[C@H]2N(C)C1] |
| 10-77 | 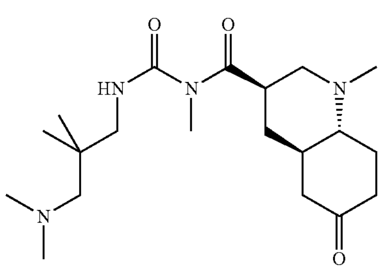 |
| 10-78 | 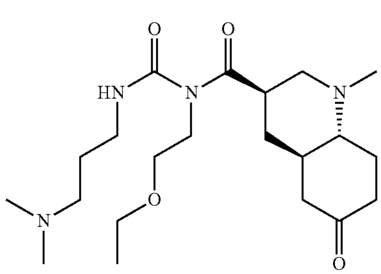 |

TABLE 9-continued

| Reference example | Structure |
|---|---|
| 10-79 | 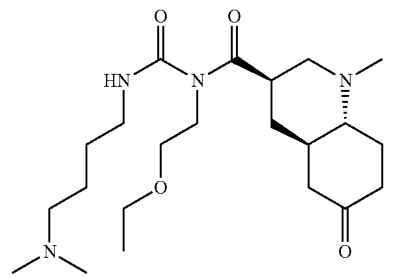 |
| 10-80 | 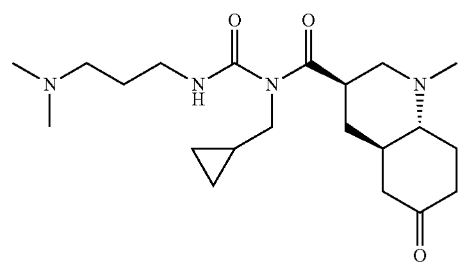 |
| 10-81 | 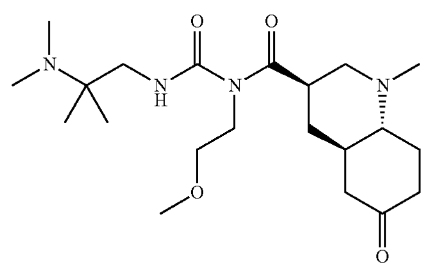 |
| 10-82 | 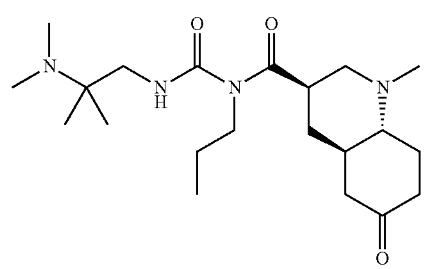 |
| 10-83 | 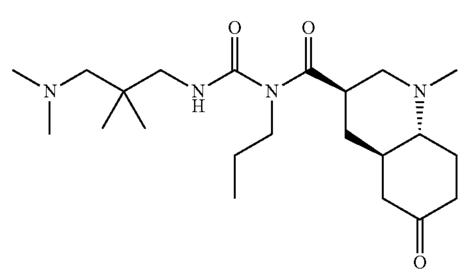 |

TABLE 9-continued

| Reference example | Structure |
|---|---|
| 10-84 | 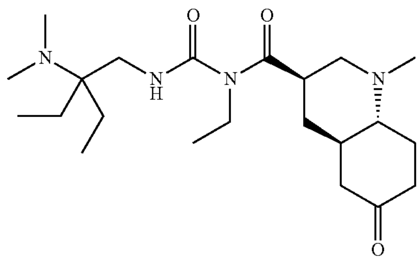 |
| 10-85 | 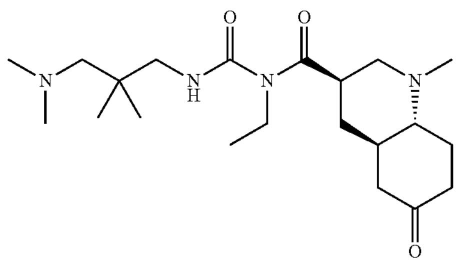 |
| 10-86 | 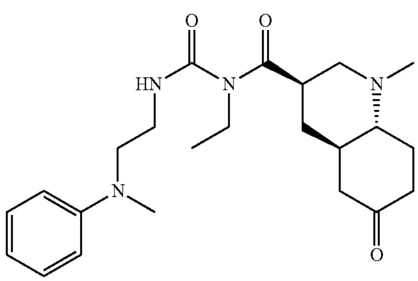 [SMILES: CCN(C(=O)NCCN(C)c1ccccc1)C(=O)[C@@H]1C[C@@H]2CC(=O)CC[C@H]2N(C)C1] |
| 10-87 | 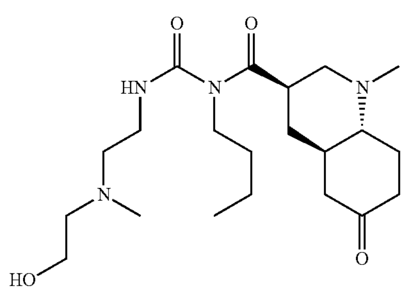 [SMILES: CCCCN(C(=O)NCCN(C)CCO)C(=O)[C@@H]1C[C@@H]2CC(=O)CC[C@H]2N(C)C1] |
| 10-88 | 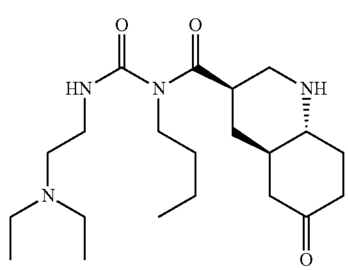 [SMILES: CCCCN(C(=O)NCCN(CC)CC)C(=O)[C@H]1CN[C@@H]2CCC(=O)C[C@H]2C1] |
| 10-89 | |
| 10-90 | |
| 10-91 | |
| 10-92 | |
| 10-93 | |

TABLE 9-continued

| Reference example | Structure |
|---|---|
| 10-94 | 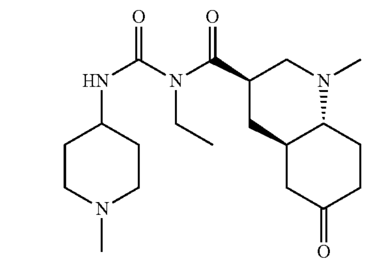 [SMILES: CCN(C(=O)NC1CCN(C)CC1)C(=O)[C@@H]1C[C@@H]2CC(=O)CC[C@H]2N(C)C1] |
| 10-95 | 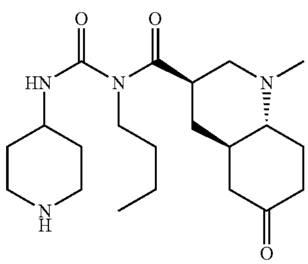 [SMILES: CCCCN(C(=O)NC1CCNCC1)C(=O)[C@@H]1C[C@@H]2CC(=O)CC[C@H]2N(C)C1] |
| 10-96 | 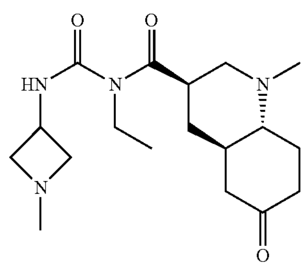 [SMILES: CCN(C(=O)NC1CN(C)C1)C(=O)[C@@H]1C[C@@H]2CC(=O)CC[C@H]2N(C)C1] |
| 10-97 | 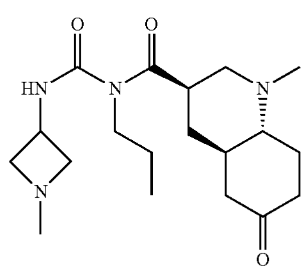 [SMILES: CCCN(C(=O)NC1CN(C)C1)C(=O)[C@@H]1C[C@@H]2CC(=O)CC[C@H]2N(C)C1] |
| 10-98 | 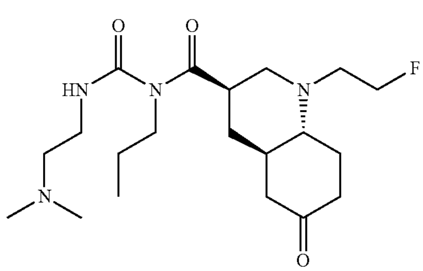 [SMILES: CCCN(C(=O)NCCN(C)C)C(=O)[C@@H]1C[C@@H]2CC(=O)CC[C@H]2N(CCF)C1] |
| 10-99 | |
| 10-100 | |
| 10-101 | |
| 10-102 | (Chiral) |
| 10-103 | (Chiral) |

TABLE 9-continued

| Reference example | Structure |
|---|---|
| 10-104 | (Chiral) |
| 10-105 | (Chiral) |
| 10-106 | (Chiral) |
| 10-107 | (Chiral) |
| 10-108 | 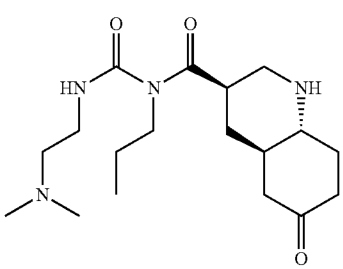 [SMILES: CCCN(C(=O)NCCN(C)C)C(=O)[C@H]1CN[C@@H]2CCC(=O)C[C@H]2C1] |

The structures of the reference example 10-1 to 10-6, 10-57 and 10-102 to 10-107 in Table 9 indicate absolute configuration, and the structures of the reference example 10-7 to 10-56, 10-58 to 10-101 and 10-108 in Table 9 indicate relative configuration.

The physical data of reference examples 10-2 to 10-6 and reference examples 10-8 to 10-108 were shown below.

Reference Example 10-2

MS (ESI, m/z): 353 (M+H)+

Reference Example 10-3

MS (ESI, m/z): 409 (M+H)+

Reference Example 10-4

$^1$H-NMR (CDCl$_3$) δ ppm: 0.91 (6H, s), 1.23 (3H, t, J=7.2 Hz), 1.50-1.65 (2H, m), 1.70-1.90 (2H, m), 1.95-2.10 (1H, m), 2.10-2.60 (17H, m), 2.95-3.15 (2H, m), 3.20 (2H, d, J=5.6 Hz), 3.75-3.90 (2H, m), 9.35 (1H, brs)

Reference Example 10-5

MS (ESI, m/z): 441 (M+H)+

Reference Example 10-6

MS (ESI, m/z): 379 (M+H)+

Reference Example 10-8

MS (ESI, m/z): 395 (M+H)+

Reference Example 10-9

MS (ESI, m/z): 381 (M+H)+

Reference Example 10-10

MS (ESI, m/z): 353 (M+H)+

Reference Example 10-11

MS (ESI, m/z): 381 (M+H)+

Reference Example 10-12

MS (ESI, m/z): 379 (M+H)+

Reference Example 10-13

$^1$H-NMR (CDCl$_3$) δ ppm: 0.86 (3H, t, J=7.3 Hz), 1.16 (3H, t, J=7.3 Hz), 1.40-1.65 (4H, m), 1.65-1.95 (4H, m), 2.10-2.25 (7H, m), 2.25-2.60 (9H, m), 2.60-2.75 (1H, m), 3.00-3.10 (1H, m), 3.10-3.35 (3H, m), 3.60-3.85 (2H, m), 9.40 (1H, brs)

Reference Example 10-14

$^1$H-NMR (CDCl$_3$) δ ppm: 1.03 (3H, t, J=7.1 Hz), 1.17 (3H, t, J=7.3 Hz), 1.40-1.65 (2H, m), 1.65-1.95 (4H, m), 2.10-2.25 (7H, m), 2.25-2.50 (7H, m), 2.55 (1H, t, J=11.1 Hz), 2.70-2.90 (2H, m), 2.95-3.10 (1H, m), 3.10-3.35 (3H, m), 3.60-3.85 (2H, m), 9.41 (1H, brs)

Reference Example 10-15

$^1$H-NMR (CDCl$_3$) δ ppm: 0.94 (3H, t, J=7.6 Hz), 1.40-1.70 (4H, m), 1.70-1.90 (2H, m), 1.90-2.10 (1H, m), 2.10-2.60 (17H, m), 2.90-3.10 (2H, m), 3.30-3.50 (2H, m), 3.60-3.80 (2H, m), 9.22 (1H, brs)

Reference Example 10-16

MS (ESI, m/z): 367 (M+H)+

Reference Example 10-17

MS (ESI, m/z): 353 (M+H)+

Reference Example 10-18

MS (ESI, m/z): 381 (M+H)+

Reference Example 10-19

MS (ESI, m/z): 324 (M+H)+

Reference Example 10-20

MS (ESI, m/z): 386 (M+H)+

Reference Example 10-21

MS (ESI, m/z): 354 (M+H)+

Reference Example 10-22

MS (ESI, m/z): 340 (M+H)+

Reference Example 10-23

MS (ESI, m/z): 296 (M+H)+

Reference Example 10-24

MS (ESI, m/z): 381 (M+H)+

Reference Example 10-25

MS (ESI, m/z): 373 (M+H)+

Reference Example 10-26

MS (ESI, m/z): 365 (M+H)+

Reference Example 10-27

MS (ESI, m/z): 397 (M+H)+

Reference Example 10-28

MS (ESI, m/z): 415 (M+H)+

Reference Example 10-29

MS (ESI, m/z): 354 (M+H)+

Reference Example 10-30

MS (ESI, m/z): 429 (M+H)+

Reference Example 10-31

MS (ESI, m/z): 387 (M+H)+

Reference Example 10-32

MS (ESI, m/z): 393 (M+H)+

Reference Example 10-33

MS (ESI, m/z): 373 (M+H)+

Reference Example 10-34

MS (ESI, m/z): 381 (M+H)+

Reference Example 10-35

MS (ESI, m/z): 381 (M+H)+

Reference Example 10-36

MS (ESI, m/z): 379 (M+H)+

Reference Example 10-37

MS (ESI, m/z): 421 (M+H)+

Reference Example 10-38

MS (ESI, m/z): 422 (M+H)+

Reference Example 10-39

MS (ESI, m/z): 365 (M+H)+

Reference Example 10-40

MS (ESI, m/z): 395 (M+H)+

Reference Example 10-41

MS (ESI, m/z): 421 (M+H)+

Reference Example 10-42

MS (ESI, m/z): 429 (M+H)+

Reference Example 10-43

MS (ESI, m/z): 395 (M+H)+

Reference Example 10-44

MS (ESI, m/z): 457 (M+H)+

Reference Example 10-45

MS (ESI, m/z): 409 (M+H)+

Reference Example 10-46

MS (ESI, m/z): 421 (M+H)+

Reference Example 10-47

MS (ESI, m/z): 407 (M+H)+

Reference Example 10-48

$^1$H-NMR (CDCl$_3$) δ ppm: 0.94 (3H, t, J=6.0 Hz), 1.02 (6H, t, J=5.6 Hz), 1.45-1.90 (6H, m), 1.95-2.10 (1H, m), 2.15-2.25 (1H, m), 2.30-2.65 (14H, m), 2.90-3.10 (2H, m), 3.30-3.40 (2H, m), 3.60-3.80 (2H, m), 9.17 (1H, brs)

Reference Example 10-49

$^1$H-NMR (CDCl$_3$) δ ppm: 0.94 (3H, t, J=6.0 Hz), 1.29-1.90 (12H, m), 1.95-2.05 (1H, m), 2.10-2.25 (1H, m), 2.25-2.55 (14H, m), 2.90-3.10 (2H, m), 3.30-3.45 (2H, m), 3.60-3.80 (2H, m), 9.14 (1H, brs)

Reference Example 10-50

$^1$H-NMR (CDCl$_3$) δ ppm: 1.16 (3H, t, J=7.0 Hz), 1.40-1.65 (2H, m), 1.65-2.05 (4H, m), 2.10-2.55 (16H, m), 2.95-3.10 (1H, m), 3.30-3.65 (7H, m), 3.85-4.10 (2H, m), 9.09 (1H, br)

Reference Example 10-51

MS (ESI, m/z): 390 (M+H)+

Reference Example 10-52

MS (ESI, m/z): 421 (M+H)+

Reference Example 10-53

MS (ESI, m/z): 376 (M+H)+

Reference Example 10-54

MS (ESI, m/z): 443 (M+H)+

Reference Example 10-55

MS (ESI, m/z): 367 (M+H)+

Reference Example 10-56

MS (ESI, m/z): 395 (M+H)+

Reference Example 10-57

MS (ESI, m/z): 367 (M+H)+
[α]$_D^{28}$=−8.96° (c=0.43, MeOH)

Reference Example 10-58

MS (ESI, m/z): 395 (M+H)+

Reference Example 10-59

MS (ESI, m/z): 409 (M+H)+

Reference Example 10-60

MS (ESI, m/z): 437 (M+H)+

Reference Example 10-61

MS (ESI, m/z): 435 (M+H)+

Reference Example 10-62

MS (ESI, m/z): 381 (M+H)+

Reference Example 10-63

MS (ESI, m/z): 395 (M+H)+

Reference Example 10-64

MS (ESI, m/z): 450 (M+H)+

Reference Example 10-65

MS (ESI, m/z): 381 (M+H)+

Reference Example 10-66

MS (ESI, m/z): 436 (M+H)+

Reference Example 10-67

MS (ESI, m/z): 411 (M+H)+

Reference Example 10-68

MS (ESI, m/z): 423 (M+H)+

Reference Example 10-69

MS (ESI, m/z): 397 (M+H)+

Reference Example 10-70

MS (ESI, m/z): 411 (M+H)+

Reference Example 10-71

MS (ESI, m/z): 367 (M+H)+

Reference Example 10-72

MS (ESI, m/z): 397 (M+H)+

Reference Example 10-73

MS (ESI, m/z): 365 (M+H)+

Reference Example 10-74

MS (ESI, m/z): 379 (M+H)+

Reference Example 10-75

MS (ESI, m/z): 438 (M+H)+

Reference Example 10-76

MS (ESI, m/z): 409 (M+H)+

Reference Example 10-77

$^1$H-NMR (CDCl$_3$) δ ppm: 0.92 (6H, s), 1.45-1.65 (2H, m), 1.70-1.95 (2H, m), 1.95-2.10 (1H, m), 2.10-2.55 (17H, m), 2.95-3.05 (1H, m), 3.10-3.25 (3H, m), 3.34 (3H, s), 9.30-9.50 (1H, m)

Reference Example 10-78

MS (ESI, m/z): 411 (M+H)+

Reference Example 10-79

MS (ESI, m/z): 425 (M+H)+

Reference Example 10-80

$^1$H-NMR (CDCl$_3$) δ ppm: 0.35-0.45 (2H, m), 0.45-0.55 (2H, m), 0.90-1.05 (1H, m), 1.45-1.65 (2H, m), 1.65-1.90

(4H, m), 1.95-2.10 (1H, m), 2.15-2.30 (7H, m), 2.30-2.55 (10H, m), 2.95-3.05 (1H, m), 3.15-3.40 (3H, m), 3.65-3.85 (2H, m), 9.25 (1H, brs)

Reference Example 10-81

MS (ESI, m/z): 411 (M+H)+

Reference Example 10-82

MS (ESI, m/z): 395 (M+H)+

Reference Example 10-83

MS (ESI, m/z): 409 (M+H)+

Reference Example 10-84

MS (ESI, m/z): 409 (M+H)+

Reference Example 10-85

MS (ESI, m/z): 395 (M+H)+

Reference Example 10-86

MS (ESI, m/z): 415 (M+H)+

Reference Example 10-87

MS (ESI, m/z): 411 (M+H)+

Reference Example 10-88

MS (ESI, m/z): 395 (M+H)+

Reference Example 10-89

MS (ESI, m/z): 407 (M+H)+

Reference Example 10-90

MS (ESI, m/z): 367 (M+H)+

Reference Example 10-91

MS (ESI, m/z): 381 (M+H)+

Reference Example 10-92

MS (ESI, m/z): 367 (M+H)+

Reference Example 10-93

MS (ESI, m/z): 385 (M+H)+

Reference Example 10-94

MS (ESI, m/z): 379 (M+H)+

Reference Example 10-95

MS (ESI, m/z): 393 (M+H)+

Reference Example 10-96

MS (ESI, m/z): 351 (M+H)+

Reference Example 10-97

MS (ESI, m/z): 365 (M+H)+

Reference Example 10-98

$^1$H-NMR (CDCl$_3$) δ ppm: 0.95 (3H, t, J=7.6 Hz), 1.40-1.90 (6H, m), 2.10-2.60 (14H, m), 2.60-2.80 (1H, m), 2.80-3.15 (4H, m), 3.30-3.45 (2H, m), 3.60-3.80 (2H, m), 4.40-4.80 (2H, m), 9.19 (1H, brs)

Reference Example 10-99

$^1$H-NMR (CDCl$_3$) δ ppm: 0.95 (3H, t, J=7.2 Hz), 1.40-1.90 (4H, m), 2.10-2.27 (7H, m), 2.27-2.70 (8H, m), 2.80-3.05 (2H, m), 3.05-3.34 (4H, m), 3.34-3.45 (2H, m), 3.60-3.80 (2H, m), 9.14 (1H, brs)

Reference Example 10-100

$^1$H-NMR (CDCl$_3$) δ ppm: 0.92 (6H, s), 1.24 (3H, t, J=7.0 Hz), 1.45-1.70 (2H, m), 1.70-1.90 (2H, m), 2.10-2.55 (14H, m), 2.65-2.80 (1H, m), 2.85-3.15 (4H, m), 3.20 (2H, d, J=5.5 Hz), 3.75-3.90 (2H, m), 4.40-4.75 (2H, m), 9.31 (1H, brs)

Reference Example 10-101

MS (ESI, m/z): 463 (M+H)+

Reference Example 10-102

$^1$H-NMR (CDCl$_3$) δ ppm: 0.30-0.45 (2H, m), 0.45-0.55 (2H, m), 0.70-1.10 (7H, m), 1.45-1.65 (3H, m), 1.70-1.95 (2H, m), 1.95-2.10 (1H, m), 2.10-2.55 (16H, m), 2.90-3.10 (1H, m), 3.10-3.30 (3H, m), 3.60-3.85 (2H, m), 9.35 (1H, brs)
$[α]_D^{28}$=−21.70° (c=0.39, MeOH)

Reference Example 10-103

$^1$H-NMR (CDCl$_3$) δ ppm: 1.02 (6H, t, J=7.2 Hz), 1.24 (3H, t, J=7.2 Hz), 1.45-1.65 (2H, m), 1.70-1.90 (2H, m), 1.95-2.10 (1H, m), 2.10-2.25 (1H, m), 2.28-2.65 (14H, m), 2.90-3.10 (2H, m), 3.30-3.40 (2H, m), 3.80-3.90 (2H, m), 9.18 (1H, brs)
$[α]_D^{28}$=−31.40° (c=0.28, MeOH)

Reference Example 10-104

$^1$H-NMR (CDCl$_3$) δ ppm: 1.22 (3H, t, J=7.2 Hz), 1.34 (6H, s), 1.45-1.70 (2H, m), 1.70-1.90 (2H, m), 1.95-2.10 (1H, m), 2.10-2.26 (1H, m), 2.27-2.55 (16H, m), 2.90-3.10 (2H, m), 3.70-3.90 (2H, m), 9.27 (1H, brs)
$[α]_D^{28}$=−20.69° (c=0.29, MeOH)

Reference Example 10-105

$^1$H-NMR (CDCl$_3$) δ ppm: 0.87 (6H, t, J=7.5 Hz), 1.24 (3H, t, J=7.0 Hz), 1.35-2.55 (24H, m), 2.95-3.15 (2H, m), 3.29 (2H, d, J=4.8 Hz), 3.75-3.90 (2H, m), 9.00-9.50 (1H, m)
$[α]_D^{28}$=−21.47° (c=0.44, MeOH)

Reference Example 10-106

$^1$H-NMR (CDCl$_3$) δ ppm: 1.25 (3H, t, J=7.1 Hz), 1.40-2.55 (22H, m), 2.90-3.10 (2H, m), 3.30-3.45 (2H, m), 3.80-3.90 (2H, m), 9.00-9.45 (1H, m)
$[α]_D^{27}$=−35.33° (c=0.42, MeOH)

Reference Example 10-107

$^1$H-NMR (CDCl$_3$) δ ppm: 0.30-0.45 (2H, m), 0.45-0.60 (2H, m), 0.90-1.05 (1H, m), 1.45-1.65 (2H, m), 1.70-1.90

(3H, m), 1.95-2.10 (1H, m), 2.10-2.55 (16H, m), 2.90-3.05 (1H, m), 3.10-3.25 (1H, m), 3.30-3.45 (2H, m), 3.65-3.85 (2H, m), 9.19 (1H, brs)

$[\alpha]_D^{28}$=−20.70° (c=0.28, MeOH)

Reference Example 10-108

MS (ESI, m/z): 353 (M+H)+

Example 1-1

1-{[(4aR,6R,8aR)-2-Amino-3-cyano-8-methyl-4H,4aH,5H,6H,7H,8H,8aH,9H-thieno-[3,2-g]quinolin-6-yl]carbonyl}-3-[2-(dimethylamino)ethyl]-1-propylurea (compound 1-1)

To a mixture of 1-{[(3R,4aR,8aR)-1-methyl-6-oxodecahydroquinolin-3-yl]-carbonyl}-3-[2-(dimethylamino)ethyl]-1-propylurea (reference example 10-1) (1.602 g) and ethanol (44 mL) were added malononitrile (435 mg), morpholine (0.572 mL), followed by elemental sulfer (282 mg) while stirring at room temperature. The mixture was heated at 55° C. and stirred for 1.5 hours. After cooling to room temperature, the reaction mixture was concentrated under reduced pressure. The residue was purified by aminopropyl silica gel column chromatography (eluent: 0%-5% methanol/ethyl acetate, gradient elution) to give the title compound (1.479 g) as a solid.

$^{1}$H-NMR (CDCl$_3$) δ ppm: 0.94 (3H, t, J=7.4 Hz), 1.45-1.85 (4H, m), 1.95-2.15 (2H, m), 2.15-2.30 (7H, m), 2.30-2.55 (7H, m), 2.60-2.75 (1H, m), 2.90-3.00 (2H, m), 3.00-3.10 (1H, m), 3.35-3.45 (2H, m), 3.60-3.85 (2H, m), 4.65 (2H, s), 9.27 (1H, br)

$[\alpha]_D^{29}$=−105.54° (c=0.30, MeOH)

Example 1-7

1-{[(4aR*,6R*,8aR*)-2-Amino-3-cyano-8-methyl-4H,4aH,5H,6H,7H,8H,8aH,9H-thieno[3,2-g]quinolin-6-yl]carbonyl}-1-[3-(dimethylamino)propyl]-3-ethylurea (compound 1-7)

To a mixture of 1-{[(3R*,4aR*,8aR*)-1-methyl-6-oxo-decahydroquinolin-3-yl]-carbonyl}-1-[3-(dimethylamino)propyl]-3-ethylurea (reference example 10-7) (216 mg) and ethanol (6 mL) were added malononitrile (71 mg), morpholine (0.077 mL), followed by elemental sulfer (39 mg) while stirring at room temperature, and the mixture was heated at 55° C. and stirred for 2 hours. After cooling to room temperature, the reaction mixture was concentrated under reduced pressure. The residue was purified by aminopropyl silica gel column chromatography (eluent: 0%-5% methanol/ethyl acetate, gradient elution) to give the title compound (201 mg) as a solid.

$^{1}$H-NMR (CDCl$_3$) δ ppm: 1.17 (3H, t, J=7.3 Hz), 1.40-1.55 (1H, m), 1.65-1.90 (3H, m), 1.95-2.15 (2H, m), 2.15-2.25 (7H, m), 2.25-2.45 (7H, m), 2.60-2.70 (1H, m), 2.85-3.05 (2H, m), 3.20-3.40 (3H, m), 3.65-3.85 (2H, m), 4.64 (2H, s), 9.44 (1H, brs)

Compounds 1-2 to 1-6 and compounds 1-8 to 1-110 were prepared in a manner similar to those as described in example 1-1 or example 1-7 using the corresponding octahydroquinolines and methyl 2-cyanoacetate or 2-cyanoacetamide instead of 1-{[(3R,4aR,8aR)-1-methyl-6-oxodecahydroquinolin-3-yl]carb-only}-3-[2-(dimethylamino)ethyl]-1-propylurea and malononitrile. These were illustrated in Table 10.

TABLE 10

| Compound No. | Structure |
|---|---|
| 1-1 | (structure shown) |
| 1-2 | (structure shown) |

TABLE 10-continued
| Compound No. | Structure |
|---|---|
| 1-3 | 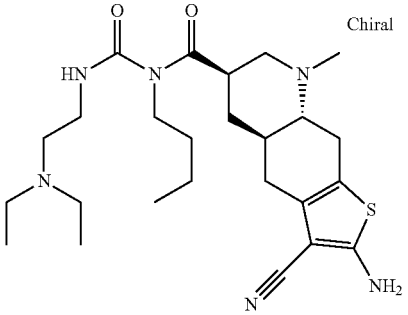 [SMILES: CCCCN(C(=O)NCCN(CC)CC)C(=O)[C@@H]1C[C@@H]2Cc3c(sc(N)c3C#N)C[C@H]2N(C)C1] |
| 1-4 | 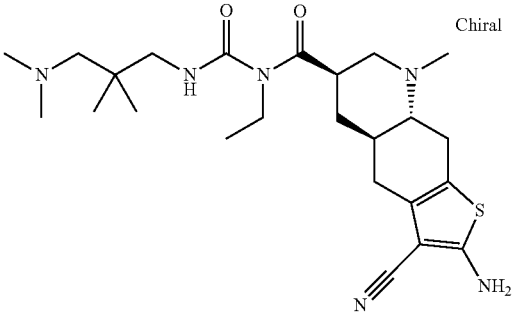 [SMILES: CCN(C(=O)NCC(C)(C)CN(C)C)C(=O)[C@@H]1C[C@@H]2Cc3c(sc(N)c3C#N)C[C@H]2N(C)C1] |
| 1-5 | 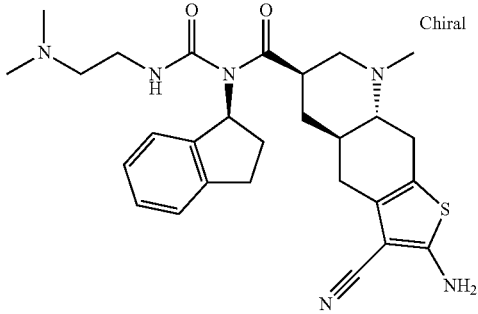 [SMILES: CN(C)CCNC(=O)N(C(=O)[C@@H]1C[C@@H]2Cc3c(sc(N)c3C#N)C[C@H]2N(C)C1)[C@H]1CCc2ccccc21] |
| 1-6 | 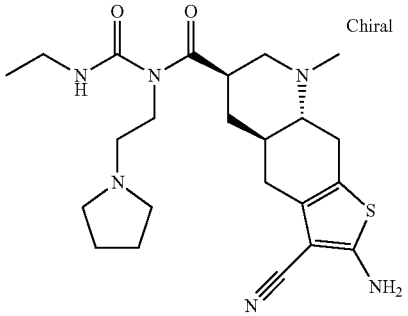 [SMILES: CCNC(=O)N(CCN1CCCC1)C(=O)[C@@H]1C[C@@H]2Cc3c(sc(N)c3C#N)C[C@H]2N(C)C1] |

TABLE 10-continued
| Compound No. | Structure |
|---|---|
| 1-7 | 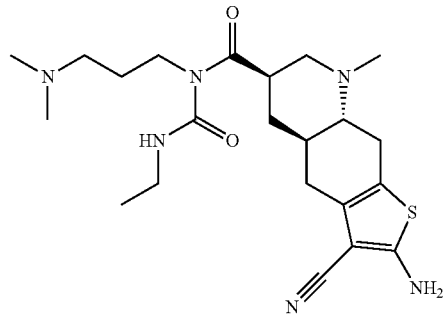 [SMILES: CCNC(=O)N(CCCN(C)C)C(=O)[C@@H]1C[C@@H]2Cc3c(sc(N)c3C#N)C[C@H]2N(C)C1] |
| 1-8 | 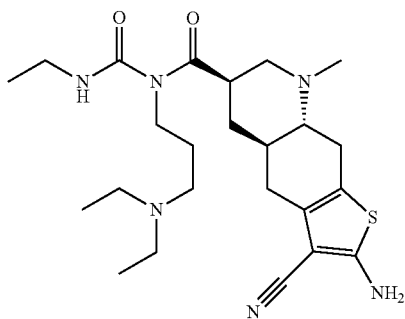 [SMILES: CCNC(=O)N(CCCN(CC)CC)C(=O)[C@@H]1C[C@@H]2Cc3c(sc(N)c3C#N)C[C@H]2N(C)C1] |
| 1-9 | 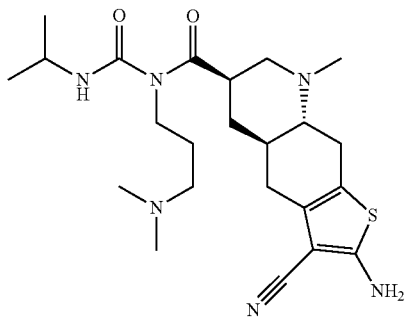 [SMILES: CC(C)NC(=O)N(CCCN(C)C)C(=O)[C@@H]1C[C@@H]2Cc3c(sc(N)c3C#N)C[C@H]2N(C)C1] |
| 1-10 | 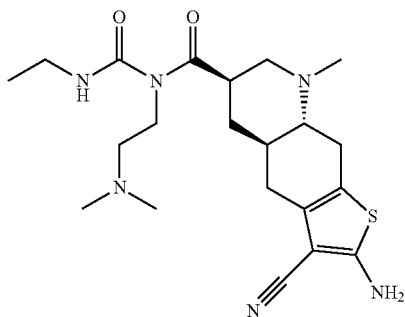 [SMILES: CCNC(=O)N(CCN(C)C)C(=O)[C@@H]1C[C@@H]2Cc3c(sc(N)c3C#N)C[C@H]2N(C)C1] |

TABLE 10-continued
| Compound No. | Structure |
|---|---|
| 1-11 | 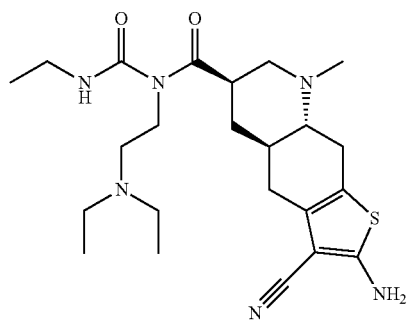 [SMILES: CCNC(=O)N(CCN(CC)CC)C(=O)[C@@H]1C[C@@H]2Cc3c(sc(N)c3C#N)C[C@H]2N(C)C1] |
| 1-12 | 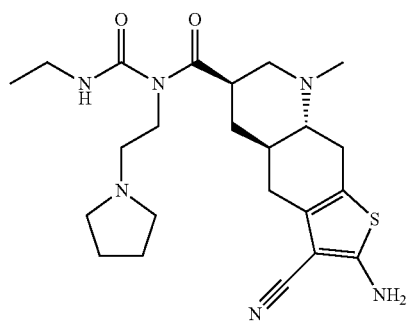 [SMILES: CCNC(=O)N(CCN1CCCC1)C(=O)[C@@H]1C[C@@H]2Cc3c(sc(N)c3C#N)C[C@H]2N(C)C1] |
| 1-13 | 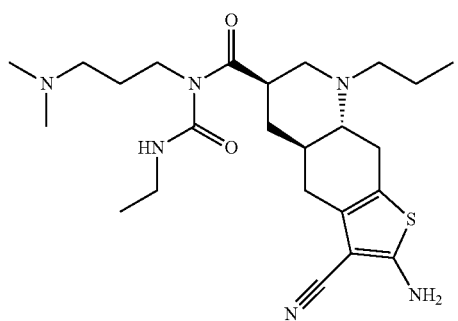 [SMILES: CCCN1C[C@H](C(=O)N(CCCN(C)C)C(=O)NCC)C[C@@H]2Cc3c(sc(N)c3C#N)C[C@H]21] |
| 1-14 | 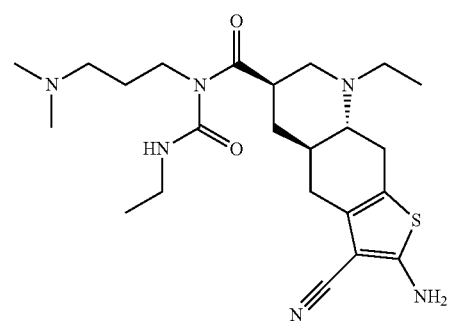 [SMILES: CCNC(=O)N(CCCN(C)C)C(=O)[C@@H]1C[C@@H]2Cc3c(sc(N)c3C#N)C[C@H]2N(CC)C1] |

TABLE 10-continued
| Compound No. | Structure |
|---|---|
| 1-15 | 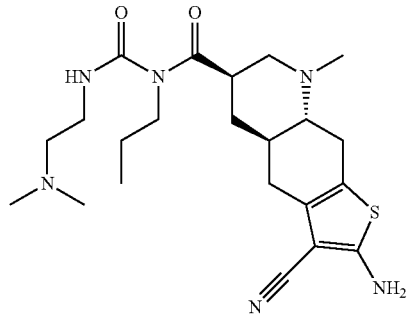 [SMILES: CCCN(C(=O)NCCN(C)C)C(=O)[C@@H]1C[C@@H]2Cc3c(sc(N)c3C#N)C[C@H]2N(C)C1] |
| 1-16 | 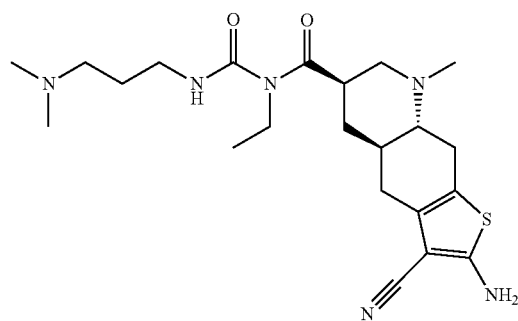 [SMILES: CCN(C(=O)NCCCN(C)C)C(=O)[C@@H]1C[C@@H]2Cc3c(sc(N)c3C#N)C[C@H]2N(C)C1] |
| 1-17 | 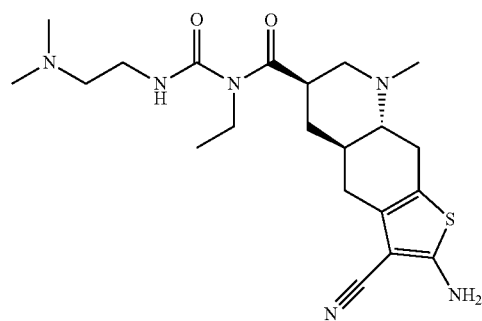 [SMILES: CCN(C(=O)NCCN(C)C)C(=O)[C@@H]1C[C@@H]2Cc3c(sc(N)c3C#N)C[C@H]2N(C)C1] |
| 1-18 | 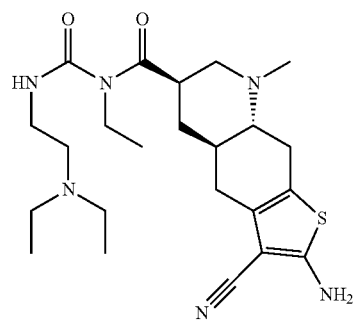 [SMILES: CCN(CC)CCNC(=O)N(CC)C(=O)[C@@H]1C[C@@H]2Cc3c(sc(N)c3C#N)C[C@H]2N(C)C1] |

TABLE 10-continued
| Compound No. | Structure |
|---|---|
| 1-19 | 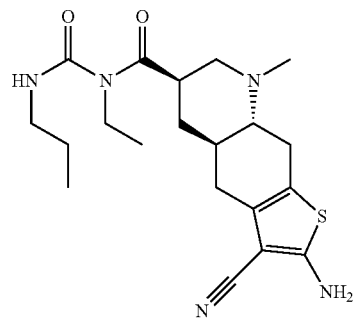 [SMILES: CCCNC(=O)N(CC)C(=O)[C@@H]1C[C@@H]2Cc3c(sc(N)c3C#N)C[C@H]2N(C)C1] |
| 1-20 | 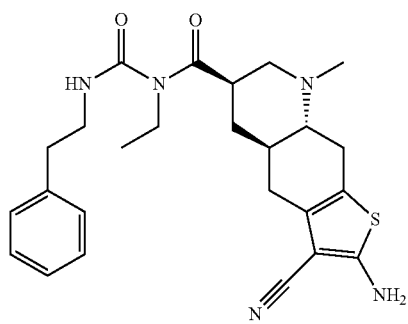 [SMILES: CCN(C(=O)NCCc1ccccc1)C(=O)[C@@H]1C[C@@H]2Cc3c(sc(N)c3C#N)C[C@H]2N(C)C1] |
| 1-21 | 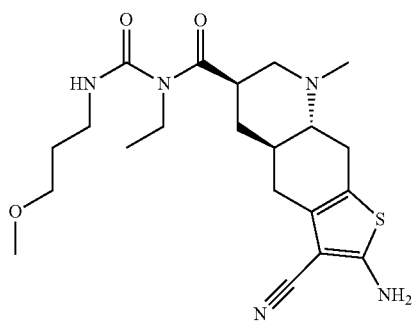 [SMILES: CCN(C(=O)NCCCOC)C(=O)[C@@H]1C[C@@H]2Cc3c(sc(N)c3C#N)C[C@H]2N(C)C1] |
| 1-22 | 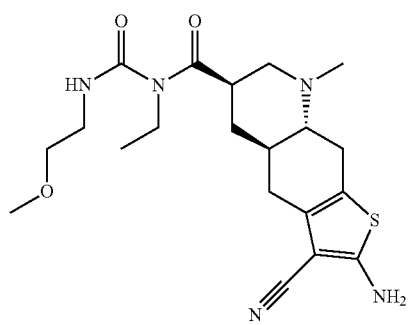 [SMILES: CCN(C(=O)NCCOC)C(=O)[C@@H]1C[C@@H]2Cc3c(sc(N)c3C#N)C[C@H]2N(C)C1] |

TABLE 10-continued

| Compound No. | Structure |
| --- | --- |
| 1-23 | 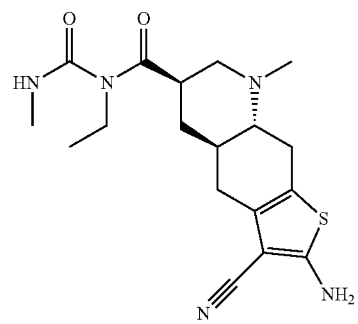 [SMILES: CCN(C(=O)NC)C(=O)[C@@H]1C[C@@H]2Cc3c(sc(N)c3C#N)C[C@H]2N(C)C1] |
| 1-24 | 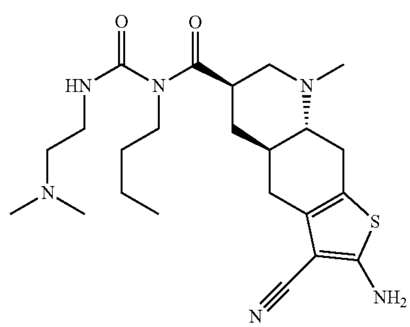 [SMILES: CCCCN(C(=O)NCCN(C)C)C(=O)[C@@H]1C[C@@H]2Cc3c(sc(N)c3C#N)C[C@H]2N(C)C1] |
| 1-25 | 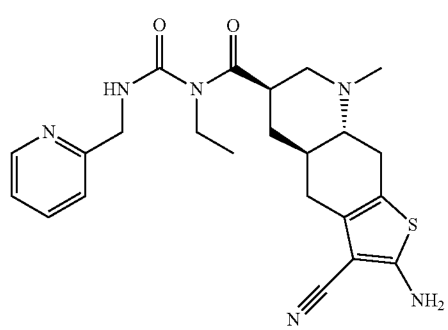 [SMILES: CCN(C(=O)NCc1ccccn1)C(=O)[C@@H]1C[C@@H]2Cc3c(sc(N)c3C#N)C[C@H]2N(C)C1] |
| 1-26 | 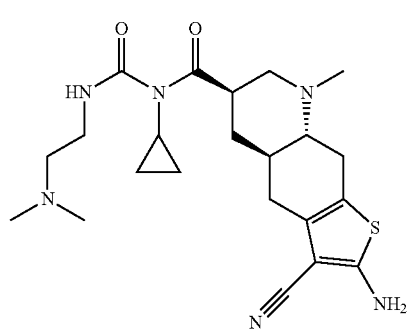 [SMILES: CN(C)CCNC(=O)N(C(=O)[C@@H]1C[C@@H]2Cc3c(sc(N)c3C#N)C[C@H]2N(C)C1)C1CC1] |

TABLE 10-continued

| Compound No. | Structure |
| --- | --- |
| 1-27 | 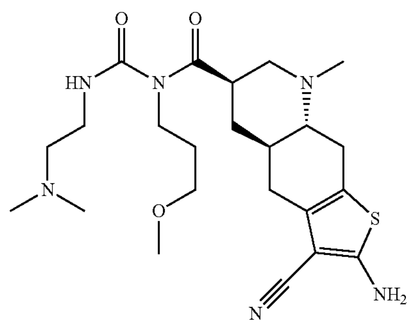 [SMILES: COCCCN(C(=O)NCCN(C)C)C(=O)[C@@H]1C[C@@H]2Cc3c(sc(N)c3C#N)C[C@H]2N(C)C1] |
| 1-28 | 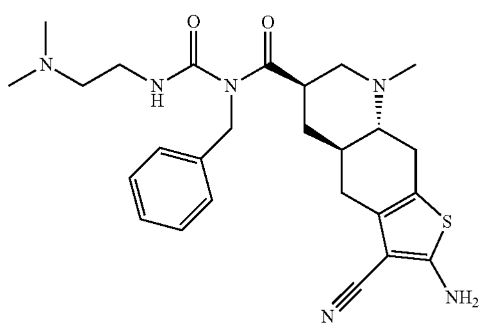 [SMILES: CN(C)CCNC(=O)N(Cc1ccccc1)C(=O)[C@@H]1C[C@@H]2Cc3c(sc(N)c3C#N)C[C@H]2N(C)C1] |
| 1-29 | 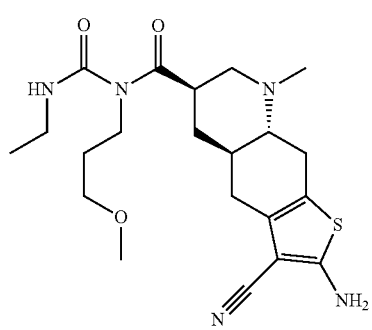 [SMILES: CCNC(=O)N(CCCOC)C(=O)[C@@H]1C[C@@H]2Cc3c(sc(N)c3C#N)C[C@H]2N(C)C1] |
| 1-30 | 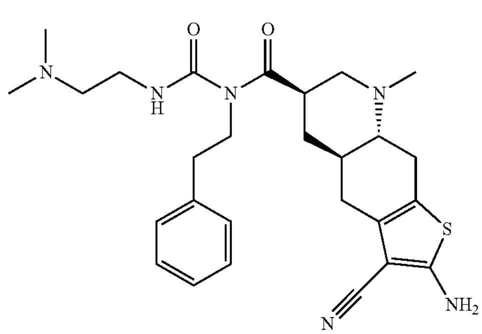 [SMILES: CN(C)CCNC(=O)N(CCc1ccccc1)C(=O)[C@@H]1C[C@@H]2Cc3c(sc(N)c3C#N)C[C@H]2N(C)C1] |

TABLE 10-continued
| Compound No. | Structure |
| --- | --- |
| 1-31 | 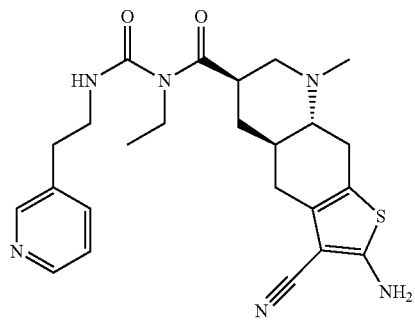 [SMILES: CCN(C(=O)NCCc1cccnc1)C(=O)[C@@H]1C[C@@H]2Cc3c(sc(N)c3C#N)C[C@H]2N(C)C1] |
| 1-32 | 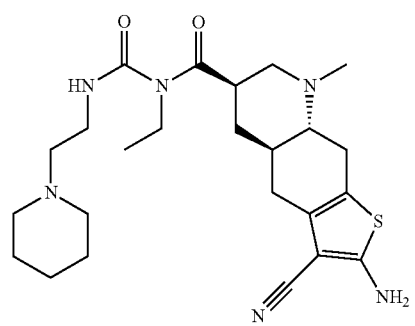 [SMILES: CCN(C(=O)NCCN1CCCCC1)C(=O)[C@@H]1C[C@@H]2Cc3c(sc(N)c3C#N)C[C@H]2N(C)C1] |
| 1-33 | 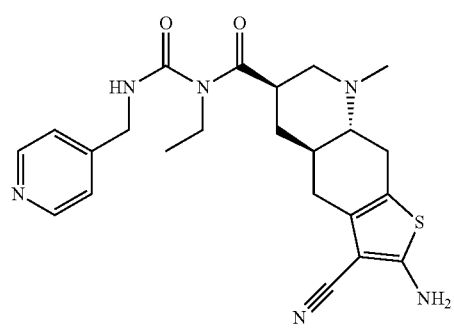 [SMILES: CCN(C(=O)NCc1ccncc1)C(=O)[C@@H]1C[C@@H]2Cc3c(sc(N)c3C#N)C[C@H]2N(C)C1] |
| 1-34 | 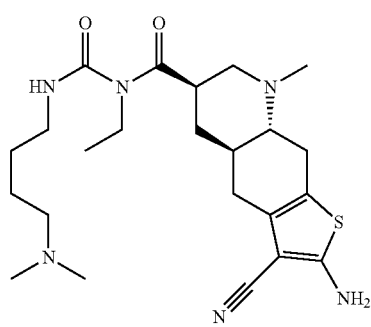 [SMILES: CCN(C(=O)NCCCCN(C)C)C(=O)[C@@H]1C[C@@H]2Cc3c(sc(N)c3C#N)C[C@H]2N(C)C1] |

TABLE 10-continued

| Compound No. | Structure |
| --- | --- |
| 1-35 | 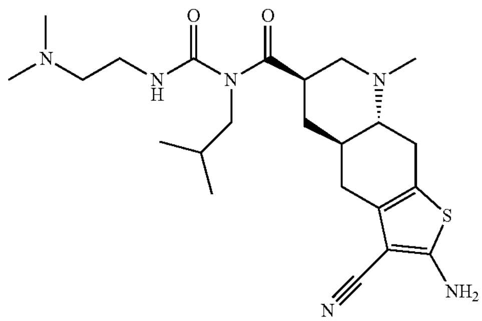 [SMILES: CC(C)CN(C(=O)NCCN(C)C)C(=O)[C@@H]1C[C@@H]2Cc3c(sc(N)c3C#N)C[C@H]2N(C)C1] |
| 1-36 | 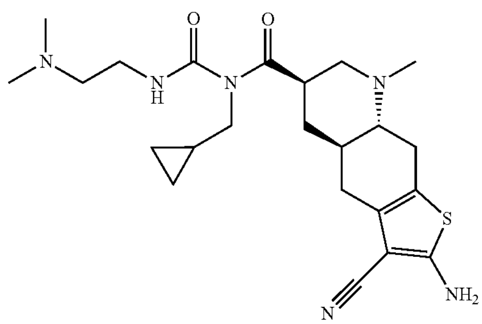 [SMILES: CN(C)CCNC(=O)N(CC1CC1)C(=O)[C@@H]1C[C@@H]2Cc3c(sc(N)c3C#N)C[C@H]2N(C)C1] |
| 1-37 | 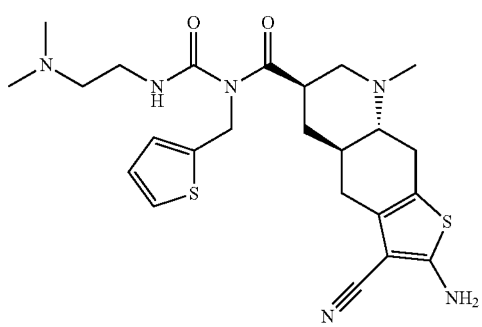 [SMILES: CN(C)CCNC(=O)N(Cc1cccs1)C(=O)[C@@H]1C[C@@H]2Cc3c(sc(N)c3C#N)C[C@H]2N(C)C1] |
| 1-38 | 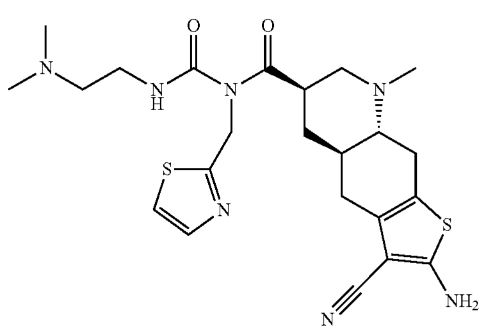 [SMILES: CN(C)CCNC(=O)N(Cc1nccs1)C(=O)[C@@H]1C[C@@H]2Cc3c(sc(N)c3C#N)C[C@H]2N(C)C1] |

TABLE 10-continued
| Compound No. | Structure |
|---|---|
| 1-39 | 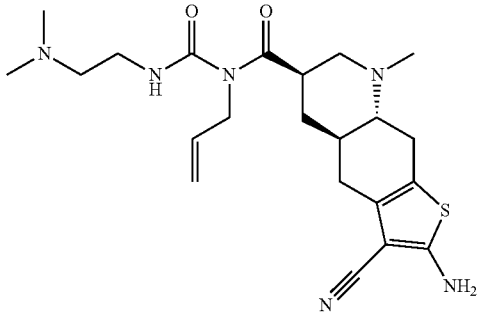 [SMILES: C=CCN(C(=O)NCCN(C)C)C(=O)[C@@H]1C[C@@H]2Cc3c(sc(N)c3C#N)C[C@H]2N(C)C1] |
| 1-40 | 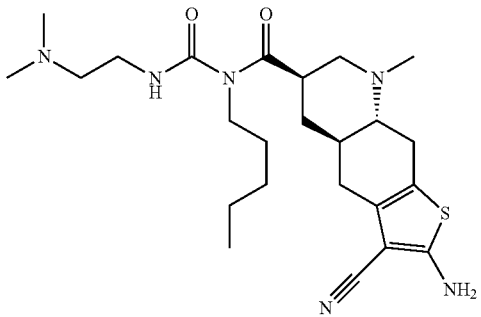 [SMILES: CCCCCN(C(=O)NCCN(C)C)C(=O)[C@@H]1C[C@@H]2Cc3c(sc(N)c3C#N)C[C@H]2N(C)C1] |
| 1-41 | 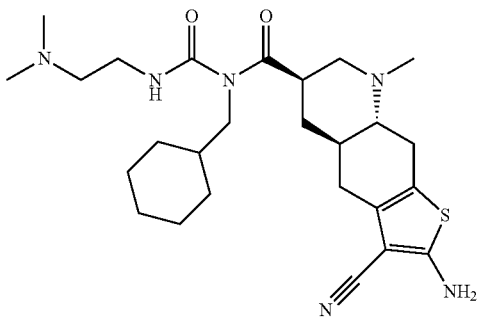 [SMILES: CN(C)CCNC(=O)N(CC1CCCCC1)C(=O)[C@@H]1C[C@@H]2Cc3c(sc(N)c3C#N)C[C@H]2N(C)C1] |
| 1-42 | 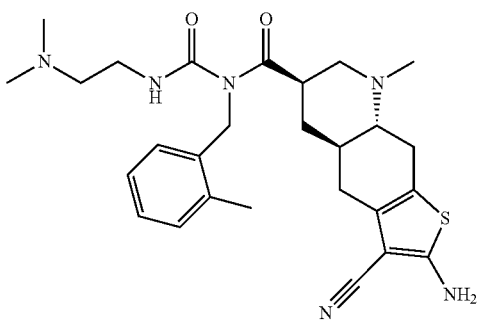 [SMILES: Cc1ccccc1CN(C(=O)NCCN(C)C)C(=O)[C@@H]1C[C@@H]2Cc3c(sc(N)c3C#N)C[C@H]2N(C)C1] |

TABLE 10-continued
| Compound No. | Structure |
|---|---|
| 1-43 | 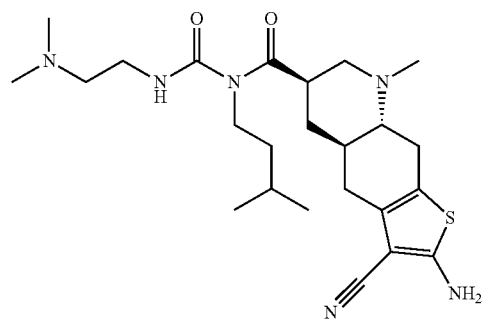 [SMILES: CC(C)CCN(C(=O)NCCN(C)C)C(=O)[C@@H]1C[C@@H]2Cc3c(sc(N)c3C#N)C[C@H]2N(C)C1] |
| 1-44 | 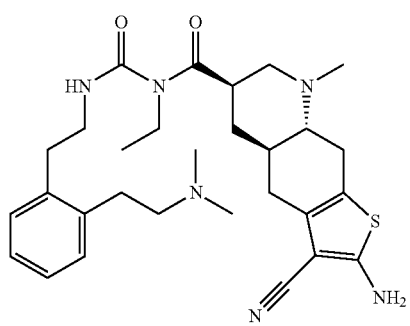 [SMILES: CCN(C(=O)NCCc1ccccc1CCN(C)C)C(=O)[C@@H]1C[C@@H]2Cc3c(sc(N)c3C#N)C[C@H]2N(C)C1] |
| 1-45 | 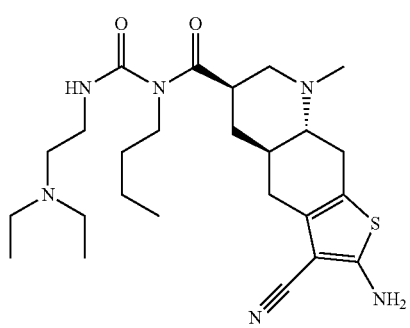 [SMILES: CCCCN(C(=O)NCCN(CC)CC)C(=O)[C@@H]1C[C@@H]2Cc3c(sc(N)c3C#N)C[C@H]2N(C)C1] |
| 1-46 | 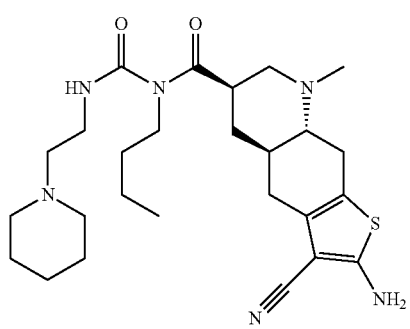 [SMILES: CCCCN(C(=O)NCCN1CCCCC1)C(=O)[C@@H]1C[C@@H]2Cc3c(sc(N)c3C#N)C[C@H]2N(C)C1] |

TABLE 10-continued

| Compound No. | Structure |
| --- | --- |
| 1-47 | 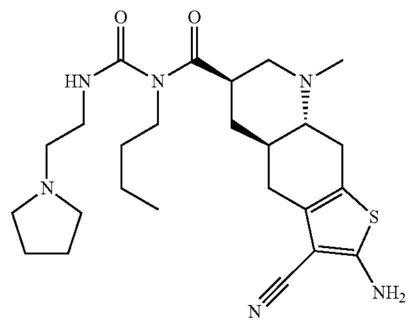 [SMILES: CCCCN(C(=O)NCCN1CCCC1)C(=O)[C@@H]1C[C@@H]2Cc3c(sc(N)c3C#N)C[C@H]2N(C)C1] |
| 1-48 | 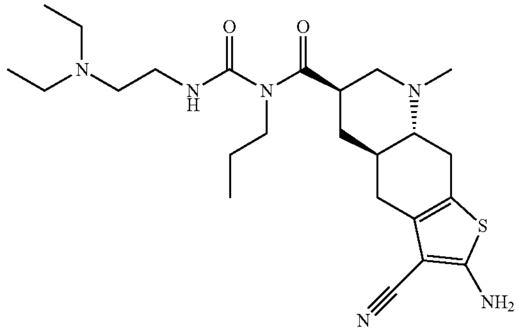 [SMILES: CCCN(C(=O)NCCN(CC)CC)C(=O)[C@@H]1C[C@@H]2Cc3c(sc(N)c3C#N)C[C@H]2N(C)C1] |
| 1-49 | 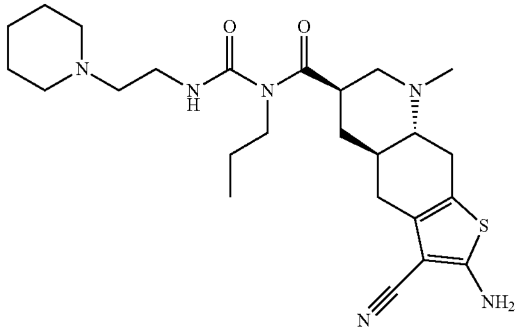 [SMILES: CCCN(C(=O)NCCN1CCCCC1)C(=O)[C@@H]1C[C@@H]2Cc3c(sc(N)c3C#N)C[C@H]2N(C)C1] |
| 1-50 | 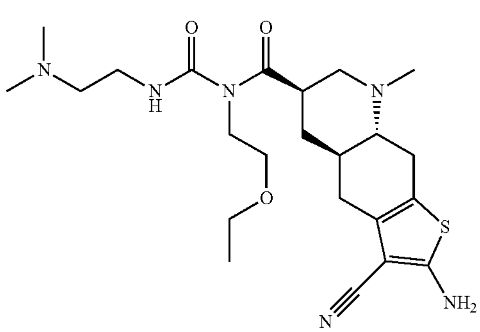 [SMILES: CCOCCN(C(=O)NCCN(C)C)C(=O)[C@@H]1C[C@@H]2Cc3c(sc(N)c3C#N)C[C@H]2N(C)C1] |

TABLE 10-continued

| Compound No. | Structure |
| --- | --- |
| 1-51 | 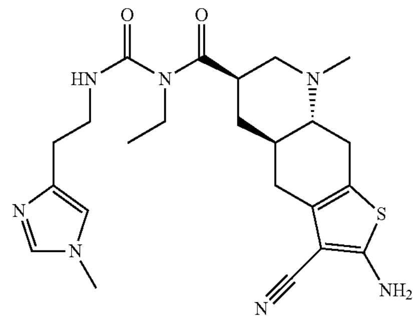 [SMILES: CCN(C(=O)NCCc1cn(C)cn1)C(=O)[C@@H]1C[C@@H]2Cc3c(sc(N)c3C#N)C[C@H]2N(C)C1] |
| 1-52 | 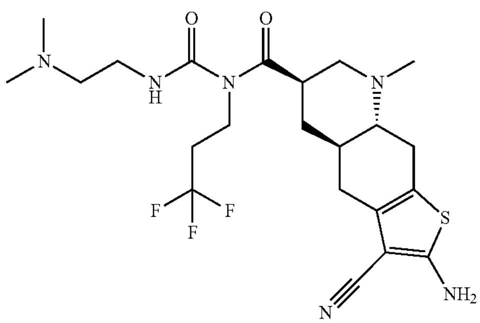 [SMILES: CN(C)CCNC(=O)N(CCC(F)(F)F)C(=O)[C@@H]1C[C@@H]2Cc3c(sc(N)c3C#N)C[C@H]2N(C)C1] |
| 1-53 | 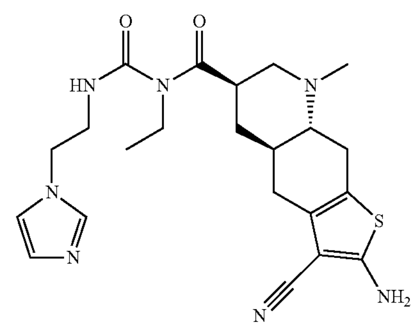 [SMILES: CCN(C(=O)NCCn1ccnc1)C(=O)[C@@H]1C[C@@H]2Cc3c(sc(N)c3C#N)C[C@H]2N(C)C1] |
| 1-54 | 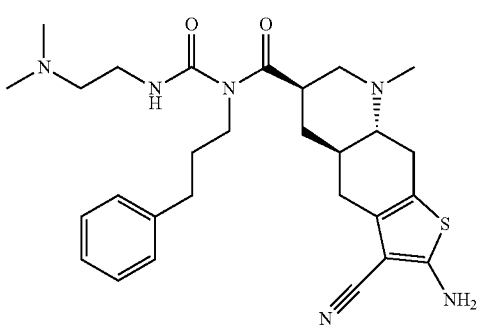 [SMILES: CN(C)CCNC(=O)N(CCCc1ccccc1)C(=O)[C@@H]1C[C@@H]2Cc3c(sc(N)c3C#N)C[C@H]2N(C)C1] |

TABLE 10-continued
| Compound No. | Structure |
|---|---|
| 1-55 | 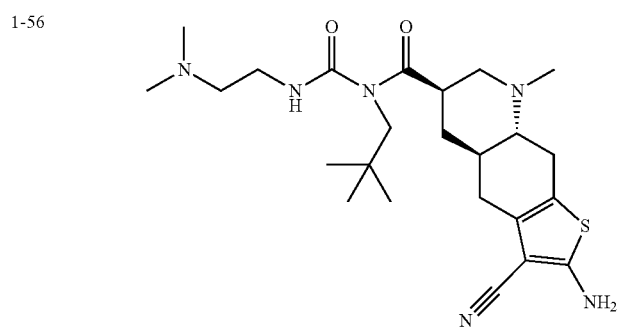 |
| 1-56 | 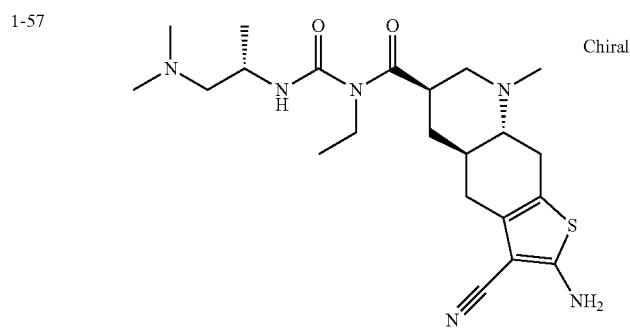 |
| 1-57 | Chiral |
| 1-58 | 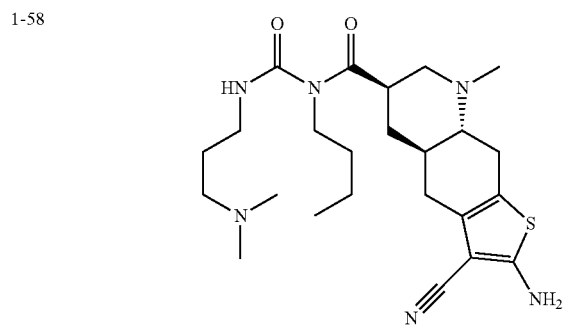 |

TABLE 10-continued

| Compound No. | Structure |
| --- | --- |
| 1-59 | 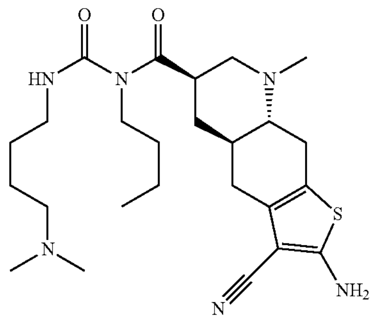 [SMILES: CCCCN(C(=O)NCCCCN(C)C)C(=O)[C@@H]1C[C@@H]2Cc3c(sc(N)c3C#N)C[C@H]2N(C)C1] |
| 1-60 | 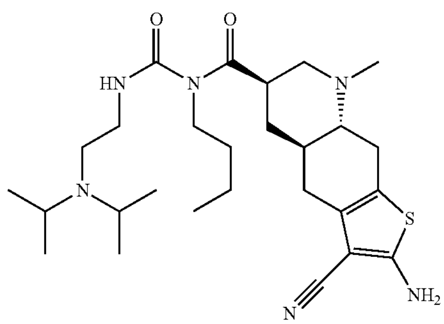 [SMILES: CCCCN(C(=O)NCCN(C(C)C)C(C)C)C(=O)[C@@H]1C[C@@H]2Cc3c(sc(N)c3C#N)C[C@H]2N(C)C1] |
| 1-61 | 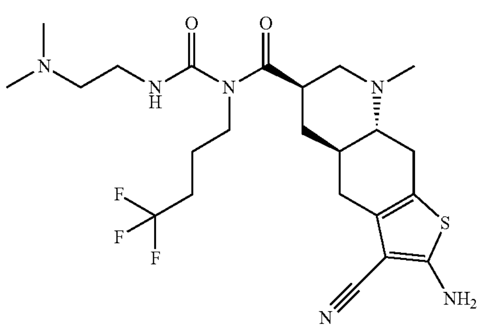 [SMILES: CN(C)CCNC(=O)N(CCCC(F)(F)F)C(=O)[C@@H]1C[C@@H]2Cc3c(sc(N)c3C#N)C[C@H]2N(C)C1] |
| 1-62 | 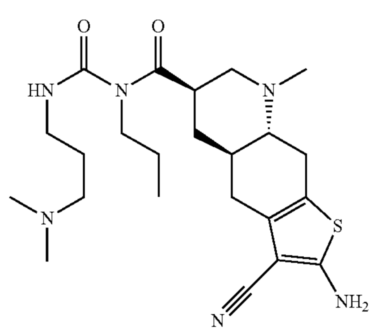 [SMILES: CCCN(C(=O)NCCCN(C)C)C(=O)[C@@H]1C[C@@H]2Cc3c(sc(N)c3C#N)C[C@H]2N(C)C1] |

TABLE 10-continued

| Compound No. | Structure |
| --- | --- |
| 1-63 | 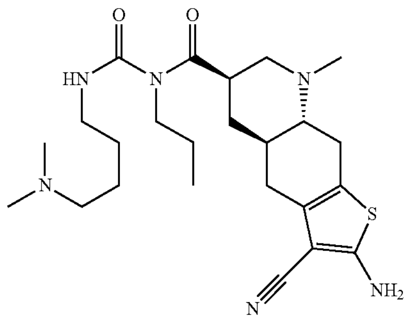 [SMILES: CCCN(C(=O)NCCCCN(C)C)C(=O)[C@@H]1C[C@@H]2Cc3c(sc(N)c3C#N)C[C@H]2N(C)C1] |
| 1-64 | 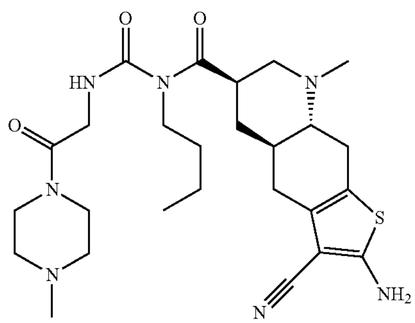 [SMILES: CCCCN(C(=O)NCC(=O)N1CCN(C)CC1)C(=O)[C@@H]1C[C@@H]2Cc3c(sc(N)c3C#N)C[C@H]2N(C)C1] |
| 1-65 | 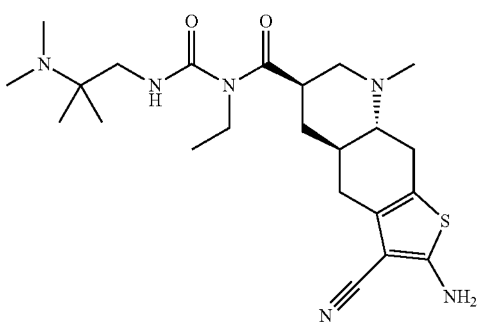 [SMILES: CCN(C(=O)NCC(C)(C)N(C)C)C(=O)[C@@H]1C[C@@H]2Cc3c(sc(N)c3C#N)C[C@H]2N(C)C1] |
| 1-66 | 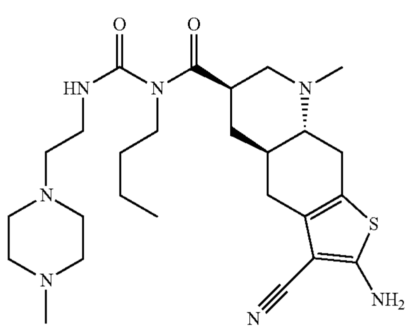 [SMILES: CCCCN(C(=O)NCCN1CCN(C)CC1)C(=O)[C@@H]1C[C@@H]2Cc3c(sc(N)c3C#N)C[C@H]2N(C)C1] |

TABLE 10-continued

| Compound No. | Structure |
| --- | --- |
| 1-67 | 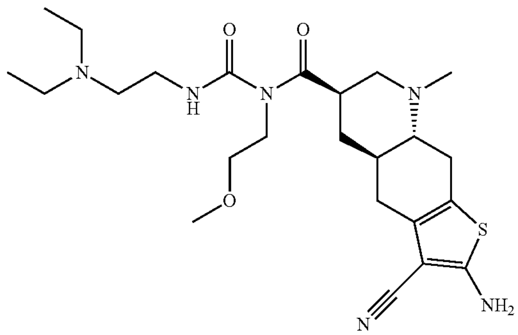 [SMILES: CCN(CC)CCNC(=O)N(CCOC)C(=O)[C@@H]1C[C@@H]2Cc3c(sc(N)c3C#N)C[C@H]2N(C)C1] |
| 1-68 | 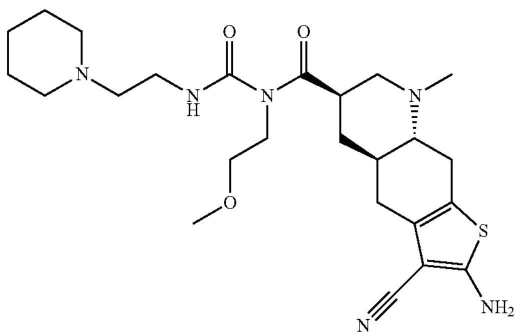 [SMILES: COCCN(C(=O)NCCN1CCCCC1)C(=O)[C@@H]1C[C@@H]2Cc3c(sc(N)c3C#N)C[C@H]2N(C)C1] |
| 1-69 | 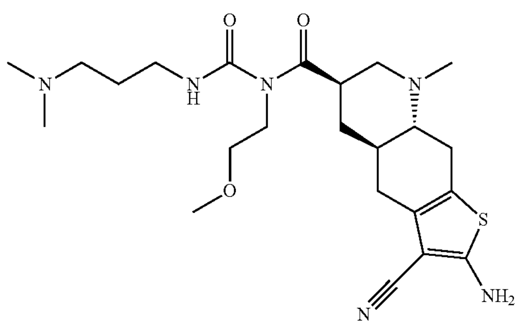 [SMILES: COCCN(C(=O)NCCCN(C)C)C(=O)[C@@H]1C[C@@H]2Cc3c(sc(N)c3C#N)C[C@H]2N(C)C1] |
| 1-70 | 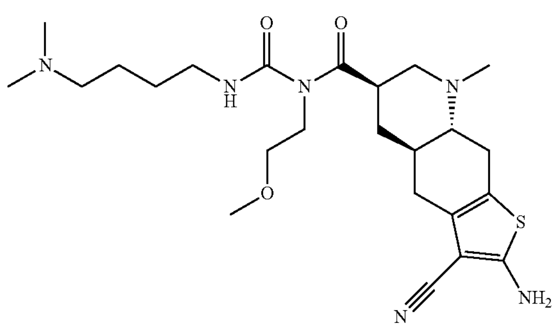 [SMILES: COCCN(C(=O)NCCCCN(C)C)C(=O)[C@@H]1C[C@@H]2Cc3c(sc(N)c3C#N)C[C@H]2N(C)C1] |

TABLE 10-continued
| Compound No. | Structure |
|---|---|
| 1-71 | 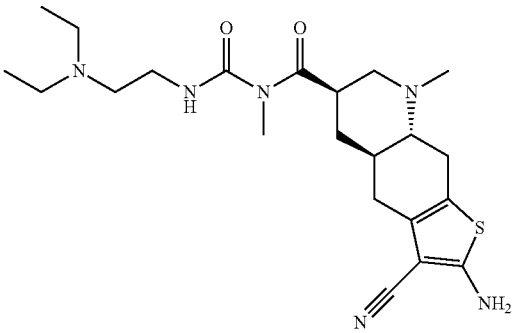 [SMILES: CCN(CC)CCNC(=O)N(C)C(=O)[C@@H]1C[C@@H]2Cc3c(sc(N)c3C#N)C[C@H]2N(C)C1] |
| 1-72 | 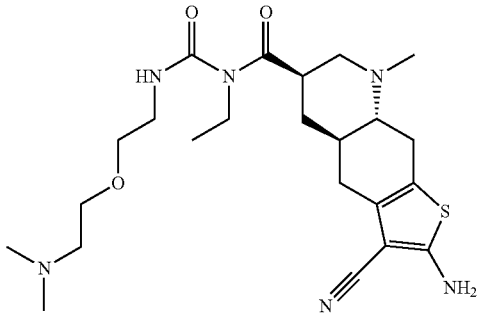 [SMILES: CCN(C(=O)NCCOCCN(C)C)C(=O)[C@@H]1C[C@@H]2Cc3c(sc(N)c3C#N)C[C@H]2N(C)C1] |
| 1-73 | 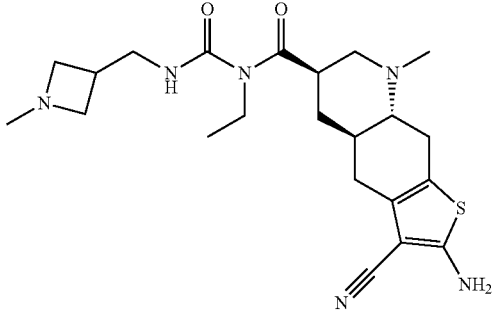 [SMILES: CCN(C(=O)NCC1CN(C)C1)C(=O)[C@@H]1C[C@@H]2Cc3c(sc(N)c3C#N)C[C@H]2N(C)C1] |
| 1-74 | 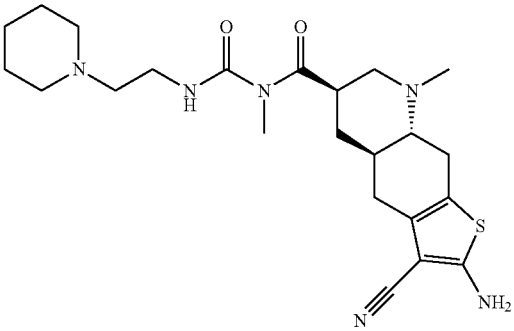 [SMILES: CN(C(=O)NCCN1CCCCC1)C(=O)[C@@H]1C[C@@H]2Cc3c(sc(N)c3C#N)C[C@H]2N(C)C1] |

TABLE 10-continued

| Compound No. | Structure |
|---|---|
| 1-75 | 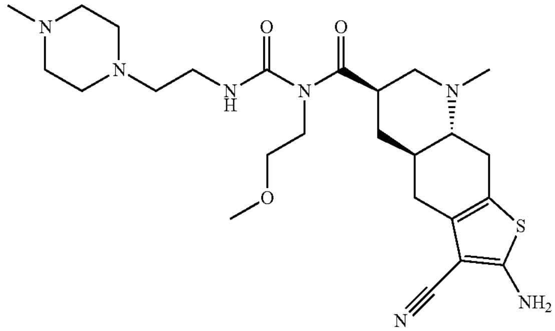 [SMILES: COCCN(C(=O)NCCN1CCN(C)CC1)C(=O)[C@@H]1C[C@@H]2Cc3c(sc(N)c3C#N)C[C@H]2N(C)C1] |
| 1-76 | 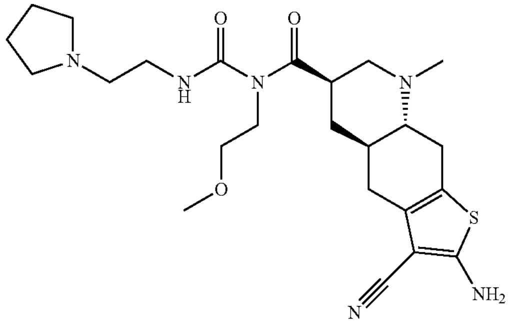 [SMILES: COCCN(C(=O)NCCN1CCCC1)C(=O)[C@@H]1C[C@@H]2Cc3c(sc(N)c3C#N)C[C@H]2N(C)C1] |
| 1-77 | 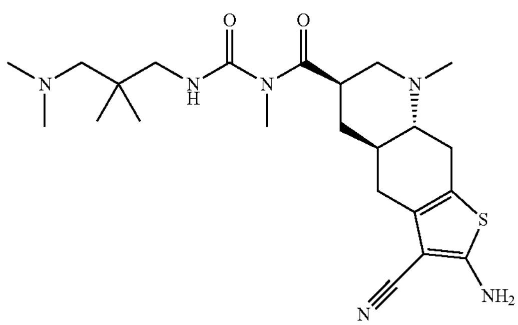 [SMILES: CN(C)CC(C)(C)CNC(=O)N(C)C(=O)[C@@H]1C[C@@H]2Cc3c(sc(N)c3C#N)C[C@H]2N(C)C1] |
| 1-78 | 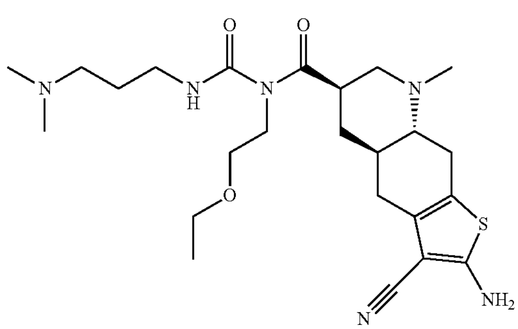 [SMILES: CCOCCN(C(=O)NCCCN(C)C)C(=O)[C@@H]1C[C@@H]2Cc3c(sc(N)c3C#N)C[C@H]2N(C)C1] |

TABLE 10-continued
| Compound No. | Structure |
| --- | --- |
| 1-79 | 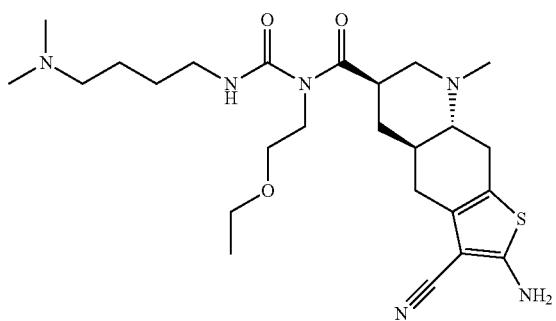 [SMILES: CCOCCN(C(=O)NCCCCN(C)C)C(=O)[C@@H]1C[C@@H]2Cc3c(sc(N)c3C#N)C[C@H]2N(C)C1] |
| 1-80 | 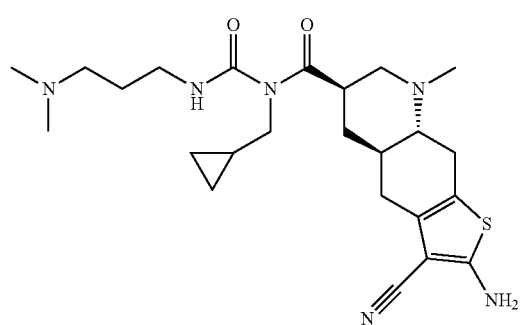 [SMILES: CN(C)CCCNC(=O)N(CC1CC1)C(=O)[C@@H]1C[C@@H]2Cc3c(sc(N)c3C#N)C[C@H]2N(C)C1] |
| 1-81 | 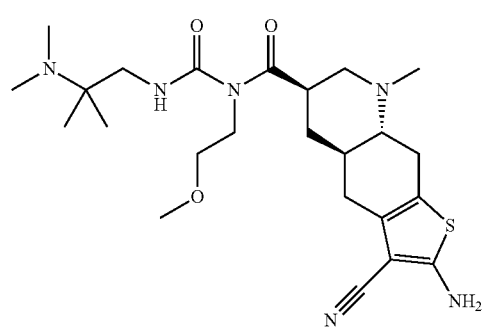 [SMILES: COCCN(C(=O)NCC(C)(C)N(C)C)C(=O)[C@@H]1C[C@@H]2Cc3c(sc(N)c3C#N)C[C@H]2N(C)C1] |
| 1-82 | 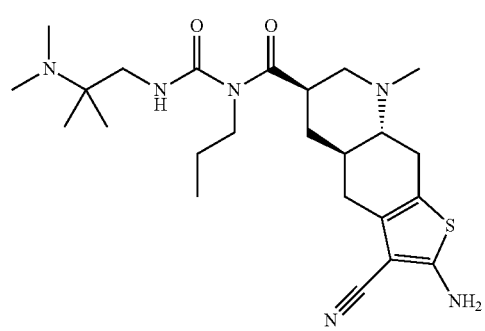 [SMILES: CCCN(C(=O)NCC(C)(C)N(C)C)C(=O)[C@@H]1C[C@@H]2Cc3c(sc(N)c3C#N)C[C@H]2N(C)C1] |

TABLE 10-continued
| Compound No. | Structure |
|---|---|
| 1-83 | 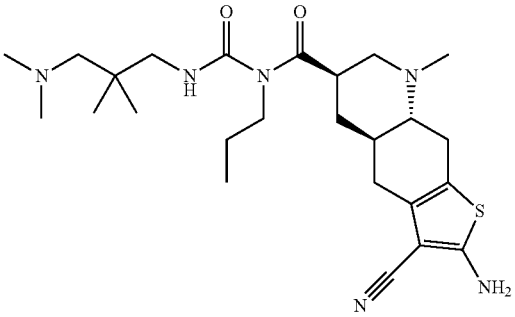 [SMILES: CCCN(C(=O)NCC(C)(C)CN(C)C)C(=O)[C@@H]1C[C@@H]2Cc3c(sc(N)c3C#N)C[C@H]2N(C)C1] |
| 1-84 | 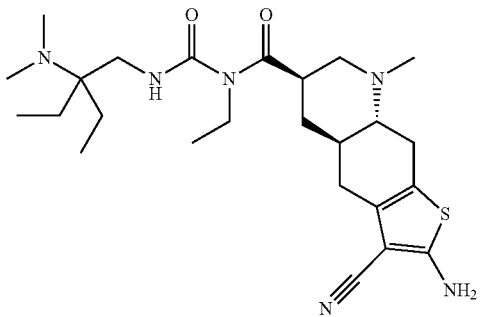 [SMILES: CCN(C(=O)NCC(CC)(CC)N(C)C)C(=O)[C@@H]1C[C@@H]2Cc3c(sc(N)c3C#N)C[C@H]2N(C)C1] |
| 1-85 | 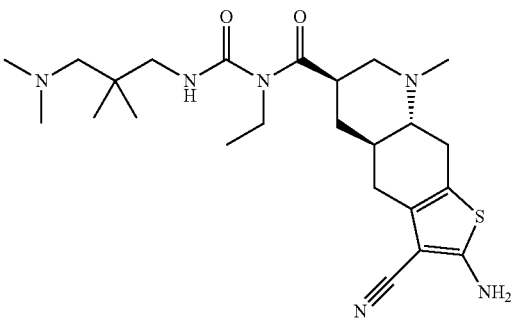 [SMILES: CCN(C(=O)NCC(C)(C)CN(C)C)C(=O)[C@@H]1C[C@@H]2Cc3c(sc(N)c3C#N)C[C@H]2N(C)C1] |
| 1-86 | 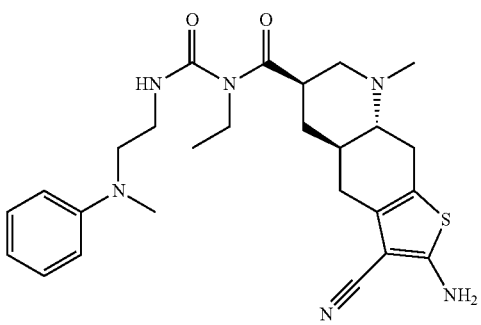 [SMILES: CCN(C(=O)NCCN(C)c1ccccc1)C(=O)[C@@H]1C[C@@H]2Cc3c(sc(N)c3C#N)C[C@H]2N(C)C1] |

TABLE 10-continued
| Compound No. | Structure |
|---|---|
| 1-87 | 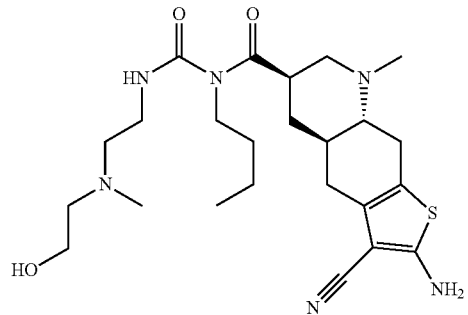 [SMILES: CCCCN(C(=O)NCCN(C)CCO)C(=O)[C@@H]1C[C@@H]2Cc3c(sc(N)c3C#N)C[C@H]2N(C)C1] |
| 1-88 | 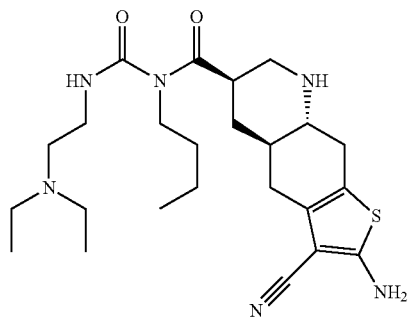 [SMILES: CCCCN(C(=O)NCCN(CC)CC)C(=O)[C@H]1CN[C@@H]2Cc3sc(N)c(C#N)c3C[C@H]2C1] |
| 1-89 | 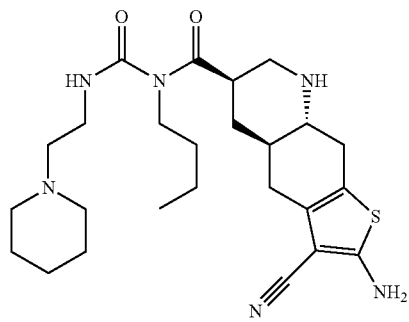 [SMILES: CCCCN(C(=O)NCCN1CCCCC1)C(=O)[C@H]1CN[C@@H]2Cc3sc(N)c(C#N)c3C[C@H]2C1] |
| 1-90 | 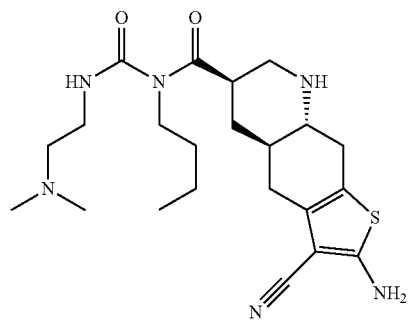 [SMILES: CCCCN(C(=O)NCCN(C)C)C(=O)[C@H]1CN[C@@H]2Cc3sc(N)c(C#N)c3C[C@H]2C1] |

TABLE 10-continued
| Compound No. | Structure |
|---|---|
| 1-91 | 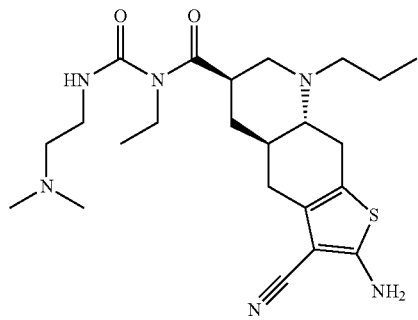 [SMILES: CCCN1C[C@H](C(=O)N(CC)C(=O)NCCN(C)C)C[C@@H]2Cc3c(sc(N)c3C#N)C[C@H]21] |
| 1-92 | 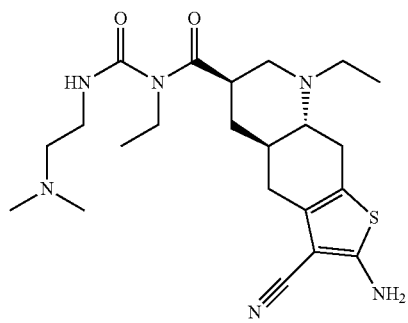 [SMILES: CCN(C(=O)NCCN(C)C)C(=O)[C@@H]1C[C@@H]2Cc3c(sc(N)c3C#N)C[C@H]2N(CC)C1] |
| 1-93 | 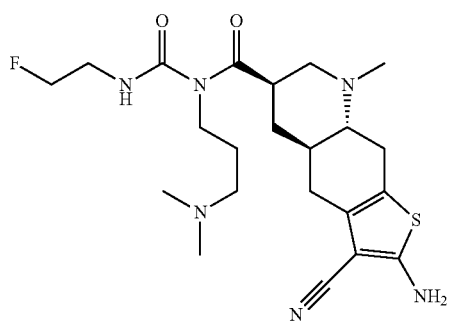 [SMILES: CN(C)CCCN(C(=O)NCCF)C(=O)[C@@H]1C[C@@H]2Cc3c(sc(N)c3C#N)C[C@H]2N(C)C1] |
| 1-94 | 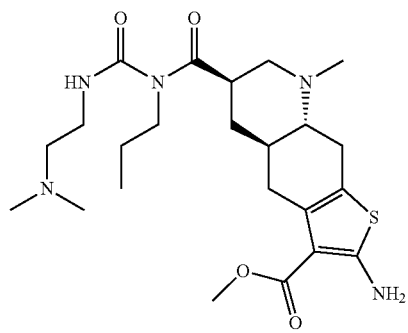 [SMILES: CCCN(C(=O)NCCN(C)C)C(=O)[C@@H]1C[C@@H]2Cc3c(sc(N)c3C(=O)OC)C[C@H]2N(C)C1] |

TABLE 10-continued
| Compound No. | Structure |
| --- | --- |
| 1-95 | 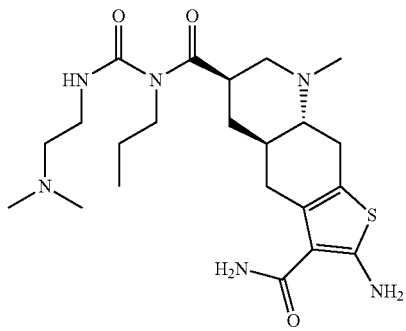 [SMILES: CCCN(C(=O)NCCN(C)C)C(=O)[C@@H]1C[C@@H]2Cc3c(sc(N)c3C(N)=O)C[C@H]2N(C)C1] |
| 1-96 | 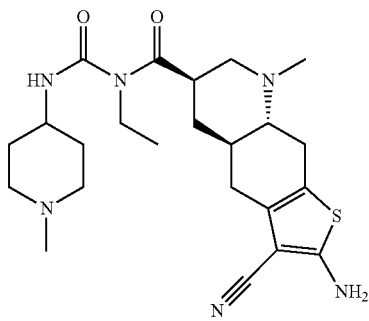 [SMILES: CCN(C(=O)NC1CCN(C)CC1)C(=O)[C@@H]1C[C@@H]2Cc3c(sc(N)c3C#N)C[C@H]2N(C)C1] |
| 1-97 | 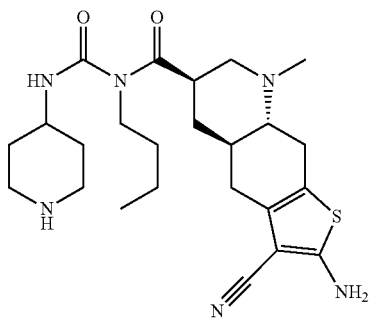 [SMILES: CCCCN(C(=O)NC1CCNCC1)C(=O)[C@@H]1C[C@@H]2Cc3c(sc(N)c3C#N)C[C@H]2N(C)C1] |
| 1-98 | 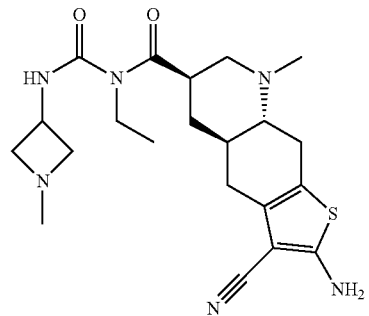 [SMILES: CCN(C(=O)NC1CN(C)C1)C(=O)[C@@H]1C[C@@H]2Cc3c(sc(N)c3C#N)C[C@H]2N(C)C1] |

TABLE 10-continued
| Compound No. | Structure |
|---|---|
| 1-99 | 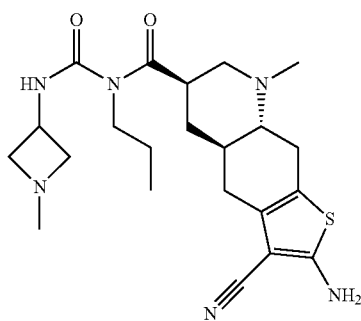 [SMILES: CCCN(C(=O)NC1CN(C)C1)C(=O)[C@@H]1C[C@@H]2Cc3c(sc(N)c3C#N)C[C@H]2N(C)C1] |
| 1-100 | 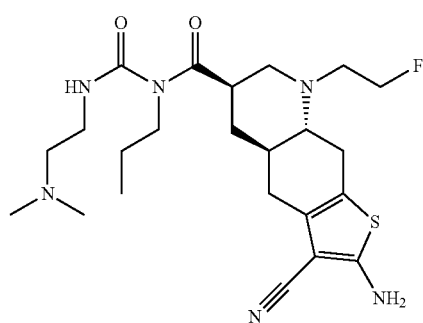 [SMILES: CCCN(C(=O)NCCN(C)C)C(=O)[C@@H]1C[C@@H]2Cc3c(sc(N)c3C#N)C[C@H]2N(CCF)C1] |
| 1-101 | 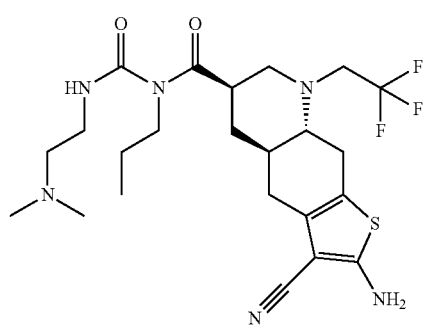 [SMILES: CCCN(C(=O)NCCN(C)C)C(=O)[C@@H]1C[C@@H]2Cc3c(sc(N)c3C#N)C[C@H]2N(CC(F)(F)F)C1] |
| 1-102 | 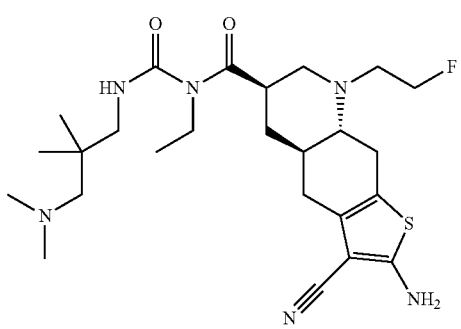 [SMILES: CCN(C(=O)NCC(C)(C)CN(C)C)C(=O)[C@@H]1C[C@@H]2Cc3c(sc(N)c3C#N)C[C@H]2N(CCF)C1] |

TABLE 10-continued

| Compound No. | Structure |
| --- | --- |
| 1-103 | 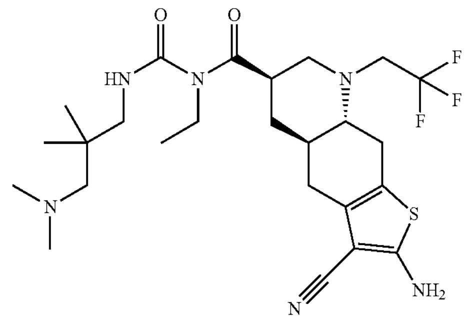 [SMILES: CCN(C(=O)NCC(C)(C)CN(C)C)C(=O)[C@@H]1C[C@@H]2Cc3c(sc(N)c3C#N)C[C@H]2N(CC(F)(F)F)C1] |
| 1-104 | 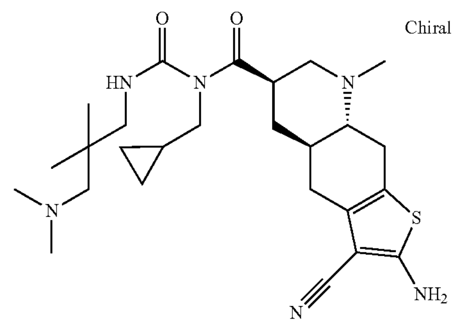 [SMILES: CN(C)CC(C)(C)CNC(=O)N(CC1CC1)C(=O)[C@@H]1C[C@@H]2Cc3c(sc(N)c3C#N)C[C@H]2N(C)C1] |
| 1-105 | 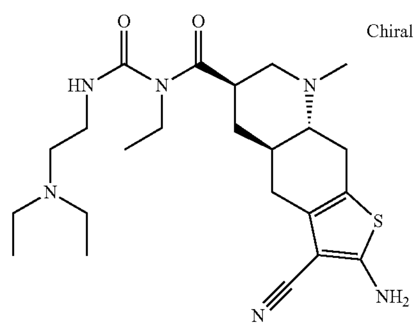 [SMILES: CCN(CC)CCNC(=O)N(CC)C(=O)[C@@H]1C[C@@H]2Cc3c(sc(N)c3C#N)C[C@H]2N(C)C1] |
| 1-106 | 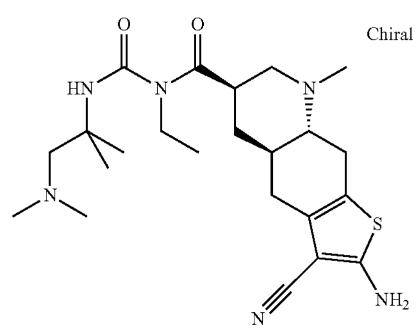 [SMILES: CCN(C(=O)NC(C)(C)CN(C)C)C(=O)[C@@H]1C[C@@H]2Cc3c(sc(N)c3C#N)C[C@H]2N(C)C1] |

TABLE 10-continued

| Compound No. | Structure |
|---|---|
| 1-107 | 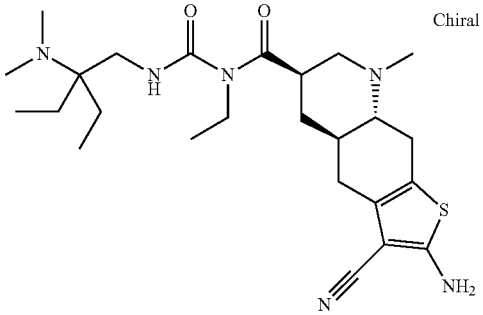 [SMILES: CCN(C(=O)NCC(CC)(CC)N(C)C)C(=O)[C@@H]1C[C@@H]2Cc3c(sc(N)c3C#N)C[C@H]2N(C)C1] |
| 1-108 | 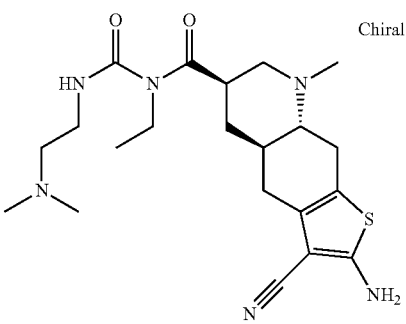 [SMILES: CCN(C(=O)NCCN(C)C)C(=O)[C@@H]1C[C@@H]2Cc3c(sc(N)c3C#N)C[C@H]2N(C)C1] |
| 1-109 | 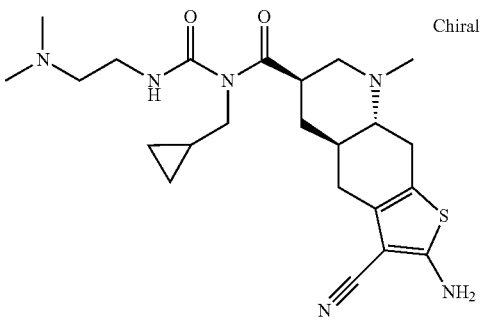 [SMILES: CN(C)CCNC(=O)N(CC1CC1)C(=O)[C@@H]1C[C@@H]2Cc3c(sc(N)c3C#N)C[C@H]2N(C)C1] |
| 1-110 | 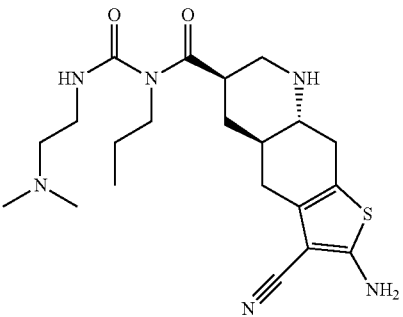 [SMILES: CCCN(C(=O)NCCN(C)C)C(=O)[C@H]1CN[C@@H]2Cc3sc(N)c(C#N)c3C[C@H]2C1] |

The structures of compound 1-1 to 1-6, 1-57 and 1-104 to 1-109 in Table 10 indicate absolute configuration, and the structures of compound 1-7 to 1-56, 1-58 to 1-103 and 1-110 in Table 10 indicate relative configuration.

The physical data of compounds 1-2 to 1-6 and compounds 1-8 to 1-110 were shown below.

Compound 1-2

$^1$H-NMR (CDCl$_3$) δ ppm: 0.95 (3H, t, J=7.5 Hz), 1.40-1.90 (4H, m), 1.95-2.15 (2H, m), 2.15-2.30 (1H, m), 2.30-2.55 (8H, m), 2.60-2.75 (1H, m), 2.77 (2H, t, J=6.1 Hz), 2.90-3.15 (3H, m), 3.41 (2H, q, J=5.8 Hz), 3.60-3.85 (2H, m), 4.60-4.70 (2H, m), 9.37 (1H, brs)

$[α]_D^{26}$=−103.02° (c=0.24, MeOH)

Compound 1-3

$^1$H-NMR (CDCl$_3$) δ ppm: 0.94 (3H, t, J=7.3 Hz), 1.02 (6H, t, J=7.2 Hz), 1.27-1.43 (2H, m), 1.46-1.64 (3H, m), 1.68-1.86 (1H, m), 1.95-2.11 (2H, m), 2.16-2.28 (1H, m), 2.31-2.72 (9H, m), 2.34 (3H, s), 2.87-3.12 (3H, m), 3.28-3.41 (2H, m), 3.63-3.89 (2H, m), 4.64 (2H, s), 9.01-9.42 (1H, m)

Compound 1-4

$^1$H-NMR (CDCl$_3$) δ ppm: 0.92 (6H, s), 1.25 (3H, t, J=7.2 Hz), 1.50-1.65 (1H, m), 1.70-1.90 (1H, m), 1.95-2.55 (16H, m), 2.60-2.75 (1H, m), 2.90-3.17 (3H, m), 3.21 (2H, d, J=5.2 Hz), 3.75-3.95 (2H, m), 4.65 (2H, s), 9.38 (1H, brs)

[α]$_D^{28}$=−88.997° (c=0.33, MeOH)

Compound 1-5

$^1$H-NMR (CDCl$_3$) δ ppm: 1.65-1.85 (4H, m), 1.95-2.25 (11H, m), 2.25-2.40 (4H, m), 2.40-2.45 (1H, m), 2.50-2.65 (2H, m), 2.85-3.00 (2H, m), 3.00-3.25 (5H, m), 4.60-4.75 (2H, m), 6.15-6.35 (1H, m) 7.10-7.30 (4H, m)

[α]$_D^{28}$=−123.09° (c=0.45, MeOH)

Compound 1-6

$^1$H-NMR (CDCl$_3$) δ ppm: 1.17 (3H, t, J=7.3 Hz), 1.37-1.51 (1H, m), 1.65-1.89 (5H, m), 1.93-2.23 (3H, m), 2.25-2.47 (2H, m), 2.31 (3H, s), 2.54-2.78 (7H, m), 2.84-2.97 (1H, m), 2.97-3.08 (1H, m), 3.16-3.43 (3H, m), 3.53-3.96 (2H, m), 4.90 (2H, s), 9.36-9.79 (1H, m)

[α]$_D^{29}$=−112.38° (c=0.25, MeOH)

Compound 1-8

$^1$H-NMR (CDCl$_3$) δ ppm: 1.02 (6H, t, J=7.2 Hz), 1.17 (3H, t, J=7.3 Hz), 1.40-1.55 (1H, m), 1.65-1.90 (3H, m), 1.95-2.10 (2H, m), 2.15-2.25 (1H, m), 2.30-2.50 (7H, m), 2.54 (4H, q, J=7.2 Hz), 2.60-2.70 (1H, m), 2.85-3.05 (2H, m), 3.15-3.35 (3H, m), 3.60-3.85 (2H, m), 4.60-4.70 (2H, m), 9.39 (1H, br)

Compound 1-9

$^1$H-NMR (CDCl$_3$) δ ppm: 1.18 (6H, d, J=6.6 Hz), 1.35-1.55 (1H, m), 1.70-1.90 (3H, m), 1.95-2.25 (9H, m), 2.25-2.45 (7H, m), 2.55-2.70 (1H, m), 2.85-3.05 (2H, m), 3.15-3.45 (1H, m), 3.55-3.85 (2H, m), 3.85-4.00 (1H, m), 4.60-4.75 (2H, m), 9.38 (1H, brs)

Compound 1-10

$^1$H-NMR (DMSO-d$_6$) δ ppm: 1.20-1.90 (8H, m), 2.00-2.10 (1H, m), 2.15-2.35 (11H, m), 2.38 (2H, t, J=6.4 Hz), 2.42-2.55 (1H, m), 2.90-3.05 (1H, m), 3.20-3.35 (2H, m), 3.90-4.01 (4H, m), 6.00-6.15 (1H, m)

Compound 1-11

$^1$H-NMR (CDCl$_3$) δ ppm: 1.03 (6H, t, J=7.2 Hz), 1.17 (3H, t, J=7.3 Hz), 1.34-1.50 (1H, m), 1.69-1.87 (1H, m), 1.92-2.25 (3H, m), 2.27-2.45 (2H, m), 2.31 (3H, s), 2.46-2.72 (7H, m), 2.86-3.08 (2H, m), 3.16-3.88 (5H, m), 4.63 (2H, s), 9.59-10.00 (1H, m)

Compound 1-12

$^1$H-NMR (CDCl$_3$) δ ppm: 1.17 (3H, t, J=7.3 Hz), 1.36-1.51 (1H, m), 1.51-1.90 (5H, m), 1.93-2.13 (2H, m), 2.13-2.25 (1H, m), 2.25-2.48 (2H, m), 2.31 (3H, s), 2.49-2.81 (7H, m), 2.83-3.11 (2H, m), 3.18-3.45 (3H, m), 3.57-3.93 (2H, m), 4.65 (2H, s), 9.31-9.79 (1H, m)

Compound 1-13

$^1$H-NMR (CDCl$_3$) δ ppm: 0.87 (3H, t, J=7.3 Hz), 1.17 (3H, t, J=7.3 Hz), 1.40-1.55 (3H, m), 1.65-1.90 (3H, m), 2.00-2.10 (1H, m), 2.15-2.55 (13H, m), 2.55-2.70 (2H, m), 2.85-3.00 (1H, m), 3.00-3.10 (1H, m), 3.10-3.35 (3H, m), 3.65-3.85 (2H, m), 4.68 (2H, brs), 9.42 (1H, br)

Compound 1-14

$^1$H-NMR (CDCl$_3$) δ ppm: 1.01 (3H, t, J=7.1 Hz), 1.17 (3H, t, J=7.3 Hz), 1.35-1.55 (1H, m), 1.65-1.90 (3H, m), 2.00-2.10 (1H, m), 2.15-2.45 (11H, m), 2.53 (1H, t, J=11.1 Hz), 2.60-2.75 (2H, m), 2.75-3.10 (3H, m), 3.15-3.35 (3H, m), 3.65-3.85 (2H, m), 4.60-4.70 (2H, m), 9.42 (1H, brs)

Compound 1-15

$^1$H-NMR (DMSO-d$_6$) δ ppm: 0.75-0.90 (3H, m), 1.20-1.40 (1H, m), 1.40-1.70 (3H, m), 1.80-2.25 (14H, m), 2.25-2.50 (3H, m), 2.80-2.95 (2H, m), 2.95-3.10 (1H, m), 3.15-3.30 (2H, m), 3.45-3.65 (2H, m), 7.01 (2H, s), 8.67 (1H, brs)

Compound 1-16

$^1$H-NMR (CDCl$_3$) δ ppm: 1.18-1.35 (5H, m), 1.45-1.88 (3H, m), 1.95-2.12 (2H, m), 2.14-2.29 (7H, m), 2.29-2.50 (6H, m), 2.60-2.72 (1H, m), 2.90-3.16 (3H, m), 3.27-3.38 (2H, m), 3.77-3.92 (2H, m), 4.67 (2H, s), 9.25 (1H, brs)

Compound 1-17

$^1$H-NMR (CDCl$_3$) δ ppm: 1.26 (3H, t, J=7.1 Hz), 1.50-1.65 (1H, m), 1.65-1.90 (1H, m), 1.95-2.15 (2H, m), 2.15-2.55 (14H, m), 2.60-2.75 (1H, m), 2.90-3.15 (3H, m), 3.35-3.45 (2H, m), 3.75-4.00 (2H, m), 4.60-4.75 (2H, m), 9.28 (1H, brs)

Compound 1-18

$^1$H-NMR (CDCl$_3$) δ ppm: 1.03 (6H, t, J=7.2 Hz), 1.26 (3H, t, J=7.1 Hz), 1.56 (1H, q, J=12.3 Hz), 1.70-1.85 (1H, m), 1.95-2.15 (2H, m), 2.15-2.30 (1H, m), 2.30-2.45 (4H, m), 2.46 (1H, t, J=11.2 Hz), 2.50-2.75 (7H, m), 2.90-3.15 (3H, m), 3.30-3.40 (2H, m), 3.75-3.95 (2H, m), 4.60-4.70 (2H, m), 9.24 (1H, brs)

Compound 1-19

$^1$H-NMR (CDCl$_3$) δ ppm: 0.95 (3H, t, J=7.4 Hz), 1.26 (3H, t, J=7.1 Hz), 1.45-1.65 (3H, m), 1.70-1.90 (1H, m), 1.95-2.15 (2H, m), 2.15-2.30 (1H, m), 2.30-2.50 (5H, m), 2.60-2.75 (1H, m), 2.90-3.15 (3H, m), 3.20-3.30 (2H, m), 3.80-4.00 (2H, m), 4.60-4.75 (2H, m), 9.25 (1H, brs)

Compound 1-20

$^1$H-NMR (CDCl$_3$) δ ppm: 1.25 (3H, t, J=7.0 Hz), 1.45-1.63 (1H, m), 1.68-1.86 (1H, m), 1.92-2.12 (2H, m), 2.15-2.29 (1H, m), 2.31-2.48 (2H, m), 2.34 (3H, s), 2.61-2.74 (1H, m), 2.80-3.13 (5H, m), 3.48-3.60 (2H, m), 3.78-3.95 (2H, m), 4.65 (2H, s), 7.16-7.36 (5H, m), 9.18-9.41 (1H, m)

Compound 1-21

$^1$H-NMR (CDCl$_3$) δ ppm: 1.26 (3H, t, J=7.0 Hz), 1.47-1.65 (1H, m), 1.70-1.87 (3H, m), 1.96-2.13 (2H, m), 2.17-2.29 (1H, m), 2.32-2.50 (2H, m), 2.35 (3H, s), 2.62-2.73 (1H, m), 2.91-3.15 (3H, m), 3.31-3.48 (4H, m), 3.35 (3H, s), 3.80-3.95 (2H, m), 4.65 (2H, s), 9.17-9.36 (1H, m)

Compound 1-22

$^1$H-NMR (CDCl$_3$) δ ppm: 1.26 (3H, t, J=6.9 Hz), 1.48-1.64 (1H, m), 1.70-1.87 (1H, m), 1.94-2.12 (2H, m), 2.17-2.28 (1H, m), 2.30-2.52 (2H, m), 2.34 (3H, s), 2.61-2.73 (1H, m), 2.90-3.15 (3H, m), 3.38 (3H, s), 3.44-3.56 (4H, m), 3.79-3.95 (2H, m), 4.65 (2H, s), 9.30-9.45 (1H, m)

Compound 1-23

$^1$H-NMR (CDCl$_3$) δ ppm: 1.27 (3H, t, J=7.0 Hz), 1.48-1.64 (1H, m), 1.70-1.86 (1H, m), 1.95-2.13 (2H, m), 2.15-2.29 (1H, m), 2.30-2.49 (2H, m), 2.35 (3H, s), 2.61-2.73 (1H, m), 2.87 (3H, d, J=4.8 Hz), 2.91-3.17 (3H, m), 3.81-3.97 (2H, m), 4.65 (2H, s), 9.02-9.26 (1H, m)

Compound 1-24

$^1$H-NMR (DMSO-d$_6$) δ ppm: 0.80-0.95 (3H, m), 1.20-1.37 (3H, m), 1.38-1.54 (2H, m), 1.54-1.70 (1H, m), 1.80-2.25 (14H, m), 2.26-2.37 (2H, m), 2.37-2.47 (1H, m), 2.80-2.95 (2H, m), 2.95-3.10 (1H, m), 3.15-3.30 (2H, m), 3.45-3.70 (2H, m), 7.02 (2H, s), 8.20-9.00 (1H, m)

Compound 1-25

$^1$H-NMR (CDCl$_3$) δ ppm: 1.29 (3H, t, J=7.0 Hz), 1.50-1.70 (1H, m), 1.70-1.90 (1H, m), 1.95-2.15 (2H, m), 2.15-2.30 (1H, m), 2.30-2.45 (4H, m), 2.49 (1H, t, J=11.3 Hz), 2.60-2.75 (1H, m), 2.90-3.05 (2H, m), 3.05-3.15 (1H, m), 3.80-4.00 (2H, m), 4.60-4.70 (4H, m), 7.15-7.25 (1H, m), 7.25-7.35 (1H, m), 7.60-7.70 (1H, m), 8.55-8.65 (1H, m), 9.97 (1H, brs)

Compound 1-26

$^1$H-NMR (CDCl$_3$) δ ppm: 0.64-0.77 (2H, m), 1.08-1.34 (4H, m), 1.41-1.56 (1H, m), 1.70-1.86 (1H, m), 1.98-2.11 (2H, m), 2.16-2.49 (12H, m), 2.60-2.73 (1H, m), 2.76-2.85 (1H, m), 2.90-3.05 (1H, m), 3.30-3.43 (2H, m), 3.61-3.78 (1H, m), 4.64 (2H, brs), 8.48 (1H, brs)

Compound 1-27

$^1$H-NMR (DMSO-d$_6$) δ ppm: 1.21-1.40 (1H, m), 1.50-1.78 (3H, m), 1.83-2.25 (14H, m), 2.29-2.48 (3H, m), 2.80-2.94 (2H, m), 3.00-3.13 (1H, m), 3.17-3.48 (7H, m), 3.53-3.75 (2H, m), 7.02 (2H, s), 8.71 (1H, brs)

Compound 1-28

$^1$H-NMR (DMSO-d$_6$) δ ppm: 1.16-1.34 (1H, m), 1.39-1.57 (1H, m), 1.70-1.92 (2H, m), 1.95-2.23 (11H, m), 2.26-2.42 (3H, m), 2.70-2.88 (2H, m), 2.93-3.11 (1H, m), 3.15-3.53 (3H, m), 4.77-5.09 (2H, m), 7.02 (2H, s), 7.17-7.30 (3H, m), 7.31-7.39 (2H, m), 8.88 (1H, brs)

Compound 1-29

$^1$H-NMR (CDCl$_3$) δ ppm: 1.10-1.22 (3H, m), 1.40-1.60 (1H, m), 1.70-2.10 (5H, m), 2.15-2.50 (6H, m), 2.60-2.75 (1H, m), 2.90-3.00 (2H, m), 3.10-3.50 (8H, m), 3.75-4.00 (2H, m), 4.67 (2H, brs), 9.08 (1H, brs)

Compound 1-30

$^1$H-NMR (CDCl$_3$) δ ppm: 1.30-1.45 (1H, m), 1.50-1.65 (2H, m), 1.90-2.05 (1H, m), 2.05-2.20 (1H, m), 2.20-2.45 (11H, m), 2.47 (2H, t, J=6.2 Hz), 2.50-2.60 (1H, m), 2.75-3.05 (5H, m), 3.35-3.50 (2H, m), 3.90-4.20 (2H, m), 4.60-4.75 (2H, m), 7.15-7.40 (5H, m), 9.29 (1H, brs)

Compound 1-31

$^1$H-NMR (CDCl$_3$) δ ppm: 1.25 (3H, t, J=6.9 Hz), 1.44-1.62 (1H, m), 1.69-1.87 (1H, m), 1.94-2.12 (2H, m), 2.16-2.28 (1H, m), 2.31-2.48 (2H, m), 2.34 (3H, s), 2.61-2.74 (1H, m), 2.81-3.12 (5H, m), 3.48-3.58 (2H, m), 3.76-3.96 (2H, m), 4.66 (2H, s), 7.19-7.30 (1H, m), 7.51-7.60 (1H, m), 8.44-8.52 (2H, m), 9.25-9.45 (1H, m)

Compound 1-32

$^1$H-NMR (CDCl$_3$) δ ppm: 1.26 (3H, t, J=7.1 Hz), 1.38-1.48 (2H, m), 1.51-1.64 (5H, m), 1.72-1.85 (1H, m), 1.96-2.11 (2H, m), 2.17-2.28 (1H, m), 2.34 (3H, s), 2.36-2.52 (8H, m), 2.62-2.71 (1H, m), 2.90-3.12 (3H, m), 3.37-3.45 (2H, m), 3.79-3.93 (2H, m), 4.65 (2H, s), 9.09-9.32 (1H, m)

Compound 1-33

$^1$H-NMR (DMSO-d$_6$) δ ppm: 1.10 (3H, t, J=7.1 Hz), 2.19 (3H, s), 3.58-3.78 (2H, m), 4.39 (2H, d, J=5.7 Hz), 7.02 (2H, s), 7.22-7.33 (2H, m), 8.45-8.54 (2H, m), 9.04-9.21 (1H, m)

Compound 1-34

$^1$H-NMR (CDCl$_3$) δ ppm: 1.26 (3H, t, J=7.1 Hz), 1.44-1.66 (5H, m), 1.68-1.87 (1H, m), 1.95-2.12 (2H, m), 2.17-2.30 (3H, m), 2.21 (6H, s), 2.32-2.49 (2H, m), 2.35 (3H, s), 2.61-2.73 (1H, m), 2.90-3.13 (3H, m), 3.24-3.35 (2H, m), 3.79-3.93 (2H, m), 4.65 (2H, s), 9.19-9.32 (1H, m)

Compound 1-35

$^1$H-NMR (CDCl$_3$) δ ppm: 0.85-1.00 (6H, m), 1.40-1.65 (1H, m), 1.65-2.10 (4H, m), 2.15-2.50 (14H, m), 2.60-2.75 (1H, m), 2.85-3.00 (2H, m), 3.05-3.20 (1H, m), 3.30-3.45 (2H, m), 3.60-3.80 (2H, m), 4.60-4.70 (2H, m), 9.22 (1H, brs)

Compound 1-36

$^1$H-NMR (CDCl$_3$) δ ppm: 0.30-0.45 (2H, m), 0.45-0.60 (2H, m), 0.80-1.10 (1H, m), 1.50-1.65 (1H, m), 1.65-1.90 (1H, m), 1.95-2.15 (2H, m), 2.15-2.55 (14H, m), 2.60-2.75 (1H, m), 2.90-3.05 (2H, m), 3.15-3.30 (1H, m), 3.35-3.45 (2H, m), 3.70-3.85 (2H, m), 4.65-4.75 (2H, m), 9.26 (1H, brs)

Compound 1-37

$^1$H-NMR (CDCl$_3$) δ ppm: 1.35-1.55 (1H, m), 1.60-1.80 (2H, m), 1.95-2.10 (1H, m), 2.10-2.20 (1H, m), 2.20-2.50 (13H, m), 2.50-2.60 (1H, m), 2.85-3.00 (2H, m), 3.20-3.35 (1H, m), 3.35-3.50 (2H, m), 4.60-4.70 (2H, m), 5.10 (1H, d, J=16.5 Hz), 5.35 (1H, d, J=16.5 Hz), 6.90-7.05 (2H, m), 7.20-7.30 (1H, m), 9.20 (1H, br)

Compound 1-38

$^1$H-NMR (CDCl$_3$) δ ppm: 1.46 (1H, q, J=12.3 Hz), 1.65-1.80 (1H, m), 1.80-1.95 (1H, m), 1.95-2.10 (1H, m), 2.10-2.25 (1H, m), 2.26 (6H, s), 2.30 (3H, s), 2.30-2.65 (5H, m), 2.85-3.05 (2H, m), 3.35-3.50 (3H, m), 4.60-4.70 (2H, m), 5.15-5.50 (2H, m), 7.32 (1H, d, J=3.3 Hz), 7.72 (1H, d, J=3.3 Hz), 9.24 (1H, br)

Compound 1-39

$^1$H-NMR (CDCl$_3$) δ ppm: 1.40-1.80 (1H, m), 1.90-2.10 (2H, m), 2.15-2.50 (13H, m), 2.55-2.70 (1H, m), 2.85-3.15 (3H, m), 3.30-3.50 (2H, m), 3.65-3.80 (2H, m), 4.35-4.60 (2H, m), 4.60-4.75 (2H, m), 5.05-5.30 (2H, m), 5.80-6.05 (1H, m), 9.28 (1H, m)

Compound 1-40

$^1$H-NMR (CDCl$_3$) δ ppm: 0.90 (3H, t, J=7.0 Hz), 1.20-1.45 (4H, m), 1.45-1.85 (4H, m), 1.95-2.15 (2H, m), 2.15-2.30 (7H, m), 2.30-2.55 (7H, m), 2.60-2.75 (1H, m), 2.90-3.00 (2H, m), 3.00-3.10 (1H, m), 3.35-3.45 (2H, m), 3.65-3.90 (2H, m), 4.65-4.75 (2H, m), 9.28 (1H, br)

Compound 1-41

$^1$H-NMR (CDCl$_3$) δ ppm: 0.90-1.10 (2H, m), 1.10-1.30 (3H, m), 1.45-1.85 (8H, m), 1.95-2.10 (2H, m), 2.15-2.30 (7H, m), 2.30-2.50 (7H, m), 2.60-2.75 (1H, m), 2.90-3.00 (2H, m), 3.05-3.20 (1H, m), 3.35-3.45 (2H, m), 3.55-3.80 (2H, m), 4.65-4.75 (2H, m), 9.26 (1H, br)

Compound 1-42

$^1$H-NMR (CDCl$_3$) δ ppm: 1.40-1.65 (2H, m), 1.75-1.90 (1H, m), 1.90-2.20 (1H, m), 2.20-2.35 (14H, m), 2.40-2.60 (4H, m), 2.80-2.95 (3H, m), 3.35-3.50 (2H, m), 4.55-4.70 (2H, m), 4.90-5.15 (2H, m), 6.85-7.00 (1H, m), 7.10-7.25 (3H, m), 9.36 (1H, brs)

Compound 1-43

$^1$H-NMR (CDCl$_3$) δ ppm: 0.95 (6H, d, J=6.6 Hz), 1.45-1.85 (5H, m), 1.95-2.15 (2H, m), 2.15-2.30 (7H, m), 2.30-2.55 (7H, m), 2.60-2.75 (1H, m), 2.90-3.10 (3H, m), 3.35-3.45 (2H, m), 3.65-3.90 (2H, m), 4.60-4.80 (2H, m), 9.27 (1H, brs)

Compound 1-44

$^1$H-NMR (CDCl$_3$) δ ppm: 1.26 (3H, t, J=7.0 Hz), 1.47-1.63 (1H, m), 1.69-1.86 (1H, m), 1.94-2.12 (2H, m), 2.16-2.54 (5H, m), 2.32 (6H, s), 2.35 (3H, s), 2.62-2.72 (1H, m), 2.77-3.16 (7H, m), 3.43-3.55 (2H, m), 3.78-3.96 (2H, m), 4.65 (2H, s), 7.10-7.23 (4H, m), 9.23-9.42 (1H, m)

Compound 1-45

$^1$H-NMR (CDCl$_3$) δ ppm: 0.94 (3H, t, J=7.3 Hz), 1.02 (6H, t, J=7.2 Hz), 1.27-1.43 (2H, m), 1.46-1.64 (3H, m), 1.68-1.86 (1H, m), 1.95-2.11 (2H, m), 2.16-2.28 (1H, m), 2.31-2.72 (9H, m), 2.34 (3H, s), 2.87-3.12 (3H, m), 3.28-3.41 (2H, m), 3.63-3.89 (2H, m), 4.64 (2H, s), 9.01-9.42 (1H, m)

Compound 1-46

$^1$H-NMR (CDCl$_3$) δ ppm: 0.94 (3H, t, J=7.5 Hz), 1.29-1.85 (12H, m), 1.96-2.12 (2H, m), 2.16-2.28 (1H, m), 2.30-2.54 (8H, m), 2.34 (3H, s), 2.60-2.74 (1H, m), 2.88-3.14 (3H, m), 3.34-3.47 (2H, m), 3.62-3.89 (2H, m), 4.66 (2H, s), 8.96-9.43 (1H, m)

Compound 1-47

$^1$H-NMR (CDCl$_3$) δ ppm: 0.94 (3H, t, J=7.5 Hz), 1.28-1.43 (2H, m), 1.46-1.66 (3H, m), 1.69-1.87 (5H, m), 1.95-2.13 (2H, m), 2.16-2.28 (1H, m), 2.30-2.74 (9H, m), 2.34 (3H, s), 2.87-3.13 (3H, m), 3.37-3.48 (2H, m), 3.63-3.89 (2H, m), 4.64 (2H, s), 9.10-9.39 (1H, m)

Compound 1-48

$^1$H-NMR (DMSO-d$_6$) δ ppm: 0.84 (3H, t, J=7.2 Hz), 0.94 (6H, t, J=7.2 Hz), 1.20-1.40 (1H, m), 1.40-1.70 (3H, m), 1.80-2.00 (2H, m), 2.00-2.30 (6H, m), 2.35-2.55 (7H, m), 2.80-2.95 (2H, m), 2.95-3.10 (1H, m), 3.10-3.25 (2H, m), 3.45-3.70 (2H, m), 7.02 (2H, brs), 8.65 (1H, brs)

Compound 1-49

$^1$H-NMR (DMSO-d$_6$) δ ppm: 0.75-0.90 (3H, m), 1.25-1.70 (10H, m), 1.80-2.00 (2H, m), 2.00-2.25 (6H, m), 2.25-2.50

(7H, m), 2.80-2.95 (2H, m), 2.95-3.10 (1H, m), 3.15-3.30 (2H, m), 3.45-3.65 (2H, m), 7.01 (2H, brs), 8.57 (1H, brs)

Compound 1-50
$^1$H-NMR (CDCl$_3$) δ ppm: 1.18 (3H, t, J=7.0 Hz), 1.40-1.60 (1H, m), 1.65-1.85 (1H, m), 1.95-2.10 (2H, m), 2.10-2.50 (14H, m), 2.55-2.70 (1H, m), 2.85-3.05 (2H, m), 3.30-3.65 (7H, m), 3.80-4.15 (2H, m), 4.60-4.75 (2H, m), 9.24 (1H, br)

Compound 1-51
$^1$H-NMR (CDCl$_3$) δ ppm: 1.25 (3H, t, J=7.1 Hz), 1.48-1.60 (1H, m), 1.70-1.84 (1H, m), 1.95-2.11 (2H, m), 2.16-2.27 (1H, m), 2.30-2.48 (2H, m), 2.34 (3H, s), 2.61-2.71 (1H, m), 2.76-2.84 (2H, m), 2.89-3.13 (3H, m), 3.53-3.61 (2H, m), 3.64 (3H, s), 3.80-3.93 (2H, m), 4.69 (2H, s), 6.66-6.71 (1H, m), 7.32-7.37 (1H, m), 9.13-9.37 (1H, m)

Compound 1-52
$^1$H-NMR (DMSO-d$_6$) δ ppm: 1.20-1.40 (1H, m), 1.50-1.70 (1H, m), 1.80-2.25 (15H, m), 2.30-2.70 (4H, m), 2.80-2.95 (2H, m), 3.00-3.15 (1H, m), 3.20-3.30 (2H, m), 3.70-3.90 (2H, m), 7.02 (2H, brs), 8.61 (1H, brs)

Compound 1-53
$^1$H-NMR (CDCl$_3$) δ ppm: 1.26 (3H, t, J=7.0 Hz), 1.45-1.59 (1H, m), 1.69-1.86 (1H, m), 1.93-2.12 (2H, m), 2.15-2.28 (1H, m), 2.31-2.48 (2H, m), 2.34 (3H, s), 2.61-2.72 (1H, m), 2.87-3.12 (3H, m), 3.51-3.71 (2H, m), 3.76-3.97 (2H, m), 4.06-4.21 (2H, m), 4.71 (2H, s), 6.89-6.98 (1H, m), 7.06-7.10 (1H, m), 7.45-7.50 (1H, m), 9.36-9.49 (1H, m)

Compound 1-54
$^1$H-NMR (CDCl$_3$) δ ppm: 1.40-1.70 (2H, m), 1.80-2.10 (4H, m), 2.10-2.50 (14H, m), 2.50-2.80 (3H, m), 2.85-3.00 (3H, m), 3.30-3.45 (2H, m), 3.65-3.95 (2H, m), 4.68 (2H, brs), 7.10-7.24 (3H, m), 7.24-7.32 (2H, m), 9.24 (1H, brs)

Compound 1-55
$^1$H-NMR (CDCl$_3$) δ ppm: 0.97 (3H, d, J=6.5 Hz), 1.26 (3H, t, J=7.2 Hz), 1.50-1.66 (1H, m), 1.69-1.86 (1H, m), 1.94-2.12 (2H, m), 2.15-2.29 (1H, m), 2.26 (6H, s), 2.30-2.53 (2H, m), 2.34 (3H, s), 2.60-2.77 (2H, m), 2.90-3.25 (4H, m), 3.30-3.41 (1H, m), 3.78-3.96 (2H, m), 4.66 (2H, s), 9.10-9.37 (1H, m)

Compound 1-56
$^1$H-NMR (CDCl$_3$) δ ppm: 0.93 (9H, s), 1.45-1.60 (1H, m), 1.65-1.85 (1H, m), 1.90-2.10 (2H, m), 2.10-2.50 (14H, m), 2.60-2.75 (1H, m), 2.85-3.00 (2H, m), 3.15-3.30 (1H, m), 3.30-3.45 (2H, m), 3.65-3.95 (2H, m), 4.60-4.75 (2H, m), 8.77 (1H, br)

Compound 1-57
$^1$H-NMR (CDCl$_3$) δ ppm: 1.21 (3H, d, J=6.5 Hz), 1.26 (3H, t, J=7.0 Hz), 1.47-1.65 (1H, m), 1.68-1.87 (1H, m), 1.94-2.11 (2H, m), 2.13-2.28 (2H, m), 2.25 (6H, s), 2.29-2.50 (3H, m), 2.34 (3H, s), 2.61-2.74 (1H, m), 2.90-3.13 (3H, m), 3.77-4.03 (3H, m), 4.65 (2H, s), 9.04-9.31 (1H, m)
[α]$_D^{28}$=−78.58° (c=0.31, MeOH)

Compound 1-58
$^1$H-NMR (CDCl$_3$) δ ppm: 0.94 (3H, t, J=7.3 Hz), 1.30-1.42 (2H, m), 1.45-1.86 (6H, m), 1.95-2.12 (2H, m), 2.15-2.51 (5H, m), 2.22 (6H, s), 2.34 (3H, s), 2.61-2.73 (1H, m), 2.90-3.18 (3H, m), 3.27-3.38 (2H, m), 3.62-3.88 (2H, m), 4.66 (2H, s), 9.07-9.43 (1H, m)

Compound 1-59
$^1$H-NMR (CDCl$_3$) δ ppm: 0.94 (3H, t, J=7.4 Hz), 1.29-1.42 (2H, m), 1.44-1.85 (8H, m), 1.96-2.12 (2H, m), 2.14-2.49 (5H, m), 2.21 (6H, s), 2.34 (3H, s), 2.62-2.74 (1H, m), 2.88-3.18 (3H, m), 3.24-3.35 (2H, m), 3.62-3.89 (2H, m), 4.67 (2H, s), 9.14-9.37 (1H, m)

Compound 1-60
$^1$H-NMR (CDCl$_3$) δ ppm: 0.94 (3H, t, J=7.4 Hz), 1.00 (12H, d, J=6.5 Hz), 1.28-1.42 (2H, m), 1.45-1.64 (3H, m), 1.69-1.86 (1H, m), 1.95-2.12 (2H, m), 2.16-2.28 (1H, m), 2.30-2.51 (2H, m), 2.34 (3H, s), 2.53-2.61 (2H, m), 2.62-2.73 (1H, m), 2.88-3.16 (5H, m), 3.21-3.34 (2H, m), 3.64-3.88 (2H, m), 4.64 (2H, s), 9.00-9.36 (1H, m)

Compound 1-61
$^1$H-NMR (DMSO-d$_6$) δ ppm: 1.50-2.50 (23H, m), 2.80-2.95 (2H, m), 2.95-3.15 (1H, m), 3.15-3.30 (2H, m), 3.50-3.75 (2H, m), 7.02 (2H, brs), 8.65 (1H, brs)

Compound 1-62
$^1$H-NMR (CDCl$_3$) δ ppm: 0.94 (3H, t, J=7.4 Hz), 1.45-1.90 (6H, m), 1.95-2.15 (2H, m), 2.15-2.50 (14H, m), 2.60-2.75 (1H, m), 2.90-3.15 (3H, m), 3.25-3.40 (2H, m), 3.60-3.85 (2H, m), 4.65-4.75 (2H, m), 9.26 (1H, brs)

Compound 1-63
$^1$H-NMR (CDCl$_3$) δ ppm: 0.94 (3H, t, J=7.4 Hz), 1.45-1.85 (8H, m), 1.95-2.15 (2H, m), 2.15-2.30 (9H, m), 2.30-2.50 (5H, m), 2.60-2.75 (1H, m), 2.90-3.15 (3H, m), 3.25-3.35 (2H, m), 3.60-3.85 (2H, m), 4.65-4.75 (2H, m), 9.26 (1H, brs)

Compound 1-64
$^1$H-NMR (CDCl$_3$) δ ppm: 0.94 (3H, t, J=7.3 Hz), 1.29-1.43 (2H, m), 1.48-1.84 (4H, m), 1.92-2.11 (2H, m), 2.15-2.27 (1H, m), 2.28-2.44 (5H, m), 2.31 (3H, s), 2.34 (3H, s), 2.46-2.55 (1H, m), 2.61-2.72 (1H, m), 2.90-3.14 (3H, m), 3.38-3.47 (2H, m), 3.57-3.91 (4H, m), 4.05-4.21 (2H, m), 4.70 (2H, s), 9.61-10.05 (1H, m)

Compound 1-65
$^1$H-NMR (CDCl$_3$) δ ppm: 1.03 (6H, s), 1.26 (3H, t, J=6.9 Hz), 1.48-1.69 (1H, m), 1.71-1.86 (1H, m), 1.94-2.13 (2H, m), 2.16-2.28 (1H, m), 2.23 (6H, s), 2.30-2.43 (1H, m), 2.34 (3H, s), 2.45-2.54 (1H, m), 2.62-2.72 (1H, m), 2.89-3.14 (3H, m), 3.27 (2H, d, J=5.0 Hz), 3.78-3.97 (2H, m), 4.66 (2H, s), 9.05-9.42 (1H, m)

Compound 1-66
$^1$H-NMR (CDCl$_3$) δ ppm: 0.95 (3H, t, J=7.3 Hz), 1.29-1.43 (2H, m), 1.47-1.66 (3H, m), 1.70-1.86 (1H, m), 1.96-2.14 (2H, m), 2.16-2.73 (14H, m), 2.29 (3H, s), 2.34 (3H, s), 2.89-3.14 (3H, m), 3.36-3.46 (2H, m), 3.65-3.88 (2H, m), 4.64 (2H, s), 9.07-9.38 (1H, m)

Compound 1-67
$^1$H-NMR (CDCl$_3$) δ ppm: 1.02 (6H, t, J=7.2 Hz), 1.40-1.55 (1H, m), 1.65-1.85 (1H, m), 1.95-2.10 (2H, m), 2.10-2.45 (6H, m), 2.50-2.75 (7H, m), 2.80-3.10 (2H, m), 3.25-3.47 (6H, m), 3.47-3.60 (2H, m), 3.85-4.05 (2H, m), 4.63 (2H, brs)

Compound 1-68
$^1$H-NMR (CDCl$_3$) δ ppm: 1.30-1.90 (8H, m), 1.90-2.10 (2H, m), 2.10-2.55 (12H, m), 2.55-2.75 (1H, m), 2.80-3.10 (2H, m), 3.30-3.45 (6H, m), 3.45-3.60 (2H, m), 3.80-4.05 (2H, m), 4.62 (2H, brs)

Compound 1-69
$^1$H-NMR (CDCl$_3$) δ ppm: 1.30-2.10 (8H, m), 2.10-2.50 (14H, m), 2.55-2.75 (1H, m), 2.80-3.10 (2H, m), 3.20-3.60 (8H, m), 3.90-4.05 (2H, m), 4.78 (2H, brs)

Compound 1-70
$^1$H-NMR (CDCl$_3$) δ ppm: 1.35-1.65 (3H, m), 1.70-1.85 (1H, m), 1.95-2.10 (2H, m), 2.10-2.50 (16H, m), 2.55-2.70 (1H, m), 2.80-3.10 (2H, m), 3.20-3.45 (6H, m), 3.50-3.60 (2H, m), 3.85-4.05 (2H, m), 4.90 (2H, brs)

Compound 1-71
$^1$H-NMR (CDCl$_3$) δ ppm: 1.03 (6H, t, J=7.2 Hz), 1.43-1.57 (1H, m), 1.68-1.85 (1H, m), 1.94-2.11 (2H, m), 2.17-2.29 (1H, m), 2.30-2.46 (2H, m), 2.34 (3H, s), 2.51-2.62 (6H, m), 2.62-2.72 (1H, m), 2.90-3.03 (2H, m), 3.09-3.21 (1H, m), 3.30-3.42 (2H, m), 3.37 (3H, s), 4.66 (2H, s), 9.12-9.36 (1H, m)

Compound 1-72
$^1$H-NMR (CDCl$_3$) δ ppm: 1.26 (3H, t, J=7.1 Hz), 1.48-1.62 (1H, m), 1.70-1.86 (1H, m), 1.94-2.13 (2H, m), 2.17-2.30 (1H, m), 2.27 (6H, s), 2.32-2.56 (4H, m), 2.34 (3H, s), 2.62-

2.73 (1H, m), 2.90-3.13 (3H, m), 3.41-3.64 (6H, m), 3.76-3.96 (2H, m), 4.67 (2H, s), 9.12-9.55 (1H, m)

Compound 1-73

$^1$H-NMR (CDCl$_3$) δ ppm: 1.26 (3H, t, J=7.0 Hz), 1.47-1.62 (1H, m), 1.70-1.87 (1H, m), 1.96-2.13 (2H, m), 2.16-2.49 (3H, m), 2.30 (3H, s), 2.35 (3H, s), 2.57-2.73 (2H, m), 2.85-3.13 (5H, m), 3.34-3.40 (2H, m), 3.42-3.50 (2H, m), 3.78-3.96 (2H, m), 4.66 (2H, s), 9.23-9.43 (1H, m)

Compound 1-74

$^1$H-NMR (CDCl$_3$) δ ppm: 1.35-1.67 (7H, m), 1.70-1.85 (1H, m), 1.95-2.12 (2H, m), 2.17-2.29 (1H, m), 2.30-2.53 (8H, m), 2.35 (3H, s), 2.61-2.72 (1H, m), 2.90-3.03 (2H, m), 3.08-3.20 (1H, m), 3.34-3.46 (2H, m), 3.37 (3H, m), 4.65 (2H, s), 9.09-9.38 (1H, m)

Compound 1-75

MS (ESI, m/z): 518 (M+H)+

Compound 1-76

$^1$H-NMR (CDCl$_3$) δ ppm: 1.40-1.55 (1H, m), 1.65-1.90 (4H, m), 1.90-2.12 (3H, m), 2.13-2.26 (1H, m), 2.26-2.46 (5H, m), 2.47-2.74 (7H, m), 2.85-3.10 (2H, m), 3.25-3.47 (6H, m), 3.47-3.61 (2H, m), 3.81-4.07 (2H, m), 4.79 (2H, brs)

Compound 1-77

$^1$H-NMR (CDCl$_3$) δ ppm: 0.92 (6H, s), 1.43-1.57 (1H, m), 1.68-1.88 (1H, m), 1.96-2.12 (2H, m), 2.14-2.47 (3H, m), 2.16 (2H, s), 2.29 (6H, s), 2.35 (3H, s), 2.59-2.72 (1H, m), 2.88-3.27 (3H, m), 3.21 (2H, d, J=5.5 Hz), 3.36 (3H, s), 4.64 (2H, s), 9.35-9.51 (1H, m)

Compound 1-78

$^1$H-NMR (CDCl$_3$) δ ppm: 1.18 (3H, t, J=6.9 Hz), 1.39-1.55 (1H, m), 1.55-1.83 (3H, m), 1.95-2.10 (2H, m), 2.14-2.27 (1H, m), 2.23 (6H, s), 2.28-2.44 (4H, m), 2.32 (3H, s), 2.54-2.74 (1H, m), 2.83-3.09 (2H, m), 3.23-3.37 (2H, m), 3.40-3.65 (5H, m), 3.77-4.14 (2H, m), 4.66 (2H, s), 8.42-9.79 (1H, m)

Compound 1-79

$^1$H-NMR (CDCl$_3$) δ ppm: 1.18 (3H, t, J=6.9 Hz), 1.38-1.85 (6H, m), 1.95-2.10 (2H, m), 2.13-2.45 (5H, m), 2.22 (6H, s), 2.32 (3H, s), 2.58-2.70 (1H, m), 2.85-3.10 (2H, m), 3.20-3.34 (2H, m), 3.39-3.63 (5H, m), 3.78-4.11 (2H, m), 4.63 (2H, s), 8.30-9.74 (1H, m)

Compound 1-80

$^1$H-NMR (CDCl$_3$) δ ppm: 0.35-0.45 (2H, m), 0.45-0.60 (2H, m), 0.90-1.05 (1H, m), 1.45-1.65 (1H, m), 1.65-1.90 (3H, m), 1.95-2.15 (2H, m), 2.15-2.50 (14H, m), 2.60-2.75 (1H, m), 2.90-3.05 (2H, m), 3.15-3.40 (3H, m), 3.70-3.85 (2H, m), 4.60-4.70 (2H, m), 9.28 (1H, brs)

Compound 1-81

$^1$H-NMR (CDCl$_3$) δ ppm: 1.03 (6H, s), 1.38-1.55 (1H, m), 1.69-1.84 (1H, m), 1.95-2.12 (2H, m), 2.12-2.28 (1H, m), 2.23 (6H, s), 2.29-2.47 (2H, m), 2.32 (3H, s), 2.56-2.72 (1H, m), 2.85-3.10 (2H, m), 3.17-3.29 (2H, m), 3.30-3.47 (1H, m), 3.34 (3H, s), 3.48-3.61 (2H, m), 3.77-4.04 (2H, m), 4.61 (2H, s)

Compound 1-82

$^1$H-NMR (CDCl$_3$) δ ppm: 0.94 (3H, t, J=7.4 Hz), 1.03 (6H, s), 1.47-1.87 (4H, m), 1.94-2.12 (2H, m), 2.14-2.29 (1H, m), 2.23 (6H, s), 2.29-2.43 (1H, m), 2.34 (3H, s), 2.44-2.54 (1H, m), 2.61-2.72 (1H, m), 2.87-3.18 (3H, m), 3.27 (2H, d, J=5.0 Hz), 3.59-3.88 (2H, m), 4.69 (2H, s), 8.85-9.59 (1H, m)

Compound 1-83

$^1$H-NMR (CDCl$_3$) δ ppm: 0.88-0.98 (3H, m), 0.92 (6H, s), 1.47-1.86 (4H, m), 1.95-2.11 (2H, m), 2.12-2.52 (3H, m), 2.16 (2H, s), 2.29 (6H, s), 2.34 (3H, s), 2.58-2.75 (1H, m), 2.89-3.16 (3H, m), 3.20 (2H, d, J=5.5 Hz), 3.62-3.85 (2H, m), 4.66 (2H, s), 9.22-9.48 (1H, m)

Compound 1-84

$^1$H-NMR (CDCl$_3$) δ ppm: 0.88 (6H, t, J=7.5 Hz), 1.26 (3H, t, J=7.1 Hz), 1.37-1.66 (5H, m), 1.70-1.87 (1H, m), 1.94-2.13 (2H, m), 2.15-2.54 (12H, m), 2.59-2.73 (1H, m), 2.89-3.18 (3H, m), 3.31 (2H, d, J=4.8 Hz), 3.75-3.97 (2H, m), 4.65 (2H, s), 8.96-9.55 (1H, m)

Compound 1-85

$^1$H-NMR (CDCl$_3$) δ ppm: 0.92 (6H, s), 1.25 (3H, t, J=7.1 Hz), 1.46-1.66 (1H, m), 1.71-1.87 (1H, m), 1.95-2.12 (2H, m), 2.12-2.53 (3H, m), 2.16 (2H, s), 2.29 (6H, s), 2.34 (3H, s), 2.60-2.74 (1H, m), 2.89-3.17 (3H, m), 3.21 (2H, d, J=5.5 Hz), 3.77-3.94 (2H, m), 4.65 (2H, s), 9.23-9.50 (1H, m)

Compound 1-86

$^1$H-NMR (CDCl$_3$) δ ppm: 1.25 (3H, t, J=7.1 Hz), 1.43-1.61 (1H, m), 1.69-1.85 (1H, m), 1.91-2.12 (2H, m), 2.15-2.28 (1H, m), 2.30-2.46 (2H, m), 2.34 (3H, s), 2.60-2.73 (1H, m), 2.86-3.15 (3H, m), 2.97 (3H, s), 3.41-3.57 (4H, m), 3.76-3.93 (2H, m), 4.65 (2H, s), 6.64-6.79 (3H, m), 7.17-7.26 (2H, m), 9.25-9.41 (1H, m)

Compound 1-87

$^1$H-NMR (CDCl$_3$) δ ppm: 0.95 (3H, t, J=7.3 Hz), 1.29-1.42 (2H, m), 1.45-1.66 (2H, m), 1.68-1.84 (1H, m), 1.93-2.11 (2H, m), 2.14-2.52 (3H, m), 2.28 (3H, s), 2.33 (3H, s), 2.53-2.72 (5H, m), 2.87-3.13 (4H, m), 3.34-3.46 (2H, m), 3.53-3.92 (4H, m), 4.64 (2H, s), 9.40-9.72 (1H, m)

Compound 1-88

$^1$H-NMR (CDCl$_3$) δ ppm: 0.95 (3H, t, J=7.3 Hz), 1.02 (6H, t, J=7.1 Hz), 1.30-1.44 (2H, m), 1.47-1.73 (4H, m), 1.99-2.46 (3H, m), 2.49-2.80 (9H, m), 2.84-3.03 (2H, m), 3.09-3.41 (3H, m), 3.63-3.89 (2H, m), 4.64 (2H, s), 8.81-9.57 (1H, m)

Compound 1-89

$^1$H-NMR (CDCl$_3$) δ ppm: 0.95 (3H, t, J=7.3 Hz), 1.30-1.48 (4H, m), 1.49-1.71 (8H, m), 1.98-2.54 (9H, m), 2.57-2.79 (3H, m), 2.83-3.04 (2H, m), 3.14-3.28 (1H, m), 3.33-3.47 (2H, m), 3.64-3.87 (2H, m), 4.66 (2H, s), 8.82-9.51 (1H, m)

Compound 1-90

$^1$H-NMR (CDCl$_3$) δ ppm: 0.96 (3H, t, J=7.3 Hz), 1.31-1.44 (2H, m), 1.48-1.69 (4H, m), 1.99-2.29 (2H, m), 2.26 (6H, s), 2.32-2.49 (3H, m), 2.55-2.79 (3H, m), 2.83-3.04 (2H, m), 3.15-3.29 (1H, m), 3.34-3.45 (2H, m), 3.64-3.88 (2H, m), 4.66 (2H, s), 8.93-9.47 (1H, m)

Compound 1-91

$^1$H-NMR (CDCl$_3$) δ ppm: 0.80-1.00 (3H, m), 1.20-1.40 (3H, m), 1.40-1.90 (4H, m), 1.90-2.10 (1H, m), 2.10-2.30 (7H, m), 2.30-2.80 (8H, m), 2.80-3.10 (3H, m), 3.25-3.50 (2H, m), 3.80-3.95 (2H, m), 4.50-4.70 (2H, m), 9.31 (1H, brs)

Compound 1-92

$^1$H-NMR (CDCl$_3$) δ ppm: 0.95-1.10 (3H, m), 1.50-1.65 (1H, m), 1.95-2.10 (2 nH, m), 2.15-2.30 (7H, m), 2.35-2.50 (4H, m), 2.50-3.10 (7H, m), 3.35-3.45 (2H, m), 3.80-3.95 (2H, m), 4.66 (2H, s), 9.31 (1H, brs)

Compound 1-93

$^1$H-NMR (CDCl$_3$) δ ppm: 1.40-1.54 (1H, m), 1.69-1.88 (3H, m), 1.96-2.12 (2H, m), 2.15-2.47 (5H, m), 2.22 (6H, s), 2.32 (3H, s), 2.58-2.73 (1H, m), 2.87-3.07 (2H, m), 3.23-3.87 (5H, m), 4.47 (1H, t, J=4.8 Hz), 4.58 (1H, t, J=4.8 Hz), 4.65 (2H, s), 9.87-10.42 (1H, m)

Compound 1-94

$^1$H-NMR (CDCl$_3$) δ ppm: 0.94 (3H, t, J=7.6 Hz), 1.40-1.90 (4H, m), 1.90-2.15 (4H, m), 2.20-2.55 (13H, m), 2.80-3.20 (4H, m), 3.30-3.50 (2H, m), 3.60-3.90 (4H, m), 5.99 (2H, s), 9.30 (1H, brs)

Compound 1-95

$^1$H-NMR (CDCl$_3$) δ ppm: 0.84 (3H, t, J=7.2 Hz), 1.10-1.70 (4H, m), 1.70-2.05 (2H, m), 2.05-2.28 (10H, m), 2.28-2.41 (3H, m), 2.60-2.75 (1H, m), 2.80-2.95 (2H, m), 2.95-3.15

(1H, m), 3.15-3.30 (2H, m), 3.45-3.75 (3H, m), 6.51 (2H, brs), 6.92 (2H, s), 8.64 (1H, brs)

Compound 1-96

¹H-NMR (CDCl₃) δ ppm: 1.19-1.31 (3H, m), 1.46-1.64 (3H, m), 1.71-1.86 (1H, m), 1.90-2.30 (7H, m), 2.27 (3H, s), 2.30-2.50 (2H, m), 2.34 (3H, s), 2.61-2.80 (3H, m), 2.90-3.22 (3H, m), 3.64-3.97 (3H, m), 4.64 (2H, s), 9.13-9.39 (1H, m)

Compound 1-97

¹H-NMR (CDCl₃) δ ppm: 0.95 (3H, t, J=7.3 Hz), 1.29-1.67 (7H, m), 1.71-1.86 (1H, m), 1.90-2.12 (4H, m), 2.16-2.28 (1H, m), 2.30-2.51 (2H, m), 2.35 (3H, s), 2.63-2.75 (3H, m), 2.90-3.12 (5H, m), 3.62-3.92 (3H, m), 4.65 (2H, s), 9.18-9.40 (1H, m)

Compound 1-98

¹H-NMR (CDCl₃) δ ppm: 1.20-1.34 (3H, m), 1.46-1.62 (1H, m), 1.70-1.85 (1H, m), 1.95-2.15 (2H, m), 2.15-2.30 (1H, m), 2.30-2.50 (8H, m), 2.60-2.75 (1H, m), 2.80-3.15 (5H, m), 3.60-3.75 (2H, m), 3.76-3.95 (2H, m), 4.35-4.50 (1H, m), 4.60-4.75 (2H, m), 9.50-9.65 (1H, m)

Compound 1-99

¹H-NMR (CDCl₃) δ ppm: 0.80-1.00 (3H, m), 1.40-1.90 (4H, m), 1.90-2.15 (2H, m), 2.15-2.29 (1H, m), 2.29-2.50 (8H, m), 2.60-2.75 (1H, m), 2.80-3.15 (5H, m), 3.55-3.85 (4H, m), 4.35-4.50 (1H, m), 4.60-4.75 (2H, m), 9.50-9.65 (1H, m)

Compound 1-100

¹H-NMR (CDCl₃) δ ppm: 0.90-1.00 (3H, m), 1.50-2.10 (5H, m), 2.15-2.31 (7H, m), 2.31-2.55 (4H, m), 2.55-2.77 (2H, m), 2.77-2.94 (1H, m), 2.94-3.17 (4H, m), 3.35-3.45 (2H, m), 3.51-3.86 (2H, m), 4.40-4.80 (4H, m), 9.24 (1H, brs)

Compound 1-101

¹H-NMR (CDCl₃) δ ppm: 0.96 (3H, t, J=7.2 Hz), 1.40-1.85 (2H, m), 1.90-2.10 (1H, m), 2.15-2.35 (7H, m), 2.35-2.55 (3H, m), 2.55-2.75 (2H, m), 2.80-2.95 (3H, m), 2.95-3.35 (5H, m), 3.35-3.45 (2H, m), 3.60-3.85 (2H, m), 4.65 (2H, brs), 9.19 (1H, brs)

Compound 1-102

MS (ESI, m/z): 507 (M+H)+

Compound 1-103

¹H-NMR (CDCl₃) δ ppm: 0.93 (6H, s), 1.26 (3H, t, J=7.1 Hz), 1.50-1.65 (1H, m), 1.70-1.85 (1H, m), 1.95-2.35 (10H, m), 2.35-2.55 (1H, m), 2.55-2.75 (2H, m), 2.80-3.00 (2H, m), 3.00-3.40 (6H, m), 3.70-3.95 (2H, m), 4.70 (2H, s), 9.32 (1H, brs)

Compound 1-104

¹H-NMR (CDCl₃) δ ppm: 0.30-0.45 (2H, m), 0.45-0.55 (2H, m), 0.92 (6H, s), 0.95-1.05 (1H, m), 1.50-1.70 (1H, m), 1.70-1.85 (1H, m), 2.00-2.13 (2H, m), 2.13-2.55 (14H, m), 2.60-2.75 (1H, m), 2.90-3.10 (2H, m), 3.15-3.35 (3H, m), 3.70-3.90 (2H, m), 4.64 (2H, brs), 9.39 (1H, brs)

[α]_D^28=−99.54° (c=0.31, MeOH)

Compound 1-105

¹H-NMR (CDCl₃) δ ppm: 1.03 (6H, t, J=7.2 Hz), 1.26 (3H, t, J=6.8 Hz), 1.49-1.65 (1H, m), 1.70-1.90 (1H, m), 1.90-2.15 (2H, m), 2.15-2.30 (1H, m), 2.30-2.75 (12H, m), 2.80-3.15 (3H, m), 3.30-3.45 (2H, m), 3.75-4.00 (2H, m), 4.66 (2H, brs), 9.23 (1H, brs)

[α]_D^27=−100.82° (c=0.34, MeOH)

Compound 1-106

¹H-NMR (CDCl₃) δ ppm: 1.15-1.32 (3H, m), 1.35 (6H, s), 1.70-1.85 (1H, m), 1.90-2.14 (2H, m), 2.14-2.55 (15H, m), 2.60-2.75 (1H, m), 2.90-3.15 (3H, m), 3.74-3.92 (2H, m), 4.63 (2H, brs), 9.31 (1H, brs)

[α]_D^28=−85.40° (c=0.30, MeOH)

Compound 1-107

¹H-NMR (CDCl₃) δ ppm: 0.88 (6H, t, J=7.6 Hz), 1.26 (3H, t, J=7.0 Hz), 1.40-1.65 (5H, m), 1.70-1.85 (1H, m), 1.95-2.15 (2H, m), 2.15-2.45 (11H, m), 2.49 (1H, t, J=11.2 Hz), 2.60-2.75 (1H, m), 2.90-3.15 (3H, m), 3.31 (2H, d, J=4.7 Hz), 3.80-3.95 (2H, m), 4.64 (2H, s), 9.24 (1H, brs)

[α]_D^28=−86.48° (c=0.29, MeOH)

Compound 1-108

¹H-NMR (CDCl₃) δ ppm: 1.26 (3H, t, J=7.0 Hz), 1.50-1.60 (1H, m), 1.70-1.85 (1H, m), 1.95-2.15 (2H, m), 2.15-2.25 (1H, m), 2.26 (6H, s), 2.30-2.45 (7H, m), 2.60-2.75 (1H, m), 2.90-3.15 (3H, m), 3.35-3.45 (2H, m), 3.75-3.95 (2H, m), 4.66 (2H, s), 9.27 (1H, brs)

[α]_D^27=−118.60° (c=0.31, MeOH)

Compound 1-109

¹H-NMR (CDCl₃) δ ppm: 0.35-0.45 (2H, m), 0.45-0.60 (2H, m), 0.90-1.10 (1H, m), 1.50-1.65 (1H, m), 1.70-1.90 (1H, m), 1.95-2.15 (2H, m), 2.15-2.55 (14H, m), 2.60-2.75 (1H, m), 2.90-3.05 (2H, m), 3.15-3.30 (1H, m), 3.35-3.45 (2H, m), 3.70-3.85 (2H, m), 4.70 (2H, s), 9.25 (1H, brs)

[α]_D^27=−89.37° (c=0.35, MeOH)

Compound 1-110

¹H-NMR (CDCl₃) δ ppm: 0.96 (3H, t, J=7.4 Hz), 1.40-1.80 (4H, m), 2.00-2.50 (11H, m), 2.55-2.80 (3H, m), 2.80-3.05 (2H, m), 3.15-3.30 (1H, m), 3.30-3.45 (2H, m), 3.60-3.85 (2H, m), 4.66 (2H, s), 9.00-9.50 (1H, m)

Example 2-1

N-[(4aR*,6R*,8aR*)-3-Cyano-6-[({[2-(dimethylamino)ethyl]carbamoyl}(propyl)amino)carbonyl]-8-methyl-4H,4aH,5H,6H,7H,8H,8aH,9H-thieno[3,2-g]quinolin-2-yl]-acetamide (compound 2-1)

To 1-{[(4aR*,6R*,8aR*)-2-amino-3-cyano-8-methyl-4H,4aH,5H,6H,7H,8H,8aH,9H-thieno[3,2-g]quinolin-6-yl]carbonyl}-3-[2-(dimethylamino)ethyl]-1-propylurea (example 1-15) (100 mg) was added acetic acid (2 mL) and the mixture was heated at 135° C. and refluxed for 12 hours. After cooling to room temperature, the reaction mixture was concentrated under reduced pressure. To the residue were added ethyl acetate and a saturated aqueous solution of sodium bicarbonate. After the separated organic layer was dried over anhydrous sodium sulfate, it was concentrated under reduced pressure. The residue was purified by silica gel column chromatography (eluent: 0%-5% methanol/ethyl acetate, gradient elution) to give the title compound (26 mg). The structure was illustrated in Table 11.

¹H-NMR (CDCl₃) δ ppm: 0.94 (3H, t, J=7.2 Hz), 1.50-1.90 (4H, m), 1.90-2.20 (2H, m), 2.20-2.40 (12H, m), 2.40-2.60 (4H, m), 2.70-2.90 (1H, m), 2.90-3.20 (3H, m), 3.30-3.50 (2H, m), 3.60-3.90 (2H, m), 8.54 (1H, s), 9.26 (1H, brs)

Example 2-2

Methyl N-[(4aR*,6R*,8aR*)-3-cyano-6-[({[2-(dimethylamino)ethyl]carbamoyl}(propyl)amino)carbonyl]-8-methyl-4H,4aH,5H,6H,7H,8H,8aH,9H-thieno[3,2-g]quinolin-2-yl]carbamate (compound 2-2)

To a mixture of 1,1'-carbonyldiimidazole (13 mg) and methylene chloride (1 mL) was added 4-dimethylaminopyridine (8 mg), followed by 1-{[(4aR*,6R*,8aR*)-2-amino-3-cyano-8-methyl-4H,4aH,5H,6H,7H,8H,8aH,9H-thieno[3,2-g]quinolin-6-yl]carbonyl}-3-[2-(dimethylamino)ethyl]-1-propylurea (example 1-15) (30 mg) while stirring under ice bath cooling, and the mixture was stirred at the same temperature for 1 hour. To the reaction mixture was added 1,1'-carbonyldiimidazole (13 mg), followed by 4-dimethylaminopyridine (8 mg) and warmed to room temperature and stirred for 1 hour. To the reaction mixture was added 1,1'-carbonyldiimidazole (50 mg), followed by 4-dimethylaminopyridine (32 mg) while stirring at room temperature and stirred at the same temperature for 12 hours. To the reaction mixture was added methanol (0.003 mL) while stirring at room temperature and stirred at the same temperature for 1 hour. The mixture was purified by aminopropyl silica gel column chromatography (eluent: 0%-10% methanol/methylene chloride, gradient elution) to give the title compound (18 mg). The structure was illustrated in Table 11.

$^1$H-NMR (CDCl$_3$) δ ppm: 0.95 (3H, t, J=7.2 Hz), 1.50-1.90 (4H, m), 1.90-2.20 (2H, m), 2.20-2.34 (1H, m), 2.26 (6H, s), 2.36 (3H, s), 2.38-2.54 (4H, m), 2.70-2.85 (1H, m), 2.90-3.15 (3H, m), 3.35-3.45 (2H, m), 3.60-3.85 (2H, m), 3.67 (3H, s), 7.12 (1H, brs), 9.26 (1H, brs)

Compound 2-3 was prepared in a manner similar to those as described in example 2-2 using 1-{[(4aR*,6R*,8aR*)-2-amino-3-cyano-8-methyl-4H,4aH,5H, 6H,7H,8H,8aH,9H-thieno[3,2-g]quinolin-6-yl]carbonyl}-3-[3-(dimethylamino)-2,2-dimethylpropyl]-1-ethylurea (example 1-85) instead of 1-{[(4aR*,6R*,8aR*)-2-amino-3-cyano-8-methyl-4H,4aH,5H,6H,7H,8H,8aH,9H-thieno[3,2-g]quinolin-6-yl]carbonyl}-3-[2-(dimethylamino)ethyl]-1-propylurea (example 1-15). This was illustrated in Table 11.

$^1$H-NMR (CDCl$_3$) δ ppm: 0.92 (6H, s), 1.25 (3H, t, J=7.0 Hz), 1.50-1.65 (1H, m), 1.70-1.90 (1H, m), 1.95-2.15 (2H, m), 2.17 (2H, s), 2.20-2.55 (12H, m), 2.65-2.80 (1H, m), 2.95-3.25 (5H, m), 3.75-3.95 (5H, m), 7.70 (1H, br), 9.37 (1H, brs)

Example 3-1

1-{[(4aR*,6R*,8aR*)-3-Cyano-8-methyl-2-(methylamino)-4H,4aH,5H,6H,7H,8H,8aH,9H-thieno[3,2-g]quinolin-6-yl]carbonyl}-3-[2-(dimethylamino)ethyl]-1-propylurea di hydrochloride salt (compound 3-1)

To (3'R*,4'aR*,8'aR*)-1'-methyl-N-propyloctahydro-1'H-spiro[1,3-dioxolane-2,6'-quinoline]-3'-carboxamide (reference example 4-5) (2.137 g) was added 2 mol/L hydrochloric acid (100 mL) and the mixture was stirred at room temperature for 2 hours. The reaction mixture was made alkaline with potassium carbonate. The mixture was extracted with methylene chloride/methanol mixed solvent (methylene chloride:methanol=9:1). After the organic layer was dried over anhydrous sodium sulfate, it was concentrated under reduced pressure to give (3R*,4aR*,8aR*)-1-methyl-6-oxo-N-propyl-decahydroquinoline-3-carboxamide (1.840 g).

$^1$H-NMR (CDCl$_3$) δ ppm: 0.85-1.00 (4H, m), 1.40-1.90 (5H, m), 1.90-2.00 (1H, m), 2.10-2.25 (1H, m), 2.25-2.55 (9H, m), 2.95-3.05 (1H, m), 3.15-3.25 (2H, m), 5.43 (1H, brs)

To a mixture of (3R*,4aR*,8aR*)-1-methyl-6-oxo-N-propyldecahydroquinoline-3-carboxamide (1.819 g) and ethanol (72 mL) were added malononitrile (622 mg), morpholine (0.943 mL), followed by elemental sulfer (303 mg) while stirring at room temperature, and the mixture was heated at 54° C. and stirred for 1.5 hours. After cooling to room temperature, the reaction mixture was concentrated under reduced pressure. The residue was triturated with ethyl acetate to give (4aR*,6R*,8aR*)-2-amino-3-cyano-8-methyl-N-propyl-4H,4aH,5H,6H,7H,8H,8aH,9H-thieno[3,2-g]quinoline-6-carboxamide (1.991 g).

$^1$H-NMR (DMSO-d$_6$) δ ppm: 0.83 (3H, t, J=7.4 Hz), 1.20-1.45 (3H, m), 1.45-1.65 (1H, m), 1.75-1.95 (2H, m), 2.00-2.25 (6H, m), 2.35-2.60 (2H, m), 2.75-3.05 (4H, m), 7.00 (2H, s), 7.81 (1H, t, J=5.6 Hz)

A mixture of (4aR*,6R*,8aR*)-2-amino-3-cyano-8-methyl-N-propyl-4H,4aH, 5H,6H,7H,8H,8aH,9H-thieno[3,2-g]quinoline-6-carboxamide (1.99 g) and (diethoxymethoxy)ethane (20 mL) was heated at 155° C. and stirred for 3 hours. After cooling to room temperature, it was diluted with diethyl ether and the solid was collected by filtration to give ethyl N-[(4aR*,6R*S,8aR*)-3-cyano-8-methyl-6-(propylcarbamoyl)-4H,4aH,5H,6H,7H,8H,8aH,9H-thieno[3,2-g]quinolin-2-yl]carboximidate (1.70 g).

MS (ESI, m/z): 389 (M+H)+

To a mixture of ethyl N-[(4aR*,6R*,8aR*)-3-cyano-8-methyl-6-(propylcarbamoyl)-4H,4aH,5H,6H,7H,8H,8aH,9H-thieno[3,2-g]quinolin-2-yl]carboximidate (499 mg) and ethanol (13 mL) was added sodium borohydride (59 mg) while stirring under ice bath cooling, and the mixture was stirred at the same temperature for 2.5 hours. To the reaction mixture was added water, and extracted with methylene chloride. After the separated organic layer was dried over anhydrous sodium sulfate, it was concentrated under reduced pressure to give (4aR*,6R*,8aR*)-3-cyano-8-methyl-2-(methylamino)-N-propyl-4H,4aH,5H,6H,7H,8H,8aH,9H-thieno[3,2-g]quinoline-6-carboxamide (446 mg).

$^1$H-NMR (CDCl$_3$) δ ppm: 0.93 (3H, t, J=7.4 Hz), 1.40-1.60 (3H, m), 1.65-1.80 (1H, m), 1.95-2.10 (2H, m), 2.15-2.30 (1H, m), 2.30-2.55 (6H, m), 2.60-2.70 (1H, m), 2.90-3.10 (5H, m), 3.15-3.30 (2H, m), 4.75-4.85 (1H, m), 5.40-5.50 (1H, m)

To a mixture of (4aR*,6R*,8aR*)-3-cyano-8-methyl-2-(methylamino)-N-propyl-4H,4aH,5H,6H,7H,8H,8aH,9H-thieno[3,2-g]quinoline-6-carboxamide (446 mg) and acetonitrile (12 mL) was added 4-dimethylaminopyridine (79 mg), followed by di-tert-butyldicarbonate (561 mg) while stirring at room temperature, and the mixture was stirred at the same temperature for 12 hours. To the reaction mixture was added water, and extracted with ethyl acetate. After the separated organic layer was dried over anhydrous sodium sulfate, it was concentrated under reduced pressure. The residue was purified by aminopropyl silica gel column chromatography (eluent: 0%-5% methanol/ethyl acetate, gradient elution) to give tert-butyl N-[(4aR*,6R*,8aR*)-3-cyano-8-methyl-6-(propylcarbamoyl)-4H,4aH,5H,6H,7H,8H,8aH,9H-thieno[3,2-g]quinolin-2-yl]-N-methylcarbamate (517 mg).

$^1$H-NMR (CDCl$_3$) δ ppm: 0.93 (3H, t, J=7.4 Hz), 1.45-1.60 (12H, m), 1.65-1.85 (1H, m), 1.95-2.10 (2H, m), 2.20-2.55 (7H, m), 2.70-2.85 (1H, m), 2.95-3.15 (5H, m), 3.15-3.30 (2H, m), 5.40-5.50 (1H, m)

To a mixture of tert-butyl N-[(4aR*,6R*,8aR*)-3-cyano-8-methyl-6-(propylcarbamoyl)-4H,4aH,5H,6H,7H,8H,8aH, 9H-thieno[3,2-g]quinolin-2-yl]-N-methylcarbamate (412 mg) and tetrahydrofuran (5 mL) was added a 1 mol/L sodium hexamethyldisilazide-tetrahydrofuran solution (1.2 mL) at −40° C. After stirring at the same temperature for 20 minutes, 4-nitrophenyl chloroformate (242 mg) was added to the mixture, and then stirred for 1 hour. After warming to room temperature and stirring for 1.5 hours, water and ethyl acetate were added. After the separated organic layer was dried over anhydrous sodium sulfate, it was concentrated under reduced pressure. The residue was purified by silica gel column chromatography (eluent: 80%-100% ethyl acetate/hexane, gradient elution) to give 4-nitrophenyl N-{[(4aR*,6R*,8aR*)-2-{[(tert-butoxy)carbonyl](methyl)amino}-3-cyano-8-methyl-4H,4aH,5H,6H,7H,8H,8aH,9H-thieno[3,2-g]quinolin-6-yl]carbonyl}-N-propylcarbamate (405 mg).

¹H-NMR (CDCl₃) δ ppm: 0.98 (3H, t, J=7.5 Hz), 1.35-1.52 (1H, m), 1.50 (9H, s), 1.64-1.76 (2H, m), 1.76-1.86 (1H, m), 2.01-2.11 (1H, m), 2.14-2.34 (2H, m), 2.35 (3H, s), 2.37-2.53 (2H, m), 2.71-2.82 (1H, m), 3.02-3.12 (2H, m), 3.38 (3H, s), 3.71-3.92 (3H, m), 7.32-7.40 (2H, m), 8.28-8.36 (2H, m)

To a mixture of 4-nitrophenyl N-{[(4aR*,6R*,8aR*)-2-{[(tert-butoxy)carbonyl](methyl)amino}-3-cyano-8-methyl-4H,4aH,5H,6H,7H,8H,8aH,9H-thieno[3,2-g]-quinolin-6-yl]carbonyl}-N-propylcarbamate (200 mg) and tetrahydrofuran (3 mL) was added N,N-dimethyl ethylenediamine (0.071 mL) while stirring at room temperature, and the mixture was stirred at the same temperature for 22 hours. The reaction mixture was concentrated under reduced pressure. The residue was purified by aminopropyl silica gel column chromatography (eluent: 0%-5% methanol/ethyl acetate, gradient elution) to give tert-butyl N-[(4aR*,6R*,8aR*)-3-cyano-6-[({[2-(dimethylamino)ethyl]-carbamoyl}(propyl)amino)carbonyl]-8-methyl-4H,4aH,5H,6H,7H,8H,8 aH,9H-thieno-[3,2-g]quinolin-2-yl]-N-methylcarbamate (160 mg).

¹H-NMR (CDCl₃) δ ppm: 0.95 (3H, t, J=7.4 Hz), 1.51 (9H, s), 1.51-1.72 (3H, m), 1.73-1.90 (1H, m), 1.99-2.15 (2H, m), 2.24-2.39 (1H, m), 2.26 (6H, s), 2.36 (3H, s), 2.40-2.54 (4H, m), 2.74-2.86 (1H, m), 2.93-3.18 (3H, m), 3.32-3.47 (5H, m), 3.63-3.86 (2H, m), 9.12-9.42 (1H, m)

To a mixture of tert-butyl N-[(4aR*,6R*,8aR*)-3-cyano-6-[({[2-(dimethylamino)ethyl]carbamoyl}(propyl)amino)carbonyl]-8-methyl-4H,4aH,5H,6H,7H,8H,8aH,9H-thieno[3,2-g]quinolin-2-yl]-N-methylcarbamate (160 mg) and ethyl acetate (10 mL) was added a 4 mol/L hydrogen chloride-ethyl acetate solution (5 mL) while stirring at room temperature, and the mixture was stirred at the same temperature for 11 hours. To the reaction mixture was added a 4 mol/L hydrogen chloride-ethyl acetate solution (5 mL) while stirring at room temperature, and then stirred at the same temperature for 13 hours. The solid was collected by filtration to give the title compound (compound 3-1) (116 mg). The structure was illustrated in Table 11.

¹H-NMR (DMSO-d₆) δ ppm: 0.87 (3H, t, J=7.4 Hz), 1.42-1.61 (3H, m), 2.09-2.30 (3H, m), 2.57-2.72 (1H, m), 3.08-3.42 (5H, m), 3.42-3.87 (19H, m), 7.59-7.75 (1H, m), 8.64-8.83 (1H, m), 10.02-10.29 (1H, m), 11.37-11.55 (1H, m)

Example 3-2

1-{[(4aR*,6R*,8aR*)-3-Cyano-8-methyl-2-(methylamino)-4H,4aH,5H,6H,7H,8H,8aH,9H-thieno[3,2-g]quinolin-6-yl]carbonyl}-3-[3-(dimethylamino)propyl]-1-propylurea di hydrochloride salt (compound 3-2)

To a mixture of 4-nitrophenyl N-{[(4aR*,6R*,8aR*)-2-{[(tert-butoxy)carbonyl](methyl)amino}-3-cyano-8-methyl-4H,4aH,5H,6H,7H,8H,8aH,9H-thieno[3,2-g]-quinolin-6-yl]carbonyl}-N-propylcarbamate (200 mg) and tetrahydrofuran (3 mL) was added (3-aminopropyl)dimethylamine (0.082 mL) while stirring at room temperature, and then stirred at the same temperature for 22 hours. The reaction mixture was concentrated under reduced pressure. The residue was purified by aminopropyl silica gel column chromatography (eluent: 0%-5% methanol/ethyl acetate, gradient elution) to give tert-butyl N-[(4aR*,6R*,8aR*)-3-cyano-6-[({[3-(dimethylamino)propyl]carbamoyl}(propyl)amino)carbonyl]-8-methyl-4H,4aH,5H,6H,7H,8H,8aH,9H-thieno-[3,2-g]quinolin-2-yl]-N-methylcarbamate (118 mg).

¹H-NMR (CDCl₃) δ ppm: 0.95 (3H, t, J=7.5 Hz), 1.50-1.76 (5H, m), 1.51 (9H, s), 1.76-1.88 (1H, m), 2.00-2.16 (2H, m), 2.20-2.40 (3H, m), 2.23 (6H, s), 2.37 (3H, s), 2.40-2.56 (2H, m), 2.75-2.85 (1H, m), 2.94-3.03 (1H, m), 3.03-3.17 (2H, m), 3.27-3.38 (2H, m), 3.40 (3H, s), 3.63-3.84 (2H, m), 9.15-9.35 (1H, m)

To a mixture of tert-butyl N-[(4aR*,6R*,8aR*)-3-cyano-6-[({[3-(dimethylamino)propyl]carbamoyl}(propyl)amino)carbonyl]-8-methyl-4H,4aH,5H,6H,7H,8H,8a H,9H-thieno[3,2-g]quinolin-2-yl]-N-methylcarbamate (118 mg) and ethyl acetate (10 mL) was added a 4 mol/L hydrogen chloride-ethyl acetate solution (5 mL) while stirring at room temperature, and the mixture was stirred at the same temperature for 11 hours. To the reaction mixture were added a 4 mol/L hydrogen chloride-ethyl acetate solution (5 mL) while stirring at room temperature, and then stirred at the same temperature for 14 hours. The solid was collected by filtration to give the title compound (compound 3-2) (45 mg). The structure was illustrated in Table 11.

¹H-NMR (DMSO-d₆) δ ppm: 0.86 (3H, t, J=7.4 Hz), 1.40-1.61 (3H, m), 1.82-1.96 (2H, m), 2.06-2.29 (3H, m), 2.50-4.00 (25H, m), 7.58-7.74 (1H, m), 8.44-8.76 (1H, m), 9.91-10.15 (1H, m), 11.33-11.55 (1H, m)

Example 4-1

1-{[(4aR,6R,8aR)-2-Amino-3-cyano-8-methyl-4H,4aH,5H,6H,7H,8H,8aH,9H-thieno-[3,2-g]quinolin-6-yl]carbonyl}-3-[2-(dimethylamino)ethyl]-1-propylurea di hydrochloride salt (compound 4-1)

To a mixture of 1-{[(4aR,6R,8aR)-2-amino-3-cyano-8-methyl-4H,4aH,5H, 6H,7H,8H,8aH,9H-thieno[3,2-g]quinolin-6-yl]carbonyl}-3-[2-(dimethylamino)ethyl]-1-propylurea (compound 1-1) (10.0 g) and ethanol (200 mL) was added dropwise a mixture of 12 mol/L hydrochloric acid (3.91 mL) and ethanol (30 mL) while stirring under ice bath cooling, and the mixture was stirred at the same temperature for 3 hours. The resulting solid was collected by filtration, and washed twice with ethanol (20 mL) to give 1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[2-(dimethylamino)ethyl]-1-propylurea di hydrochloride salt (11.5 g).

A mixture of 1-{[(4aR,6R,8aR)-2-amino-3-cyano-8-methyl-4H,4aH,5H,6H,7H, 8H,8aH,9H-thieno[3,2-g]quinolin-6-yl]carbonyl}-3-[2-(dimethylamino)ethyl]-1-propylurea di hydrochloride salt (8.0 g), ethanol (80 mL) and water (6.5 mL) was dissolved by heating at 60° C. while string. To the solution was added dropwise ethanol (80 mL) and heated at the same temperature for 1 hour. While stirring at the same temperature, ethanol (160 mL) was additionally added dropwise, and it was stirred at room temperature for 1 hour, then for 1 hour under ice bath cooling. The resulting solid was collected by filtration, and washed twice with ethanol (10 mL). After the obtained solid was air-dried overnight and dried at 75° C. for 5 hours under reduced pressure, it was additionally air-dried overnight to give the title compound (7.3 g) as a crystal. The structure was illustrated in Table 11.

¹H-NMR (MeOH-d₄) δ ppm: 0.97 (3H, t, J=7.4 Hz), 1.55-1.75 (3H, m), 2.15-2.40 (3H, m), 2.65-2.85 (2H, m), 2.97 (9H, s), 3.15-3.45 (5H, m), 3.55-3.90 (6H, m)

The crude crystal of compound 4-4 was prepared by carrying out a salt formation reaction in a manner similar to those as described in example 4-1 using the corresponding octahydrothienoquinoline instead of 1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[2-(dimethylamino)ethyl]-1-propylurea. The crude crystal was recrystallized from ethanol and water to give compound 4-4 as a crystal. The structure was illustrated in Table 11.

Example 4-2

1-{[(4aR,6R,8aR)-2-Amino-3-cyano-8-methyl-4H, 4aH,5H,6H,7H,8H,8aH,9H-thieno-[3,2-g]quinolin-6-yl]carbonyl}-3-[(2S)-1-(dimethylamino)propan-2-yl]-1-ethylurea di hydrochloride salt (compound 4-2)

To a mixture of 1-{[(4aR,6R,8aR)-2-amino-3-cyano-8-methyl-4H,4aH,5H,6H, 7H,8H,8aH,9H-thieno[3,2-g]quinolin-6-yl]carbonyl}-3-[(2S)-1-(dimethylamino)propan-2-yl]-1-ethylurea (compound 1-57) (0.88 g) and 2-propanol (17.6 mL) was added 12 mol/L hydrochloric acid (0.36 mL) while stirring under water bath cooling. To the solution was added dropwise diisopropyl ether (17.6 mL), and stirred at the room temperature for 1 hour, then for 1 hour under ice bath cooling. The resulting solid was collected by filtration, and washed twice with ice-cold 2-propanol/diisopropyl ether mixed solvent (2-propanol:diisopropyl ether=1:1) (4.4 mL) to give 1-{[(4aR,6R,8aR)-2-amino-3-cyano-8-methyl-4H,4aH,5H, 6H,7H,8H,8aH,9H-thieno-[3,2-g]quinolin-6-yl]carbonyl}-3-[(2S)-1-(dimethylamino)propan-2-yl]-1-ethylurea di hydrochloride salt (0.92 g).

A mixture of 1-{[(4aR,6R,8aR)-2-amino-3-cyano-8-methyl-4H,4aH,5H,6H,7H, 8H,8aH,9H-thieno[3,2-g]quinolin-6-yl]carbonyl}-3-[(2S)-1-(dimethylamino)propan-2-yl]-1-ethylurea di hydrochloride salt (1.0 g), acetonitrile (4.0 mL) and water (2.0 mL) was dissolved by heating at 60° C. while stirring. To the solution was added dropwise acetonitrile (20 mL) and cooled to the room temperature. While stirring at the same temperature, acetonitrile (15 mL) was additionally added dropwise, and it was stirred for 35 minutes under ice bath cooling. The resulting solid was collected by filtration, and washed three times with ice-cold water/acetonitrile mixed solvent (water:acetonitrile=1:50) (5.0 mL). The obtained solid was dried at 50° C. for 13 hours under reduced pressure to give the title compound (0.80 g) as a crystal. The structure was illustrated in Table 11.

$^1$H-NMR (DMSO-d$_6$) δ ppm: 1.11 (3H, t, J=7.0 Hz), 1.22 (3H, d, J=6.8 Hz), 1.40-1.60 (1H, m), 2.10-2.30 (3H, m), 2.55-2.70 (1H, m), 2.70-2.90 (10H, m), 3.05-3.30 (3H, m), 3.45-3.60 (1H, m), 3.60-3.80 (3H, m), 4.10-4.30 (1H, m), 7.18 (2H, s), 8.45-8.70 (1H, m), 9.75-9.95 (1H, m), 11.25-11.60 (1H, m)

The crude crystal of compound 4-3 was prepared by carrying out a salt formation reaction in a manner similar to those as described in example 4-2 using the corresponding octahydrothienoquinoline instead of 1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[(2S)-1-(dimethylamino)propan-2-yl]-1-ethylurea. The crude crystal was recrystallized from acetonitrile and water to give compound 4-3 as a crystal. The structure was illustrated in Table 11.

TABLE 11

| Compound No. | Structure |
|---|---|
| 2-1 | (structure) |
| 2-2 | (structure) |
| 2-3 | (structure) |
| 3-1 | (structure) |

TABLE 11-continued

| Compound No. | Structure |
|---|---|
| 3-2 | 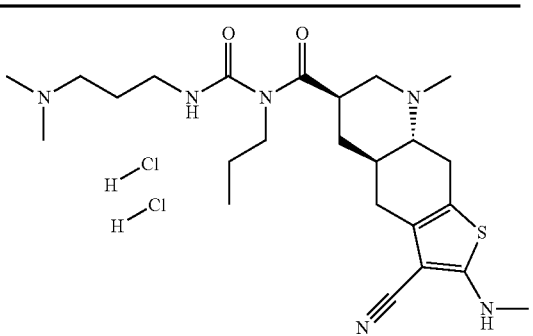 |
| 4-1 | 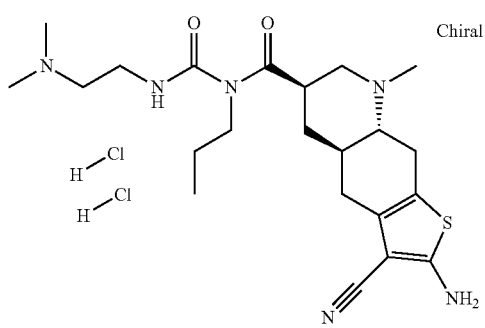 |
| 4-2 | 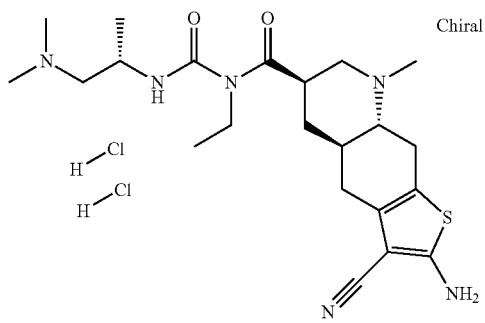 |
| 4-3 | 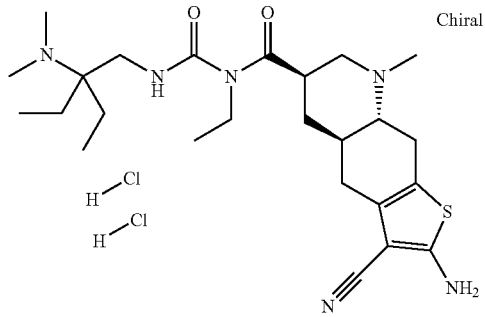 |
| 4-4 | 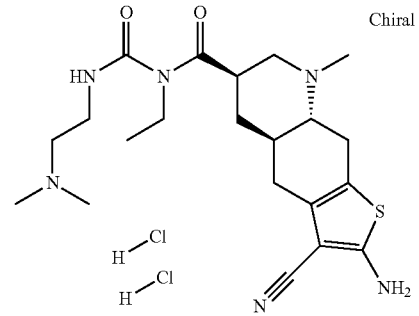 |

The structures of compound 2-1 to 2-3 and 3-1 to 3-2 in Table 11 indicate relative configuration, and the structures of compound 4-1 to 4-4 in Table 11 indicate absolute configuration.

The physical data of compounds 4-3 to 4-4 were shown below.

Compound 4-3

$^1$H-NMR (DMSO-$d_6$) δ ppm: 0.94 (6H, t, J=7.6 Hz), 1.14 (3H, t, J=6.9 Hz), 1.45-1.65 (1H, m), 1.65-1.85 (4H, m), 2.05-2.35 (3H, m), 2.55-2.85 (11H, m), 3.05-3.30 (2H, m), 3.50-3.90 (6H, m), 7.18 (2H, s), 8.75-9.10 (1H, m), 9.55-9.80 (1H, m), 11.40-11.70 (1H, m)

Compound 4-4

$^1$H-NMR (DMSO-$d_6$) δ ppm: 1.12 (3H, t, J=7.1 Hz), 1.40-1.60 (1H, m), 2.05-2.30 (3H, m), 2.55-2.90 (11H, m), 3.05-3.25 (2H, m), 3.45-3.85 (6H, m), 7.18 (2H, s), 8.55-8.85 (1H, m), 10.00-10.25 (1H, m), 11.25-11.60 (1H, m)

Test Example 1

Identification Test of Stimulating Activities on Human Dopamine $D_2$ Receptor

1) Construction of Human Dopamine $D_2$ Receptor Expression Plasmid

The PCR was performed using forward primer depicted as sequence ID No. 1, reverse primer depicted as sequence ID No. 2 and Herculase (Stratagene) as template of human brain cDNA (Japan Becton, Dickinson and Company). The PCR product was inserted into a plasmid (pcDNA3.1/V5-His-Topo (registered mark), Invitrogen). The PCR product-inserted plasmid was transformed in E. coli (One Shot TOP10 Chemically Competent, Invitrogen). That E. coli was incubated in LB agar medium contained 50 μg/mL ampicillin for a day. A selected colony was incubated in LB medium contained 50 μg/mL ampicillin and PCR product-inserted plasmid was purified with QIAprep Spin Miniprep Kit (QIAGEN). The base sequence of protein expression site in the plasmid (sequence ID No. 3) accorded to the base sequence of human dopamine $D_2$ receptor ($NM_{1-000795}$) registered on the public database (NCBI), except 1 base. But, the sequence of amino acids translated by base sequence of that plasmid accorded to it of human dopamine $D_2$ receptor ($NM_{1-000795}$) registered on NCBI completely. Therefore, the proteins induced from this plasmid were identified with human dopamine $D_2$ receptor. The pcDNA3.1/V5-His-Topo (registered mark) that the base sequence depicted as sequence ID No. 3 was inserted, was identified as human dopamine $D_2$ receptor expression plasmid.

2) Preparation of Human Dopamine $D_2$ Receptor Expression Cells (1) Cell Culture HEK 293 cells (Dainippon Sumitomo Pharma Co., Ltd.) were cultured in 5% $CO_2$ incubator at 37° C. in D-MEM (Dulbecco's Modified Eagle Medium) liquid medium (low glucose, pyruvic acid and L-glutamine were contained, Invitrogen) in which penicillin-streptomycin solution (Invitrogen, final concentration: 100 U/mL as penicillin, 100 µg/mL as streptomycin) and fetal bovine serum (final concentration: 10%).

(2) the Passage of Cells

Mostly confluent HEK293 cells were washed with PBS (Phosphate Buffered Saline, Invitrogen), followed by exfoliation with 0.05% trypsin-EDTA (Invitrogen) and they were suspended with above-mentioned liquid medium. After centrifuging, the supernatant was removed and the cells were diluted with medium and cell number was counted. After that, the cells were scattered at appropriate cell concentration.

(3) Establishment of HEK293 Cells Expressed Human Dopamine $D_2$ Receptor Stably Human dopamine $D_2$ receptor expression plasmid was digested with ScaI and changed to linear plasmid. The linear plasmid was transfected in HEK293 cells using lipofection method (Lipofectamine (registered mark) 2000 (Invitrogen)). After procurement of neomycin resistant cell using 1 mg/mL Geneticin (registered mark) (Invitrogen), cell line was selected according to the method of 3) seeing below. 3) Identification and selection of HEK293 cells expressed human dopamine $D_2$ receptor stably (1) the Passage of Cells Mostly confluent HEK293 cells expressed human dopamine $D_2$ receptor stably were washed with PBS, followed by exfoliation with 0.05% trypsin-EDTA and D-MEM liquid medium (low glucose, pyruvic acid and L-glutamine were contained) containing Geneticin (registered mark) (final concentration: 0.1 mg/mL) as antibiotics and fetal bovine serum (final concentration: 10%) was added. After centrifuging, the supernatant was removed and the cells were diluted with above-mentioned liquid medium. After counting cell number, the cells were scattered at appropriate concentration.

(2) Preparation of Cells

Mostly confluent HEK293 cells expressed human dopamine $D_2$ receptor stably were washed with PBS, followed by exfoliation with 0.05% trypsin-EDTA and the cells were suspended in D-MEM liquid medium (phenol red-free, low glucose and pyruvic acid were contained, Invitrogen) containing fetal bovine serum (final concentration: 10%) and GlutaMax (registered mark) I (Invitrogen, final concentration: 2 mM). The suspension was scattered at $5 \times 10^4$ cells/100 µL/well on poly-D-lysine-coated 96-well microplate (BD BioCoat (registered mark), Japan Becton, Dickinson and Company). The scattered cells were cultured in 5% $CO_2$ incubator at 37° C. To change signal of human dopamine $D_2$ receptor cAMP reaction interacting $G_{i/o}$ protein to carcium reaction, pLEC1-Gqo5-HA (Molecular Devices) was transfected in that cells according to the procedure seeing below.

(3) Transfection of pLEC1-Gqo5-HA pLEC1-Gqo5-HA and Lipofectamine (registered mark) 2000 were diluted to 0.008 g/L and 0.016 g/L each other with OPTI-MEM (registered mark) I Reduced-Serum Medium (Invitrogen) and incubated at room temperature. After incubation, the pLEC1-Gqo5-HA-diluted solution and Lipofectamine (registered mark) 2000-diluted solution were mixed at an equal volume and incubated at room temperature to form a complex. The complex was dispensed at 50 µL/well on the cells prepared above. The cells were incubated in 5% $CO_2$ incubator at 37° C. for 2 days and used in measurement of intracellular calcium concentration.

(4) Identification with Measurement of Intracellular Calcium Concentration

The measurement of intracellular calcium concentration induced by each test compound was performed using the forced expression cells mentioned above. Each dimethyl sulfoxide (DMSO) solution contained test compounds at 30 mM was diluted to appropriate concentration with assay buffer (Hank's Balanced Salt Solution (HBSS, Invitrogen), 20 mM HEPES (Invitrogen), 1.3 mM calcium chloride, 0.5 mM magnesium chloride and 0.4 mM magnesium sulfate were contained, pH7.4). The forced expression cells were washed with assay buffer, and 100 µL/well of fluorescent calcium indicator (Fluo-4 NW Calcium Assay Kit (Molecular Probes™)) was added and incubated in 5% $CO_2$ incubator at 37° C. After incubation, 50 µL/well of each test compound was added, and the concentration of intracellular calcium was measured as fluorescent signal with FlexStation (registered mark) II (Molecular Devices). The cell line expressed human dopamine $D_2$ receptor stably having good response was named as $hD_2R\#7$ cells.

4) Preparation of Membrane Homogenates from $hD_2R\#7$ Cells (1) the Passage of $hD_2R\#7$ Cells Mostly confluent $hD_2R\#7$ cells were washed with PBS, followed by exfoliation with 0.05% trypsin-EDTA and D-MEM liquid medium (low glucose, pyruvic acid and L-glutamine were contained) containing Geneticin (registered mark) (final concentration: 0.1 mg/mL) as antibiotics and fetal bovine serum (final concentration: 10%) were added. After centrifuging, the supernatant was removed and the cells were diluted with above-mentioned liquid medium. After counting cell number, and the cells were scattered at appropriate concentration.

(2) Preparation of Membrane Homogenates from $hD_2R\#7$ Cells

The cells, which were grown to confluence in 150 mm dishes (IWAKI), were harvested with isotonic buffer (50 mM Tris (Sigma), 2 mM ethylenediamine-tetraacetic acid (Invitrogen), and 125 mM sodium chloride (Wako Pure Chemicals), pH 7.4) and centrifuged at 1880×g and 4° C. for 10 minutes, and the cell pellets were then suspended in isotonic buffer. After being subjected to one cycle of freezing and thawing, the cells were centrifuged at 1880×g and 4° C. for 10 minutes, and the cell pellets were suspended in isotonic buffer. The cells were centrifuged at 1880×g and 4° C. for 10 minutes, and the cell pellets were suspended in isotonic buffer and homogenate buffer (10 mM sodium bicarbonate (Nacalai) and 5 mM ethylenediamine-tetraacetic acid, pH 7.5). The volume ratio of isotonic-to-homogenate buffer was 2. The cells were sonicated and centrifuged at 1880×g and 4° C. for 10 minutes, and the supernatants were ultracentrifuged at 80000×g and 4° C. for 30 minutes. The final cell pellets were suspended in homogenate buffer containing protease inhibitor cocktail (Nacalai) and stored at −80° C. until use. The protein concentration was determined using BCA Protein Assay Kit (Pierce) in accordance with the manufacturer's instructions.

5) Determination of Stimulating Activities of Human Dopamine $D_2$ Receptor

The stimulating activities of human dopamine $D_2$ receptor was determined by measuring the binding potential of $[^{35}S]$-guanosine 5'-[gamma-thio]triphosphate ($[^{35}S]GTP\gamma S$, PerkinElmer) according to the method described by Newman-Tancredi A. et al. (Naunyn-Schmiedeberg's Arch Pharmacol, 1999, vol. 359, pp. 447-453) with a minor modification. Test compounds and dopamine hydrochloride (Fluka) as positive control were dissolved in dimethyl sulfoxide (CARLBIOCHEM), resulting in 30 mM. The both compounds were diluted with assay buffer (50 mM Tris, 100 mM sodium chloride, 5 mM magnesium chloride (Nacalai), 1 mM ethylenediamine-tetraacetic acid, 1 mM dithiothreitol (Wako Pure Chemicals), 10 µM guanosine diphosphate (Wako Pure Chemicals) and 0.5% bovine serum albumin (Sigma), pH 7.4) to a final concentration of 100 pM (only test compounds), 1 nM, 10 nM, 100 nM, 1 µM, 10 µM and 100 µM (only dopamine hydrochloride). The above membrane homogenates and [$^{35}$S]GTPγS were diluted with assay buffer to a final concentration of 0.06 mg/mL and 0.6 nM, respectively. The serial diluted compounds (50 µL), the diluted membrane homogenates (50 µL) and the diluted [$^{35}$S]GTPγS (50 µL) were mixed on multi-screen 96-well plate (Millipore) and shaken lightly at room temperature for 60 minutes. The reaction was terminated by vacuum filtration with three times washes of ice-cold wash buffer (50 mM Tris, 100 mM sodium chloride, 5 mM magnesium chloride, and 1 mM ethylenediamine-tetraacetic acid, pH 7.4). After drying the bottoms of the plate at 60° C., MicroScinti-40 (PerkinElmer) (30 µL) was added in the plate. The tops of the plate were sealed by TopSeal-A (PerkinElmer), and the radioactivity was determined in a TopCount NXT (registered mark) (PerkinElmer) after shaking lightly for 5-10 minutes. The data was analyzed by nonlinear regression and sigmoidal dose-response curve fitting using GraphPad PRISM 4.0 (GraphPad Software), and values of $EC_{50}$ (concentration of the compound producing half the maximal effect of the compound) were calculated. The data was presented as mean value (n=2). As comparative examples, ropinirole as non-ergot dopamine $D_2$ receptor agonist and pergolide as ergot dopamine $D_2$ receptor agonist, were examined in a similar fashion. These results were shown in Table 12.

TABLE 12

| Compound No. | $EC_{50}$(µmol/L) |
|---|---|
| 1-1 | 0.006 |
| 1-2 | 0.012 |
| 1-3 | 0.007 |
| 1-4 | 0.003 |
| 1-6 | 0.011 |
| 1-13 | 0.007 |
| 1-21 | 0.021 |
| 1-23 | 0.008 |
| 1-24 | 0.017 |
| 1-25 | 0.015 |
| 1-30 | 0.004 |
| 1-36 | 0.010 |
| 1-37 | 0.006 |
| 1-39 | 0.017 |
| 1-43 | 0.032 |
| 1-44 | 0.013 |
| 1-46 | 0.010 |
| 1-56 | 0.009 |
| 1-57 | 0.005 |
| 1-61 | 0.011 |
| 1-66 | 0.014 |
| 1-68 | 0.012 |
| 1-82 | 0.013 |
| 1-83 | 0.006 |
| 1-84 | 0.007 |
| 1-86 | 0.013 |
| 1-87 | 0.022 |
| 1-88 | 0.024 |
| 1-99 | 0.008 |
| 1-104 | 0.004 |
| 1-105 | 0.005 |
| 1-106 | 0.004 |
| 1-107 | 0.002 |
| 1-108 | 0.006 |

TABLE 12-continued

| Compound No. | $EC_{50}$(µmol/L) |
|---|---|
| 1-109 | 0.003 |
| Ropinirole | 0.892 |
| Pergolide | 0.023 |

These results clearly showed that the compounds of the present invention exhibited potent stimulating activities of human dopamine $D_2$ receptor.

Test Example 2

Identification Test of Stimulating Activities on Human Serotonin 5-$HT_{2B}$ Receptor 1) Construction of Human Serotonin 5-$HT_{2B}$ Receptor Expression Plasmid The PCR was performed using forward primer depicted as sequence ID No. 4, reverse primer depicted as sequence ID No. 5 and KOD-Plus-Ver.2 (TOYOBO) as template of human brain hippocampus cDNA (Clontech). The PCR product was inserted into a plasmid (pcDNA3.1/V5-His-Topo (registered mark)). The PCR product-inserted plasmid was transformed in E. coli (One Shot TOP10 Chemically Competent). That E. coli was incubated in LB agar medium contained 50 µg/mL ampicillin for a day. A selected colony was incubated in LB medium contained 50 µg/mL ampicillin and PCR product-inserted plasmid was purified with QIAprep Spin Miniprep Kit (QIAGEN). The base sequence of protein expression site in the plasmid (sequence ID No. 6) accorded to the base sequence of human serotonin 5-$HT_{2B}$ receptor ($NM_{1-000867}$) registered on the public database (NCBI) completely. Therefore, the proteins induced from this vector were identified with human serotonin 5-$HT_{2B}$ receptor. The pcDNA3.1/V5-His-Topo (registered mark) that the base sequence depicted as sequence ID No. 6 was inserted, was identified as human serotonin 5-$HT_{2B}$ receptor expression plasmid.

2) Preparation of human serotonin 5-$HT_{2B}$ receptor expression cells (1) Cell Culture HEK 293 cells were cultured in 5% $CO_2$ incubator at 37° C. in D-MEM liquid medium (low glucose, pyruvic acid and L-glutamine were contained) in which penicillin-streptomycin solution (final concentration: 100 U/mL as penicillin, 100 µg/mL as streptomycin) as antibiotics and fetal bovine serum (final concentration: 10%) were contained.

(2) the Passage of a Cell

Mostly confluent HEK293 cells were washed with PBS, followed by exfoliation with 0.05% trypsin-EDTA and above-mentioned liquid medium was added. After centrifuging, the supernatant was removed and the cells were diluted with medium. After counting cell number of the diluted cells, the cells were scattered at appropriate cell concentration.

(3) Preparation of Cells

Mostly confluent HEK293 cells were washed with PBS, followed by exfoliation with 0.05% trypsin-EDTA and the cells were suspended in D-MEM liquid medium (phenol red-free, low glucose, pyruvic acid were contained) containing fetal bovine serum (final concentration: 10%) and GlutaMax (registered mark)I (final concentration: 2 mM). The suspension was scattered at $5 \times 10^4$ cells/100 L/well on poly-D-lysine-coated 96-well microplate (BD BioCoat (registered mark)). The scattered cells were cultured in 5% $CO_2$ incubator at 37° C. Human serotonin 5-$HT_{2B}$ receptor expression plasmid was transfected in that cells according to the procedure seeing below.

(4) Transfection of Human Serotonin 5-$HT_{2B}$ Receptor Plasmid

Human serotonin 5-$HT_{2B}$ receptor expression plasmid and Lipofectamine (registered mark) 2000 (Invitrogen) were diluted to 0.008 g/L and 0.016 g/L each other with OPTI-MEM (registered mark)I Reduced-Serum Medium and incubated at room temperature. After incubation, the human serotonin 5-$HT_{2B}$ receptor exoression plasmid-diluted liquid and Lipofectamine (registered mark) 2000-diluted liquid were mixed at an equal volume and incubated at room temperature to form a complex. The complex was dispensed at 50 μL/well on the cells prepared above. The cells were incubated in 5% $CO_2$ incubator at 37° C. for 2 days. After incubation, the cells were used as human serotonin 5-$HT_{2B}$ receptor forced expression cells for measurement of intracellular calcium concentration.

3) Determination of Stimulating Activities of Human Serotonin 5-$HT_{2B}$ Receptor The stimulating activities of human serotonin 5-$HT_{2B}$ receptor was determined by measuring of intracellular calcium concentration. The 30 mM dimethyl sulfoxide (DMSO) solution contained test compounds or serotonin hydrochloride (Sigma) as positive control, was diluted with assay buffer ((HBSS), 20 mM HEPES, 1.3 mM calcium chloride, 0.5 mM magnesium chloride and 0.4 mM magnesium sulfate were contained, pH7.4) to appropriate concentration.

The forced expression cells were washed with assay buffer, and 100 μL/well of fluorescent calcium indicator (Fluo-4 NW Calcium Assay Kit) was added and incubated in 5% $CO_2$ incubator at 37° C. After incubation, 50 μL/well of each test compound was added, and the concentration of intracellular calcium was measured as fluorescent signal with FlexStation (registered mark) II (Molecular Devices). The data was analyzed by nonlinear regression and sigmoidal dose-response curve fitting using GraphPad PRISM 4.0, and values of $EC_{50}$ (concentration of the compound producing half the maximal effect of the compound) were calculated. The data was presented as mean value (n=2). As comparative examples, ropinirole as non-ergot dopamine $D_2$ receptor agonist and pergolide as ergot dopamine $D_2$ receptor agonist, were examined in a similar fashion. These results were shown in Table 13.

TABLE 13

| Compound No. | $EC_{50}$(μmol/L) |
| --- | --- |
| 1-1 | >10 |
| 1-2 | >10 |
| 1-3 | >10 |
| 1-4 | >10 |
| 1-6 | >10 |
| 1-23 | >10 |
| 1-24 | >10 |
| 1-30 | >10 |
| 1-43 | >10 |
| 1-46 | >10 |
| 1-57 | >10 |
| 1-82 | >10 |
| 1-83 | >10 |
| 1-84 | >10 |
| 1-99 | >10 |
| 1-104 | >10 |
| 1-105 | >10 |
| 1-106 | >10 |
| 1-107 | >10 |
| 1-108 | >10 |
| 1-109 | >10 |
| Ropinirole | 2.593 |
| Pergolide | 0.287 |

These results clearly showed that the compounds of the present invention exhibited extremely minor stimulating activities of human serotonin 5-$HT_{2B}$ receptor as compared with ropinirole and pergolide.

Test Example 3

The Drug Efficiency Evaluation in Unilateral 6-Hydroxydopamine-Lesioned Hemi-Parkisonian Rats 1) Materials The following materials were used:
6-hydroxydopamine hydrochloride (6-OHDA, Sigma); desipramine hydrochloride (desipramine, Sigma); L-ascorbic acid (Sigma); pentobarbital sodium (somnopentyl injection, Kyoritsu Seiyaku); R-(−)-apomorphine hydrochloride hemihydrate (apomorphine, Sigma); ropinirole hydrochloride (ropinirole; Sequoia); 0.5% methyl cellulose solution (Wako Pure Chemicals); N,N-Dimethylacetamide (DMA, Wako Pure Chemicals); hydrochloric acid (Wako Pure Chemicals); distilled water (Otsuka Pharmaceutical Factory, Inc.); physiological saline (Otsuka Pharmaceutical Factory, Inc.).

6-OHDA was dissolved at 2 mg/mL in a physiolosical saline solution containing 0.2% L-ascorbic acid. Desipramine was dissolved at 10 mg/mL in a physiolosical saline solution in a hot-water bath. Apomorphine was dissolved at 0.1 mg/mL in a physiolosical saline solution. Ropinirole was dissolved in distilled water. Test compounds were dissolved in a solution containing 2% DMA, 100 or 200 mol % hydrochloric acid, and 98% of a 0.5% methyl cellulose solution.

2) Preparation of 6-OHDA-Lesioned Model

Preparation of 6-OHDA-lesioned model was performed according to the method described by Koga K. et al. (Eur J Pharmacol, 2000, vol. 408, P. 249-255) with a minor modification. Male Sprague-Dawley rats (6-weeks-old, Charles River Laboratories Japan Inc.) were anaesthetized with intraperitoneal somnopentyl (45 mg/kg) injection and placed in a stereotaxic frame (Narishige). In order to prevent 6-OHDA-induced damage of noradrenergic neurons, desipramine (25 mg/kg) was intraperitoneally injected 30 minutes before the 6-OHDA injection. After the bregma identification via a middle calvarial incision, the skull was drilled using a dental drill at the site of 6-OHDA injection. The lesion was made by injecting 6-OHDA (8 μg in 4 μL at a speed of 1 μL/minute) unilaterally into the left medial forebrain bundle by using a injection cannula (30 gauge needle) connected to a microsyringe (Hamilton) (the lesion coordinates; A/P −2.5 mm, L/M −1.8 mm, and V/D −8.0 mm, from the bregma point and surface of the skull). The cannula was carefully removed from the animal after keeping placed on the lesion site for 5 minutes. The skull was filled its hole with dental cement, disinfected, and the scalp incision was surgically sutured. Animals recovered from anesthesia were housed as usual until the day of the experiment.

3) Determining of Contralateral Rotational Behavior

Three weeks after the lesion, rats were tested on the basis of their contralateral rotational behavior (single rotation was defined as a 360° turn) in response to 0.1 mg/kg apomorphine given subcutaneously. For behavioral observation, rats were placed in plastic cylinders of a diameter of 30 cm, and its contralateral rotational behaviors were videotaped and quantified by rat-rotation auto counting system R-RACS (Kissei Wellcom). On the experimental day, animals were fasted overnight, and test compounds were orally administered at doses of 10 mg/kg. The drug potency was measured until up to 24 hours after administration as the number of contralateral rotation. Duration of the response was defined as a total time period except for a time period that the animal exhibited less than 10 counts of rotation per 5 minutes for more than 60 minutes period. Total number of rotations and the duration of the response in experimental period were presented as mean value. As comparative example, ropinirole as non-ergot dopamine $D_2$ receptor agonist, was examined in a similar fashion. These results were shown in Table 14.

TABLE 14

| Compound No. | Duration (minutes) | Total number or rotations |
| --- | --- | --- |
| 1-1 | 1101.3 | 9431.8 |
| 1-3 | 845.0 | 4478.3 |
| 1-4 | 1131.3 | 6338.8 |
| 1-24 | 766.3 | 5230.0 |
| 1-43 | 843.8 | 7557.5 |
| 1-46 | 1158.8 | 10329.8 |
| 1-57 | 1190.0 | 9976.5 |
| 1-107 | 1068.3 | 4033.3 |
| 1-108 | 698.8 | 2577.5 |
| Ropinirole | 61.3 | 276.3 |

As a result of these experiments, it was recognized that the compounds of the present invention have remarkable long-lasting drug effects as compared with ropinirole.

INDUSTRIAL APPLICABILITY

Compounds of the present invention exhibit excellent dopamine $D_2$ receptor stimulating activities, and are accordingly useful for treating or preventing Parkinson's disease, restless legs syndrome or hyperprolactinemia.

SEQUENCE LISTING FREE TEXT

[SEQ ID No. 1]
Sequence ID No. 1 indicates the sequence of forward primer employed to amplify the DNA sequence shown in sequence ID No. 3.

[SEQ ID No. 2]
Sequence ID No. 2 indicates the sequence of reverse primer employed to amplify the DNA sequence shown in sequence ID No. 3.

[SEQ ID No. 3]
Sequence ID No. 3 indicates the DNA sequence, which was intended to express the recombinant human dopamine $D_2$ receptor, amplified by using primer pair shown in sequence ID No. 1 and 2.

[SEQ ID No. 4]
Sequence ID No. 4 indicates the sequence of forward primer employed to amplify the DNA sequence shown in sequence ID No. 6.

[SEQ ID No. 5]
Sequence ID No. 5 indicates the sequence of reverse primer employed to amplify the DNA sequence shown in sequence ID No. 6.

[SEQ ID No. 6]
Sequence ID No. 6 indicates the DNA sequence, which was intended to express the recombinant human serotonin 5-$HT_{2B}$ receptor, amplified by using primer pair shown in sequence ID No. 4 and 5.

The invention claimed is:

1. A compound represented by the general formula (I):

[Chem. 1]

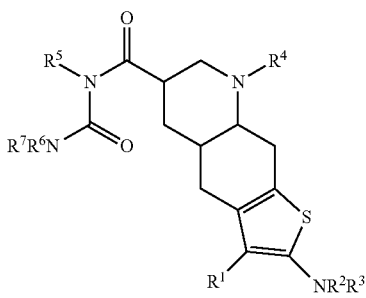

or a pharmaceutically acceptable salt thereof, wherein
$R^1$ is
a cyano group,
$R^2$ and $R^3$ are each a hydrogen atom;
$R^4$ is a hydrogen atom, a $C_{1-6}$ alkyl group, or a halo-$C_{1-6}$ alkyl group;
$R^5$ is any one of the following a) to j):
a) a $C_{1-6}$ alkyl group,
b) a halo-$C_{1-6}$ alkyl group,
c) a cycloalkyl group,
d) a benzo-fuzed cycloalkyl group,
e) a cycloalkyl-$C_{1-6}$ alkyl group,
f) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group, and a hydroxy-$C_{1-6}$ alkyl group,
g) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and a $C_{1-6}$ alkoxy group,
h) a $C_{2-6}$ alkenyl group,
i) a $C_{1-6}$ alkoxy-$C_{1-6}$ alkyl group, or
j) a $R^{10}R^{11}N$—$C_{1-6}$ alkyl group;
$R^6$ and $R^7$ are each independently any one of the following a) to k):
a) a hydrogen atom,
b) a $C_{1-6}$ alkyl group,
c) a halo-$C_{1-6}$ alkyl group,
d) a heterocycloalkyl group,
e) a heterocycloalkyl-$C_{1-6}$ alkyl group,
f) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group, and a $R^{10}R^{11}N$—$C_{1-6}$ alkyl group,
  g) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and
  a $C_{1-6}$ alkoxy group,
  h) a $C_{1-6}$ alkoxy-$C_{1-6}$ alkyl group,
  i) a $R^{12}R^{13}N$—$C_{1-6}$ alkyl group,
  j) a $R^{12}R^{13}N$—$C_{1-6}$ alkoxy-$C_{1-6}$ alkyl group, or
  k) a $R^{12}R^{13}N$—C(O)—$C_{1-6}$ alkyl group;
  $R^{10}$ and $R^{11}$ are each independently a hydrogen atom, a $C_{1-6}$ alkyl group or a hydroxy-$C_{1-6}$ alkyl group, or $R^{10}$ and $R^{11}$, together with the nitrogen atom to which they are bonded, form a cyclic amino group unsubstituted or substituted with 1 or 2 $C_{1-6}$ alkyl groups; and
  $R^{12}$ and $R^{13}$ are each independently a hydrogen atom, a $C_{1-6}$ alkyl group, a hydroxy-$C_{1-6}$ alkyl group or an aryl group, or $R^{12}$ and $R^{13}$, together with the nitrogen atom to which they are bonded, form a cyclic amino group unsubstituted or substituted with 1 or 2 $C_{1-6}$ alkyl groups.

2. The compound according to claim 1, or a pharmaceutically acceptable salt thereof, wherein $R^4$ is a hydrogen atom or a $C_{1-6}$ alkyl group.

3. The compound according to claim 2, or a pharmaceutically acceptable salt thereof, wherein
  $R^6$ is a hydrogen atom; and
  $R^7$ is any one of the following a) to i):
    a) a $C_{1-6}$ alkyl group,
    b) a halo-$C_{1-6}$ alkyl group,
    c) a heterocycloalkyl-$C_{1-6}$ alkyl group,
    d) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group, and a $R^{10}R^{11}N$—$C_{1-6}$ alkyl group,
    e) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and
    a $C_{1-6}$ alkoxy group,
    f) a $C_{1-6}$ alkoxy-$C_{1-6}$ alkyl group,
    g) a $R^{12}R^{13}N$—$C_{1-6}$ alkyl group,
    h) a $R^{12}R^{13}N$—$C_{1-6}$ alkoxy-$C_{1-6}$ alkyl group, or
    i) a $R^{12}R^{13}N$—C(O)—$C_{1-6}$ alkyl group.

4. The compound according to claim 3, or a pharmaceutically acceptable salt thereof, wherein
  $R^5$ is any one of the following a) to h):
    a) a $C_{1-6}$ alkyl group,
    b) a halo-$C_{1-6}$ alkyl group,
    c) a cycloalkyl-$C_{1-6}$ alkyl group,
    d) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group, and a hydroxy-$C_{1-6}$ alkyl group,
    e) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and
    a $C_{1-6}$ alkoxy group,
    f) a $C_{2-6}$ alkenyl group,
    g) a $C_{1-6}$ alkoxy-$C_{1-6}$ alkyl group, or
    h) a $R^{10}R^{11}N$—$C_{1-6}$ alkyl group.

5. The compound according to claim 2, or a pharmaceutically acceptable salt thereof, wherein
  $R^6$ is a hydrogen atom; and
  $R^7$ is: any one of the following a) to f)
    a) a $C_{1-6}$ alkyl group,
    b) a halo-$C_{1-6}$ alkyl group,
    c) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group, and a $R^{10}R^{11}N$—$C_{1-6}$ alkyl group,
    d) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and
    a $C_{1-6}$ alkoxy group,
    e) a $C_{1-6}$ alkoxy-$C_{1-6}$ alkyl group, or
    f) a $R^{12}R^{13}N$—$C_{1-6}$ alkyl group.

6. The compound according to claim 3, or a pharmaceutically acceptable salt thereof, wherein
  $R^4$ is a methyl group;
  $R^5$ is any one of the following a) to f):
    a) a $C_{1-6}$ alkyl group,
    b) a cycloalkyl-$C_{1-6}$ alkyl group,
    c) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group, and a hydroxy-$C_{1-6}$ alkyl group,
    d) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and
    a $C_{1-6}$ alkoxy group,
    e) a $C_{1-6}$ alkoxy-$C_{1-6}$ alkyl group, or
    f) a $R^{10}R^{11}N$—$C_{1-6}$ alkyl group;
  $R^6$ is a hydrogen atom; and
  $R^7$ is any one of the following a) to d):
    a) a $C_{1-6}$ alkyl group,
    b) an aralkyl group, wherein the ring of the aralkyl group is unsubstituted or substituted with 1 to 5 substituents independently selected from the group consisting of a halogen atom, a $C_{1-6}$ alkyl group, a halo-$C_{1-6}$ alkyl group, a $C_{1-6}$ alkoxy group, and a $R^{10}R^{11}N$—$C_{1-6}$ alkyl group,
    c) a heteroaryl-$C_{1-6}$ alkyl group, wherein the ring of the heteroaryl-$C_{1-6}$ alkyl group is unsubstituted or substituted with 1 to 3 substituents independently selected from the group consisting of a $C_{1-6}$ alkyl group, a halo-$C_{1-6}$ alkyl group, and
    a $C_{1-6}$ alkoxy group, or
    d) a $R^{12}R^{13}N$—$C_{1-6}$ alkyl group.

7. The compound according to claim 4, or a pharmaceutically acceptable salt thereof, wherein
  $R^5$ is any one of the following a) to d):
    a) a $C_{1-6}$ alkyl group,
    b) a cycloalkyl-$C_{1-6}$ alkyl group,
    c) a $C_{1-6}$ alkoxy-$C_{1-6}$ alkyl group, or
    d) a $R^{10}R^{11}N$—$C_{1-6}$ alkyl group; and R⁷ is any one of the following a) to b):
a) a $C_{1-6}$ alkyl group, or
b) a $R^{12}R^{13}N-C_{1-6}$ alkyl group.

8. The compound according to claim 1, or a pharmaceutically acceptable salt thereof, wherein
the compound is represented by the general formula (II):

[Chem. 2]

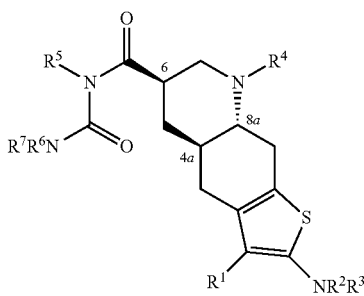

(II)

in which the configuration at 4a, 6 and 8a positions is represented by a relative configuration.

9. The compound according to claim 1, or a pharmaceutically acceptable salt thereof, wherein
the compound is represented by the general formula (III):

[Chem. 3]

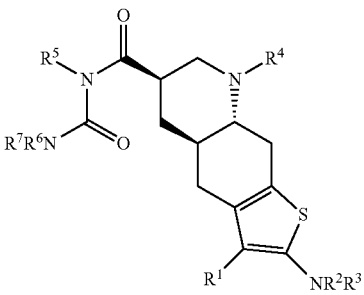

(III)

in which the configuration at 4a, 6 and 8a positions is represented by an absolute configuration.

10. A compound selected from the group consisting of:
1-{[(4aR,6R,8aR)-2-amino-3-cyano-8-methyl-4H,4aH,5H,6H,7H, 8H,8aH, 9H-thieno[3,2-g]quinolin-6-yl]carbonyl}-3-[2-(dimethylamino)ethyl]-1-propylurea;
1-{[(4aR,6R,8aR)-2-amino-3-cyano-8-methyl-4H,4aH,5H,6H,7H, 8H,8aH, 9H-thieno[3,2-g]quinolin-6-yl]carbonyl}-1-butyl-3-[2-(diethylamino)ethyl]urea;
1-{[(4aR,6R,8aR)-2-amino-3-cyano-8-methyl-4H,4aH,5H,6H,7H, 8H, 8aH, 9H-thieno[3,2-g]quinolin-6-yl]carbonyl}-3-[3-(dimethylamino)-2,2-dimethylpropyl]-1-ethylurea;
1-{[(4aR,6R,8aR)-2-amino-3-cyano-8-methyl-4H,4aH,5H,6H,7H, 8H, 8aH, 9H-thieno[3,2-g]quinolin-6-yl]carbonyl}-3-ethyl-1-[2-(pyrrolidin-1-yl)ethyl]urea;
1-{[(4aR*,6R*,8aR*)-2-amino-3-cyano-8-methyl-4H, 4aH,5H,6H,7H,8H,8aH,9H-thieno[3,2-g]quinolin-6-yl]carbonyl}-1-butyl-3-[2-(dimethylamino)-ethyl]urea;
1-{[(4aR*,6R*,8aR*)-2-amino-3-cyano-8-methyl-4H, 4aH,5H,6H,7H,8H,8aH,9H-thieno[3,2-g]quinolin-6-yl]carbonyl}-3-[2-(dimethylamino)ethyl]-1-(2-phenylethyl)urea;
1-{[(4aR*,6R*,8aR*)-2-amino-3-cyano-8-methyl-4H, 4aH,5H,6H,7H,8H,8aH,9H-thieno[3,2-g]quinolin-6-yl]carbonyl}-3-[2-(dimethylamino)ethyl]-1-(3-methylbutyl)urea;
1-{[(4aR*,6R*,8aR*)-2-amino-3-cyano-8-methyl-4H, 4aH,5H,6H,7H, 8H,8aH,9H-thieno[3,2-g]quinolin-6-yl]carbonyl}-1-butyl-3-[2-(piperidin-1-yl)ethyl]urea;
1-{[(4aR*,6R*,8aR*)-2-amino-3-cyano-8-methyl-4H, 4aH,5H,6H,7H,8H,8aH,9H-thieno[3,2-g]quinolin-6-yl]carbonyl}-3-[2-(dimethylamino)ethyl]-1-(2,2-dimethylpropyl)urea;
1-{[(4aR,6R,8aR)-2-amino-3-cyano-8-methyl-4H,4aH,5H,6H,7H, 8H, 8aH, 9H-thieno[3,2-g]quinolin-6-yl]carbonyl}-3-[(2S)-1-(dimethylamino)propan-2-yl]-1-ethlylurea;
1-{[(4aR*,6R*,8aR*)-2-amino-3-cyano-8-methyl-4H, 4aH,5H,6H,7H,8H,8aH,9H-thieno[3,2-g]quinolin-6-yl]carbonyl}-3-[2-(dimethylamino)-2-methylpropyl]-1-propylurea;
1-{[(4aR*,6R*,8aR*)-2-amino-3-cyano-8-methyl-4H, 4aH,5H,6H,7H,8H,8aH,9H-thieno[3,2-g]quinolin-6-yl]carbonyl}-3-[2-(dimethylamino)-2-ethylbutyl]-1-ethylurea;
1-{[(4aR,6R,8aR)-2-amino-3-cyano-8-methyl-4H,4aH,5H,6H,7H,8H,8aH,9H-thieno[3,2-g]quinolin-6-yl]carbonyl}-1-(cyclopropylmethyl)-3-[3-(dimethylamino)-2,2-dimethylpropyl]urea;
1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[2-(diethylamino)ethyl]-1-ethylurea;
1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[1-(dimethylamino)-2-methylpropan-2-yl]-1-ethylurea;
1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[2-(dimethylamino)-2-ethylbutyl]-1-ethylurea;
1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[2-(dimethylamino)ethyl]-1-ethylurea; and
1-{[(4aR,6R,8aR)-2-amino-3-cyano-8-methyl-4H,4aH,5H,6H,7H,8H,8aH,9H-thieno[3,2-g]quinolin-6-yl]carbonyl}-1-(cyclopropylmethyl)-3-[2-(dimethylamino)ethyl]urea;
or a pharmaceutically acceptable salt thereof.

11. A pharmaceutical composition which comprises a compound according to claim 1 or a pharmaceutically acceptable salt thereof.

12. A pharmaceutical agent comprising (1) a compound according to claim 1 or a pharmaceutically acceptable salt thereof, and (2) at least one anti-Parkinson drug selected from L-dopa, dopamine $D_2$ receptor agonists, anticholinergic agents, adenosine $A_{2A}$ receptor antagonists, NMDA receptor antagonists, monoamine oxidase B inhibitors, COMT inhibitors, aromatic L-amino acid decarboxylase inhibitors, droxidopa, melevodopa, threodops, zonisamide and amantadine hydrochloride.

13. A pharmaceutical composition as claimed in claim 9, which is an agent for treatment of a disease selected from the group consisting of Parkinson's disease, restless legs syndrome and hyperprolactinemia.

14. A pharmaceutical composition as claimed in claim 11, which is an agent for the treatment of Parkinson's disease.

15. A method for the treatment of a disease selected from the group consisting of Parkinson's disease, restless legs syndrome and hyperprolactinemia, which comprises administering to a patient in need thereof an effective amount of a compound according to claim 1 or a pharmaceutically acceptable salt thereof.

16. A method as claimed in claim 13, which is for the treatment of Parkinson's disease.

17. 1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[2-(dimethylamino)ethyl]-1-propylurea, or a pharmaceutically acceptable salt thereof.

18. 1-{[(4aR*,6R*,8aR*)-2-amino-3-cyano-8-methyl-4H,4aH,5H,6H,7H,8H,8aH,9H-thieno[3,2-g]quinolin-6-yl]carbonyl}-1-butyl-3-[2-(piperidin-1-yl)-ethyl]urea, or a pharmaceutically acceptable salt thereof.

19. 1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[2-(dimethylamino)-propan-2-yl]-1-ethylurea, or a pharmaceutically acceptable salt thereof.

20. 1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[2-(dimethylamino)-2-ethylbutyl]-1-ethylurea, or a pharmaceutically acceptable salt thereof.

21. 1-{[(4aR,6R,8aR)-2-amino-3-cyano-8-methyl-4H,4aH,5H,6H,7H,8H,8aH,9H-thieno[3,2-g]quinolin-6-yl]carbonyl}-3-[2-(dimethylamino)ethyl]-1-ethylurea, or a pharmaceutically acceptable salt thereof.

\* \* \* \* \*